US012024717B2

(12) United States Patent
Nakauchi et al.

(10) Patent No.: US 12,024,717 B2
(45) Date of Patent: Jul. 2, 2024

(54) METHOD FOR RECONSTRUCTING IMMUNE FUNCTION USING PLURIPOTENT STEM CELLS

(71) Applicant: The University of Tokyo, Tokyo-To (JP)

(72) Inventors: Hiromitsu Nakauchi, Tokyo-To (JP); Shin Kaneko, Tokyo-To (JP); Toshinobu Nishimura, Tokyo-To (JP)

(73) Assignee: The University of Tokyo, Tokyo (JP)

( * ) Notice: Subject to any disclaimer, the term of this patent is extended or adjusted under 35 U.S.C. 154(b) by 752 days.

(21) Appl. No.: 16/991,758

(22) Filed: Aug. 12, 2020

(65) Prior Publication Data

US 2021/0032595 A1 Feb. 4, 2021

Related U.S. Application Data

(60) Division of application No. 14/928,556, filed on Oct. 30, 2015, now Pat. No. 10,787,642, which is a continuation of application No. 13/565,558, filed on Aug. 2, 2012, now Pat. No. 9,206,394, which is a continuation-in-part of application No. PCT/JP2011/052260, filed on Feb. 3, 2011.

(60) Provisional application No. 61/300,991, filed on Feb. 3, 2010.

(30) Foreign Application Priority Data

May 22, 2012 (JP) ................................ 2012-116639

(51) Int. Cl.

| | |
|---|---|
| *C12N 5/0783* | (2010.01) |
| *A61K 35/17* | (2015.01) |
| *A61K 39/00* | (2006.01) |
| *A61K 39/21* | (2006.01) |
| *C12N 5/074* | (2010.01) |

(52) U.S. Cl.

CPC ............ *C12N 5/0636* (2013.01); *A61K 35/17* (2013.01); *A61K 39/00* (2013.01); *A61K 39/21* (2013.01); *C12N 5/0638* (2013.01); *C12N 5/0696* (2013.01); *A61K 2039/5158* (2013.01); *C12N 2500/02* (2013.01); *C12N 2501/065* (2013.01); *C12N 2501/2302* (2013.01); *C12N 2501/2307* (2013.01); *C12N 2501/2315* (2013.01); *C12N 2501/415* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/608* (2013.01); *C12N 2501/727* (2013.01); *C12N 2506/11* (2013.01); *C12N 2506/45* (2013.01); *C12N 2510/00* (2013.01)

(58) Field of Classification Search

CPC .. C12N 5/0636; C12N 5/0638; C12N 5/0696; C12N 2500/02; C12N 2501/065; C12N 2501/2302; C12N 2501/2307; C12N 2501/2315; C12N 2501/415; C12N 2501/602; C12N 2501/603; A61K 35/17; A61K 39/00; A61K 39/21; A61K 2039/5158

See application file for complete search history.

(56) References Cited

U.S. PATENT DOCUMENTS

| | | | |
|---|---|---|---|
| 9,206,394 | B2 | 12/2015 | Nakauchi et al. |
| 10,787,642 | B2 | 9/2020 | Nakauchi et al. |
| 2003/0217374 | A1 | 11/2003 | West |
| 2008/0166325 | A1 | 7/2008 | Sagawa et al. |
| 2009/0047263 | A1 | 2/2009 | Yamanaka et al. |
| 2011/0318828 | A1 | 12/2011 | Suzuki et al. |
| 2012/0135525 | A1 | 5/2012 | Brown et al. |
| 2013/0078226 | A1 | 3/2013 | Nakauchi et al. |
| 2017/0009206 | A1 | 1/2017 | Nakauchi et al. |

FOREIGN PATENT DOCUMENTS

| | | | |
|---|---|---|---|
| EP | 2853590 | A1 | 4/2015 |
| JP | H09500261 | A | 1/1997 |
| JP | 2012-528599 | A | 11/2012 |
| WO | WO-94/026876 | A1 | 11/1994 |
| WO | WO-2008/038579 | A1 | 4/2008 |
| WO | WO-2008/143255 | A1 | 11/2008 |
| WO | WO-2009/148057 | A1 | 12/2009 |
| WO | WO-2009/152529 | A2 | 12/2009 |
| WO | WO-2009/157593 | A1 | 12/2009 |
| WO | WO-2010/141801 | A2 | 12/2010 |
| WO | WO-2011/096482 | A1 | 8/2011 |
| WO | WO-2013/176197 | A1 | 11/2013 |

OTHER PUBLICATIONS

Cabello-Kindelan et al. “Adoptive T Regulatory Cell Therapy for Tolerance Induction.” Current Transplantation Reports vol. 2, pp. 191-201 (2015) (Year: 2015).*

NIH. National Cancer Institute. “Cell Therapy: Harnessing Cells of the Immune System to Fight Cancer.” retrieved from https://www.cancer.gov/research/annual-plan/scientific-topics/cell-therapy. accessed Mar. 10, 2023. (Year: 2023).*

Zehbe et al. “Human papillomavirus 16 E6-specific CD45RA+ CCR7+ high avidity CD8+ T cells fail to control tumor growth despite interferon-gamma production in patients with cervical cancer.” J Immunother . Jul.-Aug. 2007;30(5):523-32. (Year: 2007).*

Liu et al. “NK cell-based cancer immunotherapy: from basic biology to clinical development.” Journal of Hematology & Oncology vol. 14, Article No. 7 (2021) (Year: 2021).*

(Continued)

*Primary Examiner* — Titilayo Moloye

(74) *Attorney, Agent, or Firm* — Clark & Elbing LLP; Susan M. Michaud

(57) ABSTRACT

According to the present invention, there are provided a method for producing a human T cell, which comprises the steps of inducing an iPS cell from a human T cell, and differentiating the iPS cell into a T cell; a pharmaceutical composition comprising the T cell produced by the method; and a method for cell-based immunotherapy using the method.

11 Claims, 65 Drawing Sheets

Specification includes a Sequence Listing.

(S)

(56) References Cited

OTHER PUBLICATIONS

Stauss et al. "Immunotherapy with gene-modified T cells: limiting side effects provides new challenges." Gene Therapy vol. 20, pp. 1029-1032 (2013) (Year: 2013).*
NIH. National Cancer Institute. "Immunotherapy to Treat Cancer." retrieved from hhttps://www.cancer.gov/about-cancer/treatment/types/immunotherapy. accessed Mar. 10, 2023. (Year: 2023).*
T-cell transfer therapy—immunotherapy. National Cancer Institute. (n.d.). https://www.cancer.gov/about-cancer/treatment/types/immunotherapy/t-cell-transfer-therapy. acessed Sep. 22, 2023 (Year: 2023).*
Annunziato et al., "CXCR3 and alphaEbeta7 integrin identify a subset of CD8+ mature thymocytes that share phenotypic and functional properties with CD8+ gut intraepithelial lymphocytes," Gut. 55(7):961-8 (2006).
Appay et al., "Phenotype and function of human T lymphocyte subsets: consensus and issues," Cytometry A. 73(11):975-83 (2008).
Becker et al., "Interleukin 15 is required for proliferative renewal of virus-specific memory CD8 T cells." J Exp Med. 195(12):1541-8 (2002).
Bendle et al., "Lethal graft-versus-host disease in mouse models of T cell receptor gene therapy," Nat Med. 16(5):565-70 (2010).
Brooks et al., "Human T-cell receptor (TCR) alpha/beta + CD4-CD8-T cells express oligoclonal TCRs, share junctional motifs across TCR V beta-gene families, and phenotypically resemble memory T cells," Proc Natl Acad Sci U.S.A. 90(24):11787-91 (1993).
Brown et al., "Derivation of induced pluripotent stem cells from human peripheral blood T lymphocytes," PLoS One. 5(6):e11373 (2010).
Butler et al., "Immunologic considerations for generating memory CD8 T cells through vaccination," Cell Microbiol. 13(7):925-33 (2011).
Catalog #10-1335, BIX-01294, CAS#935693-62-2, Lot #2107097, "2-(Hexahydro-4-methyl-1H-1,4-diazepin-1-yl)-6,7-dimethoxy-N-[1-(phenylmethyl)-4-piperidinyl]-4-quinazolinamine trihydrochloride," Focus Biomolecules, Plymouth Meeting PA, accessed May 20, 2014 (1 page).
Chong et al., "Suppressor of cytokine signaling-1 is a critical regulator of interleukin-7-dependent CD8+ T cell differentiation," Immunity. 18(4):475-87 (2003).
Comments related to PCT Application No. PCT/JP2011/052260, corresponding to Publication No. WO 2011/096482, dated Dec. 3, 2015 (2 pages).
Communication pursuant to Article 94(3) EPC for European Patent Application No. 13794060.7, dated Jul. 5, 2016 (7 pages).
Components of the immune system: Biology of the immune system, <http://merckmanual.jp/mmpej/print/sec13/ch163/ch163b.html>, retrieved Oct. 28, 2015 (11 pages).
Eduardo, "Generation of CD8[+] single positive T cells in vitro from iPS cells derived from human mature T cells," cover page, pp. 1, 2, 4, 5, 6, 8, 9, 10, and 11, and figure, dated Mar. 27, 2012 (10 pages).
Eduardo, "Generation of CD8[+] single positive T cells in vitro from iPS cells derived from human mature T cells," dated Mar. 27, 2012 (16 pages).
Eminli et al., "Differentiation stage determines potential of hematopoietic cells for reprogramming into induced pluripotent stem cells," Nat Genet. 41(9):968-976 (2009).
English translation of Japanese Application No. 2012-116639, filed May 22, 2012 (106 pages).
English translation of PCT Application No. PCT/JP2011/052260, corresponding to Publication No. WO 2011/096482-A1, published Aug. 11, 2011 (85 pages).
Fusaki et al., "Efficient induction of transgene-free human pluripotent stem cells using a vector based on Sendai virus, an RNA virus that does not integrate into the host genome, " Proc Jpn Acad Ser B Phys Biol Sci. 85(8):348-62 (2009).
Galic et al., "T lineage differentiation from human embryonic stem cells," Proc Natl Acad Sci USA. 103(31):11742-7 (2006).
Gonzalez et al., "Generation of mouse-induced pluripotent stem cells by transient expression of a single nonviral polycistronic vector," Proc Natl Acad Sci USA. 106(22):8918-22 (2009).
González-García et al., "Notch 1 signalling in human T-cell development and leukemia," Immunología. 28(4):193-208 (2009).
Goto et al., "O-05-7 Attempt to induce T cells from human pluripotent stem cells (IPSCs)," University of Tokyo, 2010.
Greenberg, "Adoptive T cell therapy of tumors: mechanisms operative in the recognition and elimination of tumor cells," Adv Immunol. 49:281-355 (1991).
Hong et al., "Suppression of induced pluripotent stem cell generation by the p53-p21 pathway," Nature. 460(7259):1132-1135 (2009).
Huang et al., "Ordered and coordinated rearrangement of the TCR alpha locus: role of secondary rearrangement in thymic selection," J Immunol. 166(4):2597-601 (2001).
International Preliminary Report on Patentability for International Application No. PCT/JP2011/052260 issued Sep. 18, 2012.
International Search Report for International Patent Application No. PCT/JP2011/052260 dated Apr. 18, 2011 (3 pages).
International Search Report for PCT/JP2013/064291, mailed Aug. 27, 2013 (4 pages).
Jameson et al., "Diversity in T cell memory: an embarrassment of riches," Immunity. 31(6):859-71 (2009).
Japanese Office Action for Japanese Application No. 2014-516839, dated Apr. 26, 2016 (13 pages).
June, "Adoptive T cell therapy for cancer in the clinic," J Clin Invest. 117(6):1466-76 (2007).
Kaneko et al., "IL-7 and IL-15 allow the generation of suicide gene-modified alloreactive self-renewing central memory human T lymphocytes," Blood. 113(5):1006-15 (2009).
Kaneko, "Reprogramming of antigen-specific CD4 T cells to regulatory T cells via T-iPS cells," Journal of Japanese Society for Regenerative Medicine. 11(4):63-6 (2012). English translation provided (4 pages).
Kennedy et al., "T lymphocyte potential marks the emergence of definitive hematopoietic progenitors in human pluripotent stem cell differentiation cultures," Cell Rep. 2(6):1722-35 (2012).
Khor et al., "Allelic exclusion at the TCRbeta locus," Curr Opin Immunol. 14(2):230-4 (2002).
Kim et al., "Chemokine C receptor 7 expression and protection of circulating CD8+ T lymphocytes from apoptosis," Clin Cancer Res. 11(21):7901-10 (2005).
Kim et al., "Generation of human induced pluripotent stem cells by direct delivery of reprogramming proteins," Cell Stem Cell. 4(6):472-6 (2009).
Klebanoff et al., "CD8+ T-cell memory in tumor immunology and immunotherapy," Immunol Rev. 211:214-24 (2006).
Kouro et al., "In vitro differentiation and measurement of B cell progenitor activity in culture," Curr Protoc Immunol. Chapter 22: Unit 22F.2 (2005).
Lei et al., "T lineage differentiation from induced pluripotent stem cells," Cell Immunol. 260(1):1-5 (2009).
Lewitzky et al., "Reprogramming somatic cells towards pluripotency by defined factors," Curr Opin Biotechnol. 18(5):467-73 (2007).
MacLeod et al., "Memory CD4 T cells: generation, reactivation and re-assignment," Immunology. 130(1):10-5 (2010).
Marion et al., "Telomeres acquire embryonic stem cell characteristics in induced pluripotent stem cells," Cell Stem Cell. 4(2):141-54 (2009).
Montaudouin et al., "Endogenous TCR Recombination in TCR Tg Single RAG-deficient Mice Uncovered by Robust in Vivo T Cell Activation and Selection," PLoS One. 5(4):e10238 (2010) (8 pages).
Monteiro et al., "Shortened telomeres in clonally expanded CD28-CD8+ T cells imply a replicative history that is distinct from their CD28+CD8+ counterparts," J Immunol. 156(10):3587-90 (1996).
Morgan et al., "Cancer regression in patients after transfer of genetically engineered lymphocytes," Science. 314(5796):126-9 (2006).
Murphy et al., Chapter 7: The Development and Survival of Lymphocytes. *Janeway's Immunobiology, Seventh Edition*.Garland Science, 286-315. 2008.

(56) References Cited

OTHER PUBLICATIONS

Nishimura et al., "Development of defective and persistent Sendai virus vector: a unique gene delivery/expression system ideal for cell reprogramming," J Biol Chem. 286(6):4760-71 (2011).
Nishimura et al., "Generation of monoclonal TCR-expressing human T-lineage lymphocytes from induced pluripotent stem cells of single peripheral T-lymphocyte origin," Blood. 116(21):Abstract 490 (2 pages) (2010).
Nishimura et al., "Generation of rejuvenated antigen-specific T cells by reprogramming to pluripotency and redifferentiation," Cell Stem Cell. 12(1):114-26 (2013).
Nishimura et al., "In vitro generation of mature T lymphocytes from human iPS cells and genetic analysis of TCR gene rearrangements," Blood. 118(21): Abstract 2984 (2 pages) (2011).
Nishimura et al., "iPS cells derived from T cells and differentiation induction of T cells," Regenerative Medicine. 11 (suppl): 212 Abstract O-34-4 (2012). English translation provided.
Nishimura et al., "O-06-1 Induction of induced pluripotent stem cells (iPSCs) from human peripheral blood T cells," The University of Tokyo, 2010.
Nishimura et al., "Rejuvenation of antigen-specific T cells through reprogramming and redifferentiation," Proceedings of the Japanese Society for Immunology. 41:174 Abstract 3-D-W48-10-O/P (2012).
Niwa et al., "Quantitative expression of Oct-3/4 defines differentiation, dedifferentiation or self-renewal of ES cells," Nat Genet. 24(4):372-6 (2000).
Notification of Reasons for Refusal for Japanese Application No. 2014-516839, mailed Oct. 27, 2015 (10 pages).
Office Action dated Oct. 1, 2019 for Japanese Application No. 2018-143504, Nakauchi et al., "Method for Producing Antigen-Specific T Cells," filed Jul. 31, 2018 (7 pages).
Office Action dated Oct. 30, 2018 for Japanese Application No. 2017-194948, Nakauchi et al., "Method for Reconstructing Immune Function Using Pluripotent Stem Cells," filed Oct. 5, 2017 (10 pages).
Office Action for Japanese Patent Application No. 2011-552821, dated Apr. 7, 2015 (8 pages).
Office Action for Japanese Patent Application No. 2014-516839, dated Jan. 10, 2017 (4 pages).
Office Action for Japanese Patent Application No. 2016-022720, dated Jan. 31, 2017 (4 pages).
Okazaki et al., "PD-1 and PD-1 Ligands: From Discovery to Clinical Application," Int Immunol. 19(7):813-24 (2007).
Okita et al., "Generation of mouse induced pluripotent stem cells without viral vectors," Science. 322(5903):949-53 (2008).
Okumura et al., "3rd T-cell differentiation in thymus," <http://.or.jp/med/jbsquare/autoimmune/immunology/im03/01.php> (with full English Translation), 2011 (10 pages).
Pending Claims for Japanese Application No. 2014-516839 (1 page).
Petrie et al., "Multiple rearrangements in T cell receptor alpha chain genes maximize the production of useful thymocytes," J Exp Med. 178(2):615-22 (1993).
Porter et al., "Chimeric antigen receptor-modified T cells in chronic lymphoid leukemia," N Engl J Med. 365(8):725-33 (2011).
Prlic et al., "Multiple choices: regulation of memory CD8 T cell generation and homeostasis by interleukin (IL)-7 and IL-15," J Exp Med. 195(12):F49-52 (2002).
Reimann et al., "Further characterization of T-cellular precursors generated from $CD34^+$progenitors by exposure to immobilized notch ligand delta-like 4 in vitro," Blood. 16: Abstract 3712 (2010).
Riddell et al., "Restoration of viral immunity in immunodeficient humans by the adoptive transfer of T cell clones," Science. 257(5067):238-41 (1992).
Romero et al., "Four functionally distinct populations of human effector-memory CD8+ T lymphocytes," J Immunol. 178(7):4112-9 (2007).
Rubio et al., "Ex vivo identification, isolation and analysis of tumor-cytolytic T cells," Nat Med. 9(11):1377-82 (2003).
Sauce et al., "PD-1 expression on human CD8 T cells depends on both state of differentiation and activation status," AIDS 21(15):2005-13 (2007).
Schmitt et al., "Induction of T cell development and establishment of T cell competence from embryonic stem cells differentiated in vitro," Nat Immunol. 5(4):410-7 (2004).
Seki et al., "Generation of induced pluripotent stem cells from human terminally differentiated circulating T cells," Cell Stem Cell. 7(1):11-14 (2010).
Shi et al., "A combined chemical and genetic approach for the generation of induced pluripotent stem cells," Cell Stem Cell. 2(6):525-8 (2008).
Singer et al., "Lineage fate and intense debate: myths, models and mechanisms of CD4-versus CD8-lineage choice," Nat Rev Immunol. 8(10):788-801 (2008).
Stadtfeld et al., "Induced pluripotent stem cells generated without viral integration," Science. 322(5903):945-9 (2008).
Supplementary Search Report for European Application No. 13794060.7, mailed Nov. 10, 2015 (9 pages).
Takahashi et al., "Induction of pluripotent stem cells from adult human fibroblasts by defined factors," Cell. 131(5):861-72 (2007).
Takayama et al., "Generation of functional platelets from human embryonic stem cells in vitro via ES-sacs, VEGF-promoted structures that concentrate hematopoietic progenitors," Blood. 111(11):5298-306 (2008).
Takayama et al., "Transient activation of c-MYC expression is critical for efficient platelet generation from human induced pluripotent stem cells," J Exp Med. 207(13):2817-30 (2010).
Tan et al., "Interleukin (IL)-15 and IL-7 jointly regulate homeostatic proliferation of memory phenotype CD8+ cells but are not required for memory phenotype CD4+ cells," J Exp Med. 195(12):1523-32 (2002).
The Development and Survival of Lymphocytes. Janeway's Immunobiology. Murphy, Travers, and Walport, 286-299, 314 (2008).
Timmermans et al., "Generation of T cells from human embryonic stem cell-derived hematopoietic zones," J Immunol. 182(11):6879-88 (2009).
Topalian et al., "Cancer immunotherapy comes of age," J Clin Oncol. 29(36):4828-36 (2011).
Turka et al., "Thymocyte expression of RAG-1 and RAG-2: termination by T cell receptor cross-linking," Science. 253(5021):778-81 (1991).
Verhasselt et al., "Generation of transgenic T cells from human CD34+ cord blood cells," Methods Mol Biol. 215:327-39 (2003).
Vodyanik et al., "Human embryonic stem cell-derived CD34+ cells: efficient production in the coculture with OP9 stromal cells and analysis of lymphohematopoietic potential," Blood. 105(2):617-26 (2005).
Von Boehmer, "Selection of the T-cell repertoire: receptor-controlled checkpoints in T-cell development." Adv Immunol. 84:201-38 (2004).
Weng et al., "Regulation of telomere length and telomerase in T and B cells: a mechanism for maintaining replicative potential," Immunity. 9(2):151-7 (1998).
Wherry, "T cell exhaustion," Nat Immunol. 12(6):492-9 (2011).
Williams et al., "Generation of lytic natural killer 1.1+, Ly-49-cells from multipotential murine bone marrow progenitors in a stroma-free culture: definition of cytokine requirements and developmental intermediates," J Exp Med. 186(9):1609-14 (1997).
Woo et al., "In vitro differentiation of natural killer T cells from human cord blood CD34+ cells," Br J Haematol. 121(1):148-56 (2003).
Yamanaka et al., "Induction of pluripotent stem cells from mouse fibroblasts by four transcription factors," Cell Prolif. 41 (Suppl 1):51-6 (2008).
Yee et al., "Adoptive T cell therapy using antigen-specific CD8+ cell clones for the treatment of patients with metastatic melanoma: In vivo persistence, migration, and antitumor effect of transferred T cells," Proc Nat Acad Sci USA. 99(25):16168-73 (2002).
Zambidis et al., "Hematopoietic differentiation of human embryonic stem cells progresses through sequential hematoendothelial, primitive, and definitive stages resembling human yolk sac development," Blood. 106(3):860-70 (2005).

(56) References Cited

OTHER PUBLICATIONS

Zhang et al., "CD8(+) T cells: foot soldiers of the immune system," Immunity. 35(2):161-8 (2011).
Benigni et al., "Phenotype and homing of CD4 tumor-specific T cells is modulated by tumor bulk," J. Immunol. 175(2):739-748 (2005).
Geiger et al., "Human naive and memory CD4+ T cell repertoires specific for naturally processed antigens analyzed using libraries of amplified T cells," J. Exp. Med. 206(7):1525-1534 (2009).
Notice of Reasons for Refusal dated Oct. 6, 2020 for Japanese Patent Application No. 2017-194948, Nakauchi et al., "Method for Reconstructing Immune Function using Pluripotent Stem Cells," filed Oct. 5, 2017 (6 pages).
Decision of Dismissal of Amendment issued Jun. 8, 2021 for Japanese Patent Application No. 2019-168931, Nakauchi et al., "Method for Reconstructing Immune Function Using Pluripotent Stem Cells," filed Sep. 18, 2019 (4 pages).
Andersen R, Donia M, Ellebaek E, et al. "Long-lasting complete responses in patients with metastatic melanoma after adoptive cell therapy with tumor-infiltrating lymphocytes and an attenuated IL2 regimen." Clin Cancer Res. 2016;22(15):3734-3745.
Dudley ME, Wunderlich JR, Robbins PF, et al. "Cancer regression and autoimmunity in patients after clonal repopulation with antitumor lymphocytes," available in PMC Jan. 5, 2007, published in final edited form as: Science. 2002;298(5594):850-854 (10 pages).
Rosenberg SA, Packard BS, Aebersold PM, et al. "Use of tumor-infiltrating lymphocytes and interleukin-2 in the immunotherapy of patients with metastatic melanoma." N Engl J Med. 1988;319(25):1676-1680.
Tran E, Turcotte S, Gros A, et al. "Cancer immunotherapy based on mutation-specific CD4+ T cells in a patient with epithelial cancer," available in PMC Aug. 8, 2019, published in final edited form as: Science. 2014;344(6184):641-645 (10 pages).

* cited by examiner

Molecular Markers

Karyotype (TkT3V 1-7)

Karyotype (TkT4V 1-3)

Teratoma formation

FIG. 22

Produced TCRβ mRNA & protein sequences

| Input | V name | 3'V-REGION | N1 | D-REGION | N2 | 5'J-REGION | J name | D name | Vmut | Dmut | Jmut | Ngc |
|---|---|---|---|---|---|---|---|---|---|---|---|---|
| TCRB | TRBV29-1*01 | tgcagcgttga... | t | .ggacaggg... | a | ..aacaccggggagctgtttttt | TRBJ2-2*01 | TRBD1*01 | 0 | 0 | 0 | 0/2 |

| | 104 | 105 | 106 | 107 | 108 | 109 | 110 | 112 | 113 | 114 | 115 | 116 | 117 | 118 | Frame | CDR3-IMGT length | Molecular mass | pI |
|---|---|---|---|---|---|---|---|---|---|---|---|---|---|---|---|---|---|---|
| | C | S | V | D | G | Q | G | N | T | G | E | L | F | F | | | | |
| TCRB | tgc | agc | gtt | gat | gga | cag | gga | aac | acc | ggg | gag | ctg | ttt | ttt | + | 12 | 1,473.58 | 13.0 |

Expressed monoclonaly
&
100% match with genomic sequence

Produced TCRα mRNA & protein sequences

| Input | V name | 3'V-REGION | N | 5'J-REGION | J name | Vmut | Jmut | Ngc |
|---|---|---|---|---|---|---|---|---|
| TCRA | TRAV38-2/DV8*01 | tgtgcttat....... | tggagt | .aataacaatgccagactcatgttt | TRAJ31*01 | 0 | 0 | 3/6 |

| | 104 | 105 | 106 | 107 | 108 | 109 | 110 | 113 | 114 | 115 | 116 | 117 | 118 | Frame | CDR3-IMGT length | Molecular mass | pI |
|---|---|---|---|---|---|---|---|---|---|---|---|---|---|---|---|---|---|
| | C | A | Y | W | S | N | N | N | A | R | L | M | F | | | | |
| TCRA | tgt | gct | tat | tgg | agt | aat | aac | aat | gcc | aga | ctc | atg | ttt | + | 11 | 1,589.82 | 9.25 |

Expressed monoclonaly
&
100% match with genomic sequence

| | Vα | (P)N | Jα |
|---|---|---|---|
| Rearranged (Productive) | TRAV38-2/DV8*01<br>TGTGCTTAT ........ | TGGAGT | TRAJ31*01<br>. AATAACAATGCCAGACTCATGTTT |

| | Vβ | N1 | Dβ | N2 | Jβ |
|---|---|---|---|---|---|
| Rearranged (Productive) | TRBV29-1*01<br>TGCAGCGTTGA ... | T | TRBD1*01<br>. GGACAGGG ... | A | TRBJ2-2*01<br>.. AACACCGGGGAGCTGTTTTTT |

METHOD FOR RECONSTRUCTING IMMUNE FUNCTION USING PLURIPOTENT STEM CELLS

CROSS-REFERENCE TO RELATED APPLICATIONS

The present application enjoys the benefit of priority of the prior U.S. Provisional Application 61/300,991, filed on Feb. 3, 2010, PCT Application PCT/JP2011/052260, filed on Feb. 3, 2011, and Japanese Patent Application No. 2012-116639, filed on May 22, 2012, the entire content of which disclosures is incorporated herein by reference.

BACKGROUND OF THE INVENTION

Field of the Invention

The present invention relates to a method for reconstructing immune function using pluripotent stem cells, and more particularly to a method for producing a human T cell, a pharmaceutical composition comprising the T cell produced by the method, and a method for cell-based immunotherapy using the method. The present invention also relates to an efficient method for producing a human CD8 single-positive cell (CD8 SP cell) having antigen specificity. The present invention also relates to a pharmaceutical composition comprising a human CD8 SP cell having antigen specificity which is produced by such a method, and to a method for cell-based immunotherapy using such a method.

Description of the Related Art

If supplementation or regeneration of immunocytes (immune cells) and others can be achieved in cases of decreased immune function resulting from various causes, then highly effective tools will be provided, for example, in ameliorating pathological conditions of and improving the effect of treatment of diseases. In particular, there is a strong need for supplementation of function of or regeneration of T lymphocytes and CD8 SP cells which are responsible for cellular immunity; however, no effective treatment methods have been established at present. This is largely because while immunological effects are characterized by their specificity, it is difficult to take good advantage of their specificity.

Along with recent rapid progress of genetic manipulation technology, attempts have been made to introduce antigen-specific T-cell receptor (TCR) genes into different types of lymphoid cells, thereby to supplement or regenerate specific immune reactions (Gattinoni L. et al., Nature Reviews Immunology, 2006, Vol. 6, pp. 383-393; and Morgan R. et al., Science, 2006, Vol. 314, pp. 126-129). These attempts used, for example, CD34 positive cells, which are a subset of myeloid progenitor cells, and naive T lymphocytes as cells for gene introduction. However, these types of cells suffer from many problems, such as a reduced capacity for ex vivo self-renewal, a low efficiency of gene introduction, difficulties in controlling their differentiation by gene introduction, and others.

Embryonic stem cells (ES cells) and artificial pluripotent stem cells (induced pluripotent stem cell, iPS cells) have recently been established from many animal species, including humans. These types of pluripotent stem cells would be the most useful source of cells for regenerative medicine because these cells are capable of differentiation into almost all of the organs by appropriate induction of their differentiation, with retaining their ability of actively dividing while maintaining their pluripotency. iPS cells, in particular, can be established from self-derived somatic cells, and therefore are not likely to cause ethical and social issues, in comparison with ES cells which are produced by destruction of embryos. Further, iPS cells, which are self-derived cell, make it possible to avoid rejection reactions, which are the biggest obstacle to regenerative medicine or transplantation therapy.

iPS cells can be established by reprogramming somatic cells in various methods. It has been a subject of great interest whether it is possible that since reprogrammed iPS cells carry, without any changes, the information of genes employed for the reprogramming, reprogramming can be also achieved in cells which have undergone gene rearrangement and terminal differentiation as in cells of the immune system, especially B- and T-lymphocytes. In such circumstances, there were reported the establishment of iPS cells from mouse B lymphocytes by Jaenisch et al. in 2008 (Hanna J. et al., Cell, 2008, Vol. 133, No. 2, pp. 250-264) and the establishment of iPS cells from mouse T lymphocytes by Yamanaka et al. in 2009 (Hong H. et al., Nature, 2009, Vol. 460, pp. 1132-1135). However, it has not been reported that iPS cells have been established from human T lymphocytes.

To realize immunotherapies using T lymphocytes, it is necessary that in addition to establishing IPS cells from human T lymphocytes, established iPS cells are induced to differentiate into functional T lymphocytes and CD8 SP cells, with retaining the TCR gene rearrangement pattern which is exhibited by the originating human T lymphocytes of the iPS cells. However, there have not been established such techniques yet.

SUMMARY OF THE INVENTION

The present invention has been made in view of the problems of the prior art as described above. An object of the present invention is to provide a method which allows one to establish an iPS cell from a human T lymphocyte and further to induce the differentiation of the established iPS cell into a functional T lymphocyte, with retaining the TCR gene rearrangement pattern which is exhibited by the originating human T lymphocyte of the iPS cell. Another object of the present invention is to efficiently produce a CD8 SP cell which has the same rearrangement pattern of the TCR gene as in its originating human T cell. Still another object of the present invention is to provide a pharmaceutical composition comprising the T cell thus produced and a method for cell-based immunotherapy using the T cell thus produced.

The present inventors have intensively studied so as to achieve the above objects and successfully established an iPS cell from a human T cell, with maintaining the same TCR rearrangement pattern as in its originating human T lymphocyte. The present inventors have been also successful in inducing the differentiation from a human T-cell-derived iPS cell thus established (T-iPS cell) into a functional T cell having, for example, the ability to produce cytokines, with maintaining the same TCR rearrangement pattern as in its originating human T lymphocyte. However, when the resulting functional T cells were subjected to further differentiation to obtain CD8 SP cells, the frequency of T cells having the same gene-rearrangement pattern as in their originating T cells was reduced to one fourth or so. The present inventors have surprisingly found that CD4/CD8 DN cells which have been redifferentiated from the T-IPS cells express TCR, which is usually not expressed on DN cells.

The present inventors have also found that TCR stimulation suppresses further rearrangement of the TCR gene and makes it possible to dramatically improve the frequency of appearance of T cells having the same gene-rearrangement pattern as in their originating T cells. Based on this, the present inventors have further found that implantation of the thus-obtained human T cells in patients will allow one to carry out an ideal cell-based immunotherapy in the patients. The present invention has been made based on these findings.

Thus, the present invention provides the following inventions:

(1) A method for producing a human T cell, which comprises the steps of inducing an iPS cell from a human T cell, and differentiating the iPS cell into a T cell.

(2) The method according to the above (1), wherein the human T cell is a T cell which expresses at least one molecule selected from the group consisting of CD4 and CD8.

(3) The method according to the above (1) or (2), wherein the T cell which is to be induced into the iPS cell has antigen specificity.

(4) The method according to the above (3), wherein the antigen specificity of the T cell which is to be induced into the iPS cell is identical to that of the T cell which is differentiated from the iPS cell.

(5) A human T cell which is produced by the method according to any one of the above (1) to (4).

(6) A pharmaceutical composition comprising the human T cell according to the above (5).

(7) A method for cell-based immunotherapy, which comprises the steps of:

isolating a T cell having a desired antigen specificity from a human, inducing an iPS cell from the T cell having the desired antigen specificity, differentiating the iPS cell into a T cell, and administering to a human the resulting T cell derived from the IPS cell.

(8) A method for producing a human CD8 single-positive cell having antigen specificity, which comprises the steps of:

differentiating an iPS cell that has been induced from a human T cell, into a CD4/CD8 double-negative cell, stimulating the T cell receptor of the CD4/CD8 double-negative cell, and differentiating the CD4/CD8 double-negative cell whose T cell receptor has been stimulated, into a CD8 single-positive cell.

(9) A human CD8 single-positive cell having antigen specificity, which is produced by the method according to the above (8).

(10) A pharmaceutical composition comprising the human CD8 single-positive cell according to the above (9).

(11) A method for cell-based immunotherapy, which comprises the steps of:

differentiating an iPS cell that has been induced from a human T cell, into a CD4/CD8 double-negative cell, stimulating the T cell receptor of the CD4/CD8 double-negative cell, differentiating the CD4/CD8 double-negative cell whose T cell receptor has been stimulated, into a CD8 single-positive cell, and administering to a human the resulting human CD8 single-positive cell derived from the iPS cell.

Lymphocytes which acquire structural changes in the base sequences of the TCR or BCR genes during the process of development are a very unique population of cells as a source for establishing iPS cells. Recently, it has been reported one after another that it is possible to establish iPS cells with a rearranged TCR from mouse T or B cells, and it has been suggested that the TCR rearrangement pattern is not lost by nuclear transplantation or through reprogramming. However, any of these studies was performed using mice. By the present invention, it has been shown for the first time that iPS cells are obtained from human peripheral blood T lymphocytes, and further it has been demonstrated for the first time that when T-lineage cells are induced from iPS cells which have at least one in-frame TCR rearrangement, human T-lineage cells having such a rearranged TCR appear in a monoclonal fashion. Particularly in the induction into T-lineage cells from iPSCs (iPS cells) which have a single in-frame rearrangement in each of the TCR α and β chains, most of the appearing TCRs had the identical base sequence to that kept in the iPS cells and were monoclonal. This shows that T cells having a monoclonal TCRαβ directed to an antigen of interest can be induced with an incomparably high efficiency, relative to methods of introducing TCR genes into ES cells, CD34-positive hematopoietic stem cells, or naive T cells, in which cells account must be always taken of inhibitory effects (interfere) due to the expression of the endogenous TCR α and β chains (especially, the a chain which is not completely controlled by allelic exclusion).

Thus, according to the present invention, it is made possible to efficiently produce a human T lymphocyte, particularly a CD8 SP cell, which is specific for an antigen of interest. It is made possible that using human T lymphocytes thus produced provides a method for cell-based immunotherapy which has fewer problems due to rejection which is the biggest obstacle to regenerative medicine or transplantation therapy.

BRIEF DESCRIPTION OF THE DRAWINGS

FIG. 16(*b*) represents scatter plots showing the results of examining the expression of CD45, CD3, CD4, CD8, and TCRαβ using flow cytometry for T-lineage cells produced from respective types of pluripotent cells. In the drawing, "ES" indicates T-lineage cells derived from ES cells, "skin iPS" indicates T-lineage cells derived from skin iPS cells, "T-iPS" indicates T-lineage cells derived from T-iPS cells, and "PB" indicates peripheral blood (control data).

FIG. 17(*b*) represents scatter plots showing representative results of at least three independent experiments in which floating cells in the medium were collected at the indicated time points of culture and the expression of T-lineage markers CD45, CD34, CD3, CD4, CD8, and TCRαβ was examined using flow cytometry. The numerical value indicated in each of the scatter plots indicates the percentage of cells (%) in the indicated fraction(s). The plots in the bottom row in (B) represent the results of an analysis of fresh PBMCs (control date).

FIG. 22 represents the mRNA and amino acid sequences of TCRβ in re-differentiated T-lineage cells (T-lineage cells derived from T-iPS cells).

FIG. 23 represents the mRNA and amino acid sequences of TCRα in re-differentiated T-lineage cells (T-lineage cells derived from T-iPS cells).

FIG. 25 is a representation showing the results of a sequencing analysis of the PCR products in an acceptable size range (about 750 bp) shown in FIG. 24, which reveals that the sequences of all transcribed mRNAs are completely identical to the genome sequence of T-iPS cells (see FIG. 13) and that there have not been identified any progenies from an allele with a rearranged DJβ. The details and results of other samples are shown in Tables 8 and 9.

FIG. 49*b*** shows the results of an analysis by flow cytometry of the expression of CD45, CD56, CD3, TCRαβ, CD4, and CD8 on the cellular surface of H254SeVT-3-derived cells in a period of 35 to 42 days after the induction of re-differentiation. Shown in the drawings are representative results of the results of at least three independent experiments.

FIGS. 54*a* and 54*b* show the results of an analysis of the phenotype as T cell, and FIGS. 54*c* and 54*d* show the results of an analysis of the phenotype as memory cell. In FIG. 54*b*, it is also shown that there was no contamination with CD3+/CD8+ cells from PBMCs, because a uniform expression of HLA-A24 was observed.

DETAILED DESCRIPTION OF THE INVENTION

Figure 1:
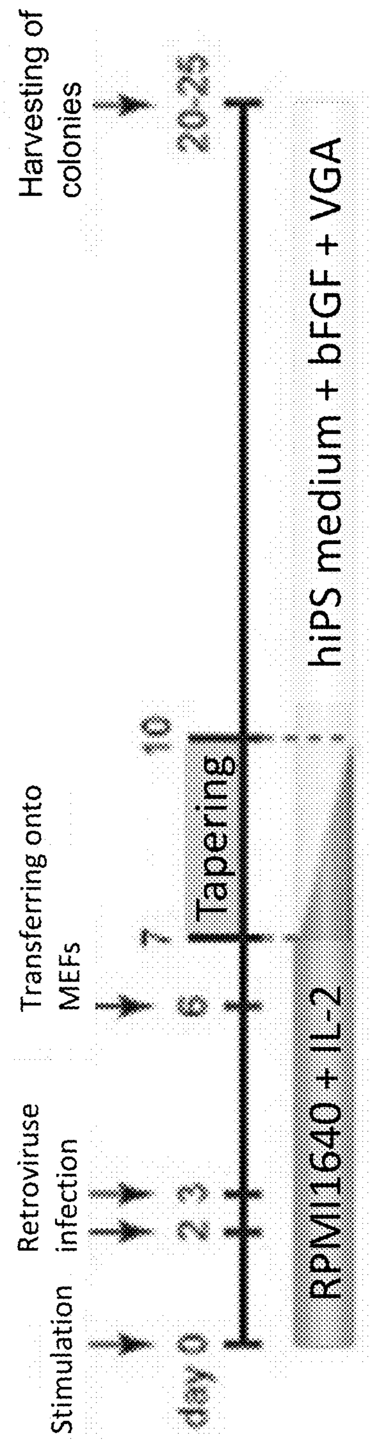
FIG. 1 represents an outline of the production of human iPS cells from peripheral blood T lymphocytes. In the drawing, "Tapering" indicates a period during which the medium was gradually replaced to human iPS cell medium (hiPS medium or the like).

<Methods for Production of Human T Cells>

The present invention provides a method for producing a human T cell, which comprises the steps of: (A-1) inducing an iPS cell from a human T cell, and (A-2) differentiating the iPS cell into a T cell. The following will describe the steps (A-1) and (A-2).

(A-1) Step of Inducing an iPS Cell from a Human T Cell

In the present invention, a "human" from which T cells are to be isolated is not limited in particular. Such a human may be a healthy individual, an individual with diminished immune function, or an individual suffering from a malignant tumor, infection, autoimmune disease, or the like. In cases where T cells obtained according to the present invention are used for a method for cell-based immunotherapy, a human from which T cells are to be isolated preferably has an HLA type identical to that of a human to which T cells obtained according to the present invention are to be administered, and more preferably is the same as a human to which T cells obtained according to the present invention are to be administered, from the viewpoint that rejection is not caused.

In the present invention, a "T cell" refers to a cell on the surface of which an antigen receptor, called a T cell receptor (TCR), is expressed, and its progenitor cells, such as a pro-T cell on which a TCR (TCRαβ) is not expressed, and a pre-T cell on which a TCRβ and a pre-TCRα are associated. A "CD4/CD8 double-negative (DN) cell" refers to a T cell on which neither CD4 nor CD8 is expressed, a "CD4/CD double-positive (DP) cell" refers to a T cell on which both CD4 and CD8 are expressed, and a "CD8 single-positive (SP) cell" refers to a T cell on which only CD8, in terms of CD4 and CD8, is expressed.

In the present invention, a "T cell which is to be induced into an iPS cell" and a "T cell which is differentiated from the iPS cell" are not limited in particular, and preferably are of a type of T cell on which CD3 is expressed and on which at least one molecule selected from the group consisting of CD4 and CD8 is expressed. Human T cells of such a type include, for example, helper/regulatory T cells, which are a subset of CD4-positive cells; cytotoxic T cells (CTLs), which are a subset of CD8-positive cells; naive T cells (CD45RA+CD62L+ cells); central memory T cells (CD45RA−CD62L+ cells); effector memory T cells (CD45RA−CD62L− cells); and terminal effector T cells (CD45RA+CD62L− cells). In cases of carrying out immunotherapy as mentioned below, it is preferable that a human T cell which is differentiated from the iPS cell has the same antigen specificity as that exhibited by a T cell which is to be induced into the iPS cell. Note that the antigen specificity of T cells is provided by their antigen-specific, rearranged TCR gene.

In the present invention, a "T cell which is to be induced into an iPS cell" can be isolated from a human tissue by known procedures. Such a human tissue is not limited in particular, if the tissue contains T cells of the above-mentioned type, and examples thereof include, for example, peripheral blood, a lymph node, bone marrow, thymus, spleen, umbilical cord blood, and a lesion site tissue. Among these, peripheral blood and umbilical cord blood are preferable from the viewpoints that their isolation is less invasive to the human body and that they are prepared with ease. Known procedures for isolating human T cells include, for example, flow cytometry using an antibody directed to a cell surface marker, such as CD4 or CD8, and a cell sorter, as shown in the below-mentioned Example. In addition, a desired type of T cell can be isolated using the secretion of cytokines or the expression of functional molecules as an indicator. In this case, for example, T cells secrete different cytokine, depending on whether they are of the Th1 or Th2 type, and thus T cells of a desired Th type can be isolated by selecting T cells using such a cytokine as an indicator. Similarly, cytotoxic (killer) T cells can be isolated using the secretion or production of granzyme, perforin, or the like as an indicator.

When a "human T cell having antigen specificity" is used as a human T cell which is to be induced into an iPS cell, isolation of cells of such a type allows one to employ methods in which they are purified from human tissue containing "T cells having a desired antigen specificity" using an affinity column on which the desired antigen is immobilized, or the like. Methods can be also employed in which "T cells having a desired antigen specificity" are purified from a human tissue using a tetramer in which an MHC (major histocompatibility complex) having the desired antigen attached thereto is tetramerized (so-called an "MHC tetramer"), or "Pro5™ MHC Class I Pentamer".

An "IPS cell" in the present invention is a cell which is also called an artificial pluripotent stem cell or an induced pluripotent stem cell, and can be induced by introducing a cell reprogramming factor into T cells of the above-mentioned type. The "cell reprogramming factor" is not limited in particular, if the factor is one which is capable of conferring the pluripotency of differentiation on somatic cells, alone or in cooperation with other factors for pluripotency of differentiation, by its introduction into T cells of the above-mentioned type, and preferably is at least one protein selected from the group consisting of Oct3/4, c-Myc, Sox2, Klf4, Klf5, LIN28, Nanog, ECAT1, ESG1, Fbx15, ERas, ECAT7, ECAT8, Gdf3, Sox15, ECAT15-1, ECAT15-2, Fthl17, Sal14, Rex1, Utf1, Tcl1, Stella, β-catenin, Stat3, and Grb2. Further, it is more preferable that among these proteins, Oct3/4, c-Myc, Sox2, and Klf4 ("4 factors") are introduced into T cells of the above-mentioned type, from the viewpoint that iPS cells can be efficiently established using a small number of factors. In addition, it is more preferable that Oct3/4, Sox2, and Klf4 ("3 factors"), with c-Myc being not included, are introduce into T cells of the above-mentioned type, from the viewpoint of reducing the risk of malignant transformation of the resulting pluripotent stems.

In cases of inducing human CD8-positive T cells into iPS cells, preference is given to introducing OCT4, SOX2, KLF4, c-MYC, and NANOG into human CD8-positive T cells, and more preference is given to introducing OCT4, SOX2, KLF4, c-MYC, NANOG, and LIN28 into human CD8-positive T cells, from the viewpoint that a higher efficiency of induction into iPS cells is achieved.

In the present invention, methods for "introducing a cell reprogramming factor into T cells" are not limited in particular, and known procedures can be selected and used as appropriate. For example, when a cell reprogramming factor as described above is introduced into T cells of the above-mentioned type in the form of proteins, such methods include ones using protein introducing reagents, fusion proteins with protein transfer domains (PTDs), electroporation, and microinjection. When a cell reprogramming factor as described above is introduced into T cells of the above-mentioned type in the form of nucleic acids encoding the cell reprogramming factor, a nucleic acid(s), such as cDNA(s), encoding the cell reprogramming factor can be inserted in an appropriate expression vector comprising a promoter that functions in T cells, which then can be introduced into T cells of the above-mentioned type by procedures using infection, lipofection, liposomes, electroporation, calcium phosphate coprecipitation, DEAE-dextran, microinjection, and electroporation.

Examples of an "expression vector" in context of the present invention include viral vectors, such as lentiviruses, retroviruses, adenoviruses, adeno-associated viruses, and herpes viruses; and expression plasmids for animal cells. Sendai virus (SeV) is preferably used to introduce a nucleic acid(s) encoding a cell reprogramming factor as described above into T cells of the described-above type, from the viewpoints that insertion mutations are unlikely to be caused, that a high efficiency of gene introduction is achieved, and that an increased number of copies of gene(s) introduced is obtained.

Promoters which are used in such expression vectors include, for example, SRα, SV40, LTR, CMV, RSV, HSV-TK promoters, and others. Such promoters may be ones which can regulate the expression of a gene inserted downstream of the promoter, for example, depending upon the presence or absence of an agent such as tetracycline. Expression vectors further may contain an enhancer, a poly A addition signal, a selective maker gene (for example, neomycin resistance gene), an SV40 origin of replication, or others, in addition to the promoter.

In the "step of inducing an iPS cell from a human T cell," it is preferable that before a cell reprogramming factor as described above is introduced, T cells of the above-mentioned type are activated by stimulation with an anti-CD3 antibody and an anti-CD28 antibody in the presence of interleukin 2 (IL-2), more preferably by stimulation with at least one substance selected from the group consisting of phytohemagglutinin (PHA), interleukin 2 (IL-2), alloantigen expressing cells, an anti-CD3 antibody and an anti-CD28 antibody, as shown in the below-mentioned Example. Such stimulation can be achieved, for example, by adding PHA, IL-2, an anti-CD3 antibody and an anti-CD28 antibody to a medium in which T cells of the above-mentioned type are then cultured for a specified period of time, as shown in the below-mentioned Example. In this case, the anti-CD3 antibody and the anti-CD28 antibody may be ones each having been attached to magnetic beads. Further, such stimulation may be achieved by culturing T cells of the above-mentioned type for a specified period of time in a culture dish to the surface of which an anti-CD3 antibody and an anti-CD28 antibody are attached, instead of adding these antibodies to the medium. Further, stimulation of T cells may be also achieved by adding an antigen peptide recognized by the human T cells, together with feeder cells to the medium.

In order to achieve such stimulation as described above, the concentrations of PHA and IL-2 added to the medium are not limited in particular, and preferably are 1 to 100 μg/mL and 1 to 200 ng/mL, respectively. The concentrations of an anti-CD3 antibody and an anti-CD28 antibody added to the medium in such stimulation as described above are not limited in particular, and preferably are one to ten times the amount of culture of the T cells of the above-mentioned type. The concentrations of an anti-CD3 antibody and an anti-CD28 antibody attached to the surface of culture dishes in such stimulation as described above are not limited in particular, and their concentrations in coating processes preferably are 1 to 100 μg/mL for an anti-CD3 antibody and 0.1 to 10 μg/mL for an anti-CD28 antibody.

The culture period for such stimulation is not limited in particular, if the culture period is a period of time which is sufficient to stimulate T cells of the above-mentioned type and which allows the T cells to proliferate to a number of cells which is necessary for introduction of a cell reprogramming factor as described above, and usually is 2 to 14 days, although the culture period may be one day. From the viewpoint of the efficiency of gene introduction, the culture period is preferably 2 to 7 days. Further, it is preferable that the culture is carried out in culture dishes having RetroNectin coated thereon, from the viewpoint that the efficiency of gene introduction is increased.

Media in which T cells of the above-mentioned type are cultured and to which PHA, IL-2, an anti-CD3 antibody, and/or an anti-CD28 antibody, and others are added can be, for example, known media suitable for culturing the T cells, more specifically Roswell Park Memorial Institute (RPMI) 1640 medium, minimal essential medium (α-MEM), Dulbecco's modified Eagle medium (DMEM), F12 medium, and others containing cytokines such as IL-2, and fetal calf serum (FCS). These media may be supplemented with amino acids necessary for culture (for example, L-glutamine), and antibiotics (for example, streptomycin, penicillin), besides PHA, IL-2, an anti-CD3 antibody and/or an anti-CD28 antibody. In cases of inducing CD8-positive T cells into iPS cells, IL-7 and IL-15 are preferably added to a medium, from the viewpoint that apoptosis is suppressed. The concentrations of IL-7 and IL-15 added are not limited in particular, and preferably are 1 to 100 ng/mL for each of IL-7 and IL-15.

Conditions in or after "introducing a cell reprogramming factor into T cells" in the present invention are not limited in particular. However, the T cells into which a cell reprogramming factor as described above has been introduced are preferably cultured on a layer of feeder cells. These feeder cells are not limited in particular, and include, for example, mouse embryonic fibroblasts (MEFs), STO cells, and SNL cells in which the cell division has been arrested by irradiation or antibiotic treatment.

Further, in the process of inducing from T cells of the above-mentioned type into iPS cells, it is preferable that basic fibroblast growth factor (bFGF) is added to the medium in or after introducing a cell reprogramming factor as described above into the T cells, from the viewpoint that cell differentiation is suppressed.

In addition, in order to achieve a higher efficiency of establishing iPS cells, it is preferable that a histone deacetylase (HDAC) inhibitor (for example, valproic acid (VPA), trichostatin A, sodium butyrate, MC 1293, M344, and other low-molecular inhibitors; an siRNA directed to HDAC), a G9a histone methyltransferase inhibitor (for example, BIX-01294 and other low-molecular inhibitors; an siRNA directed to G9a), or a p53 inhibitor (for example, Pifithrin-α (PFT-α) and other low-molecular inhibitors; an siRNA directed to p53) is added to the medium in or after introducing a cell reprogramming factor as described above into T cells of the above-mentioned type.

Further, in "introducing a cell reprogramming factor as described above into T cells," it is preferable that when a virus vector is used, protamine sulfate is added to the medium, from the viewpoint of facilitating binding of the vector to T cells of the above-mentioned type.

In addition, it is preferable that in concert with the transition from T cells of the above-mentioned type to iPS cells, culturing is performed while the medium is gradually replaced from a known medium suitable for culturing the T cells to a medium suitable for culturing the IPS cells, as shown in the below-mentioned Example. As a medium suitable for such culturing of the iPS cells, known media can be selected and used as appropriate; such media include, for example, Dulbecco's modified Eagle medium/F12 medium containing KnockOut Serum Replacement, L-glutamine, non-essential amino acids, 2-mercaptoethanol, b-FGF, and the like (human iPS cell medium).

As shown in International Publication No. WO 2011/096482, in cases of inducing human CD8-positive T cells into iPS cells, it is preferable that after transferring onto the above-mentioned feeder cells, culturing is performed under conditions of low oxygen concentrations (an oxygen concentration of 5%, for example) in a medium to which 1 to 1,000 μM of a ROCK inhibitor is further added, and it is also preferable that 1 to 1,000 μM of an MEK inhibitor (for example, PD0325901) and 1 to 1,000 μM of a GSK3 inhibitor (for example, CHIR99021) are added to the medium until there is formation of colonies as mentioned below, from the viewpoint that a higher efficiency of induction into iPS cells is achieved, as described in the below-mentioned Example.

Selection of iPS cells thus induced from T cells of the above-mentioned type (hereinafter, also referred to as "T-iPS cells") can be performed by selecting known procedures as appropriate. Such known procedures include, for example, methods in which selection is performed by observation under a microscope of the morphology of ES/iPS-cell-resembling colonies, as shown in the below-mentioned Example, and methods in which selection is performed using recombinant T cells in which a drug-resistance gene or reporter gene (GFP gene or the like) has been targeted to the locus of a gene known to be expressed specifically in iPS cells (for example, a cell reprogramming factor as described above), whereby the drug resistance or reporter activity is used as an indicator.

The fact that cells thus selected are iPS cells can be ascertained, for example, by methods in which the expression in the selected cells of markers which are specific in undifferentiated cells (such as ALP, SSEA-4, Tra-1-60, and Tra-1-81) is detected by means of immunostaining, RT-PCR, and others, or in which the selected cells are implanted into mice and then observation is made as to whether the formation of teratoma is caused by the implanted cells, as shown in the below-mentioned Example.

The fact that cells thus selected are derived from T cells as described above can be ascertained, for example, by detecting the rearrangement pattern of the TCR gene by means of genome PCR, as shown in the below-mentioned Example.

The time at which these cells are selected and harvested can be determined as appropriate with observing the condition of colony growth, and approximately 10 to 40 days, preferably 14 to 28 days, after a cell reprogramming factor as described above has been introduced into T cells of the above-mentioned type. Culture conditions preferably are those of 5% $CO_2$ and at 35 to 38° C., more preferably 37° C., unless otherwise specified above.

(A-2) Step of Differentiating a T-iPS Cell into a T Cell

In order to differentiate T-iPS cells obtained as described above into T cells, it is preferable that the T-iPS cells are first cultured on stroma cells in a medium which may not necessarily contain cytokines and contains FBS, FCS, or the like, from the viewpoint of facilitating the induction of differentiation into mesodermal cells. Alternatively, the T-iPS cells may be cultured in a medium containing cytokines, serum (for example, FBS or FCS), insulin, transferrin, sodium selenite, L-glutamine, α-monothioglycerol, ascorbic acid, and others. Media include, for example, X-VIVO medium, Iscove's Modified Dulbecco's Medium (IMDM medium), α-MEM, or DMEM, with α-MEM or IMDM being preferable; IMDM medium is preferable from the viewpoint of resulting in a high efficiency of formation of sac structures containing hematopoietic progenitor cells and the like (also referred to as "T-iPS-sacs"). Stroma cells which are to be used are preferably OP9 cells and 10T1/2 cells, such as C3H10T1/2 cells, treated by irradiation or the like, from the viewpoint of facilitating the induction of differentiation into hematopoietic cells. In cases of efficiently inducing the T-iPS cells into CD34-positive hematopoietic stem cells, the T-iPS cells are preferably cultured in a medium containing at least one cytokine selected from the group consisting of VEGF, SCF, TPO, SCF, and FLT3L, and more preferably in a medium containing VEGF, SCF, and TPO, or in a medium containing VEGF, SCF, and FLT3L. The culture period preferably is a period of time until sac structures containing blood cells and the like (also referred to as ES-sacs) are formed, and preferably 8 to 14 days, more preferably 10 to 14 days, after culturing of the T-iPS cells is started. Culture circumstances are not limited in particular, and preferably are under conditions of 5% $CO_2$ and at 35 to 38° C., more preferably 37° C. In addition, it is more preferable that culturing is performed under conditions of low oxygen concentrations (an oxygen concentration of 5 to 20%, for example), from the viewpoints that a high efficiency of formation of T-iPS-sacs is achieved and that an increased number of blood cells contained in the T-iPS-sacs is obtained.

Cells which are contained in sacs obtained as described above, such as hematopoietic progenitor cells, CD34-positive cells, and blood cells, preferably are cultured on stroma cells in a medium containing cytokines and serum (such as, FBS or FCS). Cells which are present within the sac structures can be separated by physical means, for example, by passing the cells through sterilized sieve-like apparatus (for example, cell strainers and others). Stroma cells used in the above-mentioned culture preferably are OP9-DL1, P9-DL4, 10T1/2/DL1, or 10T1/2/DL4 cells treated by irradiation or the like, from the viewpoint that the induction of differentiation into T lymphocytes is achieved through notch signals. The cytokines which are added to the medium include, for example, IL-7, FLT3L, VEGF, SCF, TPO, IL-2, and IL-15. Among these cytokines, preference is given to IL-7 and FTL3 from the viewpoint of supporting the differentiation of early T cells. However, it is preferable that SCF is not contained in the medium, from the viewpoint that the differentiation of the T-iPS cells into NKT cells is suppressed. The concentration of IL-7 added to the medium is preferably 0.1 to 9.5 ng/mL, more preferably 0.1 to 4 ng/mL, from the viewpoints of being easy in generating CD3-positive CD56-negative T-lineage cells and facilitating the induction of differentiation into CD4 single-positive (SP) T cells or CD8 SP T cells. Media include, for example, α-MEM medium, DMEM medium, and IMDM medium, with α-MEM medium being preferable from the viewpoint of being easy in maintaining feeder cells. These media may be supplemented with amino acids necessary for culture (for example, L-glutamine), and antibiotics (for example, streptomycin, penicillin), besides IL-7 and FLT3.

Step (A-2) may be carried out by steps (B-1), (B-2), and (B-3) which are described below.

The differentiation from the T-iPS cells into T cells can be induced in this way, thereby allowing one to obtain various types of cells, such as CD4/CD8 DN cells, CD4/CD8 DP cells, CD4 SP cells, and CD8 SP cells (Example A5).

For the CD8 SP cells obtained by the above-describe method, it was demonstrated that further rearrangement of the TCR gene was caused in the process of differentiation. In addition, further rearrangement of the TCR gene was found to result in a decrease to one fourth or so in the rate of cells having the same TCR rearrangement pattern as in their originating T cells (Comparative Example B1).

In order to suppress further rearrangement of the TCR gene in the course of differentiation into CD8 SP cells and to increase the rate of cells having the same condition of TCR rearrangement as in their originating T cells, the T-iPS cells are allowed to be differentiated into CD4/CD8 DN cells, of which the TCR can be then stimulated, followed by differentiation of the CD4/CD8 DN cells into CD8 SP cells. Accordingly, a CD8 SP cell having the same TCR rearrangement pattern as in its originating T cell can be produced with a very high efficiency by the steps of: differentiating a T-iPS cell into a CD4/CD8 DN cell; stimulating the T cell receptor of the CD4/CD8 DN cell; and differentiating the CD4/CD8 DN cell into a CD8 SP cell.

Description will be made on (B-1) a step of differentiating a T-iPS cell into a CD4/CD8 DN cell, (B-2) a step of stimulating the T cell receptor of the CD4/CD8 DN cell, and (B-3) a step of differentiating the CD4/CD8 DN cell into a CD8 SP cell.

(B-1) Step of Differentiating a T-iPS Cell into a CD4/CD8 DN Cell

In cases of producing CD4/CD8 DN cells, the culture period described above for culturing cells which are contained in the T-iPS-sacs is preferably a period of time until T cell receptor (TCR) is expressed on the cellular surface of CD4/CD8 DN cells obtained by differentiation as described above, and is preferably 14 to 28 days after culturing of cells contained in the T-iPS-sacs is started. Culture circumstances are not limited in particular, and preferably are under conditions of 5% $CO_2$ and at 35 to 38° C., more preferably 37° C. The T-iPS-sacs can be prepared according to the method described in step (A-2).

Whether or not T cell receptor (TCR) is expressed on the cellular surface of the resulting CD4/CD8 DN cells can be assessed by flow cytometry using an anti-TCRαβ antibody, an anti-CD3 antibody, an anti-CD4 antibody, and an anti-CD8 antibody, as shown in the below-mentioned Comparative Example B1 (see FIG. 49).

(B-2) Step of Stimulating the T Cell Receptor of the CD4/CD8 DN Cell

As shown in the below-mentioned Comparative Example B1, the present inventors have demonstrated for the first time that in T cells which have been redifferentiated from the T-iPS cells, the CD4/CD8 DP stage exhibits more intense expression of RAG1 and RAG2 than the CD4/CD8 DN stage. Further, the present inventors have demonstrated for the first time that in TCRα mRNAs from T cells into which the T-iPS cells have been redifferentiated, the DP stage has a higher frequency of having a TCR-gene rearrangement pattern different from that in their originating human T cells than the DN stage. These strongly suggest that further rearrangement of the TCRα gene (receptor revision) is caused by RAG1 and RAG2 in the process of redifferentiating the T-iPS cells into T cells, particularly in the process leading from the CD4/CD8 DN stage to the CD4/CD8 DP stage.

As shown in the below-mentioned Comparative Example B1, the present inventors have also demonstrated for the first time that in T cells obtained by redifferentiation of the T-iPS cells, TCR is expressed even at the DN stage. In a normal living body, T cells do not express TCR at the DN stage. Therefore, it was surprised that DN cells obtained by differentiation of the T-iPS cells expressed TCR.

Until now, it has been known that in the process of positive selection, TCR signals via peptide-MHC complexes arrest the expression of the RAG genes and suppress further rearrangement of the TCR gene. It has been also shown that TCR-signal-like signals by anti-CD3 antibodies exert similar effects. The present inventors have succeeded in suppressing further rearrangement of the TCR gene by stimulating the TCR which is expressed on DN cells induced from the T-iPS cells, and based on this, improving the frequency of appearance of T cells having the same rearrangement pattern of the TCR gene as in their originating human T cells.

Therefore, in the method for producing a human CD8 SP cell having antigen specificity according to the present invention, stimulating T-iPS-cell-derived CD4/CD8 DN cells via the TCR expressed on their cellular surface can suppress further rearrangement of the TCR gene, and eventually makes it possible that in CD8 SP cells obtained by redifferentiation, there is achieved a highly increased frequency of appearance of T cells having the same rearrangement pattern of the TCR gene as in their originating human T cells.

As a method for stimulating the T cell receptor of T-iPS-cell-derived CD4/CD8 DN cells, preference is given to methods of contacting at least one substances selected from the group consisting of PHA, an anti-CD3 antibody, an anti-CD28 antibody, cells expressing a complex of an antigen peptide to which the originating human T cells of the T-iPS cells binds specifically and an HLA restricted to the T cell receptor, an MHC multimer having the antigen peptide attached thereto, PMA, and ionomycin, with T-iPS-cell-derived CD4/CD8 DN cells; more preference is given to methods in which cells expressing a specific peptide/HLA complex are contacted with T-iPS-cell-derived CD4/CD8 DN cells, from the viewpoint that physiological stimulation is applied. From the viewpoint of attaching importance to the uniformity of stimulation, more preference is given to methods in which antibodies or reagents are contacted.

Contacting methods are carried out, for example, by culturing the above-mentioned T cells for a specified period of time with PHA and others added to the medium, as shown in the below-mentioned Example. The anti-CD3 antibody and the anti-CD28 antibody may be ones each having been attached to magnetic beads. Further, stimulation may be achieved by culturing the above-mentioned T cells for a specified period of time in a culture dish to the surface of which an anti-CD3 antibody and an anti-CD28 antibody are attached, instead of adding these antibodies to the medium. Further, stimulation may be also achieved by adding the above-mentioned antigen peptide with feeder cells to the medium.

In order to stimulate the TCR of CD4/CD8 DN cells, the concentration of PHA added to the medium is not limited in particular, and preferably is 1 to 100 μg/mL. The concentrations of an anti-CD3 antibody and an anti-CD28 antibody added to the medium are not limited in particular, and preferably are one to ten times the amount of culture of the above-mentioned T cells. The concentrations of an anti-CD3 antibody and an anti-CD28 antibody at which these antibodies are attached to the surface of culture dishes for stimulating the TCR of CD4/CD8 DN cells are not limited in particular, and their concentration in coating processes preferably are 0.1 to 100 μg/mL for an anti-CD3 antibody and 0.1 to 10 μg/mL for an anti-CD28 antibody.

The period for culturing cells contained in the T-iPS-sacs preferably includes a period of time around which T cell receptor (TCR) is expressed on the cellular surface of CD4/CD8 DN cells obtained by differentiation as described above, and preferably is 7 to 29 days after culturing of cells contained in the T-iPS-sacs is started. Culture circumstances are not limited in particular, and preferably are under conditions of 5% $CO_2$ and at 35 to 38° C., more preferably 37° C.

In such a culture period, a glycogen synthase kinase-313 (GSK3(3) inhibitor may be added to the medium, from the viewpoint of enhancing the self-renewal ability and the production of CD8+ memory stem cells (stem-cell-like memory T cells (TSCMs)) having a multipotency capable of differentiation into central memory T cells, effector memory T cells, and effector T cells. Such a GSK3β inhibitor is any inhibitor which can activate the Wnt signaling pathway by suppressing the phosphorylation of β-catenin by GSK3β, and includes, for example, a 4,6-disubstituted pyrrolopyrimidine (TWS119). For TSCMs, see Luca Gattinoni et al., Nature Medicine, 2011, Vol. 17, pp. 1290-1298. For the relationship between the inhibition of GSK3B and the enhancement of TSCM production, see Luca Gattinoni et al., Nature Medicine, 2009, Vol. 15, pp. 808-813.

(B-3) Step of Differentiating the CD4/CD8 DN Cell into a CD8 SP Cell

As shown in the below-mentioned Example section, it has been demonstrated that in the above-mentioned step, the stimulation of T-iPS-cell-derived CD4/CD8 DN cells through the TCR expressed on their cellular surface makes it possible to suppress further rearrangement of the TCRα gene (receptor revision) which may be caused as the T-iPS cells differentiate from the DN stage to the DP stage and further to the CD8 SP stage.

Therefore, in the method for producing a human CD8 SP cell having antigen specificity according to the present invention, stimulation of T-iPS-cell-derived CD4/CD8 DN cells via the TCR expressed on their cellular surface, followed by differentiation of the stimulated CD4/CD8 DN cells into CD8 SP cells, makes it possible that in CD8 DP cells obtained by redifferentiation, there is achieved a highly increased frequency of appearance of T cells having the same rearrangement pattern of the TCR gene as in their originating human T cells.

The above-mentioned "step of stimulating the T cell receptor of the CD4/CD8 DN cell" results in some of the T-iPS-cell-derived T-lineage cells differentiating not only into CD4/CD8 DN cells, but also into CD4/CD8 DP cells. Therefore, the "step of differentiating the CD4/CD8 DN cell whose T cell receptor has been stimulated, into a CD8 SP cell" results in the differentiation of the CD4/CD8 DN cells whose T cell receptor has been stimulated into CD8 SP cells, and yet comprises differentiating CD4/CD8 DP cells whose TCR has been stimulated at the DN stage into CD8 SP cells.

In the present invention, it is preferable that in order to differentiate the CD4/CD8 DN cells whose T cell receptor has been stimulated into CD8 SP cells, the stimulated CD4/CD8 DN cells are cultured in a medium containing cytokines, serum (for example, human serum), and others. The cytokines which are added to the medium are any ones which allow the stimulated CD4/CD8 DN cells to differentiate into CD8 SP cells, and include, for example, IL-7, IL-15, and IL-2. Among these cytokines, IL-7 and IL-15 are preferably added in combination, from the viewpoints of facilitating the production of CD8 lineage cells and further memory-type CD8+ T cells. The concentrations of IL-7 and IL-15 added are not limited in particular, and preferably are 1 to 20 ng/mL. Media include, for example, RPMI-1640 medium, X-VIVO medium, DMEM medium, and a-MEM medium, with RPMI-1640 medium and X-VIVO medium being preferable from the viewpoint that both media are more suitable for growth of blood cells. These media may be supplemented in addition to IL-7 and IL-15, with amino acids necessary for culture (for example, L-glutamine), antibiotics (for example, streptomycin, penicillin), and cytokines other than IL-7 and IL-15.

In such culture, the CD4/CD8 DN cells may be co-cultured with feeder cells. Feeder cells are not limited in particular, and preferably peripheral blood mononuclear cells (PBMCs) from the viewpoint of facilitating the differentiation into CD8 SP cells and their proliferation through cell contact and the like. Such PBMCs are preferably allo (allogeneic) to the CD4/CD8 DN cells, from the viewpoint that the TCR is effectively stimulated. Such PBMCs are preferably auto (autologous) to the CD4/CD8 DN cells, from the viewpoint that survival is conferred while excessive stimulation of the TCR is prevented. Further, it is more preferable to use peripheral blood mononuclear cells presenting an antigen peptide to which the originating human T cells of the CD4/CD8 DN cells bind specifically, from the viewpoint of continuing to stimulate the TCR and to suppress further TCR rearrangement.

The culture period for differentiating the CD4/CD8 DN cells into CD8 SP cells is preferably two to four weeks. Culture circumstances are not limited in particular, and preferably are under conditions of 5% $CO_2$ and at 35 to 38° C., more preferably 37° C.

In connection with the present invention, it has been pointed out by Serwold, T. et al. in Proc Natl Acad Sci USA, 107, 18939-18943, 2010, Vol. 107, pp. 18939-18943, that an unusually early TCR signaling in mouse thymus is likely to cause the occurrence of lymphoma. For this reason, the method for producing a human CD8 SP cell according to the present invention may incorporate a system that uses a suicide gene into the cell, from the viewpoint of avoiding the occurrence of tumors resulting from activation of TCR signals at early (CD4/CD8 DN) stages. Examples of such a "system that uses a suicide gene" include, for example, systems using a gene encoding an inducible caspase 9 (iCasp 9) consisting of human caspase 9 and a modified FK-binding protein, as described in Antonio Di Stasi et al., N Engl 3 Med, 2011, Vol. 365, pp. 1673-1683; thymidine kinase (TK) genes, as described, for example, in Kaneko, S. et. al., BLOOD, 2009, Vol. 113, pp. 1006-1015; Fabio Ciceri et al., THE LANCET, 2009, Vol. 10, pp. 489-500; and Attilio Bondanza et al., blood, 2011, Vol. 24, pp. 6469-6478.

The T-iPS cells which are used in step (B-1) can be prepared by step (A-1), a step of inducing iPS cells from human T cells. The step of differentiating into T cells in step (A-2) as mentioned above can be carried out by stimulating the TCR at the CD4/CD8-DN-cell stage, in which such stimulation can be achieved according to step (B-2).

The fact that cells which have been subjected to differentiation induction as described above are derived from the T-iPS cells and from the originating T cells of the T-iPS cells can be ascertained, for example, by detecting the TCR gene rearrangement pattern by means of PCR for genomic DNA, as shown in the below-mentioned Example.

The T cells thus produced can be isolated by selecting known procedures as appropriate. Such known procedures include, for example, flow cytometry using an antibody directed to a cell surface marker, such as CD4 or CD8, and a cell sorter, as shown in the below-mentioned Example. In cases where "T cells having a desired antigen specificity" are isolated from a human, methods can be employed in which purification of the T cells is carried out using an affinity column on which the desired antigen (for example, an antigen recognized by the originating T cells of CD8 SP cells, in cases of CD8 SP cells) is immobilized. Methods can be employed in which "T cells having a desired antigen specificity" are purified using an MHC tetramer to which the desired antigen has been attached.

The resulting T cells do not express PD-1, and yet at the same time express CCR7 together with CD27 and CD28 (expression of CD27 and CD28 is one of the representative phenotypes of central memory T cells) have a longer telomere, relative to the original T cells, and possess an improved ability of self-replication. Therefore, the present invention can provide the production of T cells (for example, CD8 SP cells) having the same rearrangement pattern of the TCR gene as in the originating T cells and expressing CD27, CD28, and CCR7, but not PD-1. T cells which have been collected from a human express PD-1, and not CD27, CD28, nor CCR7, and in this respect are different from the resulting T cells.

The resulting CD8 SP cells may be stimulated every one to two weeks, for maintaining them. Such stimulation includes contacting the cells with at least one substance selected from the group consisting of an anti-CD3 antibody, an anti-CD28 antibody, IL-2, IL-7, IL-15, an antigen recognized by the CD8 SP cells, an MHC multimer having the antigen attached thereto, feeder cells which are allo to the CD8 SP cells, and feeder cells which are auto to the CD8 SP cells.

<Human T Cells, Pharmaceutical Compositions, and Methods for Cell-Based Immunotherapy>

The human T cells produced by the method according to the present invention have antigen-specific immune functions. In addition, the human T cells produced by the method according to the present invention do not express PD-1, which is a marker of exhausted T cells (i.e., T cells having significantly decreased long-term survival capability, self-replication ability, and/or effector functions), and yet at the same time express CCR7 together with CD27 and CD28 (expression of CD27 and CD28 is one of the representative phenotypes of central memory T cells) have a longer telomere, relative to the original T cell, and possess an improved self-replication ability. Thus, the human T cells produced by the method according to the present invention can be used, for example, for treatment or prevention of diseases such as tumors, infections, autoimmune failures, and others.

Therefore, the present invention provides human T cells produced by the method according to the present invention, a pharmaceutical composition comprising the human T cells, and a method for cell-based immunotherapy using the human T cells (immunocytotherapy or immunotherapy). In particular, the present invention provides human CD8 SP cells produced by the method according to the present invention, a pharmaceutical composition comprising the human CD8 SP cells, and a method for cell-based immunotherapy using the human CD8 SP cells.

The method for cell-based immunotherapy according to the present invention can be carried out, for example, in the following way. First, T cells are collected from a human, preferably a human having an identical HLA type, more preferably a subject to be treated. Second, T-iPS cells are prepared from the T cells, and subsequently, the T-iPS cells are differentiated into T cells, preferably CD8 SP cells, having the same rearrangement pattern of the TCR gene as in their originating T cells. The resulting T cells, such as CD8 SP cells, express CCR7 together with CD27 and CD28 (expression of CD27 and CD28 is one of the representative phenotypes of central memory T cells), but not PD-1, and have a longer telomere, relative to the originating T cells, and possess an improved self-replication ability. Accordingly, the resulting cells may be identified by the expression of CD27, CD28, CCR7, and/or PD-1, if desired. The T cells thus obtained can be administered to a subject to be treated.

In the method for cell-based immunotherapy according to the present invention, the administration of the resulting T cells to a subject to be treated is not limited in particular, and can be preferably carried out by parenteral administration, such as intravenous, intraperitoneal, subcutaneous, or intramuscular administration, more preferably intravenous administration. Alternatively, topical administration to an affected site can be also done.

The pharmaceutical composition according to the present invention can be prepared by formulating the human T cells produced by the method according to the present invention into dosage forms by known pharmaceutical methods. For example, the pharmaceutical composition according to the present invention can be mainly administered parenterally, as capsules, liquids, film-coated preparations, suspensions, emulsions, injections (such as venous injections, drip injections, and the like), and others.

In formulation into these dosage forms, the T cells according to the present invention can be combined as appropriate, with pharmaceutically acceptable carriers or media, in particular, sterile water and physiological saline, vegetable oils, resolvents, bases, emulsifiers, suspending agents, surfactants, stabilizers, vehicles, antiseptics, binders, diluents, tonicity agents, soothing agents, bulking agents, disintegrants, buffering agents, coating agents, lubricants, coloring agents, solution adjuvants, or other additives. The T cells according to the present invention may be also used in combination with known pharmaceutical compositions, immunostimulants, and others which are used for the treatment or prevention of the above-mentioned diseases.

In administrating a pharmaceutical composition of the present invention, the dosage is selected as appropriate, depending upon the age, weight, symptoms, and physical condition of the subject, the type of composition (pharmaceutical, food/drink, etc.), and others.

Products (pharmaceuticals) from the compositions of the present invention or their instructions are ones having affixed thereto an indication that use is made for the treatment or prevention of decrease in immune function. Here, by "having an indication affixed to a product or its instructions," it is meant that the indication has been affixed to the body, container, packaging, or the like of the product, or alternatively its instructions, package insert, advertising materials, or other printed materials disclosing product information.

The method for cell-based immunotherapy according to the present invention comprises the steps of isolating T cells having a desired antigen specificity from a human; inducing iPS cells from the T cells having the desired antigen specificity; differentiating the iPS cells into T cells; and administering to a human the resulting T cells derived from the iPS cells. Alternatively, the method for cell-based immunotherapy according to the present invention comprises the steps of isolating T cells having a desired antigen specificity from a human; inducing iPS cells from the T cells having the desired antigen specificity; differentiating the iPS cells into CD4/CD8 DN cells; stimulating the T cell receptor of the CD4/CD8 DN cells; differentiating the CD4/CD8 DN cells whose T cell receptor has been stimulated, into CD8 SP cells; and administering to a human the resulting CD8 SP cells.

In cases of carrying out the method for cell-based immunotherapy according to the present invention, a human from which T cells are to be isolated preferably has an HLA type identical to that of a human to which T cells obtained by the method according to the present invention are to be administered, and more preferably is the same as a human to which T cells obtained by the method according to the present invention are to be administered, from the viewpoint that rejection is not caused. Regarding T cells to be administered, T cells produced by the method according to the present invention may be administered directly or in the form of formulated pharmaceutical compositions as described above.

EXAMPLES

Example A

The present invention will be described more specifically below based on Examples, but is not limited to the below-mentioned Examples. Examples A1 to A6 used the below-mentioned materials and were carried out according to the below-mentioned methods.

<Flow Cytometry>

Flow cytometry analysis was carried out using MoFlo (manufactured by Dako Cytomation), FACSAria® (manufactured by BD Bioscience), or FACSCanto II® (manufactured by BD Bioscience). Analysis of data obtained was performed using a FlowJo software (manufactured by Treestar). The antibodies used in the flow cytometry analysis were as follows:

Anti-human CD3-APC (manufactured by BD Bioscience), anti-human CD4-FITC (manufactured by BD Bioscience), anti-human CD8-PerCP/Cy5.5 (manufactured by BD Bioscience), anti-human CD56-PE (manufactured by BD Bioscience), anti-human CD45RA-Pacific Blue (manufactured by Caltag Laboratories), anti-human CD62L-PE-Cy7 (manufactured by Biolegend), anti-human CD45-Alexa 405 (manufactured by Molecular Probes-Invitrogen, Carlsbad, CA, USA), anti-human CD34-PE (manufactured by BD Bioscience), anti-human CD38-PerCP/Cy5.5 (manufactured by Biolegend), anti-human CD1a-APC (manufactured by Biolegend), anti-human CD5-PE/Cy7 and CD7-FITC (manufactured by Biolegend), anti-human CD5-PE/Cy7 (manufactured by Biolegend), anti-human CD7-FITC (manufactured by Biolegend), and anti-human TCRαβ-FITC (manufactured by Biolegend) antibodies. In the flow cytometry analysis, cells were further incubated at 4° C. for 30 minutes with a cocktail of antibodies prepared to suitable concentrations, and then washed with physiological saline. In order to eliminate dead cells, propidium iodide was added.

<Preparation of Retroviruses>

Retrovirus vectors pMXs each encoding human OCT4, SOX2, KLF4, c-MYC, or NANOG (Yamanaka's factors, YFs) were kindly provided by Professor Shinya Yamanaka, Center for iPS Cell Research and Application, Kyoto University. These YFs each were introduced via their respective retrovirus vectors into 293 GPG packaging cells having the Gag-Pol gene and a VSV-G pseudoenvelop gene under Tet-OFF control. On three days after the viruses was induced in a tetracycline-free medium, the culture supernatant of the cells was collected every day, a total of four times. The combined, collected culture supernatants were passed through a 0.45-μm cellulose acetate filter and centrifuged at 6000 g for 16 hours. The resulting supernatant was suspended in α-MEM (a-minimal essential medium) to a concentration of the supernatant of 0.5%, and stored at −80° C. until use.

<Preparation of T Cells, Infection of Retroviruses, and Production of iPS Cells>

Experimental protocols were approved by the Research Ethics Committee, The Institute of Medical Science, The University of Tokyo (Approval No. 20-6-0826). All the studies were performed according to the Declaration of Helsinki.

PBMCs were isolated from blood derived from healthy volunteers by Ficoll density-gradient centrifugation (Ficoll-Paque PLUS®, 17-1440-02, manufactured by GE Healthcare) and purified with a MoFlo (manufactured by DAKO Cytomation). T cells were isolated by gating a population of CD3+CD56− cells, in order to avoid the contamination of natural killer T (NKT) cells. Subsets of T cells were separated into CD4 (CD4+CD8−) and CD8 (CD4−CD8+) cohorts by further gating. The CD4 and/or CD8 cells were further grouped into naive (CD45RA+CD62L+), central memory (CD45RA−CD62L+), effector memory (CD45RA−CD62L−), or terminal effector (CD45RA+CD62L−) cells.

Cells of the respective subsets thus sorted were first cultured in Roswell Park Memorial Institute (RPMI) 1640 medium (manufactured by GIBCO-Invitrogen) supplemented with 10% bovine calf serum (manufactured by GIBCO-Invitrogen), 100 U/mL penicillin, 100 ng/mL streptomycin, 2 mM L-glutamine, and 20 ng/mL human interleukin 2 (hIL-2, manufactured by Novartis Vaccines & Diagnostics). Then, the cells were activated by adding anti-CD3/CD28-bound magnetic beads (Dynabeads®, ClinExVivo® CD3/CD28, manufactured by Invitrogen) in an amount three times that of the cells. In the production of iPS cells induced from T-cells (T-iPS cells), the day at which the activation was carried out is defined herein as day 0 (see FIG. 1). In some experiments, CD3+ cells which were magnetically captured from PBMCs were stimulated at the same time as their isolation, with CD3/CD28-bound magnetic beads. On day 2 and day 3, the cells were subjected to retrovirus infection by spinoculation on a RetroNectin®-coated plate (manufactured by Takara) to which 10 μg/mL protamine sulfate (Sigma-Aldrich) was added (see Kaneko, S. et al., Blood, 2009, Vol. 113, pp. 1006-1015). A complete synthetic medium for culturing T cells was replaced every day. On day 6, the infected cells were harvested and transferred onto a layer of $3\times10^5$ irradiated MEF cells in a 6-cm dish. For a period of the subsequent four days (days 6 to 10), half the volume of the medium was replaced every day with human iPS cell medium. The composition of the human iPS cell medium is as mentioned below (see Takayama, N. et al., Blood, 2008, Vol. 111, pp. 5298-5306). Dulbecco's modified Eagle medium/F12 medium (manufactured by Sigma-Aldrich) supplemented with 20% Knockout Serum Replacement® (manufactured by GIBCO-Invitrogen), 200 μM L-glutamine (manufactured by Invitrogen), 1% non-essential amino acids (manufactured by Invitrogen), 10 μM 2-mercaptoethanol (manufactured by GIBCO-Invitrogen), and 5 ng/mL b-FGF (manufactured by Wako).

Before picking up iPS-cell colonies, 0.5 mM VPA (valproic acid), an HDAC inhibitor, was added to the human iPS cell medium. On day 10, the entire medium was replaced with the human iPS cell medium containing VPA. When the colonies were allowed to be equated with human ES/iPS-cell-resembling colonies, that is, approximately on day 24, these colonies were isolated mechanically and broken into small pieces by pipetting, which were then seeded on a layer of fresh MEF cells. Human ES/iPS-cell-resembling colonies were transferred onto a layer of fresh MEF cells every three to four days using a trypsin solution (phosphate buffered saline supplemented with 0.25% trypsin, 1 mM $CaCl_2$), and 20% KnockOut Serum Replacement®).

<Chromosome Analysis>

Chromosome G-band analysis was outsourced to Nihon Gene Research Laboratories, Inc., and carried out according to a prescribed method.

<Alkaline Phosphatase (ALP) Staining and Immunocytochemical Staining>

For ALP staining, human ES/iPS-cell-resembling colonies were fixed in an ice-cold fixative solution (90% methanol, 10% formaldehyde), and stained using an ALP staining kit (manufactured by Vector Laboratories) according to the instructions of the manufacturer. For immunocytochemical staining, human ES/iPS-cell-resembling colonies were fixed in 5% paraformaldehyde and subjected to permeabilization treatment with 0.1% Triton X-100.

The colonies thus pretreated were incubated with primary antibodies. The primary antibodies used and their dilutions are as mentioned below.

PE-conjugated anti-SSEA-4 (FAB1435P, manufactured by R&D Systems, a 1:50 dilution), anti-Tra-1-60 (MAB4360, manufactured by Millipore, a 1:100 dilution), anti-Tra-1-81 (MAB4381, manufactured by Millipore, a 1:100 dilution). For the detection of the Tra-1-60 and Tra-1-81, an Alexa Fluor 488-conjugated goat anti-mouse antibody (a 1:500 dilution, A11029, manufactured by Molecular Probes-Invitrogen) was used as a secondary antibody. Further, counter staining of the nucleus was carried out using 4',6-diamidino-2-phenylindol (a 1:1,000 dilution, manufactured by Roche Diagnostics). Micrographs were taken with a fluorescence microscope Axio Observer.Z1 (manufactured by Carl Zeiss Japan).

<Teratoma Formation>

Human ES/iPS-cell-resembling colonies were aggregated and then injected into the medulla of the left testis of NOD-Scid mice as described in Masaki, H. et al., Stem Cell Res, 2007, Vol. 1, pp. 105-115. The number of cells injected was $1.0\times10^6$ cells per mouse. At 8 weeks post-injection, tumors which were formed in the testis were excised, fixed in 5% paraformaldehyde, embedded in paraffin, and then subjected to preparation of sections. The resulting sections were stained with the hematoxylin/eosin method and examined under an optical microscope as to whether the iPS cells had the ability to differentiate into the three germ layers.

<Analysis of the Expression of Pluripotent Genes and T-Cell-Related Genes>

Total RNAs were extracted from ES cells, iPS cells (cells at about day 50 after cloning), their progeny cells, and freshly isolated peripheral blood CD3+ T cells, using an RNeasy Micro Kit (manufactured by Qiagen). Each of the total RNAs obtained was used as a template to perform a reverse transcription reaction using a PrimeScript II 1st Strand Synthesis kit (manufactured by Takara).

PCR reactions were carried out using ExTaq HS (manufactured by Takara) for 30 cycles for a housekeeping gene (GAPDH or ACTB) and for 35 cycles for all pluripotent genes and T-cell-related genes. The sequences of target genes and of PCR primers used in the analysis are shown in Tables 1 and 2.

TABLE 1

PCR primers for RT-PCR

| Target gene | Primer | Sequence | SEQ ID NO |
|---|---|---|---|
| GAPDH | hGAPDH-PF1 | 5'-AACAGCCTCAAGATCATCAGC-3' | 1 |
| | hGAPDH-PR2 | 5'-TTGGCAGGTTTTTCTAGACGG-3' | 2 |
| OCT4 | total-OCT4-F.ips | 5'-ATTCAGCCAAACGACCATC-3' | 3 |
| | total-OCT4-R.ips | 5'-GGAAAGGGACCGAGGAGTA-3' | 4 |
| SOX2 | total-SOX2-F.ips | 5'-CAGCGCATGGACAGTTAC-3' | 5 |
| | total-SOX2-R.ips | 5'-GGAGTGGGAGGAAGAGGT-3' | 6 |
| c-MYC | total-c-MYC-F.ips | 5'-AGTTTCATCTGCGACCCG-3' | 7 |
| | total-c-MYC-R.ips | 5'-CCTCATCTTCTTGTTCCTCCT-3' | 8 |
| KLF4 | total-KLF4-F.ips | 5'-GCGGGAAGGGAGAAGACA-3' | 9 |
| | total-KLF4-R.ips | 5'-CCGGATCGGATAGGTGAA-3' | 10 |
| Endogenous OCT4 | endo-hOCT3/4-S1165 | 5'-GACAGGGGAGGGGAGGAGCTAGG-3' | 11 |
| | endo-hOCT3/4-AS1283 | 5'-CTTCCCTCCAACCAGTTGCCCCAAAC-3' | 12 |
| Endogenous SOX2 | endo-hSOX2-S1430 | 5'-GGGAAATGGGAGGGGTGCAAAAGAGG-3' | 13 |
| | endo-hSOX2-AS1555 | 5'-TTGCGTGAGTGTGGATGGGATTGGTG-3' | 14 |
| endogenous c-MYC | endo-hMYC-S253 | 5'-GCGTCCTGGGAAGGGAGATCCGGAGC-3' | 15 |
| | endo-hMYC-AS555 | 5'-TTGAGGGGCATCGTCGCGGGAGGCTG-3' | 16 |
| Endogenous KLF4 | endo-hKLF4-S1128 | 5'-ACGATCGTGGCCCCGGAAAAGGACC-3' | 17 |
| | endo-hKLF4-AS1826 | 5'-TGATTGTAGTGCTTTCTGGCTGGGCTCC-3' | 18 |

TABLE 1-continued

| PCR primers for RT-PCR | | | |
|---|---|---|---|
| Target gene | Primer | Sequence | SEQ ID NO |
| Tg-OCT4 | Th-OCT3/4-S880 | 5'-CAACGAGAGGATTTTGAGGCT-3' | 19 |
| Tg-SOX2 | Tg-hSOX2-S614 | 5'-TGCAGTACAACTCCATGACCA-3' | 20 |
| Tg-c-MYC | Tg-hMYC-S1011 | 5'-CAACAACCGAAATGCACCAGCCCCAG-3' | 21 |
| Tg-KLF4 | Tg-hKLF4-S1180 | 5'-TGCGGCAAAACCTACACAAAG-3' | 22 |
| Tg Vector | pMX-Tg-R | 5'-TACAGGTGGGGTCTTTCATTC-3' | 23 |
| TERT | TERT-F.ips | 5'-TGTGCACCAACATCTACAAG-3' | 24 |
| | TERT-R.ips | 5'-GCGTTCTTGGCTTTCAGGAT-3' | 25 |
| REX1 | REX1-F.ips | 5'-CAGATCCTAAACAGCTCGCAGAAT-3' | 26 |
| | REX1-R.ips | 5'-GCGTACGCAAATTAAAGTCCAGA-3' | 27 |
| GDF3 | GDF3-F.ips | 5'-AAATGTTTGTGTTGCGGTCA-3' | 28 |
| | GDF3-R.ips | 5'-TCTGGCACAGGTGTCTTCAG-3' | 29 |
| NANOG | Nanog-968S | 5'-CAGCCCTGATTCTTCCACCAGTCCC-3' | 30 |
| | Nanog-1334AS | 5'-TGGAAGGTTCCCAGTCGGGTTCACC-3' | 31 |

TABLE 2

| Primers for RT-PCR | | | |
|---|---|---|---|
| Target gene | Primer | Sequence | SEQ ID NO |
| CD3 | CD3-F.rt | 5'-GGAAGCAAACCAGAAGATGC-3' | 32 |
| | CD3-R.rt | 5'-GAGGCAGTGTTCTCCAGAGG-3' | 33 |
| CD4 | CD4-F.rt | 5'-ATGTGGCAGTGTCTGCTGAG-3' | 34 |
| | CD4-R.rt | 5'-AGAAGGGCTAGGCTTGAAGG-3' | 35 |
| CD8A | CD8A-F.rt | 5'-AAGACGTGTTTGCAAATGTCC-3' | 36 |
| | CD8A-R.rt | 5'-ACCTACTGCTCCAACCCTGA-3' | 37 |
| CD8B | CD8B-F.rt | 5'-GGTGAAGAGGTGGAACAGGA-3' | 38 |
| | CD8B-R.rt | 5'-CTTGAGGGTGGACTTCTTGC-3' | 39 |
| CD122 (IL2RB) | CD122-F.rt | 5'-CCCAGTTCACATGCTTCTAC-3' | 40 |
| | CD122-R.rt | 5'-GACAACTTGGAGGGAGATG-3' | 41 |
| CD127 (IL7R) | CD127-F.rt | 5'-GTCAACATCACCAATCTGG-3' | 42 |
| | CD127-R.rt | 5'-GTAAGATAGGATCCATCTCC-3' | 43 |
| GATA3 | GATA3-F.rt | 5'-AAGTGCATGACTCACTGGAGG-3' | 44 |
| | GATA3-R.rt | 5'-TAGGCTTCATGATACTGCTCC-3' | 45 |
| PU.1 | PU.1-F.rt | 5'-ATGTGCCTCCAGTACCCATC-3' | 46 |
| | PU.1-R.rt | 5'-TCTTCTGGTAGGTCATCTTC-3' | 47 |
| E2A | E2A-F.rt | 5'-CGAGGAGAACACGTCAGCGG-3' | 48 |
| | E2A-R.rt | 5'-GCTCGGCCTTCTGCTCTG-3' | 49 |
| ID1 | ID1-F.rt | 5'-CCCATTCTGTTTCAGCCAGT-3' | 50 |
| | ID1-R.rt | 5'-TAGTCGATGACGTGCTGGAG-3' | 51 |
| ID2 | ID2-F.rt | 5'-TCAGCCTGCATCACCAGAGA-3' | 52 |
| | ID2-R.rt | 5'-CCATTCAACTTGTCCTCC-3' | 53 |
| ID3 | ID3-F.rt | 5'-AGGGAAGGGCCCGGCAGCTG-3' | 54 |
| | ID3-R.rt | 5'-TTCCGGCAGGAGAGGTTCCC-3' | 55 |
| ID4 | ID4-F.rt | 5'-ATGGGATGAGGAAATGCTTG-3' | 56 |
| | ID4-R.rt | 5'-TGGAGGAAGGAAAGCAGAAA-3' | 57 |
| RAG1 | RAG1-F.rt | 5'-GAGCAAGGTACCTCAGCCAG-3' | 58 |
| | RAG1-R.rt | 5'-AACAATGGCTGAGTTGGGAC-3' | 59 |
| RAG2 | RAG2-F.rt | 5'-GATTCCTGCTACCTCCCTCC-3' | 60 |
| | RAG2-R.rt | 5'-AGCGTCGTCCAAAGAGAACA-3' | 61 |

TABLE 2-continued

| Primers for RT-PCR | | | |
|---|---|---|---|
| Target gene | Primer | Sequence | SEQ ID NO |
| NOTCH1 | NOTCH1-F.rt | 5'-CACTGTGGGCGGGTCC-3' | 62 |
| | NOTCH1-R.rt | 5'-GTTGTATTGGTTCGGCACCAT-3' | 63 |
| HES1 | HES1-F.rt | 5'-TCAACACGACACCGGATAAA-3' | 64 |
| | HES1-R.rt | 5'-TGGGAATGAGGAAAGCAAAC-3' | 65 |
| HEB | HEB-F.rt | 5'-CCACCTCAGCATTACCGTTT-3' | 66 |
| | HEB-R.rt | 5'-GCTTCTCCCAGTCTTTGTGC-3' | 67 |
| SLUG | SLUG-F.rt | 5'-AAAAAGCCAAACTACAGCGAAC-3' | 68 |
| | SLUG-R.rt | 5'-GAGGTGTCAGATGGAGGAGGG-3' | 69 |

<Microarray Analysis>

Whole-genome gene expression analysis was carried out on human ES cells (KhES3), T-cell-derived iPS cells (TkT3V1-7), and CD3+CD4+CD8-cells which has been stimulated with CD3/CD28. First, respective total RNAs (2 μg) were extracted from these types of cells and then subjected to probe preparation. Then, fluorescently labeled complementary RNAs from each of the total RNAs and Whole Human Genome Microarray 4×44K (G4112F, manufactured by Agilent Technologies) were hybridized in a one-color protocol (outsourcing to Takara Bio Inc.). Subsequently, the arrays were scanned and their spot images were detected on an Agilent Feature Extraction instrument (manufactured by Agilent Technologies). The signal data obtained were analyzed using a GeneSpring software (manufactured by Agilent Technologies). Two normalization procedures were applied to the normalization of the data obtained. Accordingly, when spots had a signal strength below 0.01, the values of these spots were set to be 0.01. In addition, each of the chips was normalized to the 50th percentile of the measurements obtained from the chips. In all the three samples, genes with a flag of "present" (36275 genes) were analyzed.

<Detection of TCR Rearrangement in the Genomic DNA of T-iPS Cells>

Genomic DNA was extracted form about $5\times10^6$ T-iPS cells using a QIAamp DNA kit (manufactured by Qiagen). The DNA extracted (40 ng) was used for the detection of respective rearrangement of the TCRγ, TCRβ, and TCRα genes by PCR.

PCR for detecting TCRγ rearrangement (see Benhattar, J. et al., Diagn Mol Pathol, 1995, Vol. 4, pp. 108-112) was performed using ExTaq HS (manufactured by Takara). Reaction conditions for the PCR were 95° C. for 5 minutes, followed by 5 cycles of reactions having a relatively high annealing temperature, i.e., 95° C. for 45 seconds, 65° C. for 45 seconds, and 72° C. for 45 seconds, and then 30 cycles of reactions having a relatively low annealing temperature, i.e., 95° C. for 45 seconds, 55° C. for 45 seconds, and 72° C. for 45 seconds.

In order to detect TCRβ rearrangement, PCR and heteroduplex analysis were performed according to slight modifications of the BIOMED-2 protocol (see van Dongen, J., Leukemia, 2003, Vol. 17, pp. 2257-2317).

The construction of primers for detecting TCRα rearrangement was according to Han et al. (see Han, M. et al., J Immunol, 1999, Vol. 163, pp. 301-311). Reaction conditions for PCR were 3 cycles of amplification reactions at 95° C. for 30 seconds, 68° C. for 45 seconds, and 72° C. for 6 minutes, 15 cycles of amplification reactions at 95° C. for 30 seconds, 62° C. for 45 seconds, and 72° C. for 6 minutes, and then 12 cycles of amplification reactions at 95° C. for 15 seconds, 62° C. for 30 seconds, and 72° C. for 6 minutes.

The PCR was performed using LATaq HS (manufactured by Takara). The resulting PCR products were separated on a gel, based on their size. Subsequently, the main band within an expected size range was excised from the gel, purified using a QIAquick gel extraction kit (manufactured by Qiagen), and subjected to sequencing. In the sequencing reaction, the BigDye terminator kit v3.1 (manufactured by Applied Biosystems) was used with a set of Vα, Jα, Vβ, Dβ, or Jβ primers to carry out PCR amplification and addition of the fluorescent dyes in a multifaceted approach. The resulting reaction products were analyzed on an ABI PRISM 3100 automated sequencer (manufactured by Applied Biosystems).

In the results obtained, the V, D, and J segments involved in the TCRα or TCRβ assembly were identified in comparison with published sequences and the ImMunoGeneTics (IMGT) databases (http://www.cines.fr/) using a web tool such as v-quest (see Lefranc, M. P., "IMGT databases, web resources and tools for immunoglobulin and T cell receptor sequence analysis, http://imgt.cines.fr.," Leukemia, 2003, Vol. 17, pp. 260-266). The nomenclature of gene fragments (segments) followed the IMGT nomenclature. The sequences of primers for used for detection of TCR rearrangement are shown in Tables 3 and 4.

TABLE 3

| Primers for detecting TCR rearrangement | | |
|---|---|---|
| Primer | Sequence | SEQ ID NO |
| Vβ2 | 5'-AACTATGTTTTGGTATCGTCA-3' | 70 |
| Vβ4 | 5'-CACGATGTTCTGGTACCGTCAGCA-3' | 71 |
| Vβ5/1 | 5'-CAGTGTGTCCTGGTACCAACAG-3' | 72 |

TABLE 3-continued

| Primers for detecting TCR rearrangement | | |
|---|---|---|
| Primer | Sequence | SEQ ID NO |
| Vβ8a/11 | 5'-AACCCTTTATTGGTACCGACA-3' | 73 |
| Vβ6b/25 | 5'-ATCCCTTTTTTGGTACGAACAG-3' | 74 |
| Vβ6c | 5'-AACCCTTTATTGGTATCAACAG-3' | 75 |
| Vβ7 | 5'-CGCTATGTATTGGTACAAGCA-3' | 76 |
| Vβ8a | 5'-CTCCCGTTTTCTGGTACAGACAGAC-3' | 77 |
| Vβ9 | 5'-CGCTATGTATTGGTATAAACAG-3' | 78 |
| Vβ10 | 5'-TTATGTTTACTGGTATCGTAAGAAGC-3' | 79 |
| Vβ11 | 5'-CAAAATGTACTGGTATCAACAA-3' | 80 |
| Vβ12a/3/13a/15 | 5'-ATACATGTACTGGTATCGACAAGAC-3' | 81 |
| Vβ13b | 5'-GGCCATGTACTGGTATAGACAAG-3' | 82 |
| Vβ13c/12b/14 | 5'-GTATATGTCCTGGTATAGACAAGA-3' | 83 |
| Vβ16 | 5'-TAACCTTTATTGGTATCGACGTGT-3' | 84 |
| Vβ17 | 5'-GGCCATGTACTGGTACCGACA-3' | 85 |
| Vβ18 | 5'-TCATGTTTACTGGTATCGGCAG-3' | 86 |
| Vβ19 | 5'-TTATGTTTATTGGTATCAACAGAATCA-3' | 87 |
| Vβ20 | 5'-CAACCTATACTGGTACCGACA-3' | 88 |
| Vβ21 | 5'-TACCCTTTACTGGTACCGGCAG-3' | 89 |
| Vβ22 | 5'-ATACTTCTATTGGTACAGACAAATCT-3' | 90 |
| Vβ23/8b | 5'-CACGGTCTACTGGTACCAGCA-3' | 91 |
| Vβ24 | 5'-CGTCATGTACTGGTACCAGCA-3' | 92 |
| Dβ1 | 5'-GCCAAACAGCCTTACAAAGAC-3' | 93 |
| Dβ2 | 5'-TTTCCAAGCCCCACACAGTC-3' | 94 |
| Jβ1.1 | 5'-CTTACCTACAACTGTGAATCTGGTG-3' | 95 |
| Jβ1.2 | 5'-CTTACCTACAACGGTTAACCTGGTC-3' | 96 |
| Jβ1.3 | 5'-CTTACCTAGAACAGTGAGCCAACTT-3' | 97 |
| Jβ1.4 | 5'-CATACCCAAGACAGAGAGCTGGGTTC-3' | 98 |
| Jβ1.5 | 5'-CTTACGTAGGATGGAGAGTCGAGTC-3' | 99 |
| Jβ1.6 | 5'-CATACCTGTCACAGTGAGCCTG-3' | 100 |
| Jβ2.1 | 5'-CCTTCTTACCTAGCACGGTGA-3' | 101 |
| Jβ2.2 | 5'-CTTACCCAGTACGGTCAGCCT-3' | 102 |
| Jβ2.3 | 5'-CCCGCTTACCGAGCACTGTCA-3' | 103 |
| Jβ2.4 | 5'-CCAGCTTACCCAGCACTGAGA-3' | 104 |
| Jβ2.5 | 5'-CGCGCACACCGAGCAC-3' | 105 |
| Jβ2.6 | 5'-CTCGCCCAGCACGGTCAGCCT-3' | 106 |
| Jβ2.7 | 5'-CTTACCTGTAACCGTGAGCCTG-3' | 107 |

TABLE 4

Primers for detecting TCRG rearrangement

| Primer | Sequence | SEQ ID NO |
|---|---|---|
| TV γ | 5'-AGGGTTGTGTTGGAATCAGG-3' | 108 |
| TJ γ | 5'-CGTCGACAACAAGTGTTGTTCCAC-3' | 109 |

<Induction from T-iPS Cells into T-Lineage Cells>

T-iPS cells or other pluripotent stem cells were induced so as to have a structure like an embryonic-stem-cell-derived sac (ES-sac), according to slight modifications of the method described in Takayama, N. et al., Blood, 2008, Vol. 111, pp. 5298-5306.

Pluripotent cells were co-cultured for a period of 10 to 14 days (until about day 12) on a layer of irradiated OP9 cells in a medium containing no cytokines and using α-MEM as the base, α-MEM supplemented with 20% bovine calf serum, 100 U/mL penicillin, 100 ng/mL streptomycin, and 2 mM L-glutamine.

Floating cells packed in the sac were transferred onto a layer of OP9-DL1 cells and co-cultured until day 40 in a medium using αMEM as the base and supplemented with 10 ng/mL hIL-7 and hFlt-3L. In this case, the day at which the pluripotent cells were transferred onto the layer of OP9 cells is defined as day 0. The culture medium was replaced every three days. T-lineage cells floating on the layer of OP9-DL1 cells and expressing CD45, CD3, and TCRαβ were sorted every week by flow cytometry and subjected to analysis of gene expression. OP9 and OP9-DL1 cells were obtained from the RIKEN BioResource Center through the National BioResource Project (Japan).

<Reactivity to TCR Stimulation and Cytokine Expression Profile of T-Lineage Cells Re-Differentiated from T-iPS Cells>

At the end of the induction into T cells (after being cultured on a layer of OP9-DL1 cells for about 4 weeks, i.e., on day 40), the floating cells were collected and stimulated with 30 ng/mL OKT-3 (manufactured by Janssen Pharmaceutica) and 600 IU/mL hIL-2 (manufactured by Novartis Vaccines & Diagnostics). Five days later, the number of cells was counted and the expression of CD3 was assessed. In addition, micrographs were taken to obtain morphological images.

The cytokine production (expression) of the resulting T-lineage cells was examined according to slight modifications of the method described in Uckert, W. et al., Cancer Immunol Immunother, 2008, Vol. 58, pp. 809-822. In brief, $1\times10^5$ floating cells were stimulated for 12 hours with 10 ng/mL phorbol 12-myristate 13-acetate (PMA, manufactured by Sigma-Aldrich), 0.4 µM A23187 calcium ionophore (ionomycin, manufactured by Sigma-Aldrich), and 20 IU/mL hIL-1a (manufactured by Peprotech). Further for the last three hours, brefeldin A (1 mM, manufactured by Sigma-Aldrich), an inhibitor of protein secretion, was added and the culturing was continued.

The cells which had been stimulated were labeled with anti-CD3-bound magnetic microbeads (manufactured by Miltenyi Biotec) and then retained in a magnetic column. The cells were also subjected to solid-state intracellular cytokine staining using an Inside stain kit (manufactured by Miltenyi Biotec) according to the instructions of the manufacturer. The intracellular levels of hIFN-γ and hIL-2 were measured.

<Detection of TCR Rearrangement in mRNAs from T-Lineage Cells Induced from T-iPS Cells>

On the 14th day (day 26), the 21st day (day 33), and the 28th day (day 40) after the start of culturing on a layer of OP9-DL1 cells, total RNA was extracted from CD3+ TCRαβ+ T-lineage cells induced from T-iPS cells.

By a method based on switch mechanism at the 5'-end of the reverse transcript (SMART method; see Du, G. et al., 3 Immunol Methods, 2006, Vol. 308, pp. 19-35.), cDNA was synthesized using a Super SMART® cDNA synthesis kit (manufactured by Clontech Laboratories) according to the instructions of the manufacturer. In brief, a reverse transcription reaction was performed at 42° C. for 90 minutes using a 3' SMART® CDS primer and a SMART II A oligo (Super SMART® cDNA synthesis kit), and PrimeScript Reverse Transcriptase (manufactured by Takara). Synthesis and amplification of double-stranded cDNA were carried out using 5' PCR Primer II A (Super SMART® cDNA synthesis kit), and reagents containing in the Advantage2 PCR Kit (manufactured by BD Clontech). Reaction conditions for the PCR were 20 cycles of 95° C. for 5 seconds, 65° C. for 5 seconds, and 68° C. for 3 minutes.

The amplified cDNA was used as the template in TCRα- or TCRβ-specific amplification reactions. In brief, a forward primer (2nd 5'-SMART) and a reverse primer were used to perform amplification for 25 cycles of reactions at 94° C. for 30 seconds, 55° C. for 30 seconds, and 72° C. for 3 minutes. As the reverse primer, a 3'-TRCA was used in the TCRα amplification and a 3'-TRCB in the TCRβ amplification. The resulting PCR product was inserted into a vector pGEM-T-Easy vector (manufactured by Promega, Madison) for sequencing.

<Statistical Analysis>

All the statistical analyses in Examples A1 to A6 were carried out by ANOVA or Student t-test using Excel (manufactured by Microsoft), Prism (manufactured by Graphpad Software), and Statcel 2 (manufactured by OMS Publishing). Statistical significance was determined at $P<0.05$.

Example A1

<Establishment of iPS Cells from Human Peripheral Blood T Cells>

Figure 2:
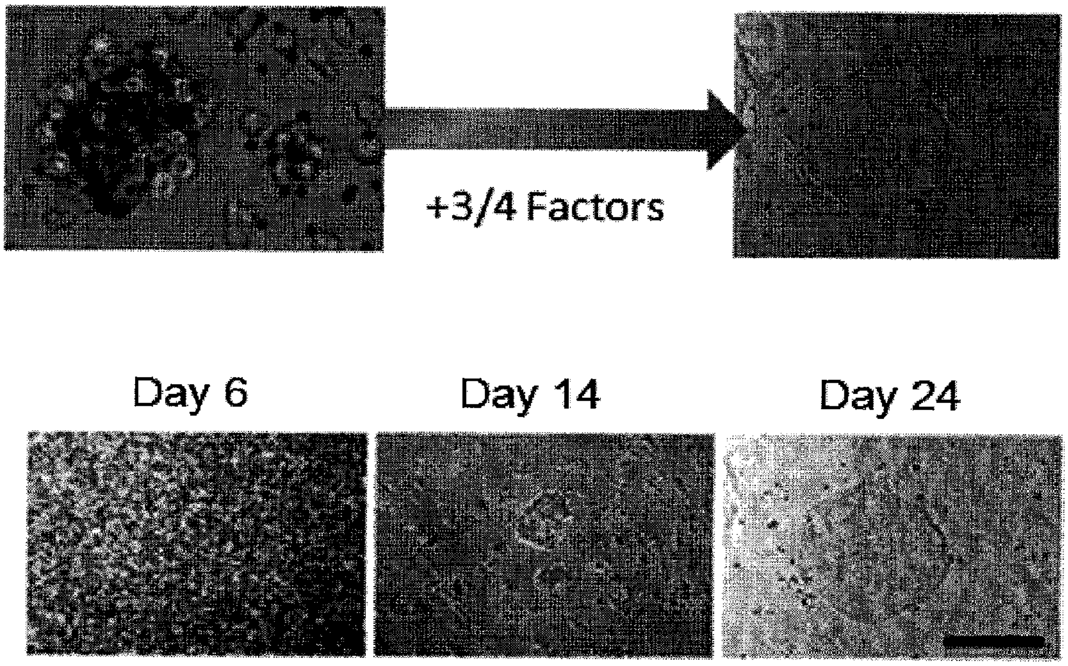
FIG. 2 represents micrographs showing T-cell-derived, ES-cell-resembling colonies formed in accordance with the method outlined in FIG. 1. In the drawing, the upper panels show a colony obtained by introducing Yamanaka's 3/4 factors into CD3 T cells; the lower panels represent, from left to right, a picture on Day 6, showing cells re-seeded onto MEF cells; a picture on Day 15, showing cells which were forming an ES-cell-resembling colony; and a picture on Day 24, showing cells which had formed a colony (for these Days, see FIG. 1). The scale bar corresponds to 200 μm.
Figure 3:
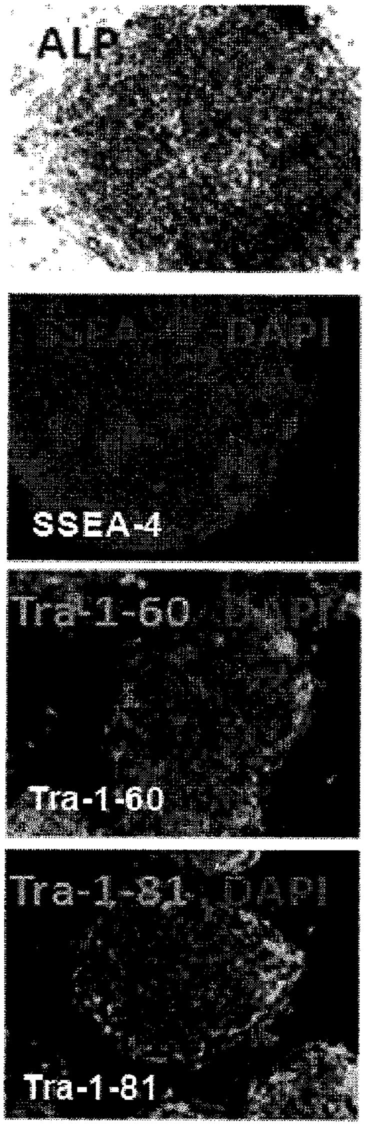
FIG. 3 represents micrographs showing the results of observing iPS-cell colonies by immunostaining.
Figure 4:
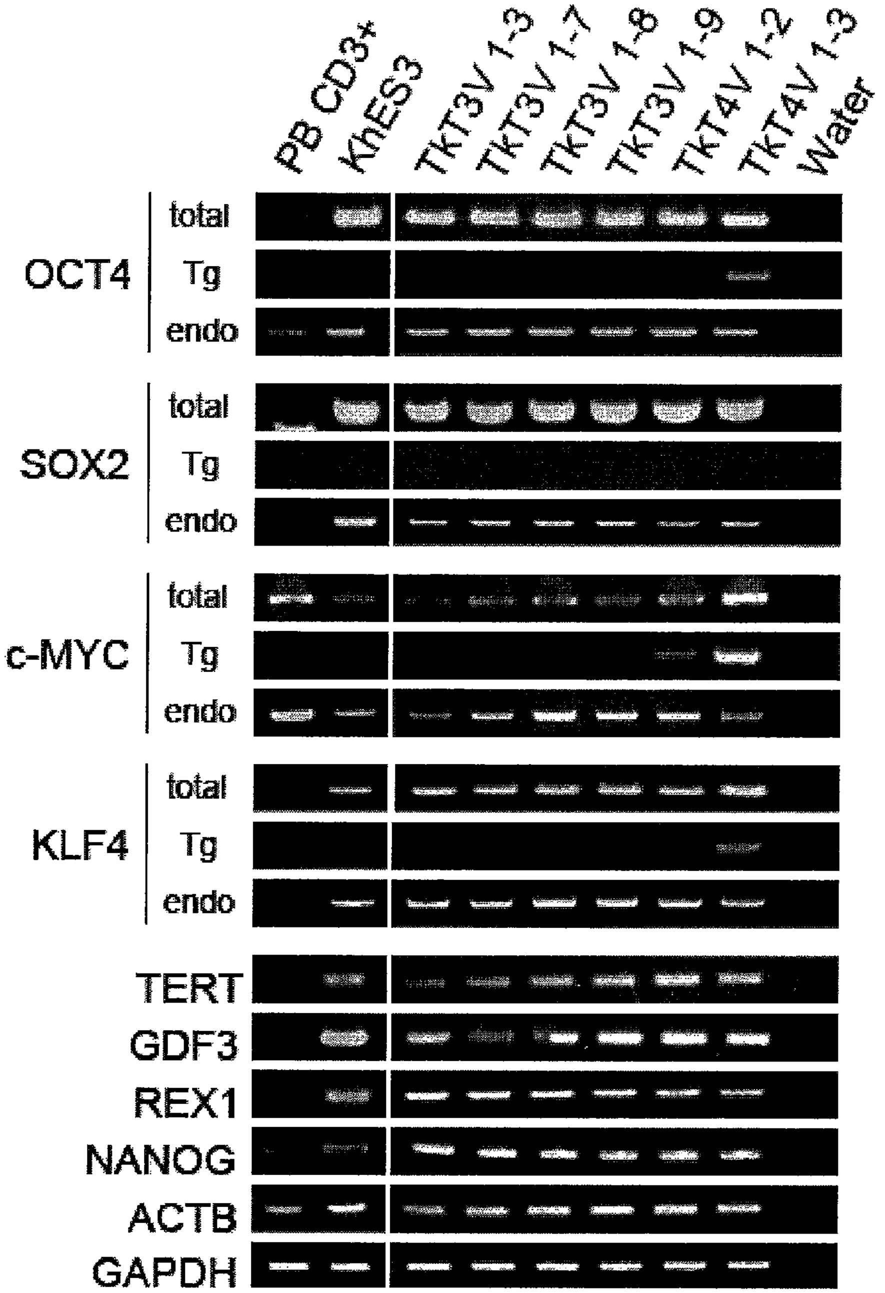
FIG. 4 represents pictures of electrophoresis showing the results of an analysis by RT-PCR of the expression of pluripotency markers in T-iPS cells, human ES cells (KhES3), and peripheral blood-derived CD3+ cells (PB CD3+). ACTB (β-actin) and GAPDH were used as loading controls.
Figure 5:
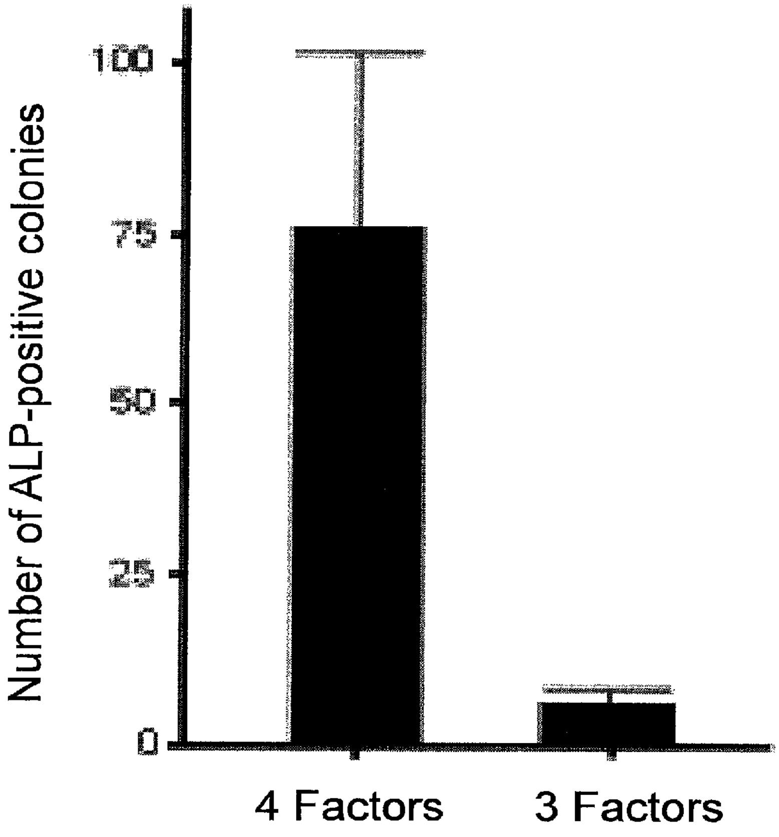
FIG. 5 represents a graph showing the efficiency of reprogramming into a pluripotent stage in peripheral blood CD3+ T cells with three factors ("3 Factors" with c-Myc being not included) or four factors ("4 Factors" with c-Myc being included). In the drawing, the ordinate axis represents the number of ALP-positive colonies derived from $3\times10^5$ T lymphocytes, on the 22nd day (day 22) (the results were: in the case of three factors, mean±S.E.M.=5.1±2.4 [n=7]; and in the case of four factors, mean S.E.M.=77.0±25.0 [n=12]).

First, T cells in human peripheral blood were used to establish iPS cells as shown in FIG. 1. In brief, PBMCs or CD3 positive cells were isolated from peripheral blood obtained from healthy individuals (of various ages (from 24 to 56 years old) and both sexes), and stimulated with CD3/CD28 ClinExVivo beads. Then, the cells were cultured for 2 days in RPMI1640+10% FBS+PSG (penicillin, streptomycin, and L-glutamine) containing 20 ng/mL hIL-2, and subjected to gene introduction using the VSV-G pseutotype retrovirus vectors pMX OCT4, pMX SOX2, pMX KLF4, and pMX c-MYCm, or alternatively pMX OCT4, pMX SOX2, and pMX KLF4. Operations for gene introduction were carried out for two successive days. Then on six days after the day of isolation, $1\times10^5$ cells were seeded on a layer of irradiated MEFs (mouse embryonic fibroblasts) grown in a 6-cm dish, and half the volume of the culture medium each time was replaced every day with iPS medium (human iPS cell medium). The culture medium was completely replaced from T cell medium to the iPS medium at four days after the cells were seeded. From about 11 days after the isolation (i.e., 5 days after the seeding), cell accumulations like cobbles were visible, and several days later (on 18 to 24 days after the start of culturing), became to exhibit an appearance like that of human ES cells (see FIG. 2, a picture of a colony (a human ES-cell-resembling colony)). Such cells were positive for ALP staining and for undifferentiation markers such as SSEA-4, TRA-1-60, and TRA-1-81 (see FIG. 3, pictures of stained colonies) and were observed to have silencing of the foreign genes and to exhibit a gene expression pattern as in ES cells (see FIG. 4, pictures of electrophoresis). In this Example, human ES-cell-resembling colonies positive for alkaline phosphatase (ALP) were obtained at a rate of 77±25 (0.03%) and of 5.1±2.4 (0.001%) from $3\times10^5$ cells into which c-Myc had or had not been introduced, respectively (see FIG. 5).

Figure 6:
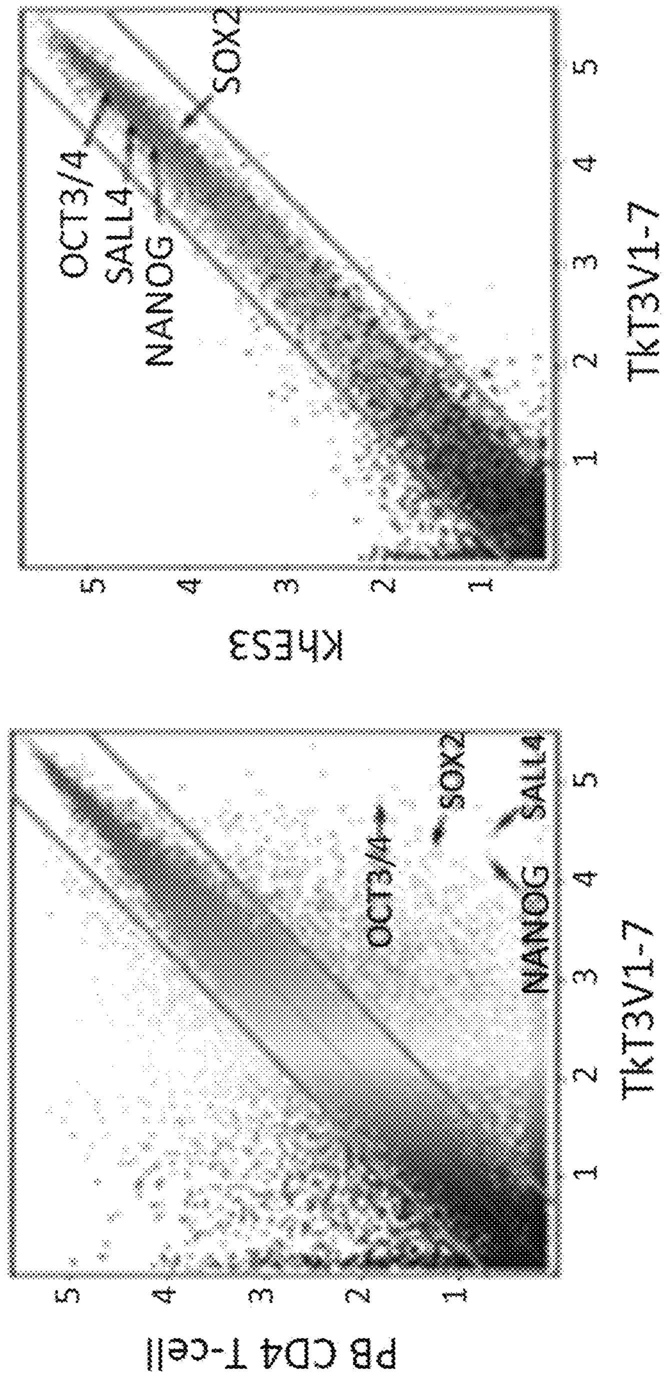
FIG. 6 represents scatter plots showing the results of comparing the comprehensive gene expression pattern between human T-iPS cells (TkT3V1-7) and active CD4 T lymphocytes (PB CD4 T-cell) (left panel) and between TkT3V1-7 cells and human ES cells (KhES3) (right panel), using oligonucleotide DNA microarrays. In each of the plots, the two parallel lines indicate that there was a fivefold difference between the corresponding samples.

Microarray analysis was performed for comparing the profile of expressed genes in CD3-derived pluripotent cells with those in human ES (KhES3) and peripheral blood T cells. The overall pattern of gene expression in the CD3-derived iPS cells was similar to that in the human ES cells and different from that in the T cells (see FIG. 6).

Figure 7:
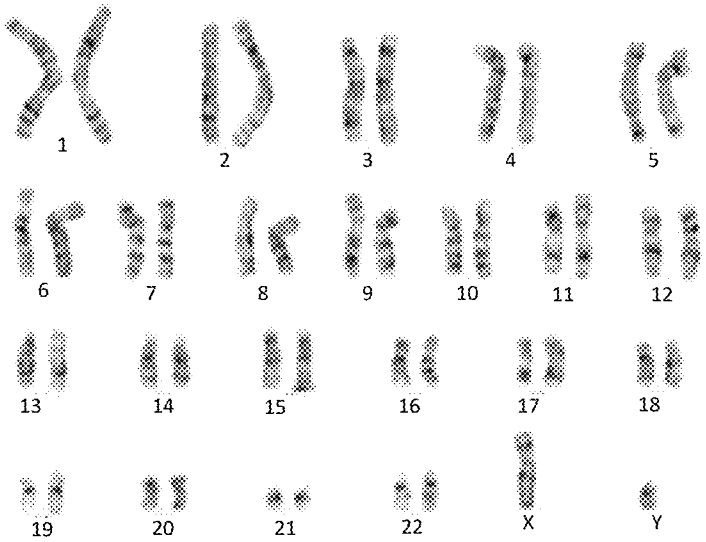
FIG. 7 represents micrographs showing the karyotype of two representative cell lines of T-iPS cells (TkT3V1-7 and TkT4V1-3). The number of passages of these T-iPS cells examined was 10 and neither of these two cell lines was observed to have any chromosomal abnormalities.
Figure 7:
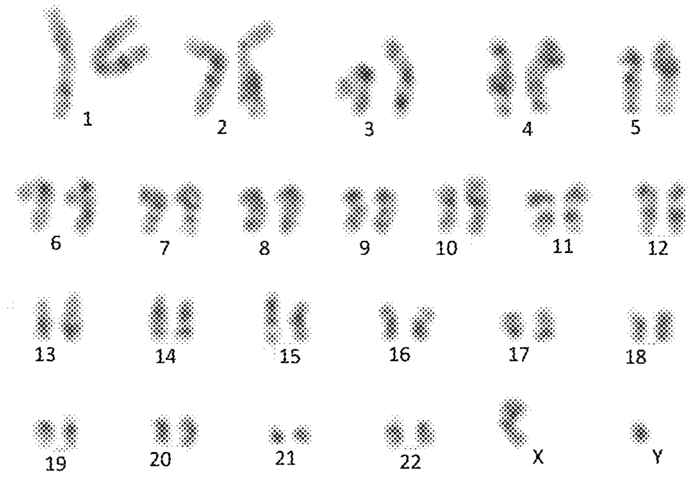
Figure 8:
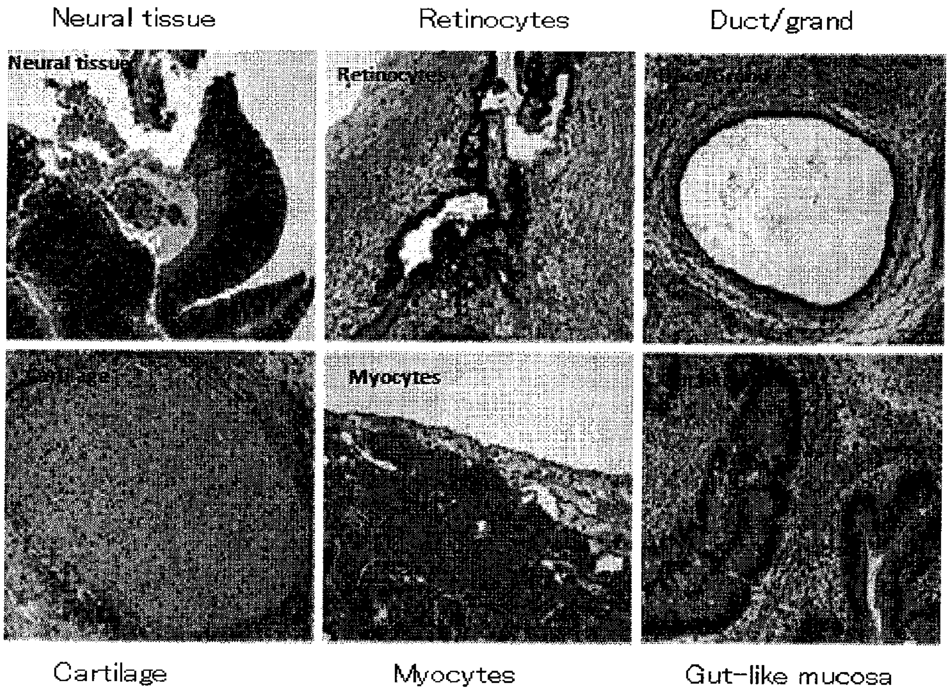
FIG. 8 represents micrographs showing representative HE-stained sections of teratomas formed in NOD-Scid mice at 8 weeks after infusion of T-iPS cells, which reveal the existence of tissues derived from the three germ layers (as ectoderm-derived tissues, neural tissue, neural plate, and retinocytes; as mesoderm-derived tissues, cartilage and myocytes; and as endoderm-derived tissues, gut-like mucosa and glands/ducts).

Furthermore, cells of resulting clones had normal karyotype (see FIG. 7, pictures of karyotype analysis) and resulted in the formation of teratomas showing the differentiation into the three germ layers by implantation into NOD/SCID mouse testes (see FIG. 8, pathological findings of formed teratoma).

Therefore, it is demonstrated that the iPS cell clones which have been established from human peripheral blood T cells are pluripotent.

Example A2

Figure 9:
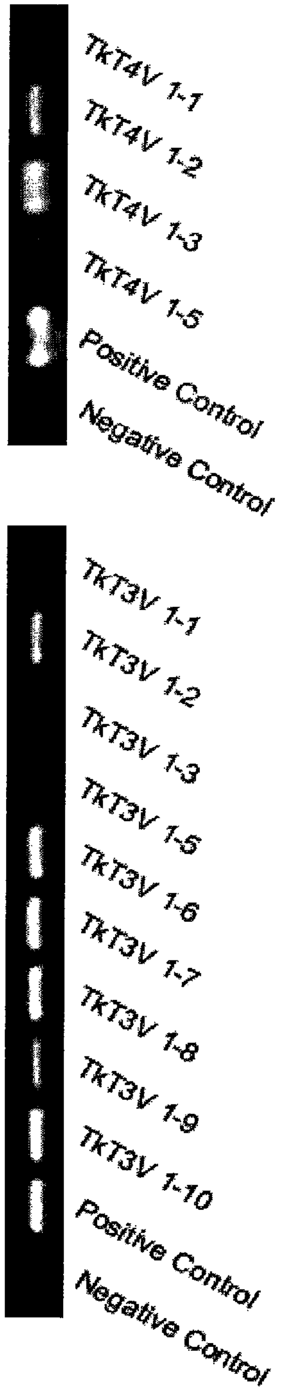
FIG. 9 represents pictures of electrophoresis showing the results of a PCR analysis for detection of gene rearrangement of the TCR γ chain.

In order to ascertain that the established iPS cell clones were derived from T cells, the rearrangement in their TCR gene was examined. In the TCR gene, three groups, TCRδ, TCRγ, and TCRβ, begin their rearrangement at early stages (almost in this order). A rearrangement of the TCRγ gene was confirmed in 2 of 4 clones derived from the "4 Factors" and in 6 of 9 clones derived from the "3 Factors" (see FIG. 9, electrophoresis). Analysis of the rearrangement in the TCRβ and TCRα genes in these clones found that all these clones had respective in-frame rearrangements of the TCRβ and TCRα genes (see Table 5, in-frame gene rearrangement in the TCRα chain region, and Table 6, in-frame gene rearrangement in the TCRβ chain region). In all of their respective rearrangements, there were not observed combinations of the NKT-cell type in which TRAV24 and TRBV11 were used specifically, and thus it was ascertained that the established iPS cell clones were ones derived from peripheral blood T cells. In Tables 5 and 6, "iPS Clone" refers to a T-cell-derived iPS cell line which has been established, "Rearrangement" refers to a combination of segments used in the rearrangement, and "Sequence of junctional region" refers to the base sequence of the junction region.

TABLE 5

| | Rearrangement | | Sequence of Junctional Region | | | TCR |
| --- | --- | --- | --- | --- | --- | --- |
| iPS Clone | Vα | Jα | 3'Vα | P(N) | 5'Jα | Protein |
| TkT3V 1-2 | | | | | | |
| TkT3V 1-3 | TRAV5*01 | TRAJ29*01 | TGTGCAGAGAGTA | TGGAGT | GGAAACACACCTCTTGTCTTT | Productive |
| | TRAV19*01 | TRAJ49*01 | TGTGCTCTGAGTGAGGC | GA | ACCGGTAACCAGTTCTATTTT | Unproductive |
| TkT3V 1-6 | TRAV9-2*01 | TRAJ8*01 | TGTGCTCTGAGTGA | TCAGG | ACACAGGCTTTCAGAAACTTGTATTT | Productive |
| TkT3V 1-7 | TRAV38-2/ DV8*01 | TRAJ31*01 | TGTGCTTAT | TGGAGT | AATAACAATGCCAGACTCATGTTT | Productive |
| TkT3V 1-8 | TRAV16*01 | TRAJ10*01 | TGTGCTCT | CAAGGG | GGGAGGAGGAAACAAACTCACCTTT | Productive |
| | TRAV12-1*01 | TRAJ12*01 | TGTGTGGTGAAC | CGAGG | TGGATAGCAGCTATAAATTGATCTTC | Unproductive |
| TkT3V 1-9 | TRAV26-1*01 | TRAJ48*01 | TGCATCGTCAG | GGCCT | TATCTAACTTTGGAAATGAGAAATTAACCTTT | Productive |
| TkT3V 1-10 | TRAV13-1*01 | TRAJ29*01 | TGTGCAGCA | CCGTCCT | ATTCAGGAAACACACCTCTTGTCTTT | Productive |
| TkT4V 1-2 | | | | | | |
| TkT4V 1-3 | TRAV8-7*01 | TRAJ6*01 | TGTGCT | TCCCTTC | GAGGAAGCTACATACCTACATTT | Productive |
| | TRAV2*01 | TRAJ42*01 | TGTGCTGIGG | TCTTAAGG | ATGGAGGAAGCCAAGGAAATCTCATCTTT | Unproductive |

| | Rearrangement | | | Sequence of junctional region | | |
|---|---|---|---|---|---|---|
| iPS Clone | Vβ | Dβ | Jβ | 3'Vβ | N-Dβ-N | 5'Jβ |
| TkT3V 1-2 | 4-2*01 | 1*01 | 1-4*01 | CTCTGTGCCAGGAGCCAAGA | GAGGACATCCCT | TAATGAAAAACTGTTT |
| TkT3V 1-3 | 28*01 | 1*01 | 1-3*01 | TGTGCCAGCA | TCCCCGGGGGTA | CTGGAAACACCATATATTTT |
| TkT3V 1-6 | 19*01/02/03 | 2*01 | 2-1*01 | TCTCTGTGCCAGTAG | GGGCGGGTGGAACCTTT | TACAATGAGCAGTTCT |
| TkT3V 1-7 | 29-1*02 | 1*01 | 2-2*01 | TATATCTCTGCAGCGTTGA | TGGACAGGGA | AACACCGGGGAGCTGTTT |
| TkT3V 1-8 | 18*01 | 1*01 | 1-2*01 | TTCTGTGCCAGCTCACCA | GACGGCG | ACTATGGCTACACCTTC |
| TkT3V 1-9 | 5-1*02 | 2*01 | 2-5*01 | ATCTTTGCGCCAGCAGC | AGAACTAGCGG | CCAAGAGACCCAGTACTTC |
| TkT3V 1-10 | 30*01 | 2*01 | 2-1*01 | TCTATCTCTGTGCCTGGAGTG | CTAGCGGG | AATGAGCAGTTCT |
| TkT4V 1-2 | 6-1*01 | 2*02 | 2-5*01 | TTCTGTGCCAGCA | CGGCGGAGAGGGCGTGG | GAGACCCAGTACTTC |
| TkT4V 1-3 | 6-2*01/6-3*01 | 1*01 | 1-5*01 | TTCTGTGCCAGCAGT | CGTACAGGGG | GCAATCAGCCCCAGCATT |

Example A3

As in Example A2, in order to ascertain that the established iPS cell clones were derived from T cells, the rearrangement in the TCR gene was examined. In brief, humans have four TCR genes (TCRα, TCRβ, TCRγ, and TCRδ), and it is known that their respective DNA rearrangements of these genes are involved in the development of normal T lymphocytes in the thymus. The rearrangement of these TCR genes is an irreversible genetic phenomenon specific to T-lineage cells, by which T cells are provided with genetic signatures and characterized. Accordingly, examining these signatures will make it possible to retrospectively ascertain whether the iPS cell clones obtained in Example A1 are derived from mature peripheral T lymphocytes of the healthy donors.

Figure 10:
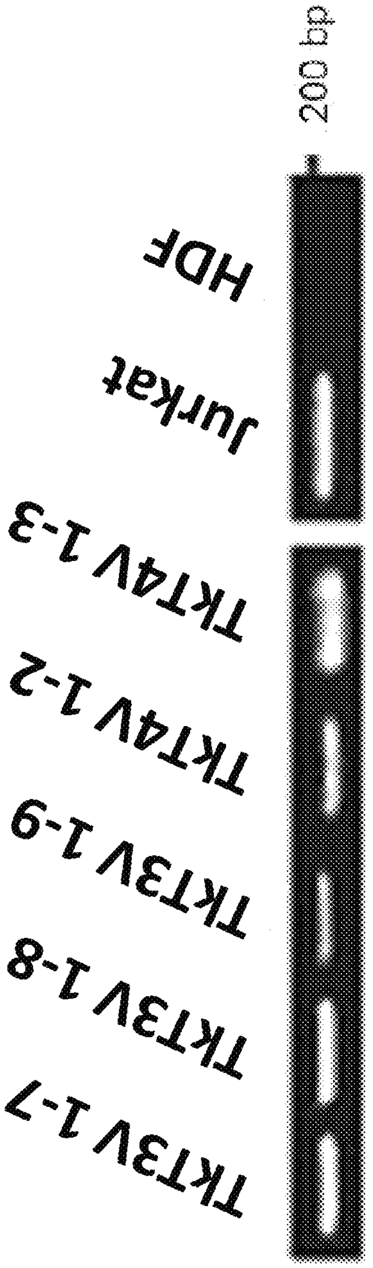
FIG. 10 represents pictures of electrophoresis showing representative results of a PCR analysis for detection of TCRγ rearrangement. Rearranged TCRγs were identified by respective PCR bands in an acceptable size range (about 200 bp).
Figure 11:
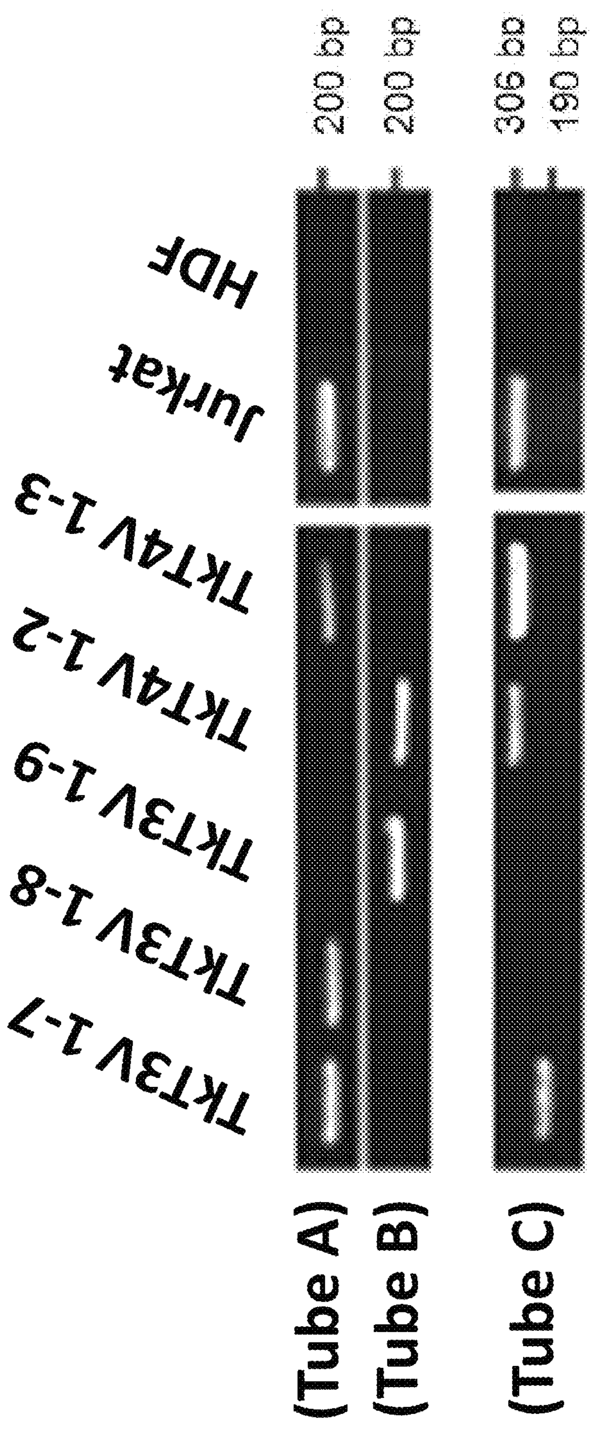
FIG. 11 represents pictures of electrophoresis showing representative results of a PCR analysis for detection of TCRβ rearrangement. In the pictures, the PCR products in the panels "Tube A" and "Tube B" indicate that a V(D)J rearrangement has been carried out (the acceptable size range of the PCR products: 240 to 285 bp), while the PCR products in the panel "Tube C" indicate that a DJ rearrangement has been carried out (the acceptable size range of the PCR products: 170 to 210 bp and 285 to 325 bp).
Figure 28:
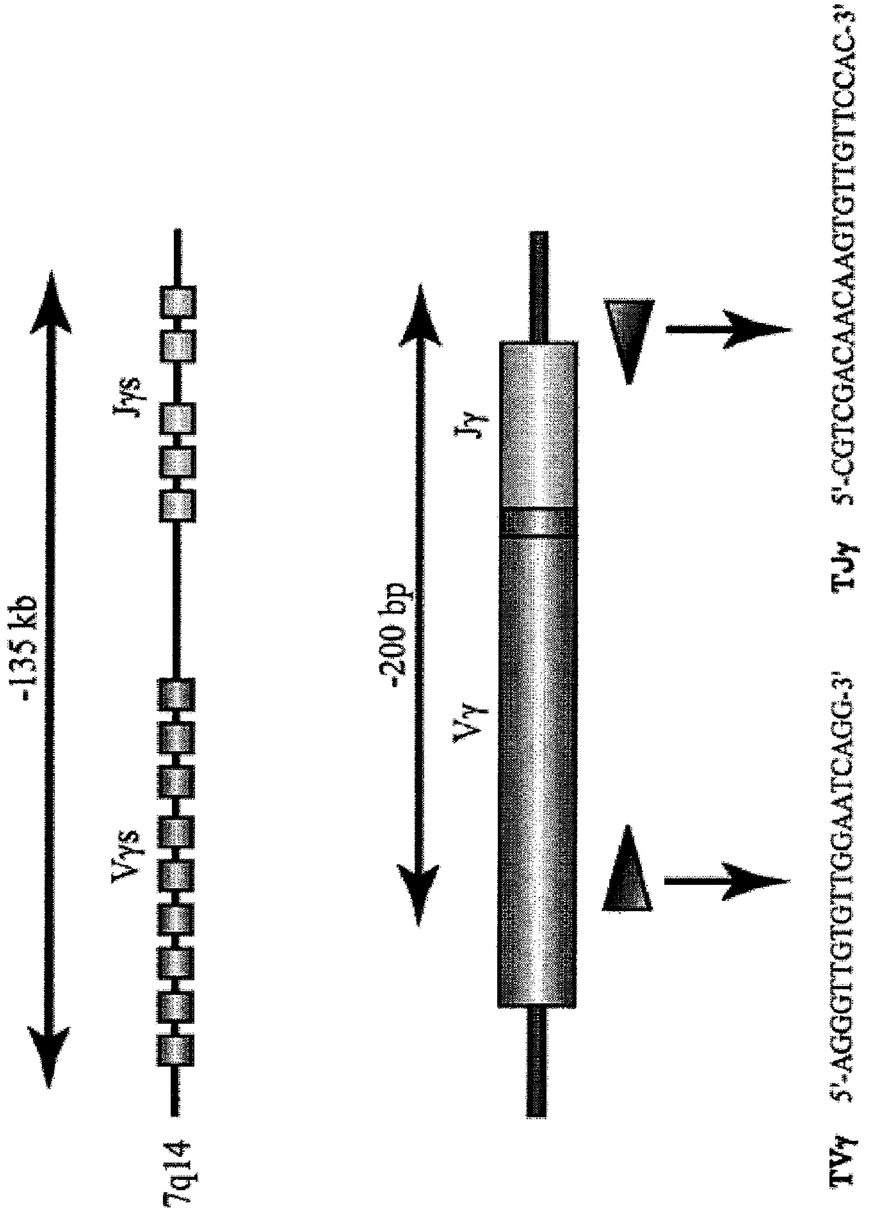
FIG. 28 is a schematic representation showing how the TCRγ gene is rearranged, and the sequences and locations of primers for detecting such rearrangement patterns. The locus of the human TCRγ gene lies in a 135-kb region on chromosome 7 (7q14). The forward primer and the reverse primer are each designed to be directed to a highly homologous region in the Vγ and Jγ segments, respectively, and allow one to detect a PCR band of about 200 bp, thereby to detect a rearranged TCRγ gene.
Figure 29:
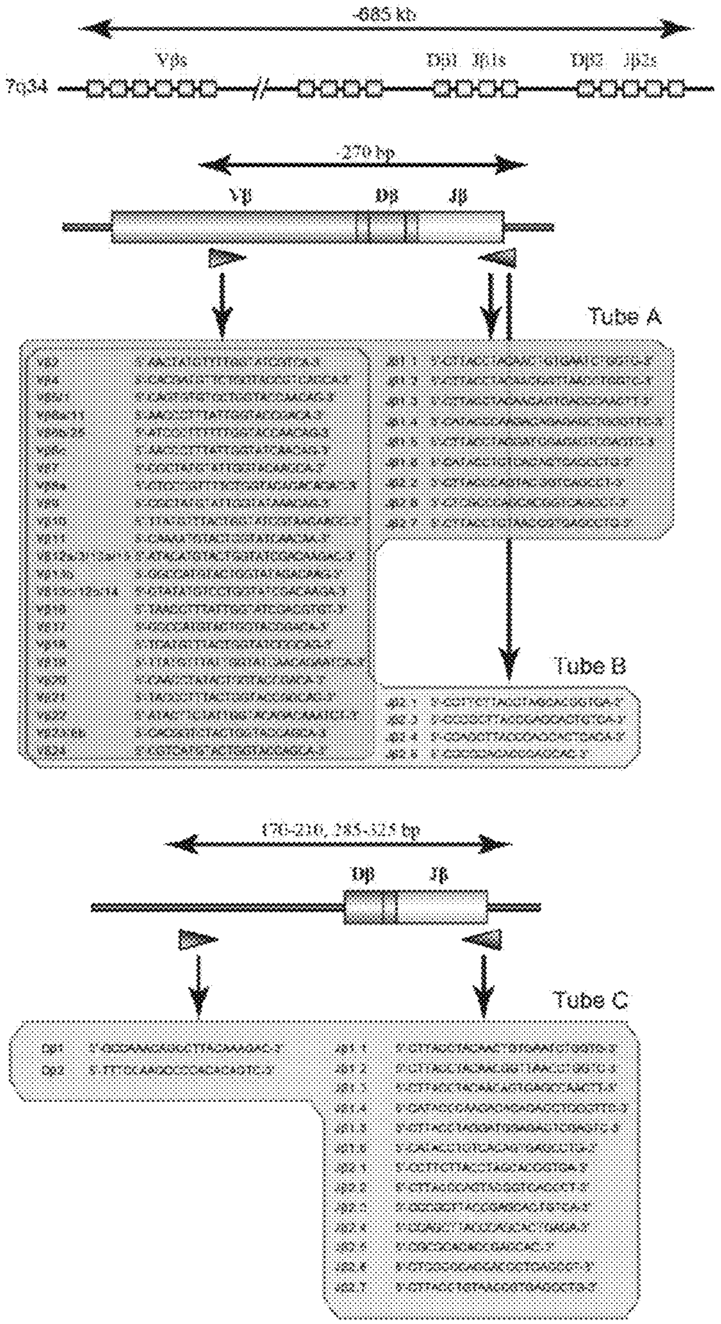
FIG. 29 is a schematic representation showing how the TCRβ gene is rearranged, and the sequences and locations of primers for detecting such rearrangement patterns. The locus of the human TCRβ gene lies in a 685-kb region on chromosome 7 (7q34). As Vβ and Jβ primers which were all capable of annealing to the same respective conserved regions in the Vβ and Jβ gene segments, 23 Vβ primers, 2 Dβ primers, and 13 Jβ primers were designed. These primers were divided into three tubes and each of the mixtures was used for analysis, as indicated under "Tube A", "Tube B", and "Tube C" in the drawing. The set of primers indicated under each of Tube A and Tube B can be used to detect a PCR band of about 270 bp, thereby to detect a rearranged V(D)Jβ, while the set of primers indicated under Tube C can be used to detect a PCR band of 170 to 210 bp or 285 to 325 bp, thereby to detect a rearranged DJβ.

First, PCR analysis using sets of PCR primers designed by Benhatter et al. and the BIOMED-2 consortium was used to detect TCRγ or TCRβ rearrangement (see FIGS. 28 and 29; see Benhattar, J. et al., Diagn. Mol. Pathol., 1995, Vol. 4, pp. 108-112; and van Dongen, J. J., Leukemia, 2003, Vol. 17, pp. 2257-2317). From the results, a TCRγ or TCRβ rearrangement was identified in cells of all the iPS cell lines examined, and thus it was ascertained that all the iPS cell lines examined were derived from peripheral blood T lymphocytes (FIGS. 10 and 11).

Figure 12:
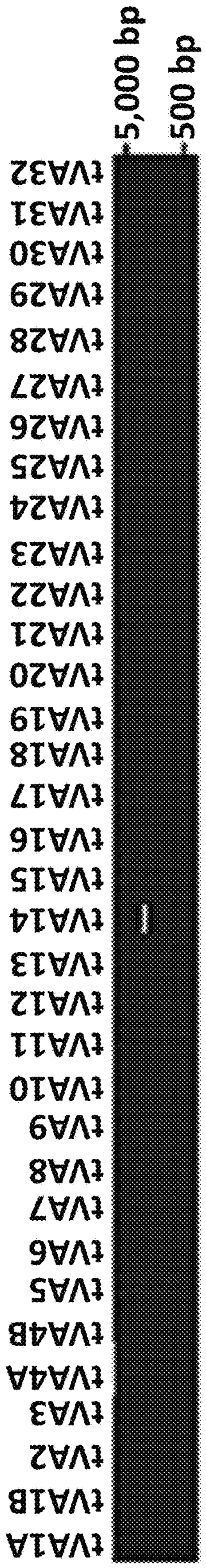
FIG. 12 represents a picture of electrophoresis showing representative results of a PCR analysis for detection of TCRα rearrangement in TkT3V1-7 cells.

Both the TCRβ chain and the TCRα chain form a heterodimer, and most of the peripheral blood T cells express TCRαβ (see Davis, M. M. et al., Nature, 1998, Vol. 334, pp. 395-402). The locus of the TCRα gene is complicated, relative to those of the TCRγ and TCRβ genes. The TCRα gene locus is a region extending more than 1,000 kb containing not only the TCRδ gene locus, but also 103 Vα segments, 61 Jα segments, and Cα segments. Based on these, in order to detect rearrangement of the TCRα gene in the genomic DNA, a set of primers was designed which included 34 forward primers directed to the Vα segments and 12 reverse primers directed to the Jα segments. When these primers were used in the analysis of multiple structures, a huge number of primer combinations were reduced, thereby allowing one to use a practical number of primer combinations. Thus, all the Jα primers were mixed in one tube, and this Jα-primers mix and each of the Vα primers were used to perform 34 PCR reactions per sample. Based on the results, this method allowed one to identify TCRα rearrangement in iPS cells having a TCRβ rearrangement (see FIG. 12).

Further, binding properties of TCR to HLA-peptide complexes are naturally determined by the three-dimensional structure of its antigen recognition site consisting of three complementarity-determining regions (CDR1, CDR2, and CDR3). In these three regions, the CDR3 is most diversifiable because the CDR3 includes the V(D)J junction region into which a variety of random nucleotides (N- or P-nucleotides) are inserted. Thus, the sequences encoding the individual TCR chains in the CDR3 region of the respective genomes of the established iPS cell clones were identified. From the results, it turned out that a functional (productive) rearrangement in the originating T cells (a gene structure with an in-frame junction and without a generated stop codon) was retained, and that all the T-iPS cell clones had single functional TCRα and TCRβ rearrangements on one allele. The other allele was found to have an intact or unfunctional (unproductive) rearrangement, including a DJβ rearrangement (see Table 7 and FIG. 13). In Table 7, "iPS Clone" refers to a T-cell-derived iPS cell line which has been established, "Productivity" refers to whether or not the rearranged T cell receptor has functions, i.e., whether the rearranged T cell receptor is functional (productive) or unfunctional (unproductive) in forming a complex with the β receptor to recognize the antigen, and "Sequence of junctional region" refers to the base sequence of the junction region. Moreover, there were not observed human NKT lymphocytes in which the TRAV24 and TRBV11 segments were specifically identified (see Godfrey, D. I. et al., Semin. Immunol., Vol. 22, pp. 61-67). Therefore, it is demonstrated that an iPS cell has been produced from a peripheral blood T cell without changes in the TCR production capability imprinted in the CDR3 sequence.

TABLE 7

| | | Rearrangement | | Sequence of junctional region | | |
|---|---|---|---|---|---|---|
| iPS clone | Productivity | Vα | Jα | 3'Vα | (P)N | 5'Jα |
| TkT3V1-3 | Productive | TRAV5*01 | TRAJ29*01 | TGTCAGAGAGTA | TGGAGT | GGAAACACACCTCTTGTCTTT |
| | Unproductive[a] | TRAV19*01 | TRAJ49*01 | TGTGCTCTGAGTGAGGC | GA | ACCGGTAACCAGTTCTATTTT |
| TkT3V1-7 | Productive | TRAV38-2/DVB*01 | TRAJ31*01 | TGTGCTTAT | TGGAGT | AATAACAATCCCAGACTCATGTTT |
| | Unproductive | Intact allele | | Intact allele | | |
| TkT3V1-8 | Productive | TRAV16*01 | TRAJ10*01 | TGTGCTCT | CAAGGG | GGGAGGAGGAAACAAACTCACCTTT |
| | Unproductive[a] | TRAV12-1*01 | TRAJ12*01 | TGTGTGGTGAAC | CGAGG | TGGATAGCAGCTATAAATTGATCTTC |
| TkT3V1-9 | Productive | TRAV28-1*01 | TRAJ48*01 | TGCATCGTCAG | GGCCT | TATCTAACTTTGGAAATGAGAAATTAACCTTT |
| | Unproductive | Intact allele | | Intact allele | | |
| TkT3V1-13 | Productive | TRAV4*01 | TRAJ39*01 | TGCCTCGTGGGTGAC | CGGGAC | GCAGGCAACATGCTCACCTTT |
| | Unproductive[a] | TRAV13-1*02 | TRAJ41*01 | TGTGCAGCAAGTA | AGGGG | ATTCCGGGTATGCACTCAACTTC |
| TkT3V1-14 | Productive | TRAV12-2*02 | TRAJ18*01 | TGTGCCGT | TATGAGG | GGCTCAACCCTGGGGAGGCTATACTTT |
| | Unproductive | TRAV1-2*01 | TRAJ28*01 | TGTGCTGTGAGAGA | TCAAAGGTT | TCTGGGGCTGGGAGTTACCAACTCACTTTC |
| TkT4V1-2 | Productive | TRAV5*01 | TRAJ16*01 | TGTGCAGAGAGTA | CCTCCTCCCTC | TTTTCAGATGGCCAGAAGCTGCTCTTT |
| | Unproductive[b] | TRAV25*01 | TRAJ8*01 | TGTGCAGGG | CCGGGA | ACAGGCTTTCAGAAACTTGTATTT |
| TkT4V1-3 | Productive | TRAV8-7*01 | TRAJ6*01 | TGTGCT | TCCCTTC | GAGGAAGCTACATACCTACATTT |
| | Unproductive[a] | TRAV2*01 | TRAJ42-01 | TGTGCTGTGG | TCTTAAGG | ATGGAGGAACCCAAGGAAATCTCATCTTT |

TABLE 7-continued

| iPS clone | | Rearrangement Vβ | Dβ | Jβ | Sequence of junctional region 3'Vβ | N1-Dβ-N2 | 6'Jβ |
|---|---|---|---|---|---|---|---|
| TkT3V1-3 | Productive | TRBV28*01 | TRBD1*01 | TRBJ-3*01 | TGTGCCAGCA | TCCCCGGGGGTA | CTGGAAACACCATATATTTT |
| | Unproductive | | Intact allele | | | Intact allele | |
| TkT3V1-7 | Productive | TRBV29-1*01 | TRBD1*01 | TRBJ2-2*01 | TGCAGCGTTGA | TGGACAGGGA | AACACCGGGGAGCTGTTTTTT |
| | Unproductive | Germline | TRBD2*01 | TRAJ2-7*01 | TATCATGGTGTAACATTGTG | GGGACTAGTTTAC | CCTACGAGCAGTACTTCG |
| TkT3V1-8 | Productive | TRBV18*01 | TRBD1*01 | TRBJ1-2*01 | TGTGCCAGCTCACCA | GACGGCG | ACTATGGCTACACCTTC |
| | Unproductive | | Intact allele | | | Intact allele | |
| TkT3V1-9 | Productive | TRBV5-1*02 | TRBD1*01 | TRBJ2-5*01 | TGCGCCAGCAGC | AGAACTAGCGG | CCAAGAGACCCAGTACTTC |
| | Unproductive | | Intact allele | | | Intact allele | |
| TkT3V1-13 | Productive | TRBV7-9*01 | TRBD2*01 | TRBJ2-7*01 | TGTGCCAGCAGC | AACCCGACGGGGTTAGT | CTACGAGCAGTACTTC |
| | Unproductive | Germline | TRBD1*01 | TRAJ2-1*01 | GTACAAAGCTGTAACATTGTG | GGGACAGCATCCCATCC | ATGAGCAGTTCTTCG |
| TkT3V1-14 | Productive | TRBV7-2*02/*03 | TRBD2*02 | TRBJ2-7*01 | TGTGCCAGCAGCTTAG | GCGGGAGTCTCA | CCTACGAGCAGTACTTC |
| | Unproductive[a] | TRBV20-1*02 | TRBD1*01 | TRBJ2-1*01 | TGCAGTGC | CCACAGGGCCT | TCCTACAATGAGCAGTTCTTC |
| TkT4V1-2 | Productive | TRBV6-1*01 | TRBD2*01 | TRBJ-25*01 | TGTGCCAGCA | CGGCGGAGAGGGCGTGG | GAGACCCAGTACTTC |
| | Unproductive | Germline | TRBD1*01 | TRBJ2-1*01 | ACAAAGCTGTAACATTGTGG | GGGACAGGGGGCGTAT | TACATTGAGCAGTTCT |
| TkT4V1-3 | Productive | TRBV6-2*01 | TRBD1*01 | TRBJ1-5*01 | TGTGCCAGCAGT | CGTACAGGGG | GCAATCAGCCCCAGCATTTT |
| | Unproductive | Germline | TRBD1*01 | TRAJ1-6*02 | TTGTACAAGCTGTACATTGT | GGGACAGGGGGC | ATTCACCCCTCC |

[a]out-of-fram junction (at CDR3)
[b]stop codon (at CR1)

Example A4

<Reprogramming from CD4+ or CD8+ Lymphocytes into iPS Cells>

Peripheral T lymphocytes are mainly derived from two functional subsets, i.e., a subset of CD4+ helper/regulatory cells and a subset of CD8+ cytotoxic cells. In the efficiency of gene introduction with viruses, it is known that there is no significant differences between CD4+ and CD8+ lymphocytes (see Berger, C. et al., Blood, 2003, Vol. 101, pp. 476-484; and Kaneko, S. et al., Blood, 2009, Vol. 113, pp. 1006-1015). Thus, the present inventors separated peripheral T lymphocytes into CD4+ and CD8+ lymphocytes, carried out reprogramming of both lymphocytes into iPS cells, and examined whether the efficiency of reprogramming into iPS cells was different, depending upon the difference in the subset of T cells from which the iPS cells were derived. Respective induction conditions for cells of these subsets are shown below.

<Induction Conditions for CD4+ T Cells>

A fraction of CD3-positive CD56-negative CD4-positive T cells of peripheral blood monocytes obtained by blood collection (hereinafter referred to as CD4-positive T cells) was sorted by flow cytometry and stimulated with anti-CD3 and anti-CD28 antibodies (whether by bound beads, or by immobilization, or by addition into medium). The medium was supplemented with about 20 ng/mL of human IL-2, and then gene introduction of Yamanaka factors was performed several times on a RetroNectin®-coated 24-well plate over a period of 48 to 96 hours after the stimulation. The Yamanaka factors which were used in this case were OCT4, SOX2, KLF4, and C-MYC, or alternatively OCT4, SOX2, and KLF4. On or after approximately 2 days after the last gene introduction, $1\times10^5$ to $5\times10^5$ T cells having these genes introduced therein were placed onto irradiated MEFs grown in a 6-cm dish. In cases where CD4-positive T cells were not used by sorting them by flow cytometry on the first day, CD4-positive T cells were sorted by flow cytometry at this time and placed onto MEFs. Half the volume of the medium was replaced with a medium for ES cells containing 0.5 μM valproic acid every day for a period of 4 days from the next day after the transferring onto the MEFs. The culture was continued during which the medium was replaced with a medium for ES cells containing 0.5 μM valproic acid every day or every other day. From around 10 days after the transferring, cell accumulations like cobbles were visible, and in several days later, completed colonies of iPS cells were observed.

<Induction Conditions for CD8+ T Cells>

A fraction of CD3-positive CD56-negative CD8-positive T cells of peripheral blood monocytes obtained by blood collection (hereinafter referred to as CD8-positive T cells) was sorted by flow cytometry and stimulated with anti-CD3 and anti-CD28 antibodies (whether by bound beads, or by immobilization, or by addition into medium). The medium was supplemented with about 20 ng/mL of human IL-2, about 10 ng/mL of IL-7, and about 10 ng/mL of IL-15, and then gene introduction of Yamanaka factors was performed several times on a RetroNectin®-coated 24-well plate over a period of 48 to 96 hours after the stimulation. The Yamanaka factors which were used in this case were OCT4, SOX2, KLF4, C-MYC, NANOG, and LIN28, or alternatively OCT4, SOX2, KLF4, C-MYC, and NANOG. On or after approximately 2 days after the last gene introduction, $1\times10^5$ to $5\times10^5$ T cells having these genes introduced therein were placed onto irradiated MEFs grown in a 6-cm dish. In cases where CD8-positive T cells were not used by sorting them by flow cytometry on the first day, CD8-positive T cells were sorted by flow cytometry at this time and placed onto MEFs. Half the volume of the medium was replaced with a medium for ES cells containing 0.5 μM valproic acid every day for a period of 4 days from the next day after the transferring onto the MEFs. The culture was continued during which the medium was replaced with a medium for ES cells containing 0.5 μM valproic acid every day or every other day. From around 2 weeks after the transferring, cell accumulations like cobbles were visible, and in 1 to 2 weeks later, completed colonies of iPS cells were observed.

From the results of an examination under the above-mentioned induction conditions, it turned out that in this Example, the success rate of the induction from CD4+T lymphocytes into T-iPS cells under conditions where NANOG was not introduced was two times that of the induction from CD8+T lymphocytes into T-iPS cells under conditions where NANOG, a re-programming factor, was further introduced. In this example, T-iPS cells were obtained from CD4+T lymphocytes by 7 or 8 trials when NANOG was not introduced.

Although not shown in any drawings, it was found that in the induction from CD8+T lymphocytes into T-iPS cells, the efficiency of induction into T-iPS cells tended to slightly increase by culturing under a reduced oxygen of 5% 02 in the presence of 10 μM ROCK inhibitor or by adding 1 μM MEK inhibitor (PD0325901) and 3 μM GSK3 inhibitor (CHIR99021) to the medium until colonies were formed, after transferring onto MEFs.

Figure 14:
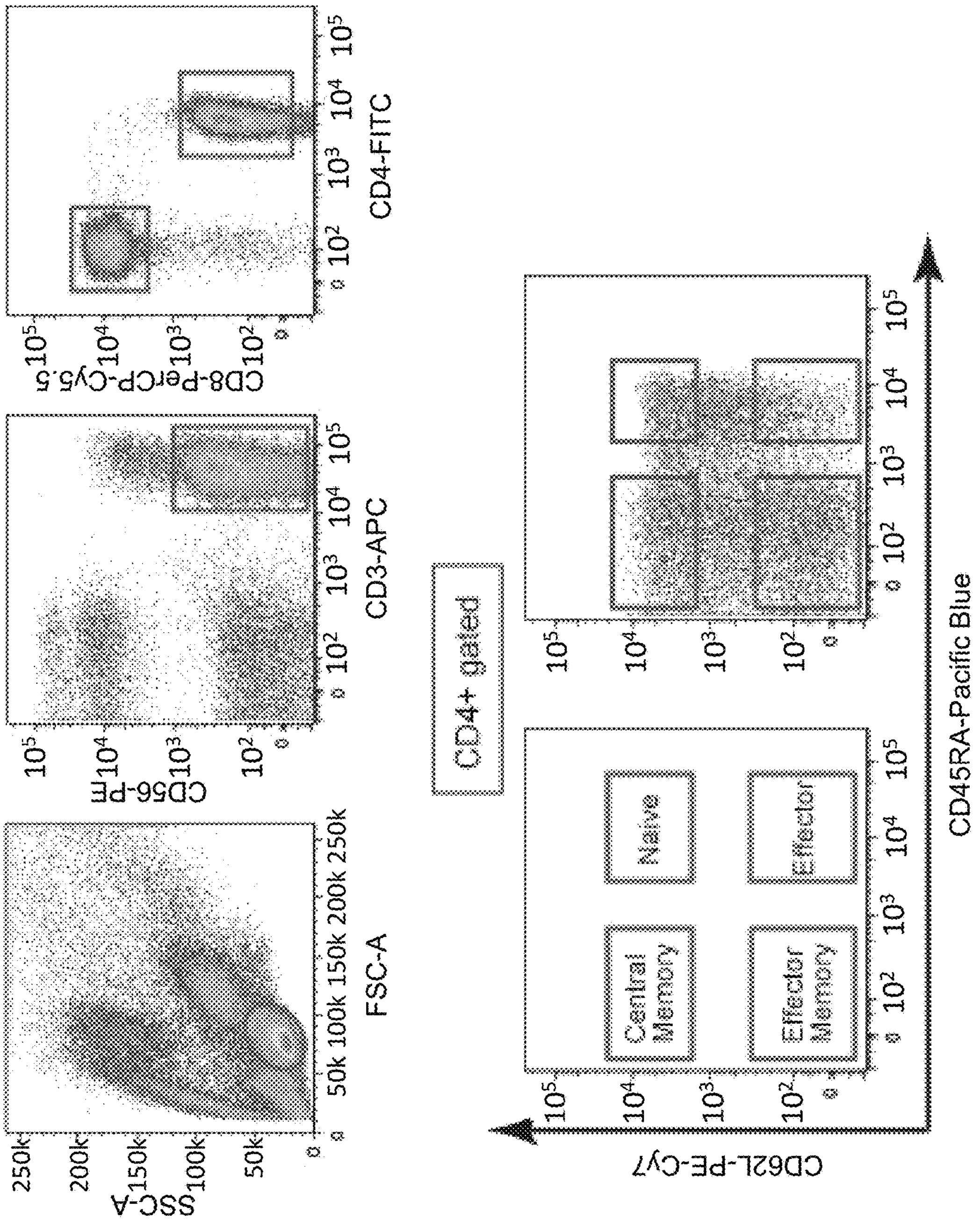
FIG. 14 represents scatter plots showing the results of first dividing CD3+CD56−peripheral blood T cells into a CD4 expressing subset and a CD8 expressing subset, followed by further classifying into a subset of naive T cells (Naive, CD45RA+CD62L+), central memory T cells (Central Memory, CD45RA−CD62L+), effector memory T cells (Effector Memory, CD45RA−CD62L−), or terminal effector T cells (Effector, CD45RA+CD62L−).
Figure 15:
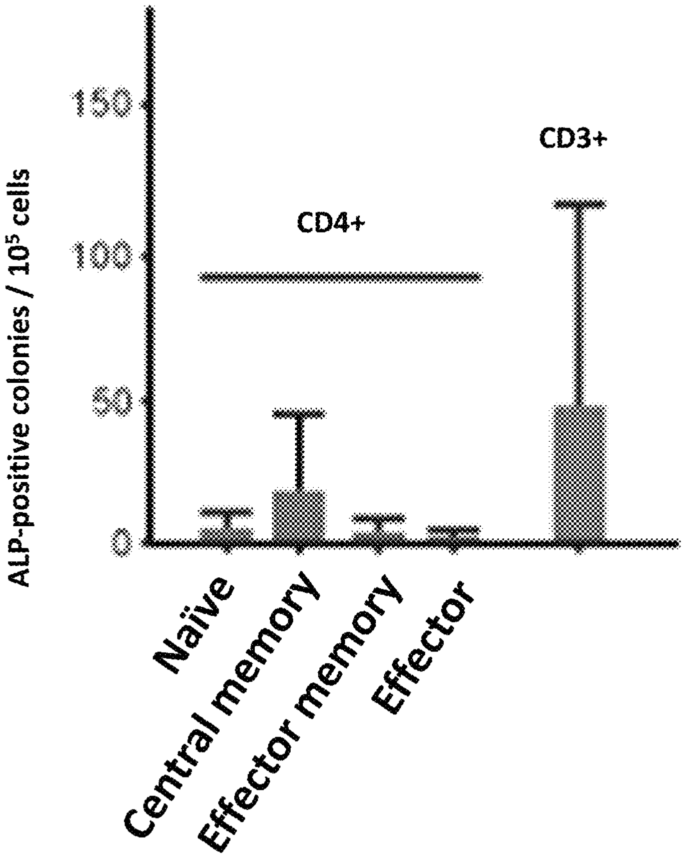
FIG. 15 represents a graph showing the results of estimating the efficiency of reprogramming in each of these T cell subsets, based on the number of ALP+ colonies yielded for each subset from $1\times10^5$ T cells re-seeded onto MEF. In the drawing, the ordinate axis represents an average number±S.D. of ALP+ colonies in three independent experiments.

On the basis of the above-mentioned results, CD4+T lymphocytes were further divided, based on the expression of CD45RA and CD62L/CCR7, into subsets of naive (CD45RA+CD62L+), central memory (CD45RA−CD62L+), effector memory (CD45RA−CD62L−), and terminal effector (CD45RA+CD62L−) T cells, which were then subjected to induction (re-programming) into iPS cells (see Sallusto, F. et al., Nature, 1999, Vol. 401, pp. 708-712; see FIG. 14). From the results, it turned out that the average efficiency of reprogramming cells of these subsets obtained from three healthy donors was 0.0041% for naive T cells, 0.017% for central memory T cells, 0.0036% for effector memory T cells, and 0.0008% for terminal effector T cells, and thus T-iPS cells were established especially from central memory T cells with a relatively good efficiency (see FIG. 15). The high efficiency of reprogramming in CD4+ central memory T cells may reflect the sensitivity to anti-CD3/CD28 stimulation.

Example A5

<Function Analysis of T-Lineage Cells Differentiated from T-iPS Cells>

Implantation into SCID-hu mice of CD34-positive cells generated from human ES cells leads to the induction of differentiation of the T cell lineage in the implanted human fetal thymus in the SCID-hu mice (see Galic, Z. et al., PNAS, 2006, Vol. 103, No. 31, pp. 11742-7). ES cells are also induced in vivo into CD3-positive TCR-positive cells which are mainly CD4/CD8 double-positive, by OP9-DL1 cells (see Timmermans et al., JI, 2009, Vol. 182, pp. 6879-6888).

Thus, the resulting iPS cells derived from T cells (T-iPS cells) were used to attempt to induce differentiation into T cells. In T cells, somatic hypermutations are not induced after they have gone through the recombination in the TCR gene during the process of development, and thus it is expected by the present inventors that cells of the T cell lineage induced from T-iPS cells retain the TCR information of their originating T-IPS cells and has a monoclonal TCR, depending upon the condition of allelic exclusion. However, it is unknown whether a T cell clone can be induced from a T-iPS cell, and whether an induced T cell clone is functional, and whether the condition of TCR rearrangement in a T cell clone induced from a T-iPS cell is identical to that in the originating T cell of the T-iPS cell clone. Thus, the present inventors examined these points as follows.

Figure 16A:
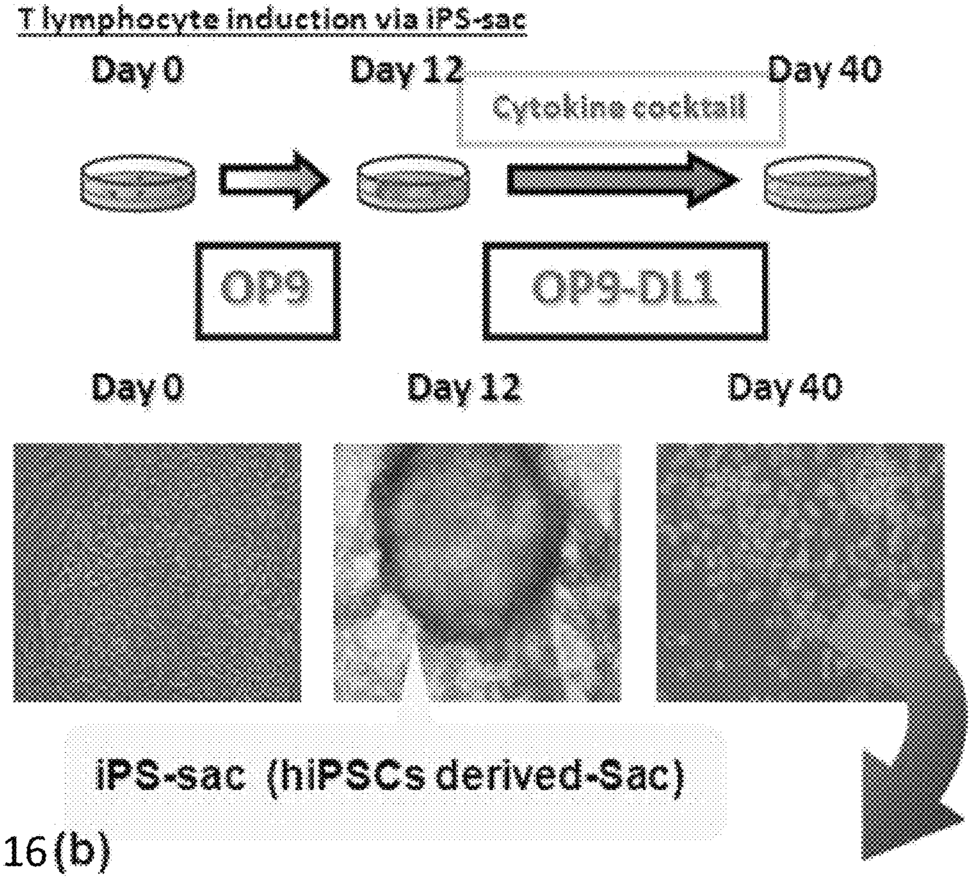
FIG. 16(*a*) represents an outline of the production of T-lineage cells from pluripotent cells by culturing on OP9 and OP9-DL1 stroma cell layers and micrographs showing the condition of cells at the indicated time points. In the drawing, "Cytokine cocktail" indicates that hIL-7, hFlt-3L, and hSCF were added.
Figure 16B:
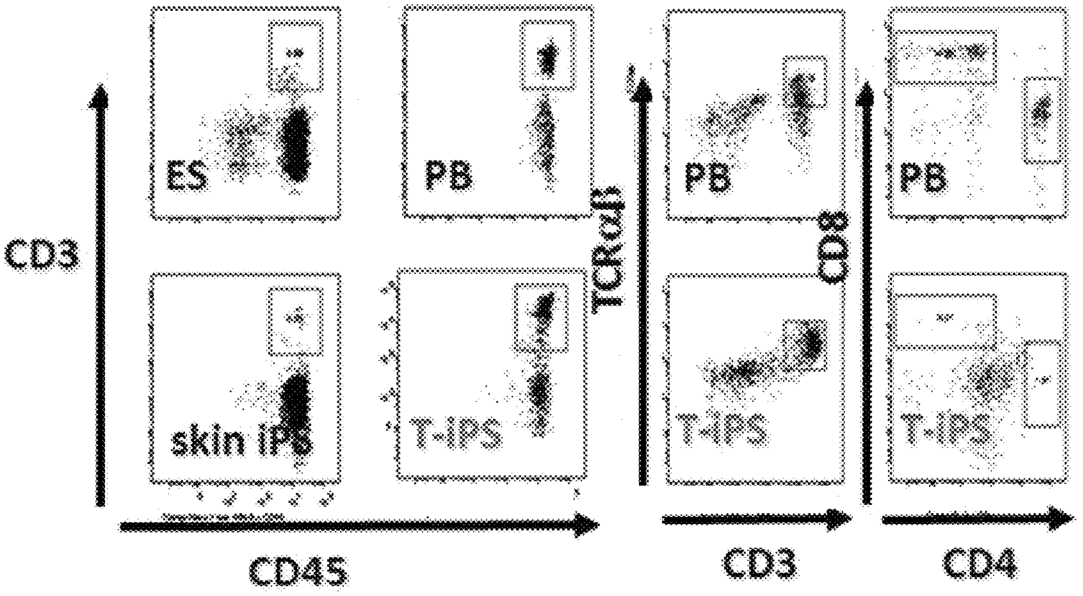

First, from the established T-iPS cell clones was selected a clone TkT3V1-7 in which one allele generated TCRα and TCRβ chains both of which had an in-frame rearrangement, whereas the other allele generated an a chain having an out-frame rearrangement and a 13 chain terminating in a DJ rearrangement, and this clone was subjected to in vitro induction of the T cell lineage. T-iPS cells which were cultured on OP9 cells in the presence of IL-7, Flt3L (human FMS-like tyrosine kinase 3 ligand), or SCF (human stem cell factor, hSCF) formed structures like ES-sacs (see Takayama et al., Blood, 2008, Vol. 111, No. 11, pp. 5298-5306) and induced CD45-positive blood cells in the inside of such structures by day 14 (see FIG. 16(*a*)). On days 12 to 14, the blood cells were transferred onto OP9-DL1 cells, and exchanging the medium was repeated every four days for continuing the culturing. On day 21 and day 40, CD3-positive cells were collected by FACS and assessed for the expression of T-cell-related genes. The CD3-positive cells on day 40 were found to be mainly cells negative for CD4/8 and in part CD8 single-positive cells (see FIG. 16(*b*)).

Figure 17B:
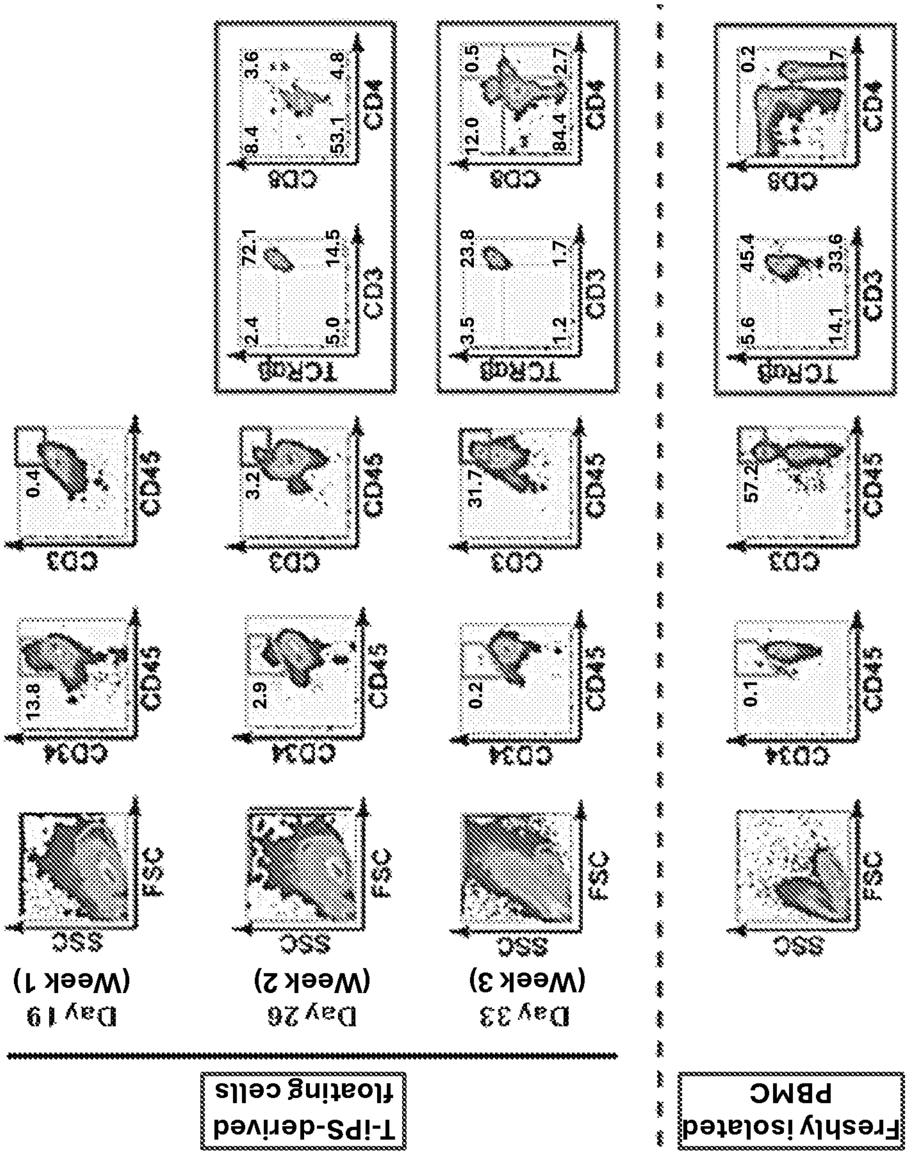
FIG. 17(*a*) represents an outline of the production of T-lineage cells from pluripotent cells, such as T-iPS cells, by culturing on OP9 and OP9-DL1 stroma cell layers, which is a representation showing that pluripotent cells were cultured for 10 to 14 days on a layer of irradiated OP9 cells in an essential medium containing no cytokines and using α-MEM as the basal medium, and then the induced hematopoietic cells were cultured for three or four weeks with OP9-DL1 cells in an essential medium supplemented with hIL-7, hFlt-3L, hSCF, and others and using α-MEM as the basal medium.
Figure 18:
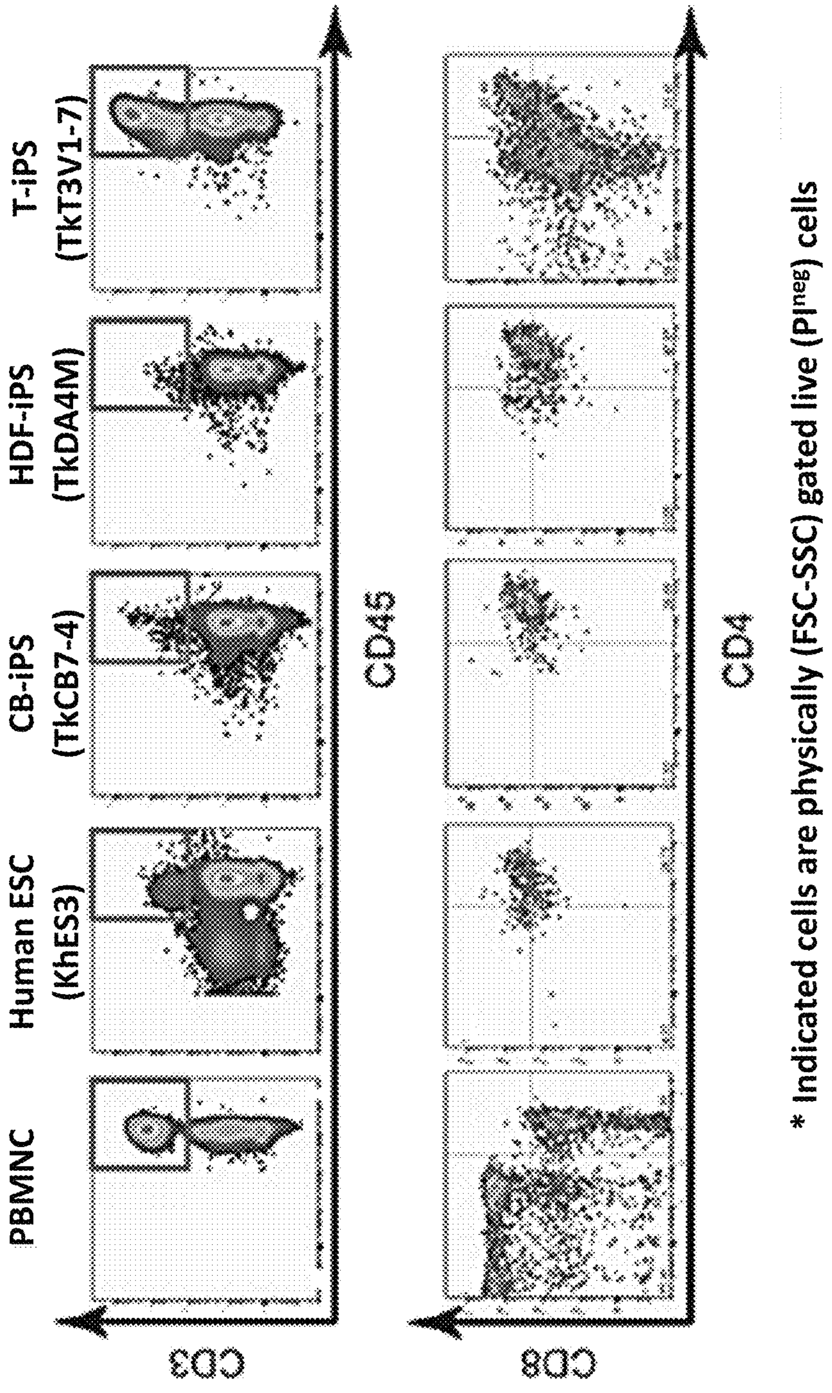
FIG. 18 represents scatter plots showing representative results of at least three independent experiments in which the expression of T-lineage markers was analyzed by flow cytometry. In the drawing, the numerical value indicated in each of the scatter plots indicates the percentage of cells (%) in the indicated fraction(s); "Human ESC" represents the results in human ES cells (KhES3), "CB-iPS" represents the results in iPS cells derived from cord blood CD34-positive cells (TkCB7-4), "HDF-iPS" represents the results in iPS cells derived from human skin fibroblasts (TkDA4M), "T-iPSC" represents the results in T-iPS cells (TkT3V1-7), and "PBMNC" represents the results in peripheral blood mononuclear cells.
Figure 19:
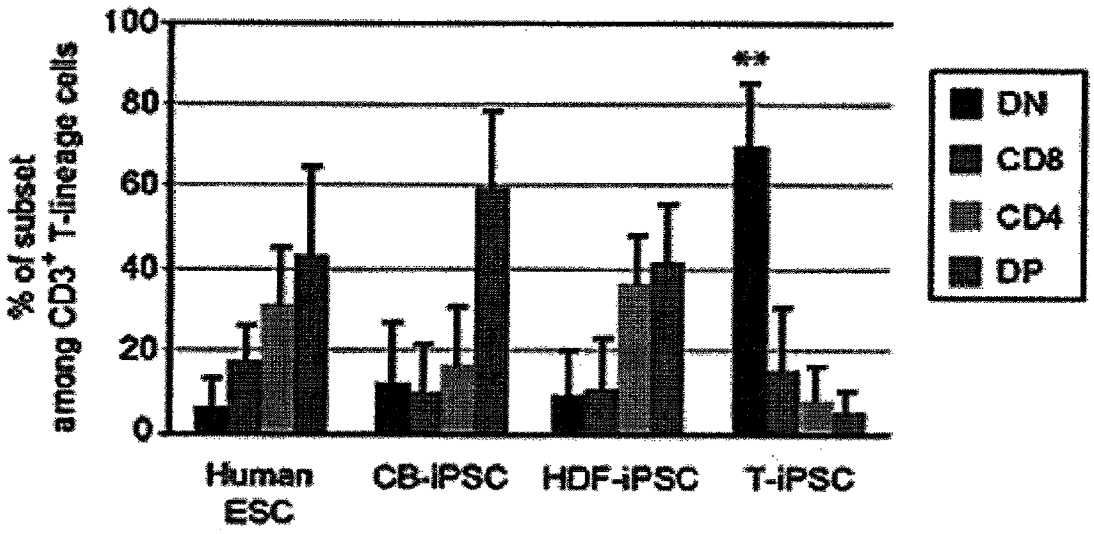
FIG. 19 represents a graph showing the expression of CD4 and CD8 in CD3+T-lineage cells, as estimated by flow cytometry. In the drawing, the ordinate axis represents a relative distribution±S.D. of each subset in the T-lineage cells derived from each of the indicated types of pluripotent cell. "Human ESC" represents the results in human ES cells, "CB-iPSC" represents the results in iPS cells derived from cord blood CD34-positive cells, "HDF-iPSC" represents the results in iPS cells derived from human skin fibroblasts, and "T-iPSC" represents the results in T-iPS cells. The columns for each of the indicated types of cell represent, from left to right, subsets "DN", "CD8", "CD4", and "DP." Here, "DN" indicates that the subset is CD4−CD8−, "CD4" indicates that the subset is CD4+CD8−, "CD8" indicates that the subset is CD4−CD8+, and "DP" indicates that the subset is CD4+ CD8+.

After the sacs were transferred onto a layer of OP9-DL1 cells, floating cells leaving the sacs were collected and analyzed every week by flow cytometry (see FIG. 17(*a*)). From the results, it followed that at the first week, most of the floating cells weakly expressed CD45 and some expressed CD34, CD7, and CD1a, while none of the cells expressed a CD3-TCRαβ complex and CD5. At the second week, most of the cells had an elevated expression of CD45 and some had begun to express a CD3-TCRαβ complex. By the third week, the CD34 cells had completely disappeared and the cells which were strongly positive for CD3-TCRαβ had formed a group of the most abundant cells in the floating cells. The CD3+ cells included no TCRαβ− cells (see FIG. 17(*b*)). Further, even after the third week, most of the redifferentiated CD3+TCRαβ+ cells were at a double-negative (DN) stage, while in some groups of cells, there were also detected cells positive only for CD4 (8.5±8.2%) and only for CD8 (15.5±15.9%) (see FIGS. 18 and 19).

Figure 20:
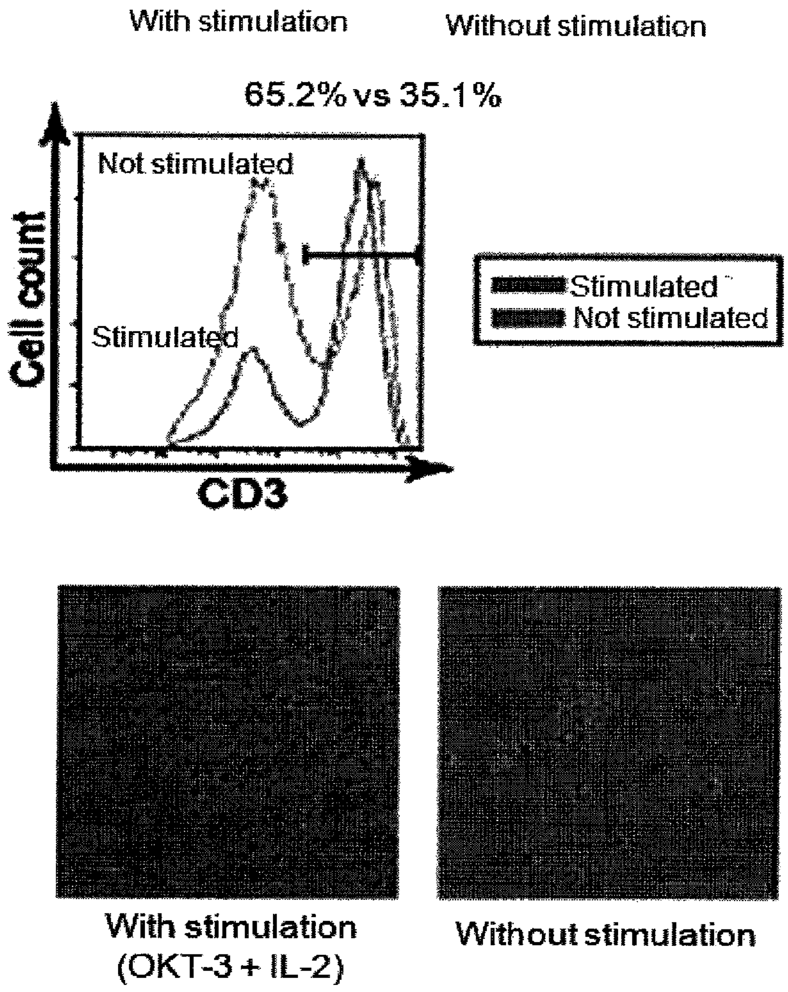
FIG. 20 represents a graph and micrographs showing proportional changes and morphological changes in re-differentiated T-lineage cells after the cells were or were not subjected to TCR stimulation with OKT-3 and hIL-2.

In general, it is known that also at thymocyte stages, TCR-expressing cells of the T lineage are capable of responding to TCR stimulation and also able to produce cytokines (see Fischer, M. et al., J. Immunol., 1991, Vol. 146, pp. 3452-3456). Thus, the present inventors stimulated the above-mentioned floating cells with OKT-3 and IL-2 and examined the activation and number of CD3 expressing cells. In brief, the floating cells were stimulated for 5 days with 30 ng/mL OKT-3 and 600 IU/mL hIL-2. The results appeared to show that a group of CD3+ cells increased in number and CD3 expressing cells were activated based on morphological criteria (see FIG. 20), but the actual CD3+ cells were found to be unchanged.

Figure 21:
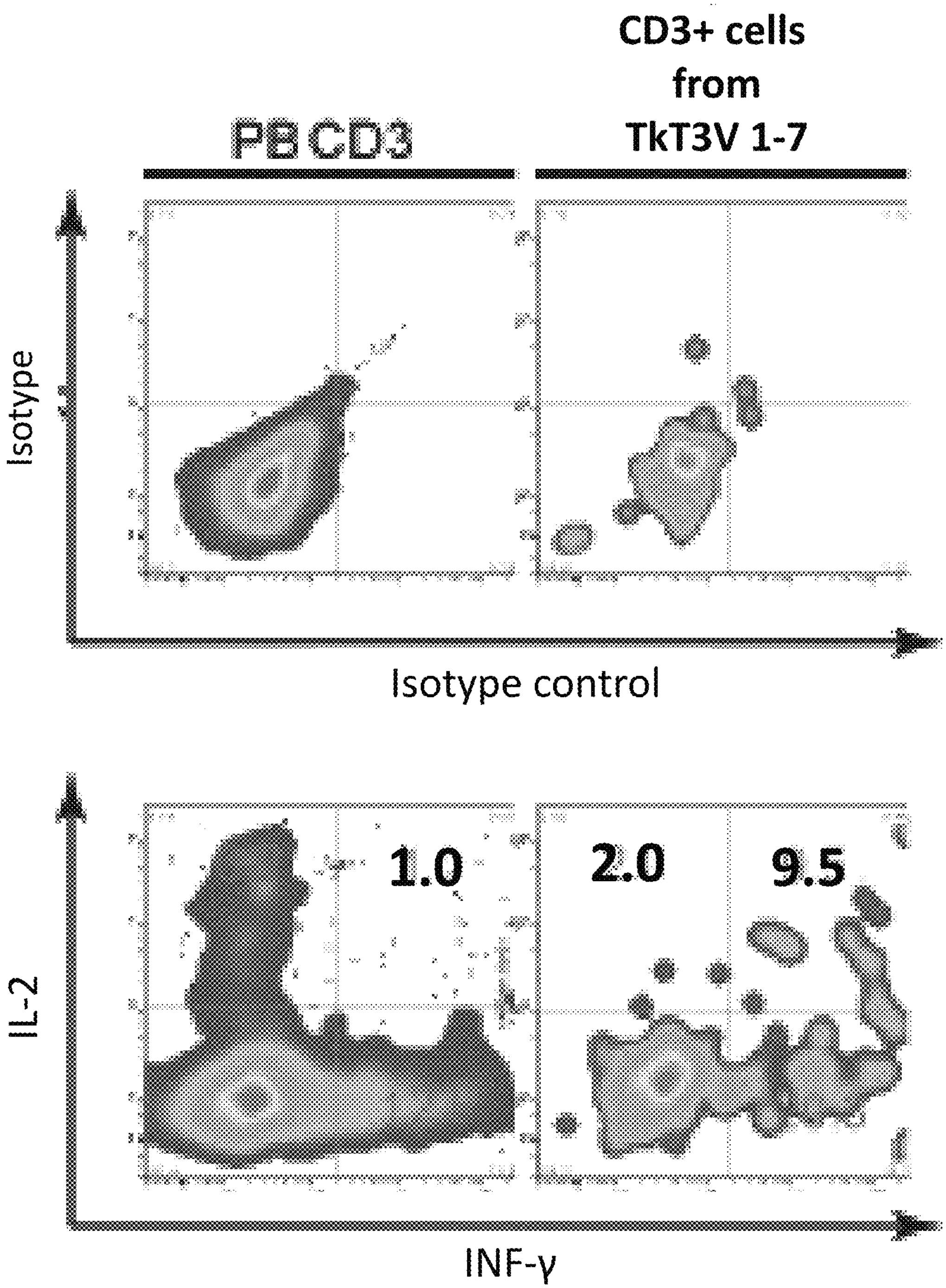
FIG. 21 represents scatter plots showing the results of an analysis by flow cytometry of the cytokine production profile of re-differentiated T-lineage cells. The re-differentiated T-lineage cells (CD3+ cells from TkT3V1-7) or PBMNCs (PB CD3, control) to be analyzed were stimulated overnight with PMA/ionomycin together with hIL-1a and then stained with antibodies. The numerical values indicated in these plots indicate the percentage (%) of cytokine producing cells.
Figure 24:
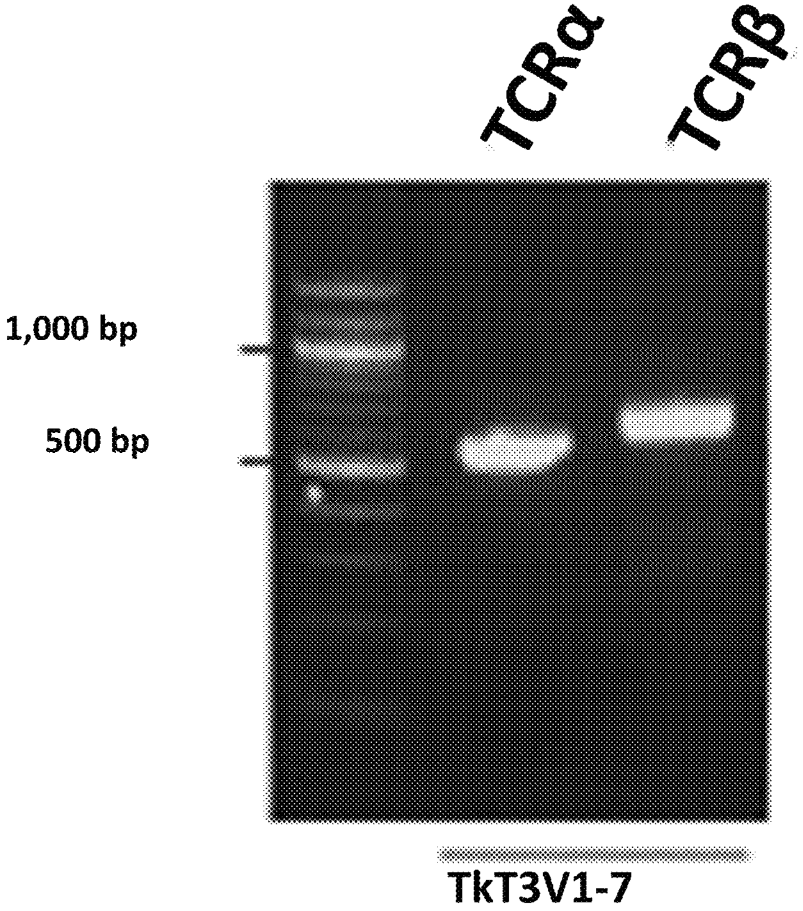
FIG. 24 represents a picture of electrophoresis showing the results of an analysis of PCR products obtained by amplifying the TCR of TkT3V1-7 cells by PCR using cDNA library constructed by SMART method.
Figure 26:
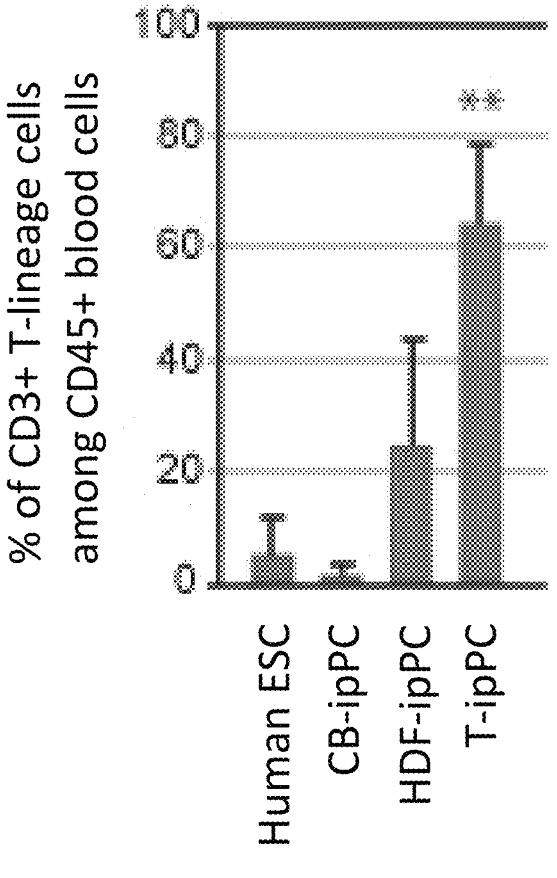
FIG. 26 represents a graph showing the results of estimating the expression of CD3 by flow cytometry. In the drawing, the ordinate axis represents the percentage of CD3+T-lineage cells in the CD45+ blood cells (an average±S.D. of three or more independent experiments for each group). "Human ESC" indicates the results in human ES cells, "CB-iPSC" indicates the results in iPS cells derived from cord blood CD34-positive cells, "HDF-iPSC" indicates the results in iPS cells derived from human skin fibroblasts, and "T-iPSC" indicates the results in T-iPS cells. ** indicates $p<0.01$, relative to the other samples.
Figure 27:
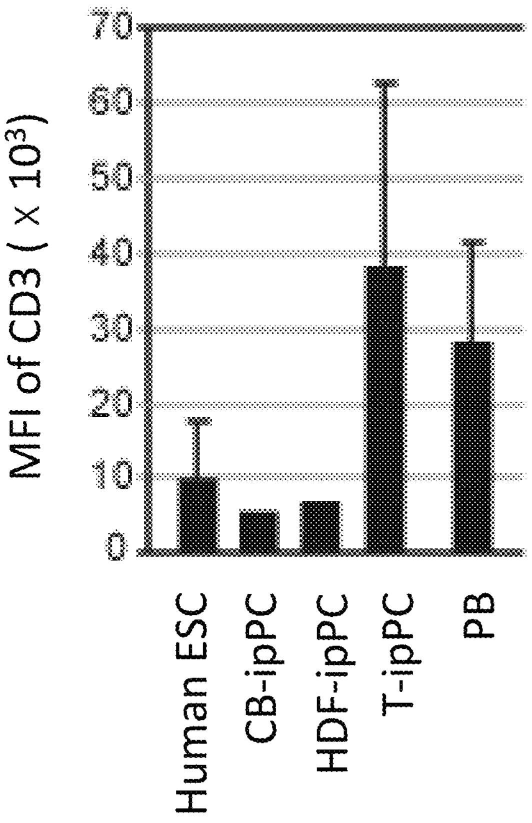
FIG. 27 represents a graph showing the mean fluorescence intensity (MFI) of CD3 cells as estimated by flow cytometry. The ordinate axis represents an average±S.D. of two independent experiments per group for CD-iPS and HDF-iPS groups and three or more independent experiments per group for the other groups. "Human ESC" indicates the results in human ES cells, "CB-iPSC" indicates the results in iPS cells derived from cord blood CD34-positive cells, "HDF-iPSC" indicates the results in iPS cells derived from human skin fibroblasts, "T-iPSC" indicates the results in T-iPS cells, and "PB" indicates the results in peripheral blood mononuclear cells.

In order to demonstrate that the induced CD3+TCRαβ+ cells functionally contribute to the induction of differentiation into cells of the T lineage, the ability to produce cytokines was assessed, as mentioned below. From the results of stimulation of these cells with PMA and calcium ionophore (ionomycin), it turned out that 12.5% of the resulting T-lineage cells produced IFN-γ, 1.0% produced IL-2, and 6.2% produced both IFN-γ and IL-2 (see FIG. 21). Therefore, it is demonstrated that the CD3+TCRαβ+ cells induced from T-iPS cells contribute not only morphologically, but also functionally to the induction into cells of the T lineage.

As mentioned above, since the TCR gene generally do not undergo somatic hyper-variable mutations (somatic hypermutations), it is expected that redifferentiated T-lineage cells derived from T-iPS cells frequently express the TCRαβ which is identical to that encoded in the genome of the originating cells of the T-iPS cells. However, it is unknown whether the TCR rearrangement pattern in redifferentiated T cells derived from T-iPS cells is identical to that in the originating T cells of the T-iPS cells. Thus, the present inventors examined this point, as mentioned below.

From the results, when the TCR expression in the induced CD3 cells was analyzed, it turned out that in TkT3V1-3 and TkT3V1-7 cells, a single TCRβ chain appeared and the sequence of a region including the CDR3 region in iPS cells post-induction was identical to that in the iPS cells pre-induction (see FIG. 22). While the TCRα chain was found to be diverse, most TCRα chains were derived from rearranged a chains (see FIG. 23). It was revealed that T cells which had been subjected to reprogramming expressed TCR in a clonal fashion when such T cells were induced again into T cells.

Analysis was also made of CD3-high TCRαβ-high cell clones of the T lineage which had been redifferentiated from T-iPS cells of four clones derived from two donors. In brief, respective cDNA libraries from these T-lineage cell clones were constructed by SMART-mediated reverse transcription reactions (see Du, G. et al., J. Immunol. Methods, 2006, Vol. 308, pp. 19-35) and subjected to amplification of the TCR gene. Then, the TCR gene amplified was inserted into a cloning vector and cloned for analysis.

Figure 13:
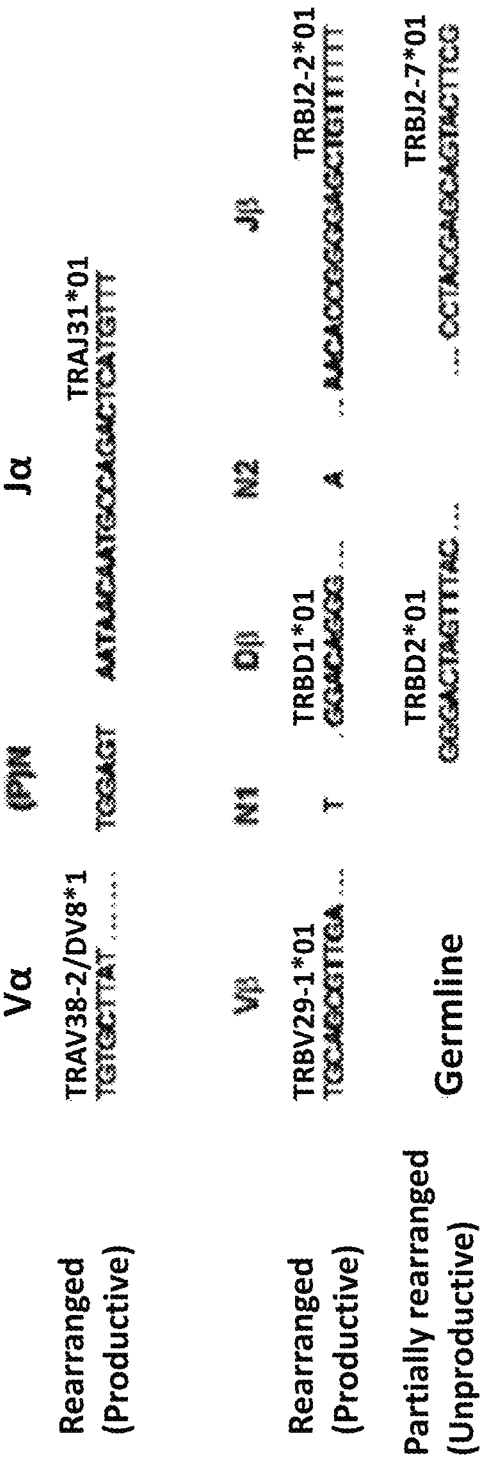
FIG. 13 represents the results of sequencing of the PCR products of TCR genes derived from TkT3V1-7 cells shown in FIGS. 11 and 12. In the drawing, a productive rearrangement in one allele of the TCRα gene is shown in the top row. A productive rearrangement in one allele of the TCRβ gene (V(D)Jβ rearrangement) is shown in the middle row. An unproductive rearrangement in the other allele of the TCRβ gene (DJβ rearrangement) is shown in the bottom row.

From the results, the sequence of the TCR gene in the clones analyzed was identical to that encoded in the genome of the originating T-iPS cells before the redifferentiation (see FIGS. 13, 23, and 25). On the other hand, most transcription products were derived from productive chains and there were also found transcription products derived from unproductive chains (see Table 8). However, there were not found transcription products of which the sequences were different from that derived from the productive or unproductive rearrangement (see Table 9). In Table 8, “iPS Clone” refers to a T-cell-derived iPS cell line which has been established, “Productivity” refers to whether or not the rearranged T cell receptor has functions, i.e., whether the rearranged T cell receptor is functional (productive) or unfunctional (unproductive) in forming a complex with the β receptor to recognize the antigen, and “Sequence of junctional region” refers to the base sequence of the junction region. In Table 9, “Productivity” refers to whether or not the rearranged T cell receptor has functions, i.e., whether the rearranged T cell receptor is functional (productive) or unfunctional (unproductive) in forming a complex with the β receptor to recognize the antigen, “No. of Sequenced Samples” refers to the number of samples analyzed for each clone in the TCR gene, and “Sequence allignment with T-iPSC’s genome” refers to the number and ratio of T-iPS cells in which the genome sequence of T-iPS cells pre-redifferentiation was identical to or different from that post-redifferentiation in the samples analyzed, in the columns “Identical” and “Different,” respectively.

TABLE 8

| iPS clone | Productivity | Vα (Rearrangement) | Jα (Rearrangement) | 3'Vα (Sequence of junctional region) | (P)N (Sequence of junctional region) | 5'Jα (Sequence of junctional region) |
|---|---|---|---|---|---|---|
| TkT3V1-3 | Productive | TRAV5*01 | TRAJ29*01 | TGTCAGAGAGTA | TGGAGT | GGAAACACACCTCTTGTCTTT |
| | Unproductive | N.D. | | N.D. | | |
| TkT3V1-7 | Productive | TRAV38-2/DVB*01 | TRAJ31*01 | TGTGCTTAT | TGGAGT | AATAACAATCCCAGACTCATGTTT |
| | Unproductive | N.D. | | N.D. | | |
| TkT3V1-13 | Productive | TRAV4*01 | TRAJ39*01 | TGCCTCGTGGGTGAC | CGGGAC | GCAGGCAACATGCTCACCTTT |
| | Unproductive | TRAV13-1*02 | TRAJ41*01 | TGTGCAGCAAGTA | AGGGG | ATTCCGGGTATGCACTCAACTTC |
| TkT3V1-14 | Productive | TRAV12-2*02 | TRAJ18*01 | TGTGCCGT | TATGAGG | GGCTCAACCCTGGGGAGGCTATACTTT |
| | Unproductive | TRAV1-2*01 | TRAJ28*01 | TGTGCTGTGAGAGA | TCAAAGGTT | TCTGGGGCTGGGAGTTACCAACTCACTTTC |

| iPS clone | Productivity | Vβ (Rearrangement) | Dβ (Rearrangement) | Jβ (Rearrangement) | 3'Vβ (Sequence of junctional region) | N1-Dβ-N2 (Sequence of junctional region) | 6'Jβ (Sequence of junctional region) |
|---|---|---|---|---|---|---|---|
| TkT3V1-3 | Productive | TRBV28*01 | TRBD1*01 | TRBJ-3*01 | TGTGCCAGCA | TCCCCGGGGGTA | CTGGAAACACCATATATTTT |
| | Unproductive | N.D. | | | N.D. | | |
| TkT3V1-7 | Productive | TRBV29-1*01 | TRBD1*01 | TRBJ2-2*01 | TGCAGCGTTGA | TGGACAGGGA | AACACCGGGGAGCTGTTTTTT |
| | Unproductive | N.D. | | | N.D. | | |
| TkT3V1-13 | Productive | TRBV7-9*03 | TRBD1*01 | TRBJ2-7*01 | TGTGCCAGCAGC | AACCCGACGGGGTTAGT | CTACGAGCAGTACTTC |
| | Unproductive | N.D. | | | N.D. | | |
| TkT3V1-14 | Productive | TRBV7-2*02/*03 | TRBD2*02 | TRBJ2-7*01 | TGTGCCAGCAGCTTAG | GCGGGAGTCTCA | CCTACGAGCAGTACTTC |
| | Unproductive | TRBV20-1*02/*04 | TRBD1*01 | TRBJ2-1*01 | TGCAGTGC | CCACAGGGCCT | TCCTACAATGAGCAGTTCTTC |

TABLE 9

| | | Productivity | No. of Sequenced Samples | Sequence alignment with T-iPSCs' genome Identical | Different |
|---|---|---|---|---|---|
| TkT3V1-3 | TCRA | Productive | 7 | 7/7 (100%) | 0/7 (0%) |
| | | Unproductive | — | — | — |
| | TCRB | Productive | 4 | 4/4 (100%) | 0/4 (0%) |
| | | Unproductive | — | — | — |
| TkT3V1-7 | TCRA | Productive | 11 | 11/11 (100%) | 0/11 (0%) |
| | | Unproductive | — | — | — |
| | TCRB | Productive | 5 | 5/5 (100%) | 0/5 (0%) |
| | | Unproductive | — | — | — |
| TkT3V1-13 | TCRA | Productive | 14 | 14/14 (100%) | 0/14 (0%) |
| | | Unproductive | 1 | 1/1 (100%) | 0/1 (0%) |
| | TCRB | Productive | 17 | 17/17 (100%) | 0/17 (0%) |
| | | Unproductive | — | — | — |
| TkT3V1-14 | TCRA | Productive | 10 | 10/10 (100%) | 0/10 (0%) |
| | | Unproductive | 3 | 3/3 (100%) | 0/3 (0%) |
| | TCRB | Productive | 15 | 15/15 (100%) | 0/15 (0%) |
| | | Unproductive | 1 | 1/1 (100%) | 0/1 (0%) |

Further, the induction into CD34-positive cells from pluripotent cells of other types was compared with that when the method according to the present invention was used. From the results, it turned out that CD3-positive cells were induced from pluripotent cells of any of the types examined, ES cells (human ES cells, Human ESCs), skin-derived iPS cells (iPS cells derived from a human dermal fibroblast, HDF-iPSCs), CD34-positive-cell-derived iPS cells (iPS cells derived from a cord blood CD34-positive cell, CB-iPSCs), and T-iPS cells (T-iPSCs), while the T-iPS cells obviously had a higher tendency to be induced into T cell, as compared with the skin-cell- and CD34-positive-cell-derived iPS cells and the ES cells (see FIGS. 16, 17, 26, and 27).

Example A6

<Induction into Functional T Cells from iPS Cells that have been Established from Human T Cells, Part 2>

Six T-iPSC clones, which were derived from CD4 or CD8 T cells obtained from donors, were used to attempt to induce a population of T cells having a monoclonal TCR. In brief, on the day of the start of induction, $3\times10^5$ T-IPS cells per clone were seeded on irradiated OP9 or 10T1/2 cells grown in a 10-cm dish and subjected to co-culturing for 14 days or so using the differentiation medium. During the co-culture, in a period from day 12 to day 14, there appeared blood cells which were present in sac structures. In this case, it turned out that although blood cells appeared without using cytokines in combination, the addition of VEGF lead to an improved harvesting of CD34-positive hematopoietic stem cells (hereinafter referred to as CD34 cells). It also turned out that the addition of VEGF, SCF, and TPO, or of VEGF, SCF, and FLT3L lead to a further improved harvesting of CD34 cells. These tendencies were also reflected in harvesting a final product, i.e., cells of the T lineage, as mentioned below.

In addition, on any of days 12 to 14, $3\times10^5$ blood cells, including their CD34 cells, were seeded on irradiated OP9/DL1, OP9/DL4, or 10T1/2/DL4 cells grown in a 10-cm dish and subjected to co-culturing in α-MEM medium containing 20% FBS in the presence of IL-7 and Flt3L. In this case, SCF was not used because it strongly promoted differentiation into NK cells. As mentioned above, the floating cells became cells of the T lineage which were CD3 positive and TCRαβ positive, which accounted for a small portion at the second week of the co-culture and a large portion at the third week, while the floating cells included cells which were double negative (DN), double positive (DP), and single positive (SP) for the expression of CD4 and CD8, and thus were not of a homogeneous population of cells (see FIG. 17). Further detailed studies resulted in the finding that the composition of DN, DP, CD4 SP, and CD8 SP cells was dependent on the concentration of IL-7. Specifically, although not shown in any drawings, when IL-7 was not added, CD3-positive CD56-negative T cells themselves accounted for a small proportion of the resulting cells and DN cells accounted for a large portion. When IL-7 was added at 5 to 10 ng/mL, a population of CD3-positive CD56-positive NKT-like cells appeared and DN cells still accounted for a large portion of the resulting cells. When IL-7 was added at 1 ng/mL, on the other hand, CD3-positive CD56-positive T-lineage cells accounted for a large portion of the resulting cells and there was observed the differentiation from the DN stage into the DP stage and then into the CD4 SP and CD8 SP stages. Analysis of these SP cells in terms of differentiation markers of peripheral blood T cells showed that about 80% of the CD8 SP cells was CD45RA+ CD62L+ naive T cells and most of the CD4 SP cells was CD45RA-CD62L+ central memory T cells, suggesting that T cells which have reached the effector memory stage are capable of rejuvenating through T-iPS cells into naive T cells (in the case of CD8 SP cells) or central memory T cells (in the case of CD4 cells).

Example B

In Examples B1 to B4, Comparative Example B1, and Preparation Example B1 which follow, examination was made on methods for efficiently obtaining CD8 SP cells which have the same rearrangement pattern of the TCR gene as in their originating human T cells. Examples B1 to B4, Comparative Example B1, and Preparation Example 61 which follow were carried out using the below-mentioned experimental methods unless otherwise specified.

<Production of CTL Clones>

CTL strain specific for Nef138-8(wt) were established from PBMCs obtained from an HIV-1-infected patient who had an HLA-A24, as described in Kawana-Tachikawa, A. et al., J. Virol., 2002, Vol. 76, pp. 11982-11988.

<Production of T-iPS Cells>

Human iPS cells were established from peripheral blood T cells or CTL clones under conditions optimized for culturing T cells, as described in Takayama, N. et al., 3. Exp. Med., 2010, Vol. 207, pp. 2817-2830.

In brief, peripheral blood T cells were first stimulated and activated with α-CD3/CD28 antibody-coated beads (manufactured by Miltenyi Biotec). CTL clones, on the other hand, were stimulated and activated with PHA (manufactured by Sigma-Aldrich). CTL clones were also stimulated and activated with irradiated PBMCs (alloantigen expressing cells) which were derived from an individual different from the HIV-1-infected patient. In these cases, there had not been observed significant differences in properties of the resulting T-iPS cells between stimulation with PHA and with alloantigen expressing cells.

Into the activated cells, reprogramming factors were introduced with retroviral vectors (pMXs retroviral vectors) or Sendai virus vectors, and then the cells were cultured with 10 ng/mL (200 U) IL-2, 5 to 10 ng/mL IL-7, and 5 to 10 ng/mL IL-15 (manufactured by Peprotech) in RH10 medium. During the culture period, the medium was gradually replaced to human iPS medium (manufactured by Wako) containing bFGF and others.

The introduction of the viral vectors into the cells was carried out by centrifugation in a RetroNectin®-coated plate (manufactured by Takara). The composition of the RH10 medium is as mentioned below: RPMI-1640 supplemented with 10% human AB serum, 2 mM L-glutamine, 100 U/mL penicillin, and 100 ng/mL streptomycin.
The composition of the human iPS medium is as mentioned below: DMEM/F12 FAM supplemented with 20% KSR, 2 mM L-glutamine, 1% non-essential amino acids, 10 μM 2-mercaptoethanol, and 5 ng/mL b-FGF.

Further, siRNA L527 (see Nishimura, K. et al., J Biol. Chem., 2011, Vol. 286, pp. 4760-4771) was introduced into the established iPS clones by Lipofectamine RNAiMAX (manufactured by Invitrogen), in order to remove SeV viruses from the cytoplasm.

<Alkaline Phosphatase Staining and Immunocytochemistry>

Alkaline phosphatase activity was assessed using an Alkaline Phosphatase Substrate Kit II (manufactured by Vector Laboratories) according to its instructions for use.

Immunocytochemical staining was carried out using the below-mentioned antibodies, as described in Takayama, N. et al., 3 Exp Med, 2010, Vol. 207, pp. 2817-2830. The ratio in the parenthesis indicates a dilution of the indicated antibody.

SSEA-4 (1:50, FAB1435P, manufactured by R&D Systems)
Tra-1-60 (1:100, MAB4360, manufactured by Millipore)
Tra-1-81 (1:100, MAB4381, manufactured by Millipore)
HLA-A24 (1:100, BIH0964, manufactured by Veritas)
Micrographs were taken using an Axio Observer Z1 fluorescence microscope (manufactured by Carl Zeiss).

<Teratoma Formation>

The pluripotency of human iPS cells was assessed through the formation of teratomas in a system using NOD-Scid mice, as described in Masaki, H. et al., Stem Cell Res., 2007, Vol. 1, pp. 105-115.

<Bisulfite Sequencing>

Genomic DNA was treated using a MethylEasy Xceed Rapid DNA Bisulphite Modification Kit (manufactured by Human Genetic Signatures) according to its instructions for use.

Promoter regions of the human Oct3/4 and Nanog genes were amplified by PCR using EpiTaq HS (manufactured by Takara). The PCR product obtained was inserted into a pGEM-T-Easy vector (manufactured by Promega), cloned, and subjected to sequencing. The sequences of primers used for the PCR (SEQ ID NOs:114 to 117) are shown in Table 10.

TABLE 10

PCR primers for bisulfite sequence

| Primer | Sequence |
|---|---|
| bisOCT4-3/F | ATTTGTTTTTTGGGTAGTTAAAGGT |
| hisOCT4-3/R | CCAACTATCTTCATCTTAATAACATCC |
| mehNANOG-F1-S | TGGTTAGGTTGGTTTTAAATTTTTG |
| mehNANOG-F1-AS | AACCCACCCTTATAAATTCTCAATTA |

<RT-PCR and Quantitative PCR>

Respective total RNAs were extracted from ES, iPS, and T cells using an RNeasy Micro Kit (manufactured by Qiagen). Then, each of the total RNAs was used as a template to perform a reverse transcription reaction using a High Capacity cDNA Reverse Transcription Kit (manufactured by Applied Biosystems) and a random 6-base primer. The RT-PCR was performed as described in Takayama, N. et al., J. Exp. Med., 2010, Vol. 207, pp. 2817-2830. The names of target genes and the sequences of PCR primers used in the analysis (SEQ ID NOs:118 to 152) are listed in Table 11.

TABLE 11

PCR primers for RT-PCR

| Target gene | Primer | Sequence (5'-3') |
|---|---|---|
| GAPDH | hGAPDH-PF1<br>hGAPDH-PR2 | AACAGCCTCAAGATCATCAGC<br>TTGGCAGGTTTTTCTAGACGG |
| 4-Oct | total-OCT4-F.ips<br>total-OCT4-R.ips | ATTCAGCCAAACGACCATC<br>GGAAAGGGACCGAGGAGTA |
| SOX2 | total-SOX2-F.ips<br>total-SOX2-R.ips | CAGCGCATGGACAGTTAC<br>GGAGTGGGAGGAAGAGGT |
| c-MYC | total-c-MYC-F.ips<br>total-c-MYC-R.ips | AGTTTCATCTGCGACCCG<br>CCTCATCTTCTTGTTCCTCCT |
| KLF4 | total-KLF4-F.ips<br>total-KLF4-R.ips | GCGGGAAGGGAGAAGACA<br>CCGGATCGGATAGGTGAA |
| endogenous<br>4-Oct | endo-hOCT3/4-S1165<br>endo-hOCT3/4-AS1283 | GACAGGGGAGGGGAGGAGCTAGG<br>CTTCCCTCCAACCAGTTGCCCCAAAC |
| endogenous<br>SOX2 | endo-hSOX2-S1430<br>endo-hSOX2-AS1555 | GGGAAATGGGAGGGGTGCAAAAGAGG<br>TTGCGTGAGTGTGGATGGGATTGGTG |
| endogenous<br>c-MYC | endo-hMYC-S253<br>endo-hMYC-AS555 | GCGTCCTGGGAAGGGAGATCCGGAGC<br>TTGAGGGGCATCGTCGCGGGAGGCTG |
| endogenous<br>KLF4 | endo-hKLF4-S1128<br>endo-hKLF4-AS1826 | ACGATCGTGGCCCCGGAAAAGGACC<br>TGATTGTAGTGCTTTCTGGCTGGGCTCC |

TABLE 11-continued

| PCR primers for RT-PCR | | |
|---|---|---|
| Target gene | Primer | Sequence (5'-3') |
| Tg-OCT4 | Th-OCT3/4-S880 | CAACGAGAGGATTTTGAGGCT |
| Tg-SOX2 | Tg-hSOX2-S614 | TGCAGTACAACTCCATGACCA |
| Tg-c-MYC | Tg-hMYC-S1011 | CAACAACCGAAATGCACCAGCCCCAG |
| Tg-KLF4 | Tg-hKLF4-S1180 | TGCGGCAAAACCTACACAAAG |
| Tg-Vector | pMX-Tg-R | TACAGGTGGGGTCTTTCATTC |
| TERT | TERT-F.ips | TGTGCACCAACATCTACAAG |
| | TERT-R.ips | GCGTTCTTGGCTTTCAGGAT |
| REX1 | REX1-F.ips | CAGATCCTAAACAGCTCGCAGAAT |
| | REX1-R.ips | GCGTACGCAAATTAAAGTCCAGA |
| GDF3 | GDF3-F.ips | AAATGTTTGTGTTGCGGTCA |
| | GDF3-R.ips | TCTGGCACAGGTGTCTTCAG |
| NANOG | Nanog-968S | CAGCCCTGATTCTTCCACCAGTCCC |
| | Nanog-1334AS | TGGAAGGTTCCCAGTCGGGTTCACC |
| RAG1 | RAG1-F.rt | GAGCAAGGTACCTCAGCCAG |
| | RAG1-R.rt | AACAATGGCTGAGTTGGGAC |
| RAG2 | RAG2-F.rt | GATTCCTGCTACCTCCCTCC |
| | RAG2-R.rt | AGCGTCCTCCAAAGAGAACA |

Quantitative PCR was performed using TaqMan® Array Human Stem Cell Pluripotency Card and customized card (manufactured by Applied Biosystems).

<Analysis of Rearrangement of the TCR Gene in Genomic DNA>

Genomic DNA was extracted from about $5\times10^6$ cells using a QIAamp DNA kit (manufactured by Qiagen) according to its instructions for use.

In order to analyze TCRβ rearrangement, multiplex PCR analysis was performed according to slight modifications of the BIOMED-2 protocol (see van Dongen, J. J. et al., Leukemia, 2003, Vol. 17, pp. 2257-2317). The primers used in the PCR for the analysis of rearrangement of the TCRβ gene (SEQ ID NOs:153 to 190) are shown in Table 12.

Figure 30:
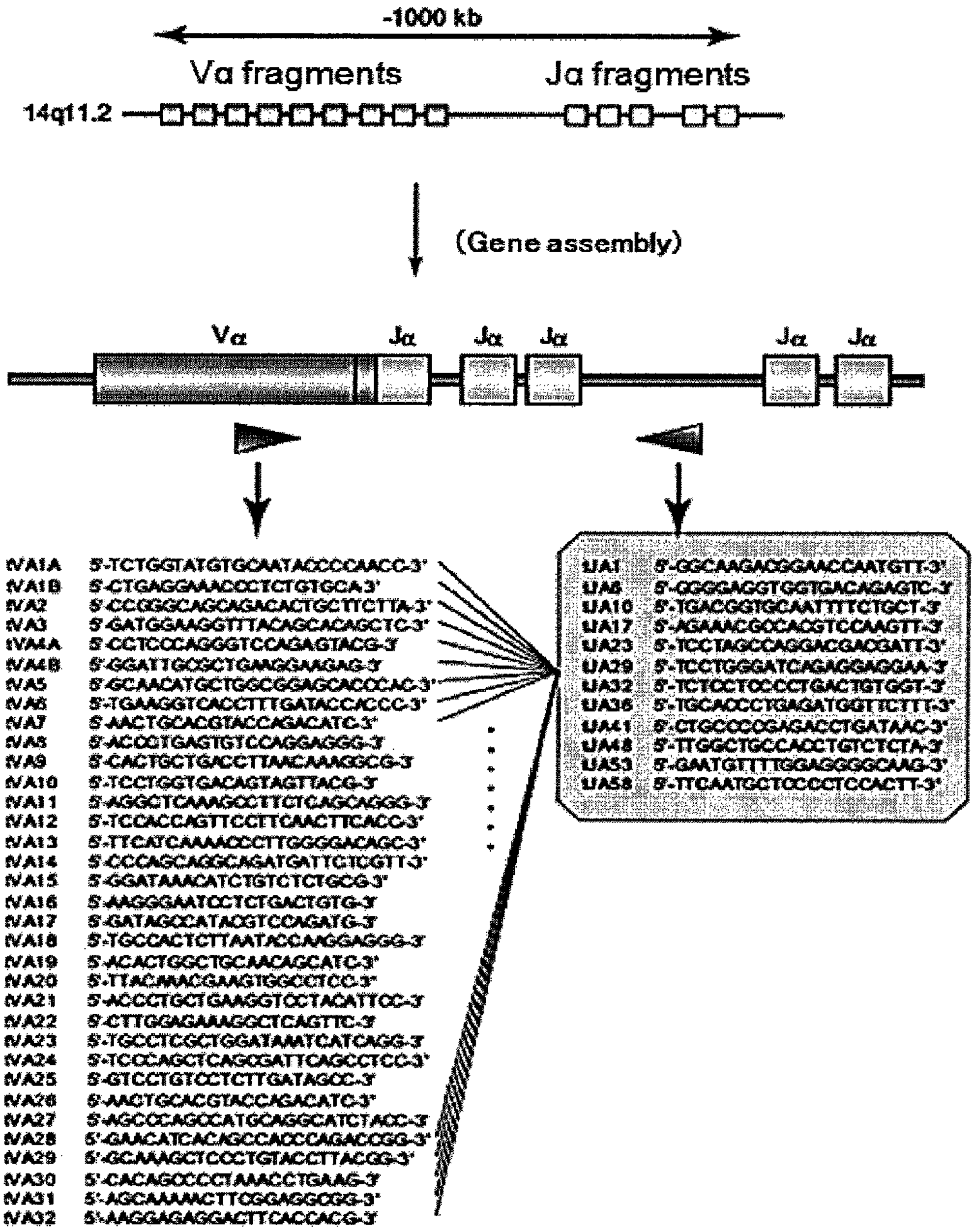
FIG. 30 represents an outline of the method for detecting rearranged TCRα genes. In brief, 34 Vα primers were designed in order to amplify all the arrangements of the Vα segments in the human TCRα gene locus, which lies in a region of more than 1,000 kb on chromosome 14 (14q11.2). In addition, 12 Ja primers were designed, downstream of the sequence of each of the segment Jα1, Jα6, Jα10, Jα17, Jα23, Jα29, Jα32, Jα36, Jα41, Jα48, Jα53, or Jα58, such that 3 to 7 different Jo segments were able to be amplified. All the Ja primers were mixed in one tube, and each of the Vα primers was used with the Jo-primers mix to perform 34 PCR reactions per sample, thereby to detect a rearranged TCRα gene.

In order to analyze rearrangement of the TCRα gene, PCR was performed using primers shown in FIG. 30 and in Table 13 (SEQ ID NOs:191 to 236) and LATaq HS (manufactured by Takara). In this case, the PCR was performed using a program to carry out 3 cycles of amplification steps at 95° C. for 30 seconds, 68° C. for 45 seconds, and 72° C. for 6 minutes, 15 cycles of amplification steps at 95° C. for 30 seconds, 62° C. for 45 seconds, and 72° C. for 6 minutes, and 12 cycles of amplification steps at 95° C. for 15 seconds, 62° C. for 30 seconds, and 72° C. for 6 minutes. A major band in the range of expected molecular sizes was purified using a QIAquick gel extraction kit (manufactured by Qiagen), and then subjected to sequencing. The use of the V, D, and J segments was identified by using an online tool (IMGT/V-Quest) for comparison to the ImMunoGeneTics (IMGT) databases (http://www.cines.fr/) (see Lefranc, M. P., Leukemia, 2003, Vol. 17, 2003, pp. 260-266). The nomenclature of gene fragments (segments) followed the IMGT nomenclature.

TABLE 12

| PCR primers for detecting TCRB rearrangement | |
|---|---|
| Primer | Sequence (5'-3') |
| Vβ2 | AACTATGTTTTGGTATCGTCA |
| Vβ4 | CACGATGTTCTGGTACCGTCAGCA |
| Vβ5/1 | CAGTGTGTCCTGGTACCAACAG |
| Vβ8a/11 | AACCCTTTATTGGTACCGACA |
| Vβ6b/25 | ATCCCTTTTTTGGTACGAACAG |
| Vβ6c | AACCCTTTATTGGTATCAACAG |
| Vβ7 | CGCTATGTATTGGTACAAGCA |
| Vβ8a | CTCCCGTTTTCTGGTACAGACAGAC |
| Vβ9 | CGCTATGTATTGGTATAAACAG |
| Vβ10 | TTATGTTTACTGGTATCGTAAGAAGC |
| Vβ11 | CAAAATGTACTGGTATCAACAA |
| Vβ12a/3/13a/15 | ATACATGTACTGGTATCGACAAGAC |
| Vβ13b | GGCCATGTACTGGTATAGACAAG |
| Vβ13c/12b/14 | GTATATGTCCTGGTATAGACAAGA |
| Vβ16 | TAACCTTTATTGGTATCGACGTGT |
| Vβ17 | GGCCATGTACTGGTACCGACA |
| Vβ18 | TCATGTTTACTGGTATCGGCAG |
| Vβ19 | TTATGTTTATTGGTATCAACAGAATCA |
| Vβ20 | CAACCTATACTGGTACCGACA |

TABLE 12-continued

PCR primers for detecting TCRB rearrangement

| Primer | Sequence (5'-3') |
|---|---|
| Vβ21 | TACCCTTTACTGGTACCGGCAG |
| Vβ22 | ATACTTCTATTGGTACAGACAAATCT |
| Vβ23/8b | CACGGTCTACTGGTACCAGCA |
| Vβ24 | CGTCATGTACTGGTACCAGCA |
| Dβ1 | GCCAAACAGCCTTACAAAGAC |
| Dβ2 | TTTCCAAGCCCCACACAGTC |
| Jβ1.1 | CTTACCTACAACTGTGAATCTGGTG |
| Jβ1.2 | CTTACCTACAACGGTTAACCTGGTC |
| Jβ1.3 | CTTACCTAGAACAGTGAGCCAACTT |
| Jβ1.4 | CATACCCAAGACAGAGAGCTGGGTTC |
| Jβ1.5 | CTTACGTAGGATGGAGAGTCGAGTC |
| Jβ1.6 | CATACCTGTCACAGTGAGCCTG |
| Jβ2.1 | CCTTCTTACCTAGCACGGTGA |
| Jβ2.2 | CTTACCCAGTACGGTCAGCCT |
| Jβ2.3 | CCCGCTTACCGAGCACTGTCA |
| Jβ2.4 | CCAGCTTACCCAGCACTGAGA |
| Jβ2.5 | CGCGCACACCGAGCAC |
| Jβ2.6 | CTCGCCCAGCACGGTCAGCCT |
| Jβ2.7 | CTTACCTGTAACCGTGAGCCTG |

TABLE 13

PCR primers for detecting TCRA rearrangement

| Primer | Sequence (5'-3') |
|---|---|
| tVA1A | TCTGGTATGTGCAATACCCCAACC |
| tVA1B | CTGAGGAAACCCTCTGTGCA |
| tVA2 | CCGGGCAGCAGACACTGCTTCTTA |
| tVA3 | GATGGAAGGTTTACAGCACAGCTC |
| tVA4A | CCTCCCAGGGTCCCAGAGTACG |
| tVA4B | GGATTGCGCTGAAGGAAGAG |
| tVA5 | GCAACATGCTGGCGGAGCACCCAC |
| tVA6 | TGAAGGTCACCTTTGATACCACCC |
| tVA7 | AACTGCACGTACCAGACATC |
| tVA8 | ACCCTGAGTGTCCAGGAGGG |
| tVA9 | CACTGCTGACCTTAACAAAGGCG |
| tVA10 | TCCTGGTGACAGTAGTTACG |
| tVA11 | AGGCTCAAAGCCTTCTCAGCAGGG |
| tVA12 | TCCACCAGTTCCTTCAACTTCACC |
| tVA13 | TTCATCAAAACCCTTGGGGACAGC |

TABLE 13-continued

PCR primers for detecting TCRA rearrangement

| Primer | Sequence (5'-3') |
|---|---|
| tVA14 | CCCAGCAGGCAGATGATTCTCGTT |
| tVA15 | GGATAAACATCTGTCTCTGCG |
| tVA16 | AAGGGAATCCTCTGACTGTG |
| tVA17 | GATAGCCATACGTCCAGATG |
| tVA18 | TGCCACTCTTAATACGAAGGAGGG |
| tVA19 | ACACTGGCTGCAACAGCATC |
| tVA20 | TTACAAACGAAGTGGCCTCC |
| tVA21 | ACCCTGCTGAAGGTCCTACATTCG |
| tVA22 | CTTGGAGAAAGGCTCAGTTC |
| tVA23 | TGCCTCGCTGGATAAATCATCAGG |
| tVA24 | TCCCAGCTCAGGGATTCAGCCTCC |
| tVA25 | GTCCTGTCCTCTTGATAGCC |
| tVA26 | AACTGCACGTACCAGACATC |
| tVA27 | AGCCCAGCCATGCAGGCATCTACC |
| tVA28 | GAACATCACAGCCACCCAGACCGG |
| tVA29 | GCAAAGCTCCCTGTACCTTACGG |
| tVA30 | CACAGCCCCTAAACCTGAAG |
| tVA31 | AGCAAAAACTTCGGAGGCGG |
| tVA32 | AAGGAGAGGACTTCACCACG |
| tJA1 | GGCAAGACGGAAGCAATGTT |
| tJA6 | GGGGAGGTGGTGACAGAGTC |
| tJA10 | TGACGGTGCAATTTTCTGCT |
| tJA17 | AGAAACGCCACGTCCAAGTT |
| tJA23 | TCCTAGCCAGGACGACGATT |
| tJA29 | TCCTGGGATCAGAGGAGGAA |
| tJA32 | TCTCCTCCCCTGACTGTGGT |
| tJA36 | TGCACCCTGAGATGGTTCTTT |
| tJA41 | CTGCCCCGAGACCTGATAAC |
| tJA48 | TTGGCTGCCACCTGTCTCTA |
| tJA53 | GAATGTTTTGGAGGGGCAAG |
| tJA58 | TTCAATGCTCCCCTCCACTT |

<Detection of Rearrangement of the TCR Gene Using mRNA>

By a method based on switch mechanism at the 5'-end of the reverse transcript (SMART method; see Du, G. et al., J. Immunol. Methods, 2006, Vol. 308, 19-35 (2006)), double-stranded cDNAs were synthesized using a Super SMART™ cDNA synthesis kit (manufactured by Clontech Laboratories) according to its instructions for use. The synthesized double-stranded cDNAs were amplified using an Advantage 2 PCR Kit (manufactured by BD Clontech), and then TCRα- or TCRβ-specific amplification from the amplified cDNAs was performed using primers listed in Table 14 (SEQ ID NOs:237 to 239). The PCR product obtained was inserted into a pGEM-T-Easy vector (manufactured by Promega), cloned, and subjected to sequencing.

TABLE 14

PCR primers for amplifying SMART cDNA

| Primer | Sequence |
|---|---|
| 2$^{nd}$ 5'-SMART | CAACGCAGAGTACGCGGG |
| 3'-TRAC | GCTGTTGTTGAAGGCGTTTG |
| 3'-TRBC | TCTCCGAGAGCCCGTAGAAC |

<Intracellular Staining>

For staining intracellular granzyme B, T cells were incubated with α-CD3/28 beads and 10 μg/mL brefeldin A (BFA, manufactured by Invitrogen).

The incubated cells were collected, fixed in a fixation/permeabilization solution (manufactured by BD Pharmingen), and subjected to intracellular staining using an FITC-conjugated anti-granzyme B antibody (manufactured by BD Bioscience) according to its instructions for use.

In order to detect CD107a which was transiently expressed on the cell surface, T cells were incubated with a-CD3/28 beads and cultured with an FITC-conjugated anti-CD107a antibody (manufactured by BioLegend).

The cells thus prepared were sorted by a FACS Aria II instrument (manufactured by BD Biosciences) and analyzed using a Flowjo software (manufactured by Treestar).

<Microarray Analysis>

Respective total RNAs were extracted from human ES cells, T-iPS cells, redifferentiated T cells, peripheral blood T cells, and peripheral blood NK cells using an RNeasy® Micro Kit (manufactured by Qiagen).

Fluorescently labeled complementary RNAs of each of the total RNAs and Whole Human Genome Microarray 4×44K (G4112F, manufactured by Agilent Technologies) or SurePrint G3 Human Gene Expression 8×60K (G4851A, manufactured by Agilent Technologies) were hybridized in a one-color protocol. The resulting signal data were analyzed using a GeneSpring GX software (manufactured by Agilent Technologies).

<Determination of the Telomere Length by Flow-FISH>

A DAKO Telomere PNA Kit/FITC (manufactured by DAKO) was used to determine the telomere length, as described in Neuber, K. et al., Immunology, 2003, Vol. 109, pp. 24-31.

<ELISPOT Assay and $^{51}$Cr-Release Assay>

Antigen-specific response properties of T cells were determined by carrying out an ELISPOT assay for IFN-γ and a standard 51 Cr-release assay, using HLA-A24-expressing autologous B-LCLs as an antigen expressing cell, as described in Kawana-Tachikawa, A. et al., J. Virol., 2002, Vol. 76, pp. 11982-11988; and Tsunetsugu-Yokota, Y. et al., J. Virol., 2003, Vol. 77, pp. 10250-10259.

<Statistical Analysis>

All the data in Examples B1 to B4 are expressed by mean±standard deviation (mean±S.D.). In all the statistical analyses in Examples B1 to B4, Excel (manufactured by Microsoft) or Prism (manufactured by Graphpad Software) was used to carry out unpaired two-tailed Student t-test. Statistical significance was determined at values of $P<0.05$.

Preparation Example B1

<Reprogramming from Antigen-Specific Cytotoxic T Cell Clones into Pluripotent Cells>

Figure 31:
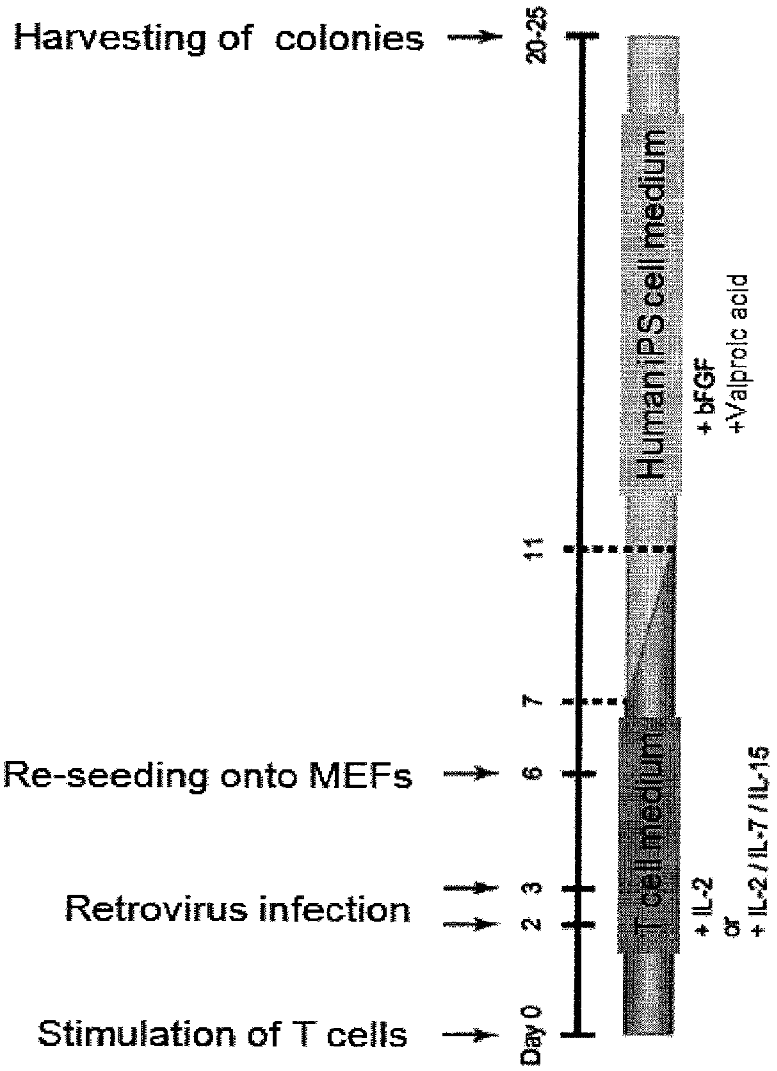
FIG. 31 is a schematic representation showing the process for producing T-cell-derived iPS (T-iPS) cells from peripheral blood T cells using retrovirus vectors, each encoding OCT3/4, SOX2, or KLF4. In the drawing, the tapering portion (a period of 7 to 11 days after the start of activation of T cells) represents a period during which the medium was gradually replaced to human iPS medium.

In order to establish T-cell-derived iPS cells, the present inventors magnetically isolated CD3+ T cells from PBMCs which were obtained from healthy subjects. Then, the isolated CD3+ T cells were stimulated in the presence of 10 ng/mL IL-2, with microbeads coated with an anti-human CD3 antibody and an anti-human CD28 antibody (α-CD3/CD28 beads) in an amount of three times that of the CD3+ T cells. After that, the CD3+ T cells thus activated were subjected to introduction of retroviruses each encoding any of OCT4, SOX2, KLF4, and c-MYC (see FIG. 31).

Figure 32:
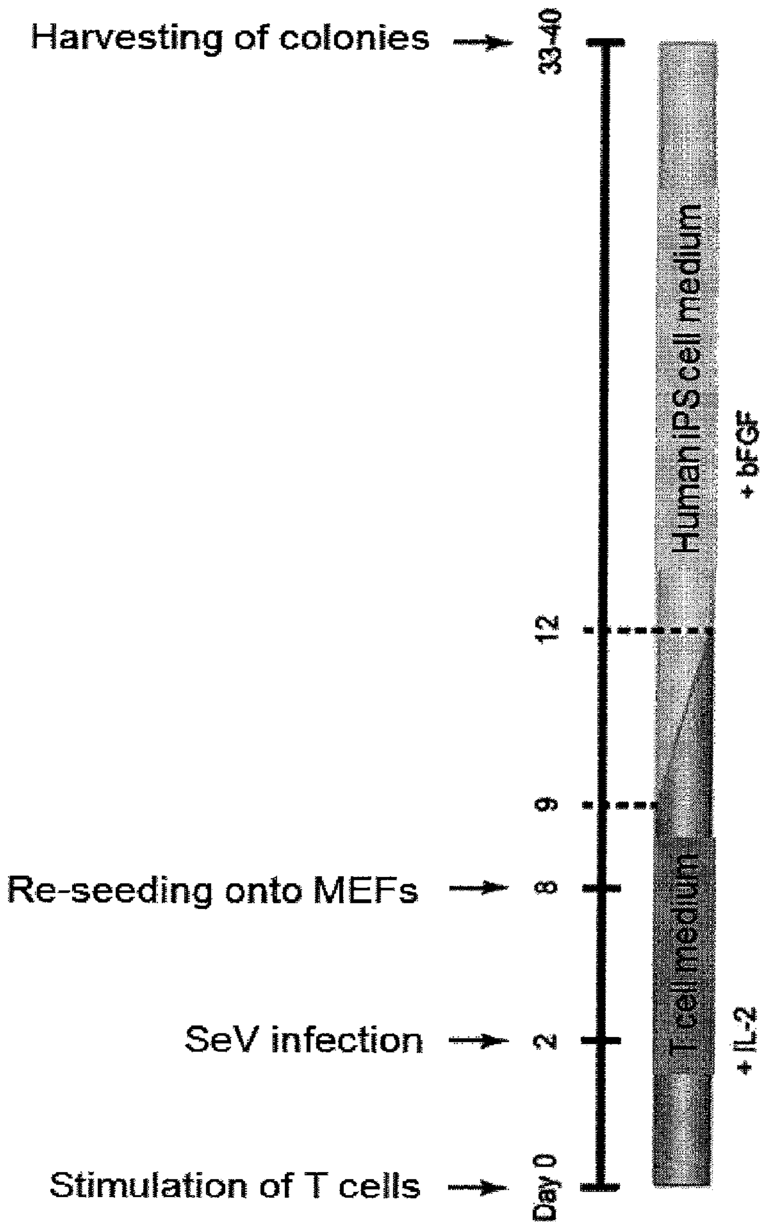
FIG. 32 is a schematic representation showing the process for producing T-iPS cells from cells of a CTL clone (H25-4T cells) using an SeV polycistronically encoding OCT3/4, SOX2, and KLF4, and an SeV encoding SV40LTAg. In the drawing, the tapering portion (a period of 9 to 12 days after the start of T cell activation) represents a period during which the medium was gradually replaced to human iPS medium.

Similarly, PBMCs derived from a person with chronic HIV infection (having an HLA type of A24) were isolated and used to establish CD8+ CTL clones specific for an antigen peptide derived from the HIV-1 Nef protein (Nef-138-8(wt), RYPLTFGW, SEQ ID NO:110; see Miyazaki, E. et al., AIDS, 2009, Vol. 23, pp. 651-660). Among these clones, a clone designated H25-4 was stimulated with 5 μg/mL PHA. The thus-activated cells of the H25-4 clone were subjected to introduction of two SeV vectors, an SeV vector encoding cistronically-expressed four factors (OCT4, SOX2, KLF4, and c-MYC) and the miR-302 target sequence (SeVp[KOSM302L]; see Nishimura, K. et al., J Biol Chem, 2011, Vol. 286, pp. 4760-4771) and an SeV vector encoding the SV40 large T antigen (SeV18+SV40/TS15ΔF; see Fusaki, N. et al., Proc. Jpn. Acad. Ser. B Phys. Biol. Sci., 2009, Vol. 85, pp. 348-362). Introducing these two SeV vectors into the PHA-activated H25-4 cells, followed by culturing for 40 days, allowed one to observe that a sufficient number of Human ES-cell-resembling colonies appeared (see FIGS. 32 and 33).

Figure 33:
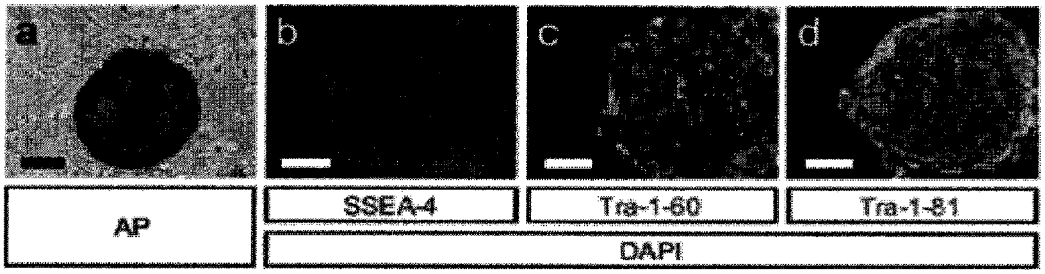
FIG. 33 represents pictures showing the results of observation under a microscope of the expression of alkaline phosphatase (AP) activity and pluripotency markers (SSEA-4, Tra-1-60, and Tra-1-81) in T-iPS cells (H254SeVT-3), cells of a cell line produced from H25-4T cells. In each of the pictures, the scale bar corresponds to 200 μm, and the pictures b to d show the result of counterstaining the nucleus with DAPI (in the pictures, blue-emitting portions).
Figure 34:
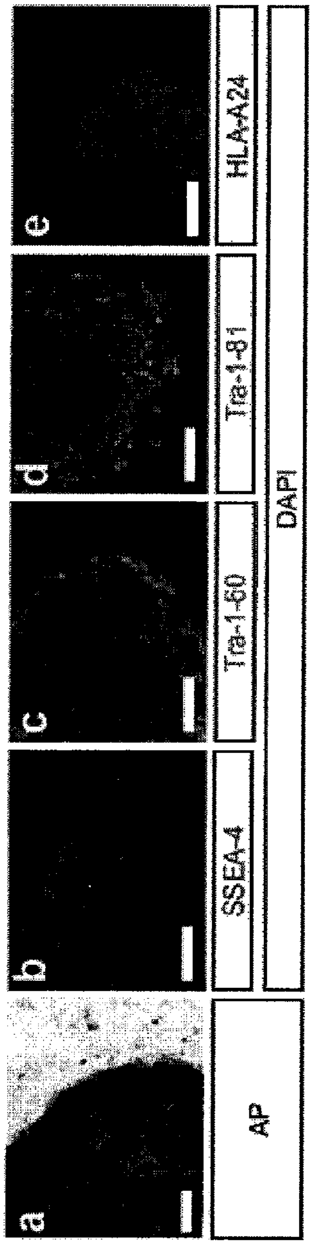
FIG. 34 represents pictures showing the results of observation under a microscope of the expression of AP activity and pluripotency markers (SSEA-4, Tra-1-60, and Tra-1-81) in iPS cells (TkT3V1-7), cells of a cell line produced from peripheral blood T cells. In the picture a, the scale bar corresponds to 500 μm. In each of the pictures b to e, the scale bar corresponds to 200 μm and the results of counterstaining the nucleus with DAPI are shown (in the pictures, blue-emitting portions).

As results, an ES-cell-resembling colonies derived from a CD3+ T cell and an ES-cell-resembling colony derived from an H25-4 clone cell (which colonies were also referred as hereinafter to "TkT3V1-7" and "H254SeVT-3," respectively) had alkaline phosphatase (AP) activity and were found to express pluripotent cell markers, SSEA-4, Tra-1-60, and Tra-1-81 (see FIGS. 33 and 34). It was also found that even after the expression of the exogenous reprogramming factors from the incorporated proviruses (in the TkT3V1-7 clone) or the cytoplasmic SeV RNAs (in the H254SeVT-3 clone) was terminated, human ES-cell-related genes were expressed (see FIGS. 35 and 36).

Figure 35:
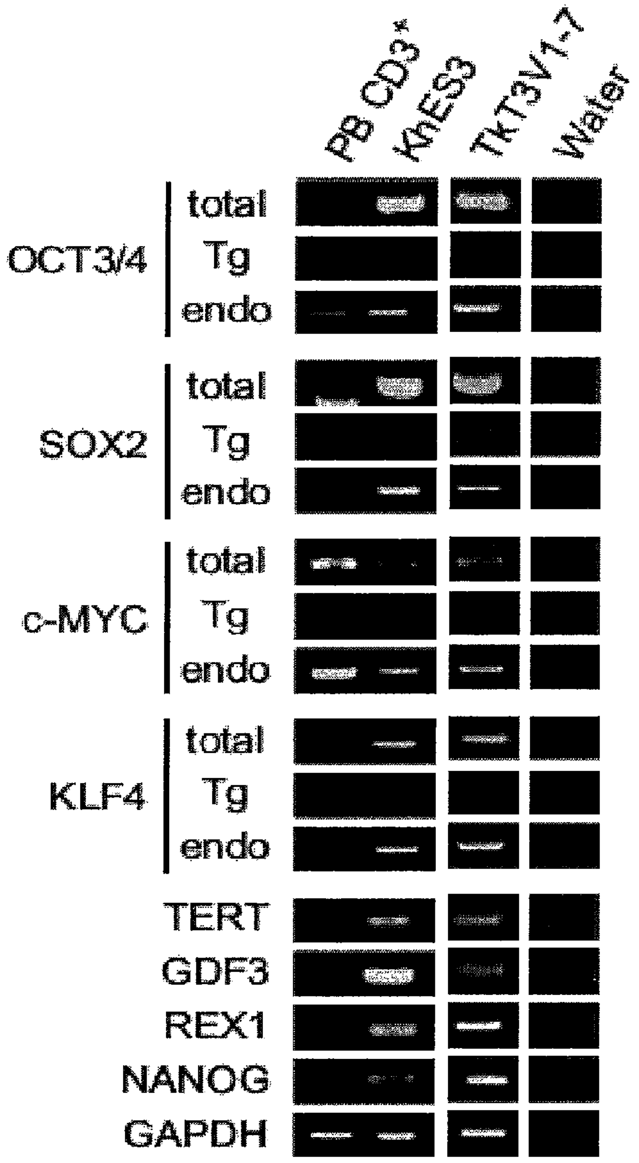
FIG. 35 represents pictures showing the results of an analysis by RT-PCR of the expression of pluripotent genes in TkT3V1-7 cells. In the drawing, "Tg" indicates the expression of the exogenous retrovirus-introduced gene, "endo" indicates the expression of the endogenous expressing gene, and "total" indicates the expression of the exogenous retrovirus-introduced gene and the endogenous expressing gene. "PB CD3+" indicates the results in the originating peripheral blood T cells of TkT3V1-7 cells, "KhES3" indicates the results (as positive control) in ES cells, which are a type of pluripotent stem cell, and "Water" indicates the results (as negative control) of RT-PCR without added template DNA. In the RT-PCR, GAPDH was used as internal standard.
Figure 36:
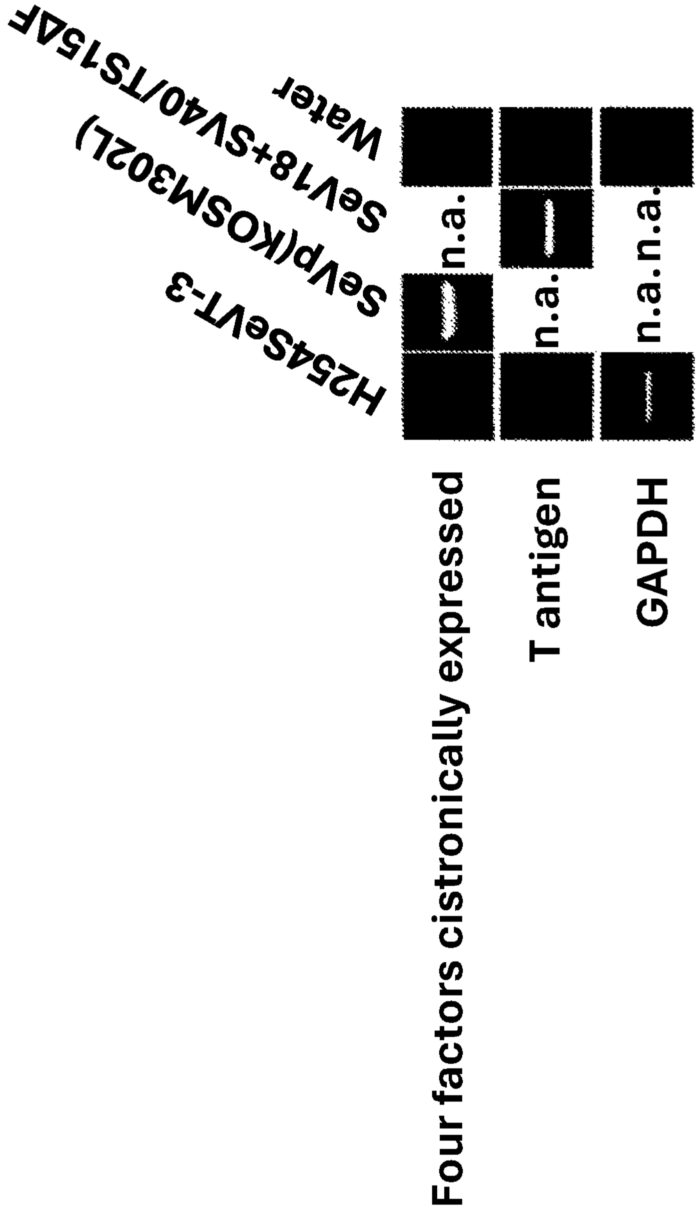
FIG. 36 represents pictures showing the results of detection by RT-PCR of the remaining SeV RNAs (four factors cistronically expressed (tetracistronic factors): OCT4, SOX2, KLF4, and c-MYC, and T antigen). In the drawing, "SeVp(KOSM302L)" and "SeV18+SV40/TS15ΔF" indicate the results in the respective SeVs which were used for establishing the H254SeVT-3, and "Water" indicates the results of RT-PCR without added template DNA (as negative control). In addition, "n.a." indicates "not assessed." In the RT-PCR, GAPDH was used as internal standard.
Figure 37:
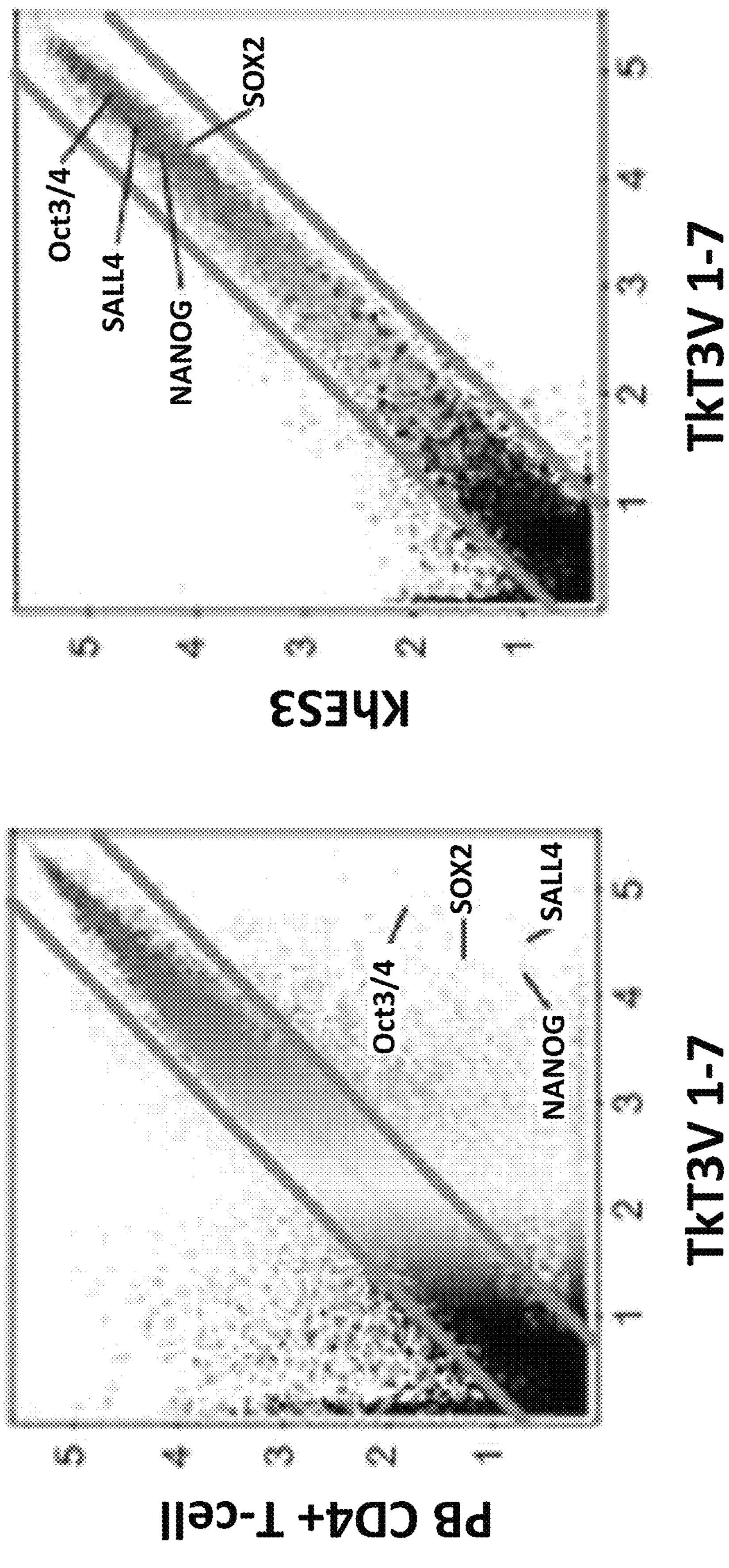
FIG. 37 represents scatter plots showing the results of a comprehensive analysis of gene expression using cDNA microarrays. The left panel shows the results of a comprehensive comparison of gene expression between CD4+ T cells (PB CD4+ T-cells) and TkT3V1-7 cells using cDNA microarrays. The right panel represents a scatter plot showing the results of a comprehensive comparison of gene expression between ES cells (KhES3) and TkT3V1-7 cells using cDNA microarrays. In each of the plots, the two parallel lines indicate that there was a fivefold difference between the corresponding samples.
Figure 38:
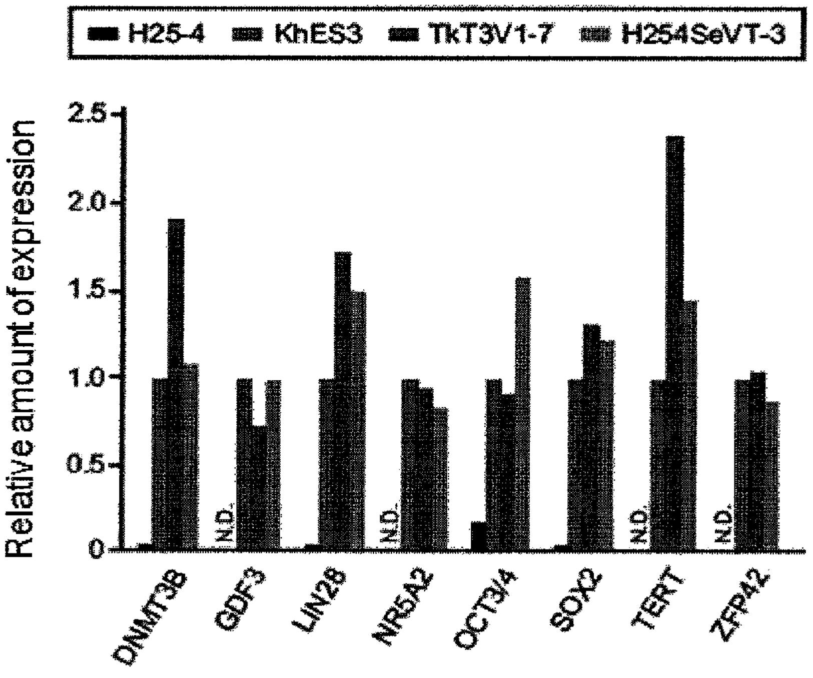
FIG. 38 represents a graph showing the results of an analysis by quantitative PCR of the expression of pluripotent genes in H25-4, KhES3, TkT3V1-7, and H254SeVT-3 cells. In each PCR reaction, the amount of expression of 18S rRNA was used as internal standard. In the graph, the abscissa axis represents, from left to right, the respective results for H25-4, KhES3, TkT3V1-7, and H254SeVT-3 cells. The ordinate axis represents a relative amount of expression when the amount of expression of each of the genes in KhES3 cells was set to be 1.0. "N.D." indicates "below detection limit (not detected)."

The results of comparing their gene expression profiles showed that the whole gene expression patterns in ES-like cells of these clones were similar to that in human ES cells and significantly different from that in peripheral blood T cells (see FIGS. 35, 37, and 38).

Figure 39:
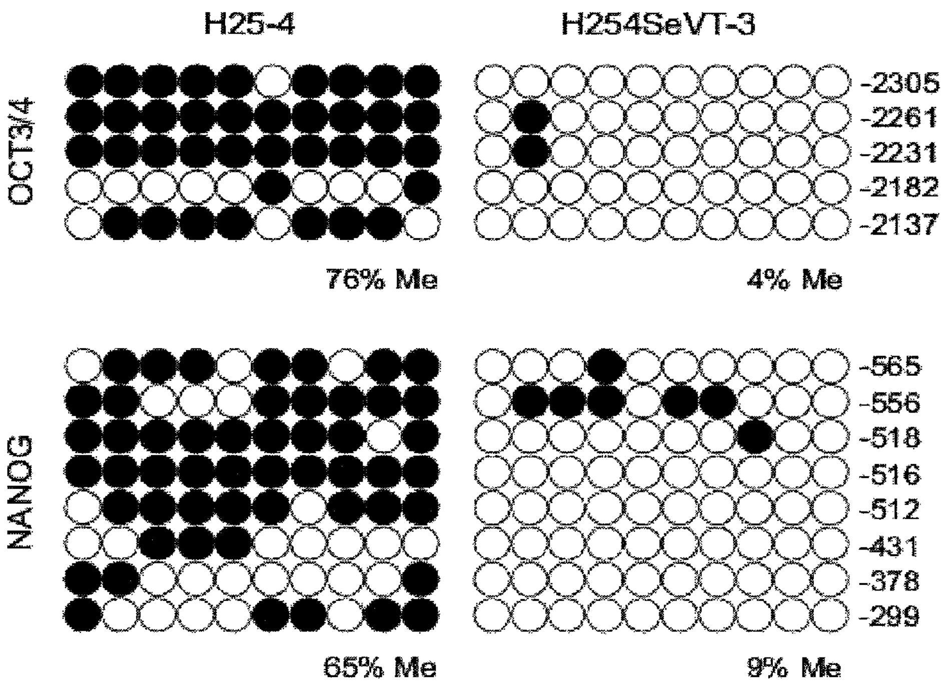
FIG. 39 is a representation showing the results of an analysis by bisulfite sequencing of the promoter region of OCT3/4 and NANOG in H25-4 and H254SeVT-3 cells. In the drawing, the open circles and the filled circles indicate a non-methylated CpG dinucleotide and a methylated CpG dinucleotide, respectively, and "% Me" indicates the percentage of methylation in the respective regions.
Figure 40:
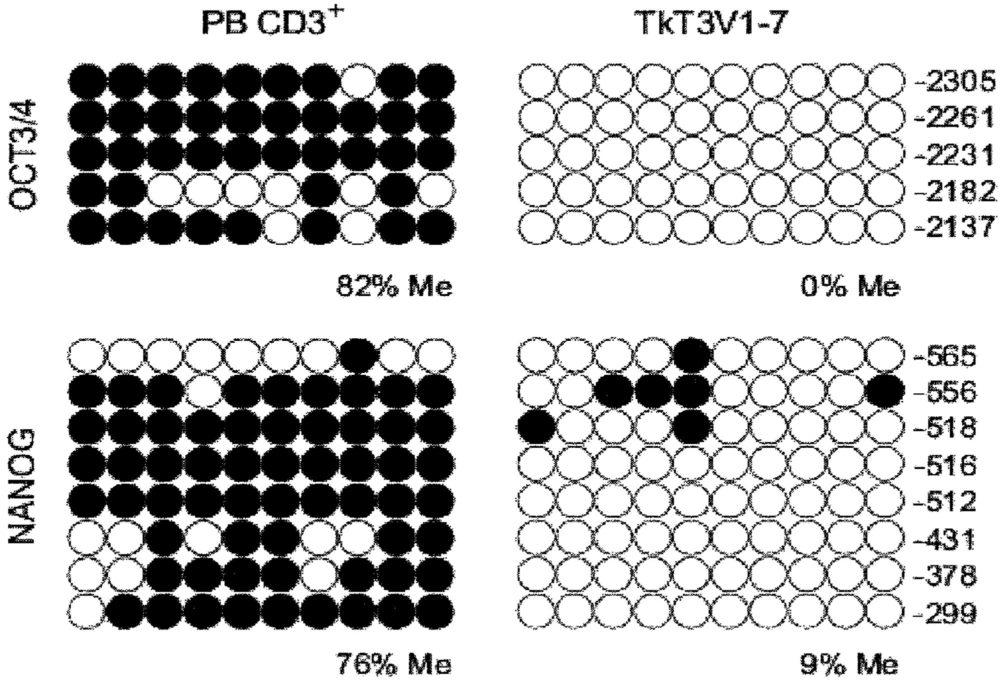
FIG. 40 is a representation showing the results of an analysis by bisulfite sequencing of the OCT3/4 and NANOG promoters in PB CD3+ and TkT3V1-7 cells. In the drawing, the open circles and the filled circles indicate a non-methylated CpG dinucleotide and a methylated CpG dinucleotide, respectively, and "% Me" indicates the percentage of methylation in the respective regions.

In addition, by bisulfite PCR assay, slight methylation was detected in the OCT4 and NANOG promoter regions. In the light of Freberg, C. T. et al., Mol. Biol. Cell, 2007, Vol. 18, pp. 1543-1553, therefore, it is demonstrated that reprogramming has been achieved in ES-like cells of these clones (see FIGS. 39 and 40).

Figure 41:
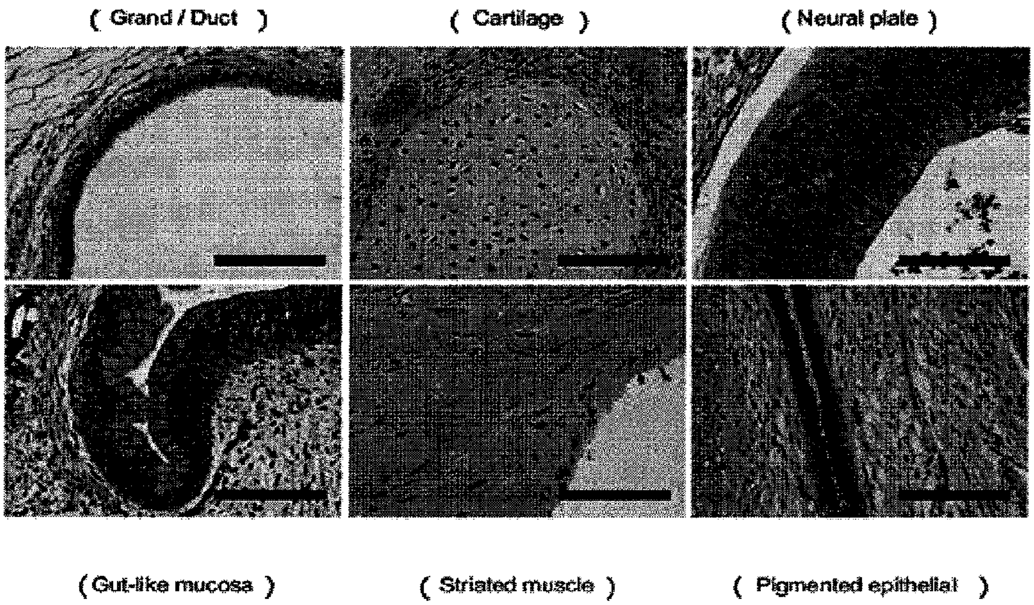
FIG. 41 represents micrographs showing representative results obtained by preparing sections from TkT3V1-7-derived teratomas formed in the testis of NOG mice, followed by HE staining of the sections for observation, which reveal that the teratomas comprise anatomical structures derived from the three germ layers. In these pictures, there are observed glands/ducts and gut-like mucosa as endoderm-derived anatomical structures, cartilage and striated muscle as mesoderm-derived anatomical structures, and neural plate and pigment epithelium as ectoderm-derived anatomical structures. In each of the micrographs, the scale bar corresponds to 100 μm.
Figure 42:
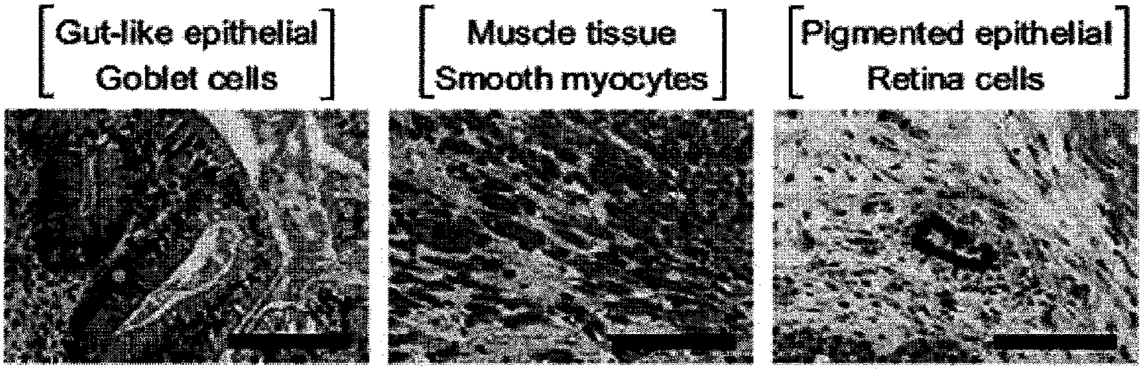
FIG. 42 represents micrographs showing representative results obtained by preparing sections from H254SeVT-3-derived teratomas formed in the testis of NOG mice, followed by HE staining of the sections for observation, which reveal that the H254SeVT-3 cells differentiated into an endoderm-derived cell lineage (goblet cells in gut-like epithelium), a mesoderm-derived cell lineage (smooth myocytes in muscle tissue), and an ectoderm-derived cell lineage (retinal cells in pigment epithelium). In each of the micrographs, the scale bar corresponds to 100 μm.
Figure 43:
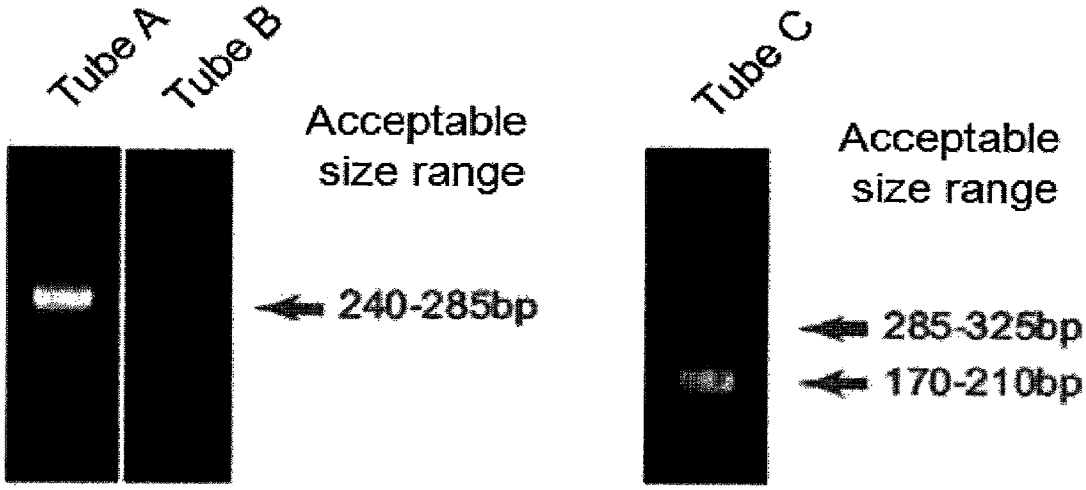
FIG. 43 represents pictures showing a result that a TCRβ gene rearrangement in the genome of TkT3V1-7 cells was detected by multiplex PCR analysis. Tubes A and B indicate that the Vβ-(D)Jβ has been rearranged and Tube C indicates that the D-Jβ has been rearranged.
Figure 44:
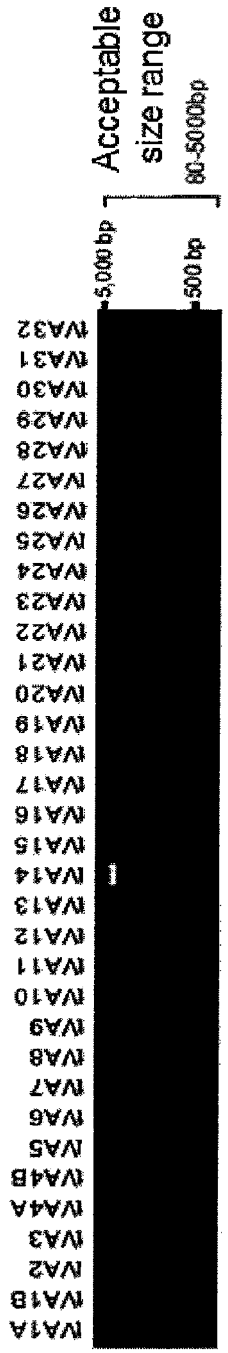
FIG. 44 represents a picture showing a result that a TCRα gene rearrangement (V-Ja rearrangement) in the genome of TkT3V1-7 cells was detected by multiplex PCR analysis.
Figure 45:
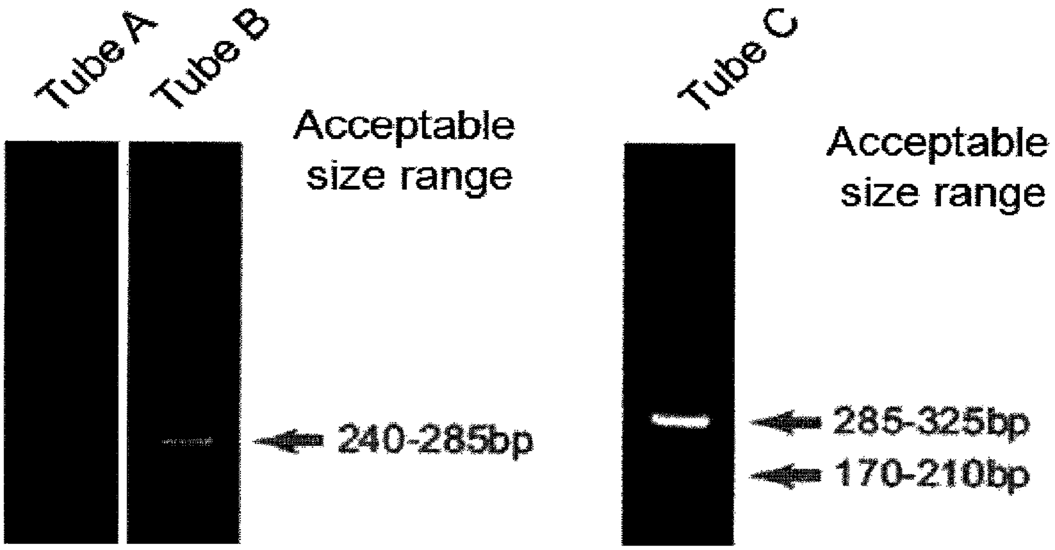
FIG. 45 represents pictures showing a result that a TCRβ gene rearrangement in the genome of H254SeVT-3 cells was detected by multiplex PCR analysis. Tubes A and B indicate that the Vβ-(D)Jβ has been rearranged and Tube C indicates that the D-Jβ has been rearranged.
Figure 46:
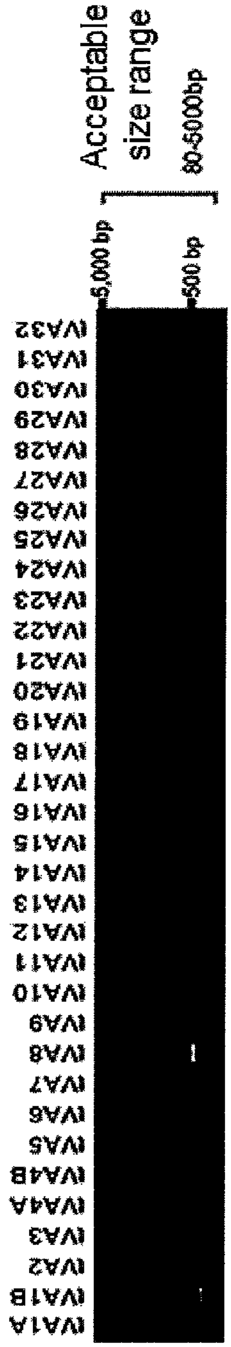
FIG. 46 represents a picture showing a result that a TCRα gene rearrangement (V-Jα rearrangement) in the genome of H254SeVT-3 cells was detected by multiplex PCR analysis.

Further, in the light of Brivanlou, A. H. et al., Science, 2003, Vol. 300, pp. 913-916, it is demonstrated that ES-like cells of these clones have pluripotency, because injection of these cells into NOD-Scid mice resulted in the formation of teratomas containing characteristic tissues, each of which was derived from any of the three germ layers (see FIGS. 41 and 42).

<Rearrangement of the TCR Gene in T-iPS Cells>

It is known that the TCRαβ gene rearrangement is involved in the process of development of normal αβ T cells in the thymus. Thus, present inventors retrospectively examined, based on TCR gene rearrangement patterns, whether the T-iPS cells established as described above were derived from αβ T cells. In brief, multiplex PCR primers for analysis of rearrangement of the TCRβ gene were designed according to the BIOMED-2 consortium (see van Dongen, J. J. et al., Leukemia, 2003, Vol. 17, pp. 2257-2317). In addition, primers for detection of rearrangement of the TCRα gene were independently designed (see FIG. 30). These primers were used to perform PCR, thereby detecting rearrangement of the TCRαβ gene in the T-iPS cells described above. The results obtained are shown in FIGS. 43 to 46.

As shown in FIGS. 43 to 46, the respective rearrangements of the TCRβ and TCRα genes were identified as a single band in the allele of cells of each of the TkT3V1-7 and H254SeVT-3 clones.

The structure of the antigen recognition site of a TCR is composed of three complementarity determining regions (CDR1, CDR2, and CDR3). Further, in these three regions, the CDR3 has a most diverse sequence because the CDR3 extends to the V(D)) junction region into which a variety of random nucleotides (N- or P-nucleotides) are inserted (see Alt, F. W. et al., Proc. Natl. Acad. Sci. USA, 1982, Vol. 79, pp. 4118-4122; and Lafaille, J. J. et al., Cell, 1989, Vol. 59, pp. 859-870).

Thus, sequencing was carried out for the CDR3 region in the TCRα and TCRβ genes rearranged in T-iPS cells of the above-mentioned clones (TkT3V1-7 and H254SeVT-3) (SEQ ID NOs: 240 to 242 and 254 to 257). The results obtained are shown in Tables 15 to 18.

TABLE 15

TCRA gene rearrangemnet in TkT3V1-7

| | Genome/ | | Rearrangement | | Sequence of junction region | | |
|---|---|---|---|---|---|---|---|
| Cell | RNA | Productivity | Vα | Jα | 3'Vα | (P)N | 5'Jα |
| TkT3V1-7 | Genome | Productive | TRAV38-2/DVB*01 | TRAJ31*01 | TGTGCTTAT | TGGAGT | AATAACAATCCCAGACTCATGTTT |
| | | Unproductive | Intact | | Intact | | |

TABLE 16

TCRB gene rearrangemnet in TkT3V1-7

| | Genome/ | | Rearrangement | | | Sequence of junction region | | |
|---|---|---|---|---|---|---|---|---|
| Cell | RNA | Productivity | Vβ | Dβ | Jβ | 3'Vβ | N1-Dβ-N2 | 5'Jβ |
| TkT3V1-7 | Genome | Productive | TRBV29-1*02 | TRBD1*01 | TRAJ31*01 | TATATCTCTGCAGCGTTGA | TGGACAGGGA | AACACCGGGGAGCTGTTT |
| | | Unproductive | Germ line | TRBD2*01/*02 | TRBJ2-7*01/*02 | TATCATGGTGTAACATTGTG | GGGACTAGTTTAC | CCTACGAGCAGTACTTCG |

TABLE 17

TCRA gene rearrangemnet in H25-4, H254SeVT-3 or redifferenciated CD8+ T Cells
TCRA

| | Genome/ | | Rearrangement | | Sequence of junction region | | |
|---|---|---|---|---|---|---|---|
| Cell | RNA | Productivity | Vα | Jα | 3'Vα | (P)N | 5'Jα |
| H25-4 | Genome | Productive | TRAV8-3*01 | TRAJ10*01 | TGTGCTGTGGGT | T | TCACGGGAGGAGGAAACAAACCTCACCTTTTAATAACAATCCCAGACTCATGTTT |
| | | Unproductive[a] | TRAV13-1*01 | TRAJ29*01 | TGTGCAGCAA | TCC | TCAGGAAACACACCTCTTGTCTTT |
| H254SeVT-3 | Genome | Productive | TRAV8-3*01 | TRAJ10-01 | TGTGCTGTGGGT | T | TCACGGGAGGAGGAAACAAACTCACCTTTT |
| | | Unproductive[a] | TRAV13-1*01 | TRAJ29*01 | TGTGCAGCAA | TCC | TCAGGAAACACACCTCTTGTCTTT |
| reT-1 | mRNA | Productive | TRAV8-3*01 | TRAJ10*01 | TGTGCTGTGGGT | T | TCACGGGAGGAGGAAACAAACTCACCTTTT |
| | | Unproductive[a] | TRAV13-1*01 | TRAJ29*01 | TGTGCAGCAA | TCC | TCAGGAAACACACCTCTTGTCTTT |
| mT-2.1 | mRNA | Productive | TRAV8-3*01 | TRAJ10*01 | TGTGCTGTGGGT | T | TCACGGGAGGAGGAAACAAACTCACCTTTT |
| | | Unproductive[a] | TRAV13-1*01 | TRAJ29*01 | TGTGCAGCAA | TCC | TCAGGAAACACACCTCTTGTCTTT |
| reT-3 | mRNA | Productive | TRAV8-3*01 | TRAJ10*01 | TGTGCTGTGGGT | T | TCACGGGAGGAGGAAACAAACTCACCTTTT |
| | | Unproductive | TRAV13-1*01 | TRAJ29*01 | TGTGCAGCAA | TCC | TCAGGAAACACACCTCTTGTCTTT |

"[a]"indicates that out-of-frame junction is caused in the CDR3.

TABLE 18

TCRB gene rearrangemnet in H25-4, H254SeVT-3 or redifferenciated CD8+ T Cells

TCRB

| | Genome/ | | Rearrangement | | | Sequence of junction region | | |
|---|---|---|---|---|---|---|---|---|
| Cell | RNA | Productivity | Vβ | Dβ | Jβ | 3'Vβ | N1-Dβ-N2 | 5'Jβ |
| H254 | Genome | Productive | TRBV7-9*01 | TRBD1*01 | TRBJ2-5*01 | TGTGCCAGCAGCTTA | CGGGACAGGGTGCCG | GAGACCCAGTACTTC |
| | | Unproductive[a] | Germ line | TRBD1*01 | TRBJ2-7*01 | TACAAAGCTGTAACATTGTG | GGGACAACT | CTACGAGCAGTACTTCGGGCCG |
| H254SeVT-3 | Genome | Productive | TRBV7-9*01 | TRBD1*01 | TRBJ2-5*01 | TGTGCCAGCAGCTTA | CGGGACAGGGTGCCG | GAGACCCAGTACTTC |
| | | Unproductive[a] | Germ line | TRBD1*01 | TRBJ2-7*01 | TACAAAGCTGTAACATTGTG | GGGACAACT | CTACGAGCAGTACTTCGGGCCG |
| reT-1 | mRNA | Productive | TRBV7-9*01 | TRBD1*01 | TRBJ2-5*01 | TGTGCCAGCAGCTTA | CGGGACAGGGTGCCG | GAGACCCAGTACTTC |
| reT-2.1 | mRNA | Productive | TRBV7-9*01 | TRBD1*01 | TRBJ2-5*01 | TGTGCCAGCAGCTTA | CGGGACAGGGTGCCG | GAGACCCAGTACTTC |
| reT-3 | mRNA | Productive | TRBV7-9*01 | TRBD1*01 | TRBJ2-5*01 | TGTGCCAGCAGCTTA | CGGGACAGGGTGCCG | GAGACCCAGTACTTC |

As shown in Tables 15 to 18, a set of respective effective rearrangements of the TCRα and TCRβ genes, for example, which had an in-frame junction and in which a stop codon was not generated was identified in the TkT3V1-7 and H254SeVT-3 clones. It was also demonstrated that the respective CDR3 sequences in the H254SeVT-3 and H25-4 clones were completely identical in the TCRα and TCRβ gene regions. From these results, it is revealed that an iPS cell is established from a single T cell and that the antigen specificity imprinted in the genomic DNA is kept also in the process of reprogramming.

Comparative Example B1

<Redifferentiation from T-iPS Cells into T Cells>

Next, in order to examine the hematopoietic differentiation potential of T-iPS cells of the above-mentioned clones, these T-iPS cells were redifferentiated into mesoderm-derived cells, particularly hematopoietic stem cells/progenitor cells (see International Publication No. WO 2011/096482; Vodyanik, M. A. et al., Blood, 2005, Vol. 105, pp. 617-626; and Takayama, N. et al., Blood, 2008, Vol. 111, pp. 5298-5306).

In brief, small aggregates (each having not more than 100 cells) of T-iPS cells of the respective above-mentioned clones were transferred onto irradiated C3H10T1/2 cells and co-cultured in EB medium in the presence of 20 ng/mL VEGF, 50 ng/mL SCF, and 50 ng/mL FLT-3L (manufactured by Peprotech). The composition of the EB medium is as mentioned below: IMDM supplemented with 15% fetal bovine serum (FBS), a cocktail of 10 μg/mL human insulin, 5.5 μg/mL human transferrin, and 5 ng/mL sodium selenite, 2 mM L-glutamine, 0.45 mM α-monothioglycerol, and 50 μg/mL ascorbic acid.

On day 14 after the cells were transferred onto the C3H10T1/2 feeder cells, hematopoietic cells (CD34+ hematopoietic stem cells/progenitor cells) contained in the iPS-sacs were collected and then transferred onto irradiated OP9-DL1 cells. OP9-DL1 cells were provided from the RIKEN BioResource Center through the National BioResource Project, the Ministry of Education, Culture, Sports, Science & Technology in Japan (Japan) (see Watarai, H. et al., Blood, 2010, Vol. 115, pp. 230-237). The hematopoietic cells were subjected to differentiation into cells of the T lineage in OP9 medium in the presence of 10 ng/mL FLT-3L and 1 ng/mL IL-7 (see Ikawa, T. et al., Science, 2010, Vol. 329, pp. 93-96). The composition of the OP9 medium is as mentioned below:

αMEM supplemented with 15% FBS, 2 mM L-glutamine, 100 U/mL penicillin, and 100 ng/mL streptomycin.

Figure 47:
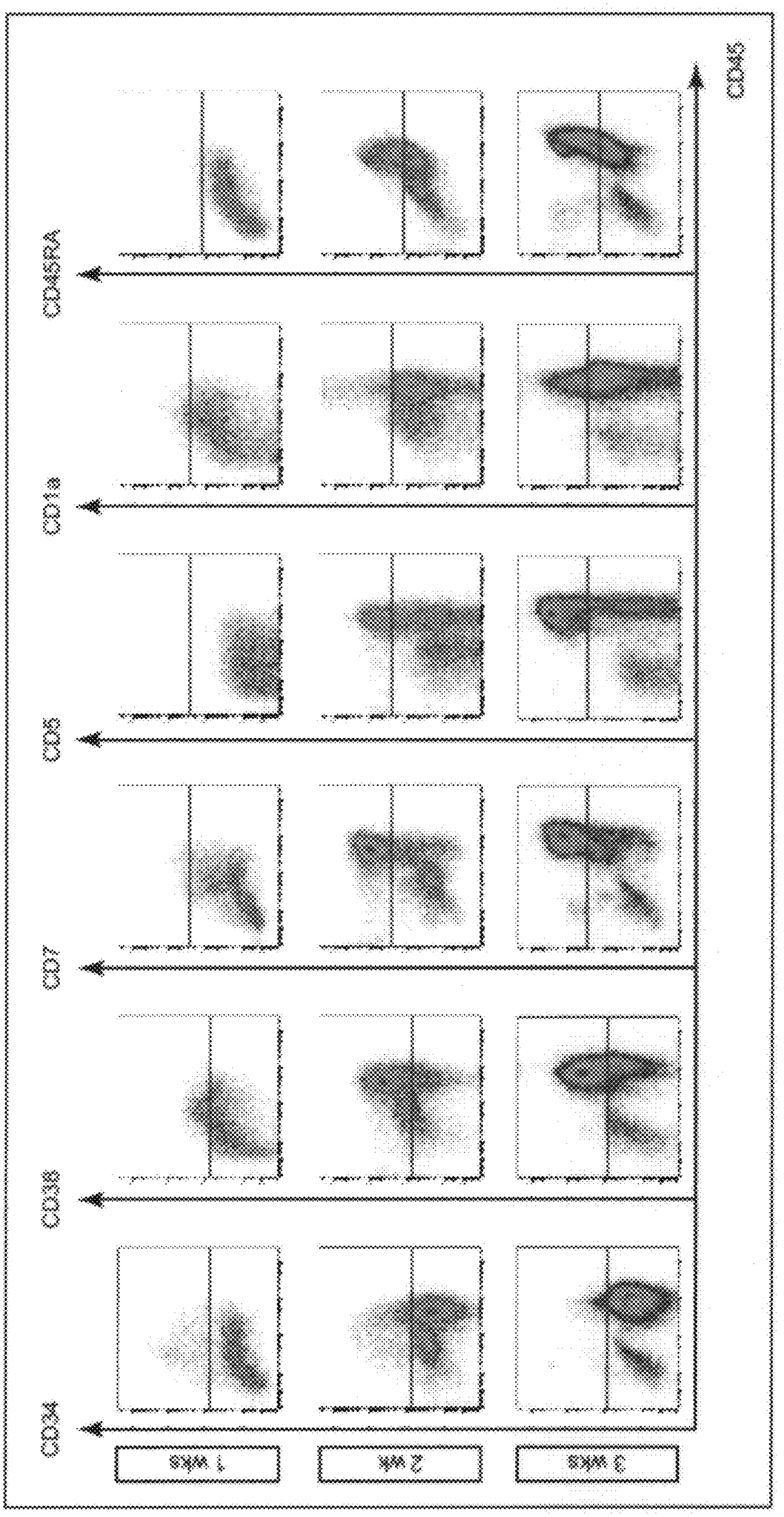
FIG. 47 represents dot plots showing the results of analyzing the course of development from TkT3V1-7-derived CD34+ hematopoietic stem/progenitor cells to human T-lineage cells by flow cytometry as mentioned below. In brief, in order to examine the hematopoietic differentiation potential of T-iPS cells, TkT3V1-7 cells were cultured with VEGF, SCF, and FLT-3L on C3H10T1/2 feeder cells. On day 14 of the culture, the TkT3V1-7-derived CD34+ hematopoietic stem/progenitor cells thus generated (T-iPS-sac cells) were transferred onto OP9 (OP9-DL1) feeder cells expressing delta-like 1. Re-differentiating cells on the OP9-DL1 cells were collected, and then the expression of CD34, CD38, CD7, CD5, CD1a, CD45RA, and CD45 on the cellular surface of TkT3V1-7-derived cells was analyzed by flow cytometry every week for a period of 22 to 36 days after the induction of re-differentiation ("1 wks" to "3 wks" in the drawing).
Figure 48:
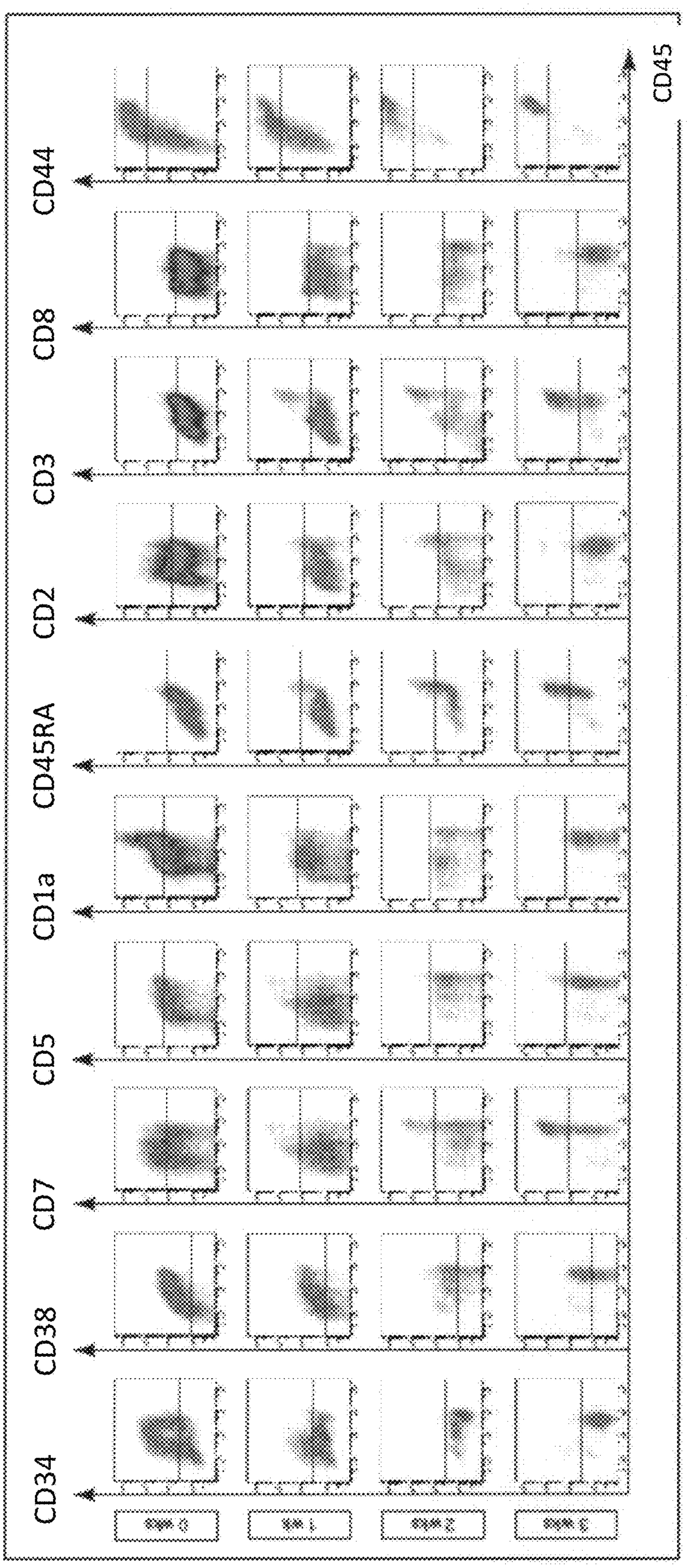
FIG. 48 represents dot plots showing the results of analyzing the course of development from H254SeVT-3-derived T-iPS-sac cells to human T-lineage cells by flow cytometry as mentioned below. In brief, in order to examine the hematopoietic differentiation potential of T-iPS cells, H254SeVT-3 cells were cultured with VEGF, SCF, and FLT-3L on C3H10T1/2 feeder cells. On day 14 of the culture, the TkT3V1-7-derived T-iPS-sac cells thus generated were transferred onto OP9-DL1 feeder cells. Re-differentiating cells on the OP9-DL1 cells were collected, and then the expression of CD34, CD38, CD7, CD5, CD1a, CD45RA, and CD45 on the cellular surface of H254SeVT-3-derived cells was analyzed by flow cytometry every week for a period of 15 to 36 days after the induction of re-differentiation ("0 wks" to "3 wks" in the drawing).

On days 21 to 28 after the start of culturing on OP9-DL1 feeder cells, there was observed the differentiation into CD45+, CD38+, CD7+, CD45RA+, CD3+, and TCRαβ+ cells of the T lineage (see FIGS. 47 and 48).

Figure 49:
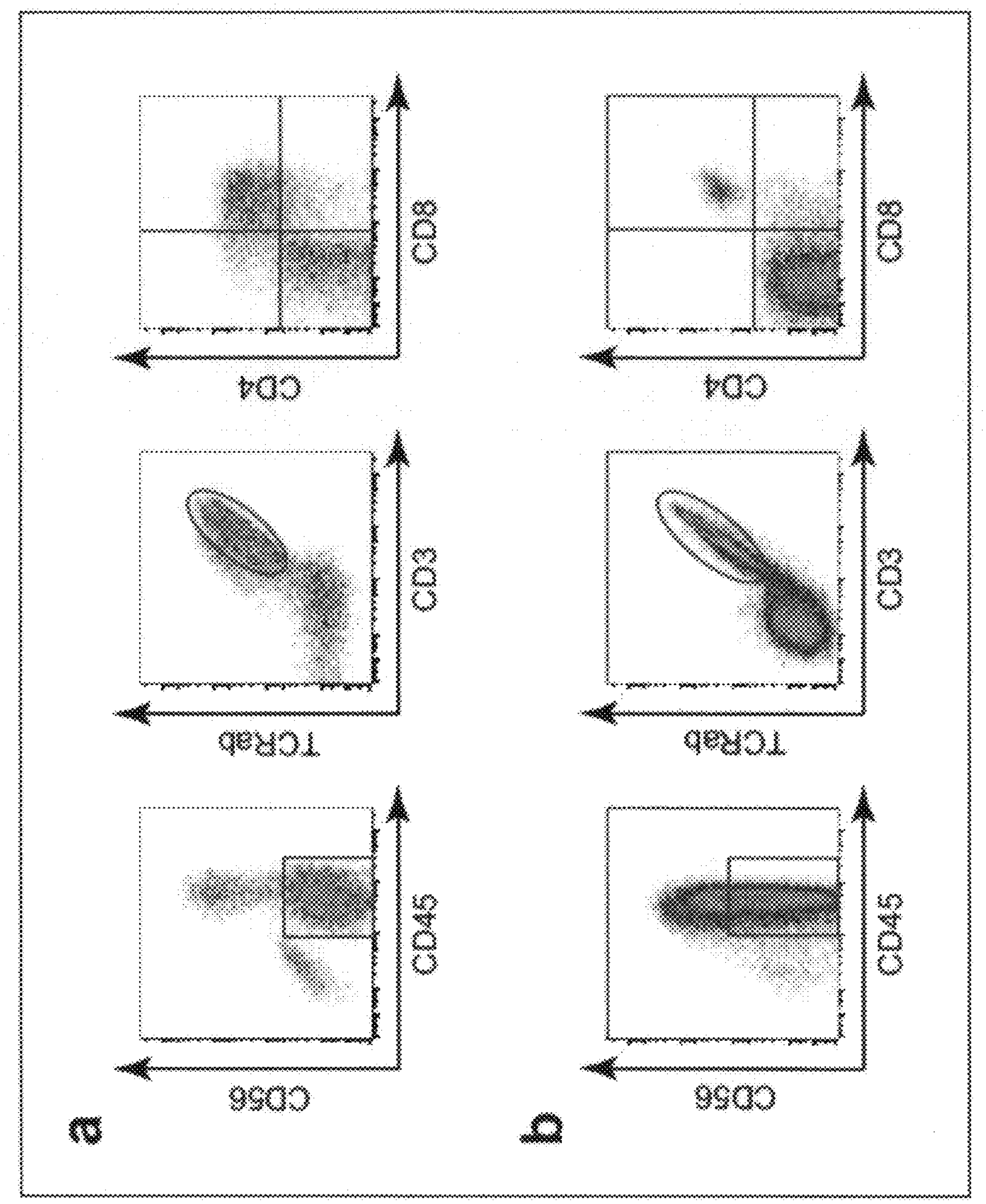
FIG. 49 represents dot plots showing the results of an analysis by flow cytometry of the existence of T-iPS-cell-derived CD4/8 DP cells established in vitro. FIG. **49*a* shows the results of an analysis by flow cytometry of the expression of CD45, CD56, CD3, TCRαβ, CD4, and CD8 on the cellular surface of TkT3V1-7-derived cells in a period of 35 to 42 days after the induction of re-differentiation.

As shown in FIG. 49, in a particular population of these T-lineage cells, there was found the differentiation into a small number of SP T-cells, which were not able to be characterized in detail by the present inventors, while there was also observed the presence of groups of cells which had been differentiated into a CD4/CD8 double-positive (DP) stage and into a mature CD4 single-positive (SP) or CD8 single-positive (SP) stage.

In the process in which T cells mature in thymus, the CD4/CD8 DN stage or the CD4/CD8 DP stage corresponds to the rearrangement stage of the β chain and the α chain, respectively (see Von Boehmer, H., Advances in Immunology, 2004, Vol. 84, pp. 201-238). In addition, the negative feedback control of gene rearrangement and the suppression of further rearrangement in the TCRβ gene locus are effected in an extremely strict manner (see Khor, B. et al., Current Opinion in Immunology, 2002, Vol. 14, pp. 230-234). On the other hand, a relatively loose negative feedback control system and further gene rearrangement of pre-rearranged genes are also effected, and these phenomena tend to take place in the TCRα gene locus and are known as "receptor revision" (see Huang, C. et al., J. Immunol., 2001, Vol. 166, pp. 2597-2601; and Krangel, M. S., Curr. Opin. Immunol., 2009, Vol. 21, pp. 133-139).

Further, in experiments using TCRα transgenic mice, genes related to the mechanism of rearrangement (for example, Rag1 and Rag2) are re-activated at the DP stage and the gene rearrangement of an endogenous gene Tcrα is also observed (see Petrie, H. T. et al., J Exp. Med., 1993, Vol. 178, pp. 615-622; and Padovan, E. et al., Science, 1993, Vol. 262, pp. 422-424).

Figure 50:
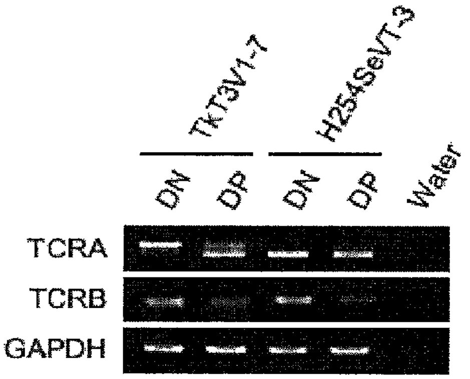
FIG. 50 represents pictures showing the results of RT-PCR amplification of the TCRα and TCRβ genes expressed in DN-cell- or DP-cell-derived cDNA libraries synthesized by SMART method. In the drawing, "Water" indicates the results of RT-PCR without added template DNA (as negative control). GAPDH was used as internal standard in each PCR.

Thus, in order to determine whether such receptor revision takes place also in the process of redifferentiation from T-iPS cells into cells of the T lineage, cells which were at each of the CD1a− DN and CD1a+ DP stages were collected from the above-mentioned CD45+, CD3+, TCRαβ+, and CD5+ cells of the T lineage, and subjected to analysis of the expression and sequences of TCR mRNAs (SEQ ID NOs: 240 to 258). The results obtained are shown in FIG. 50 and in Tables 19 to 22.

For TkT3V1-7 clone, cells at the CD8+SP stage, which was a further advanced stage of differentiation than the CD1a− DN and CD1a+ DP stages, were collected and subjected to analysis of TCR mRNA expression. The results obtained are shown in Tables 23 and 24.

TABLE 19

TCRA gene rearrangemnet in redifferenciated DN cells
TCRA

| iPS cell | Genome/ | | Rearrangement | | Sequence of junction region | | | Fequency |
|---|---|---|---|---|---|---|---|---|
| clone | RNA | Productivity | Vα | Jα | 3'Vα | (P)N | 5'Jα | cloning (%) |
| TkT3V1-7 | mRNA | Productivity | TRAV38-2/ DV8*01 | TRAJ31*01 | TGTGCTTAT | TGGAGT | AATAACAATGCCAGACTCATGTTT | 11/11 (100%) |
| H254 SeVT-3 | mRNA | Productive | TRAV8-3*01 | TRAJ10*01 | TGTGCTGTGGGT | T | TCACGGAGGAGGAAACAAACTCACTTTT | 15/16 (83%) |
| | | Productive[b] | TRAV12-1*01 | TRAJ7*01 | TGTGTGGTG | T | ACTATGGGAACAACAGACTCGTTTT | 1/16 (6%) |
| | | Unproductive[a] | TRAV13-1*01 | TRAJ29*01 | TGTGCAGCAA | TCC | TCAGGAAACACACCTCTTGTCTTT | 2/16 (11%) |

"[a]" indicates that out-of-frame junction is caused in the CDR3.
"[b]" indicates that the sequence is different from that in the genome of T-iPS cells.

TABLE 20

| TCRB gene rearrangemnet in H25-4, H254SeVT-3 or redifferenciated CD8+ T Cells TCRB | | | | | | | | | |
|---|---|---|---|---|---|---|---|---|---|
| iPS cell | Genome/ | | Rearrangement | | | Sequence of junction region | | | Frequency |
| clone | RNA | Productivity | β | Dβ | Jβ | 3'Vβ | N1-Dβ-N2 | 5'Jβ | clonging (%) |
| TkT3V1-7 | mRNA | Productive | TRBV29-1*01 | TRBD1*01 | TRBJ2-2*01 | TGCAGCGTTGA | TGGACAGGGA | AACACGGGGGAGCTGTTTTTT | 7/7 (100%) |
| H254SeVT-3 | mRNA | Productive | TRBV7-9*01 | TRBD1*01 | TRBJ2-5*01 | TGTGCCAGCAGCTTA | CGGGACAGGGTGCCG | GAGACCCAGTACTTC | 16/16 (100%) |

TABLE 21

TCRA gene rearrangemnet in redifferenciated DP cells

| iPS cell clone | Genome/ RNA | Productivity | Rearrangement Vα | Rearrangement Jα | Sequence of junction region 3'Vα | Sequence of junction region (P)N | Sequence of junction region 5'Jα | Fequency cloning (%) |
|---|---|---|---|---|---|---|---|---|
| TkT3V1-7 | mRNA | Productivity | TRAV38-2/ DV8*01 | TRAJ31*01 | TGTGCTTAT | TGGAGT | AATAACAATGCCAGACTCATGTTT | 8/9 (89%) |
| | | Productive[b] | TRAV21*02 | TRAJ16*01 | TGTCCTG | G | TTCAGATGGCCAGAAGCTGCTCTTT | 1/9 (11%) |
| H254 SeVT-3 | mRNA | Productive | TRAV8-3*01 | TRAJ10*01 | TGTGCTGTGGGT | T | TCACGGAGGAGGAAACAAACTCACTTTT | 4/16 (25%) |
| | | Productive[b] | TRAV1-2*01 | TRAJ5*01 | TGTGCTGGTGAGAG | | CATCAGGAGGAAGCTACATACCTACATTT | 3/16 (19%) |
| | | Productive[b] | TRAV1-2*01 | TRAJ7*01 | TGTGCTGTGAGACA | TTTTTATGGGAACAACG | GACTCGCTTTT | 1/16 (6%) |
| | | Productive[b] | TRAV1-2*01 | TRAJ10*01 | TGTGCTGTGAGACA | TCCGGGACCACGAAACAG | ACTCACCTTT | 1/16 (6%) |
| | | Productive[b] | TRAV1-2*01 | TRAJ16*01 | TGT | ACTGTGTTTTCACATGGCCAA | AAGCTGCTCTTT | 2/14 (13%) |
| | | Productive[b] | TRAV5-1*01 | TRAJ6*01 | TGTGCCGTGAATGC | | ATCAGGAGGAAGCTACATACCTACATTT | 1/16 (6%) |
| | | Productive[b] | TRAV12-1*01 | TRAJ6*01 | TGTGTCGTG | | TCAGGAGGAAGCTACATACCTACATTT | 1/16 (6%) |
| | | Productive[b] | TRAV12-1*01 | TRAJ9*01 | TGTGTGGTGAACA | ATACTCCACCA | TTCAAAACTATCTTT | 1/16 (6%) |
| | | Unproductive[a,b] | TRAV6*01 | TRAJ13*01 | TGTGCTCTAGACA | | TTCTGGGCGTTACCAGAAAGTTACCTTT | 1/16 (6%) |
| | | Unproductive[a,b,c] | TRAV12-1*01 | TRAJ27*01 | G | TGTGGTGAAC | AACACCAATGCAGGCAAATCAACCTTT | 1/16 (6%) |

TABLE 22

| TCRB gene rearrangemnet in redifferenciated DP Cells | | | | | | | | | |
|---|---|---|---|---|---|---|---|---|---|
| iPS cell | Genome/ | | Rearrangement | | | Sequence of junction region | | | Frequency |
| clone | RNA | Productivity | β | Dβ | Jβ | 3'Vβ | N1-Dβ-N2 | 5'Jβ | clonging (%) |
| TkT3V1-7 | mRNA | Productive | TRBV29-1*01 | TRBD1*01 | TRBJ2-2*01 | TGCAGCGTTGA | TGGACAGGGA | AACACGGGGGAGCTGTTTTTT | 10/10 (100%) |
| H254SeVT-3 | mRNA | Productive | TRBV7-9*01 | TRBD1*01 | TRBJ2-5*01 | TGTGCCAGCAGCTTA | CGGGACAGGGTGCCG | GAGACCCAGTACTTC | 15/15 (100%) |

TABLE 23

| Cell | Genome/ RNA | Productivity | Rearrangement Vα | Jα | Frequency of cloning (%) |
|---|---|---|---|---|---|
| TkT3V1-7 | Genome | Productive | TRAV38-2/DV8*01 | TRAJ31*01 | — |
| | | Unproductive | Intact | | — |
| CD8 SP cells derived from TkT3V1-7 cells | mRNA | Productive | TRAV38-2/DV8*01F | TRAJ31*01F | 75%(6/8) |
| | | Unproductive | TRAV30*01F | TRAJ29*01F | 13%(1/8) |
| | | Unproductive | TRAV20*02(F) | TRAJ28*01F | 13%(1/8) |

TABLE 24

| Cell | Genome/RNA | Productivity | Rearrangement Vβ | Dβ | Jβ | Frequency of cloning (%) |
|---|---|---|---|---|---|---|
| TkT3V1-7 | Genome | Productive | TRBV29-1*01 | TRBD1*01 | TRBJ2-2*01 | — |
| | | Unproductive | Germ line | TRBD2*01 | TRBJ2-7*01 | — |
| CD8 SP cells derived from TkT3V1-7 cells | mRNA | Productive | TRBV29-1*01 | TRBD1*01 | TRBJ2-2*01 | 89% (8/9) |
| | | Productive[b] | TRBV29-1*03 | TRBD1*01 | TRBJ2-2*01 | 11% (1/9) |

"[b]"indicates that the sequence is different from that in the genome of T-iPS cells.

As shown in FIG. 50, for both clones, the base sequence of TCRβ mRNA expressed in the resulting T-lineage cells was identical to that in their originating T-iPS cells at both the DN and DP stages.

Regarding TCRα mRNA, on the contrary, the identical sequence and a different sequence were included at the DN and DP stages, as shown in Tables 19 and 21. In addition, the DP stage was found to exhibit the different sequence more frequently than the DN stage did. Particularly in redifferentiated DP cells derived from the H254SeVT-3 clone, the frequency of T cells having the same gene rearrangement pattern as in the originating T cells was one forth or so.

Further, as shown in Tables 19, 21, and 23, it was demonstrated that in the TCRα gene of T-lineage cells derived from the TkT3V1-7 clone, the frequency of T cells having the same gene rearrangement pattern as in the originating T cells decreased to be 100%, 89%, and 75%, with differentiation to the DN stage, then to the DP stage, and then to the CD8+SP stage, respectively.

Figure 51:
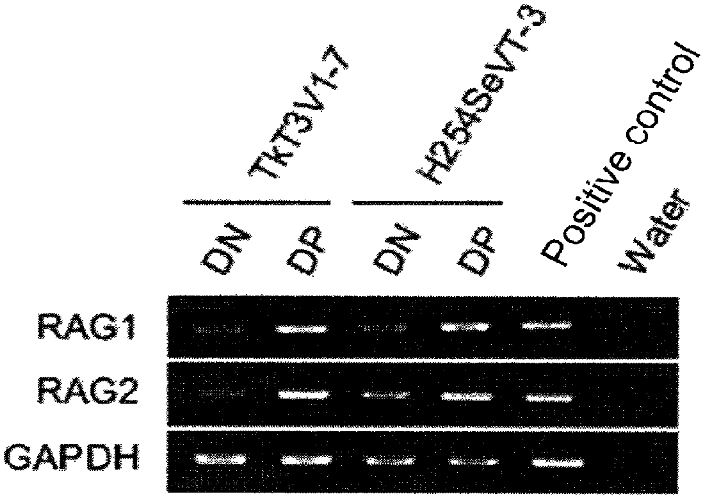
FIG. 51 represents pictures showing the results of an analysis by RT-PCR of the expression of RAG1 and RAG2 in DN cells and DP cells. In the drawing, "Water" indicates the results of RT-PCR without added template DNA (as negative control). Samples used as a PCR template were prepared, based on the expression of GAPDH.

Furthermore, as shown in FIG. 51, the expression of RAG1 and RAG2 was observed at both the DN and DP stages, and it was found that the DP stage exhibited their stronger expression than the DN stage.

Example B1

<Redifferentiation from T-iPS Cells into CD8 SP Cells According to the Method of the Present Invention>

As shown in Comparative Example B1, it was demonstrated that in TCRα mRNA in T cells into which T-iPS cells had been redifferentiated, the DP stage exhibited a TCR gene rearrangement pattern different from that exhibited by the originating human T cells, more frequently than the DN stage. It was also demonstrated that in T cells into which T-iPS cells had been redifferentiated, the DP stage exhibited a stronger expression of RAG1 and RAG2 than the DN stage.

Figure 52:
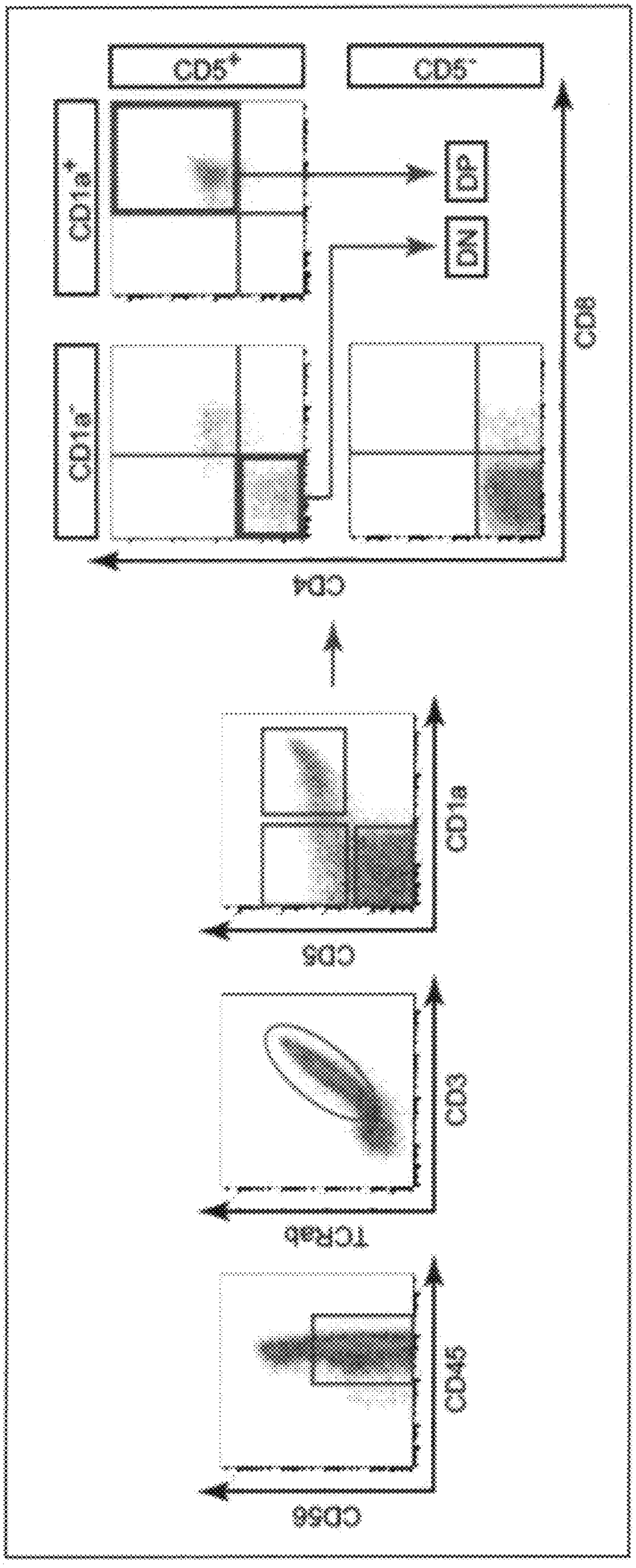
FIG. 52 represents dot plots showing the results of an analysis by flow cytometry of floating cells over OP9-DL1 cells, which were collected on day 42 after the start of the induction of re-differentiation. DN cells and DP cells were sorted from fractionated subsets of CD45+, CD56−, CD3+, TCRαβ+, CD2+, and CD5+ cells, by gating in advance for CD1a− and CD1a+, respectively.

As shown in FIG. 52, on the other hand, it was also demonstrated for the first time that T cells into which T-iPS cells had been redifferentiated expressed TCR (TCRαβ) on their surface even at the DN stage where it is known that TCR is usually not expressed on their surface at the DN stage in thymus.

As described in Turka, L. A. et al., Science, 1991, Vol. 253, pp. 778-781, it has been known in the past that in the process of "positive selection," TCR signals through peptide-MHC complexes terminate the expression of the RAG genes and suppress further rearrangement of the TCR gene. Turka et al. also found that TCR signal-like signals by anti-CD3 antibodies exerted similar effects.

Thus, the present inventors attempted to stimulate the TCR of redifferentiated T-lineage cells before the transition from the DN stage to the DP stage had been completely finished, in order to produce a mature CD8 SP cells from T-lineage cells derived from T-iPS cells without receptor revision as shown in Comparative Example B1, based on a new finding that T cells into which T-iPS cells have been redifferentiated express TCR (TCRαβ) on their surface at the DN stage and on the previous report that activation of TCR signals can lead to the termination of the expression of the RAG genes and eventually the suppression of further rearrangement of the TCR gene.

Figure 53:
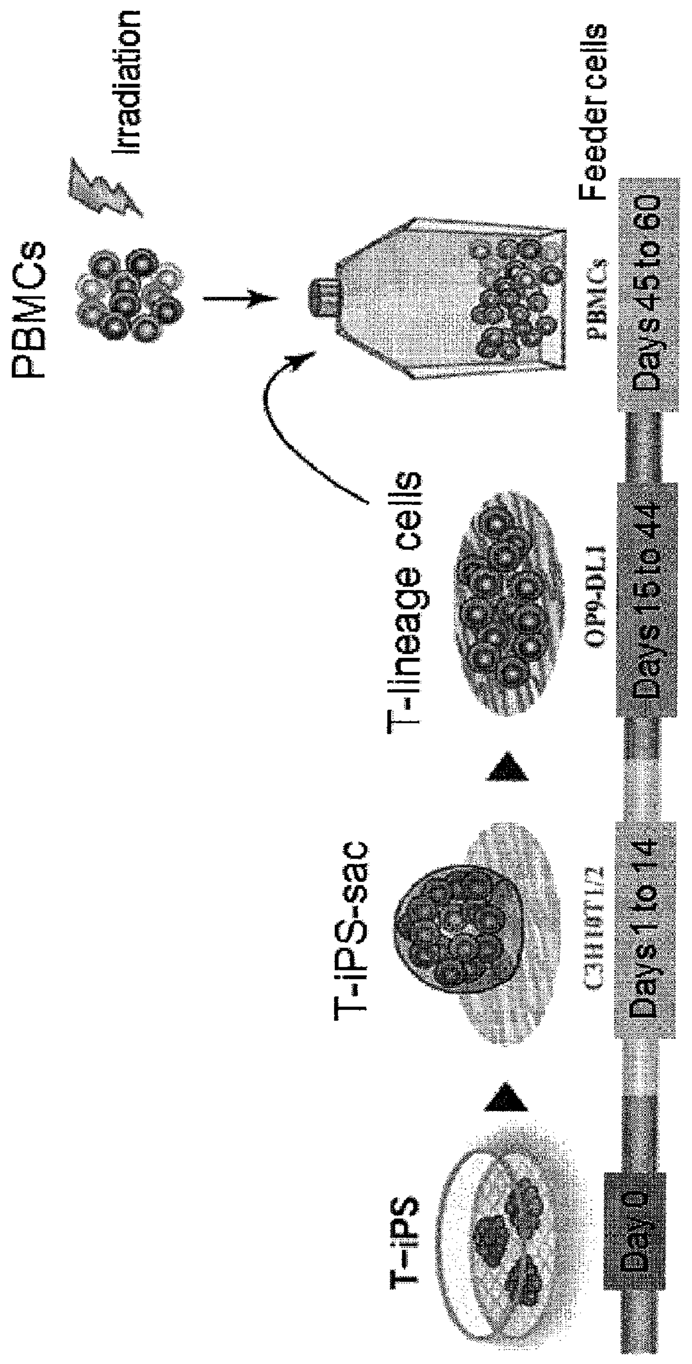
FIG. 53 is a schematic representation showing the method for producing human CD8 SP cells having antigen specificity according to the present invention, in which the process of re-differentiation from T-iPS cells into the human CD8 SP cells is shown.

In brief, as shown in FIG. 53, small aggregates (each having not more than 100 cells) of T-iPS cells obtained in Preparation Example B1 (H254SeVT-3 cells) were transferred onto irradiated C3H10T1/2 cells and co-cultured in EB medium in the presence of 20 ng/mL VEGF, 50 ng/mL SCF, and 50 ng/mL FLT-3L (manufactured by Peprotech).

On day 14 of the culture, hematopoietic cells contained in the iPS-sacs were collected, transferred onto irradiated OP9-DL1 cells, and then subjected to differentiation of the hematopoietic cells into cells of the T lineage in OP9 medium in the presence of 10 ng/mL FLT-3L and 1 ng/mL IL-7.

On day 35 of the culture, stimulation was applied by adding a-CD3/CD28 beads in an amount three times that of the hematopoietic cells or 5 μg/mL PHA to the OP9 medium, followed by continuing the culturing of cells committed to the T lineage on OP9-DL1 (the stimulation with a-CD3/CD28 beads or PHA is referred as hereinafter to the "first stimulation").

Subsequently, on day 45 of the culture, the T-lineage cells were collected and cultured with irradiated HLA-A24-PBMCs in RH10 medium in the presence of 10 ng/mL IL-7 and 10 ng/mL IL-15.

In connection with this Example, there have been reported that the IL-7 signal transduction contributes to selection of the CD8 lineage (see Chong, M. M. et al., Immunity, 2003, Vol. 18, pp. 475-487; Singer, A. et al., Nat. Rev. Immunol., 2008, Vol. 8, pp. 788-801; and Park, J. H. et al., Nat. Immunol., 2010, Vol. 11, pp. 257-264) and additionally that IL-7 and IL-15 are required for the generation of memory-type CD8+ T cells (see Becker, T. C. et al., J. Exp. Med., 2002, Vol. 195, pp. 1541-1548; Tan, J. T. et al., J. Exp. Med., 2002, Vol. 195, pp. 1523-1532; Prlic, M. et al., J. Exp. Med., 2002, Vol. 195, pp. F49-52; and Kaneko, S. et al., Blood, 2009, Vol. 113, pp. 1006-1015).

Figure 54:
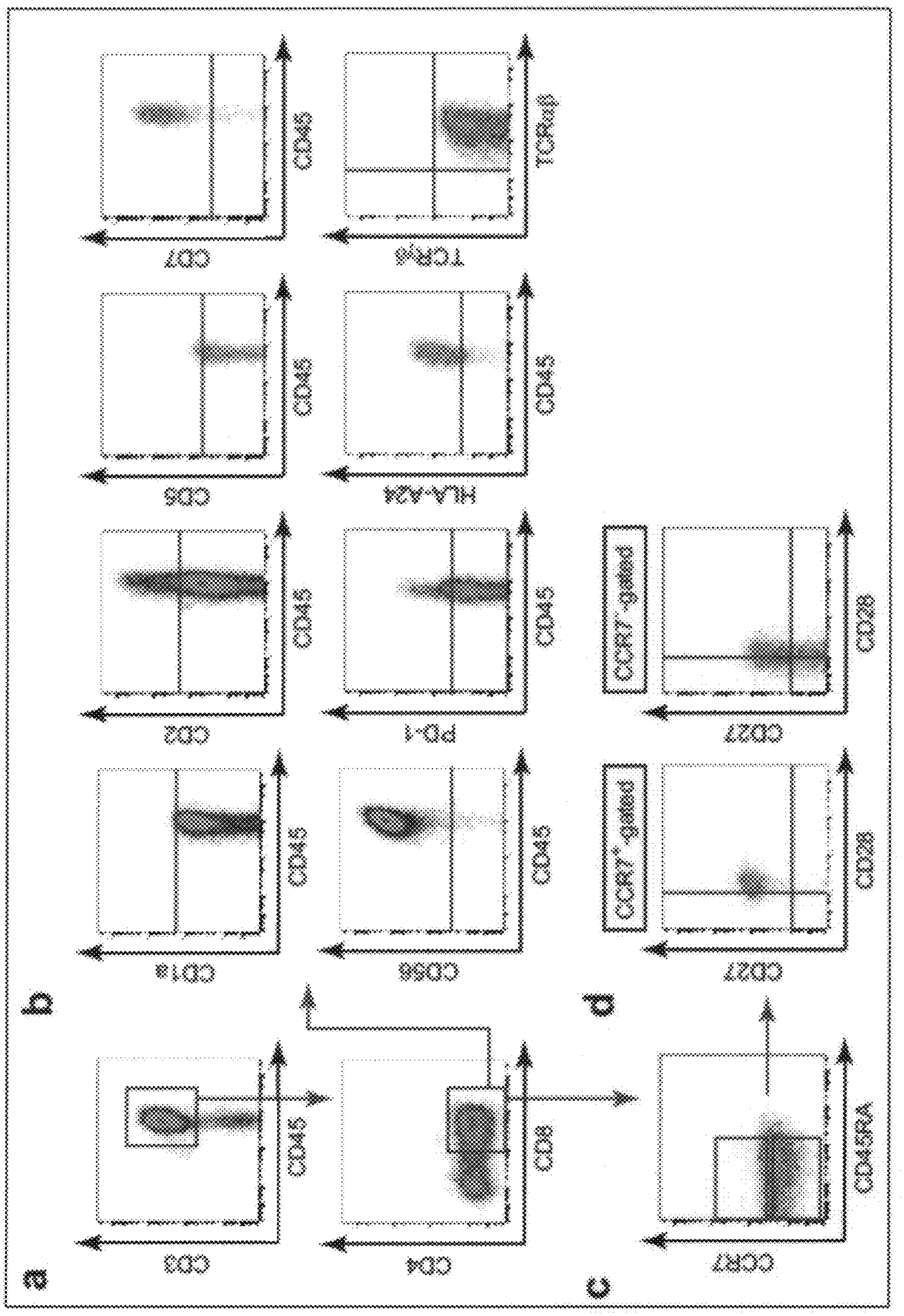
FIG. 54 represents dot plots showing results of an analysis by flow cytometry of the phenotype of cells obtained by re-differentiation of T-iPS cells by the method according to the present invention (cells on days 50 to 60 after the start of the induction of re-differentiation, as shown in FIG. 53). Shown in the drawings are representative results of the results of at least three independent experiments.

On day 60 of the culture, CD8 SP cells appeared, and these cells were found to be derived from H254SeV-3 cells because of the expression of HLA-A24, as shown in FIG. 54. In addition, the expression of CD56, which was expressed on in vitro cultured CD8+ T cells, was found on these CD8 SP cells (for CD56, see Lu, P. H. et al., J. Immunol., 1994, Vol. 153, pp. 1687-1696). Further, these CD8 SP cells also expressed CD7 and some of these cells were found to express CD2. Furthermore, most of the CD8 SP cells did not express PD-1, which is a marker of exhausted T cells. Meanwhile, some of these CD8 SP cells were found to express CCR7 together with CD27 and CD28, which are representative of the phenotype of central memory T cells. FIG. 54, FIGS. 55 to 67 described below, and Tables 17 and 18 show the results in cases where the above-mentioned T-lineage cells were stimulated with PHA as the first stimulation. Although not shown in any drawings, it was ascertained that the stimulation of the above-mentioned T-lineage cells with a-CD3/CD28 beads as the first stimulation resulted in similar results to those obtained by the stimulation with PHA.

Example B2

<Antigen Specificity of CD8 SP Cells Obtained by the Method According to the Present Invention>

An examination was made as to whether redifferentiated CD8 SP cells obtained in Example B1 were capable of recognizing antigen peptides for which the specificity was exhibited by the originating H25-4 cells, by having the same rearrangement pattern as in the originating TCR gene of the H25-4 cells. In brief, all redifferentiated T cells obtained in Example B1 and A24/Nef-138-8(wt) tetramer were mixed, and then subjected to flow cytometry analysis as described in Kawana-Tachikawa, A. et al., J. Virol., 2002, Vol. 76, pp. 11982-11988. "A24/Nef-138-8(wt) tetramer" is a tetramer in which Nef-138-8(wt), an antigen which is recognized by H25-4 cells, and HLA(A24) are tetramerized. The results obtained are shown in FIG. 55.

Figure 55:
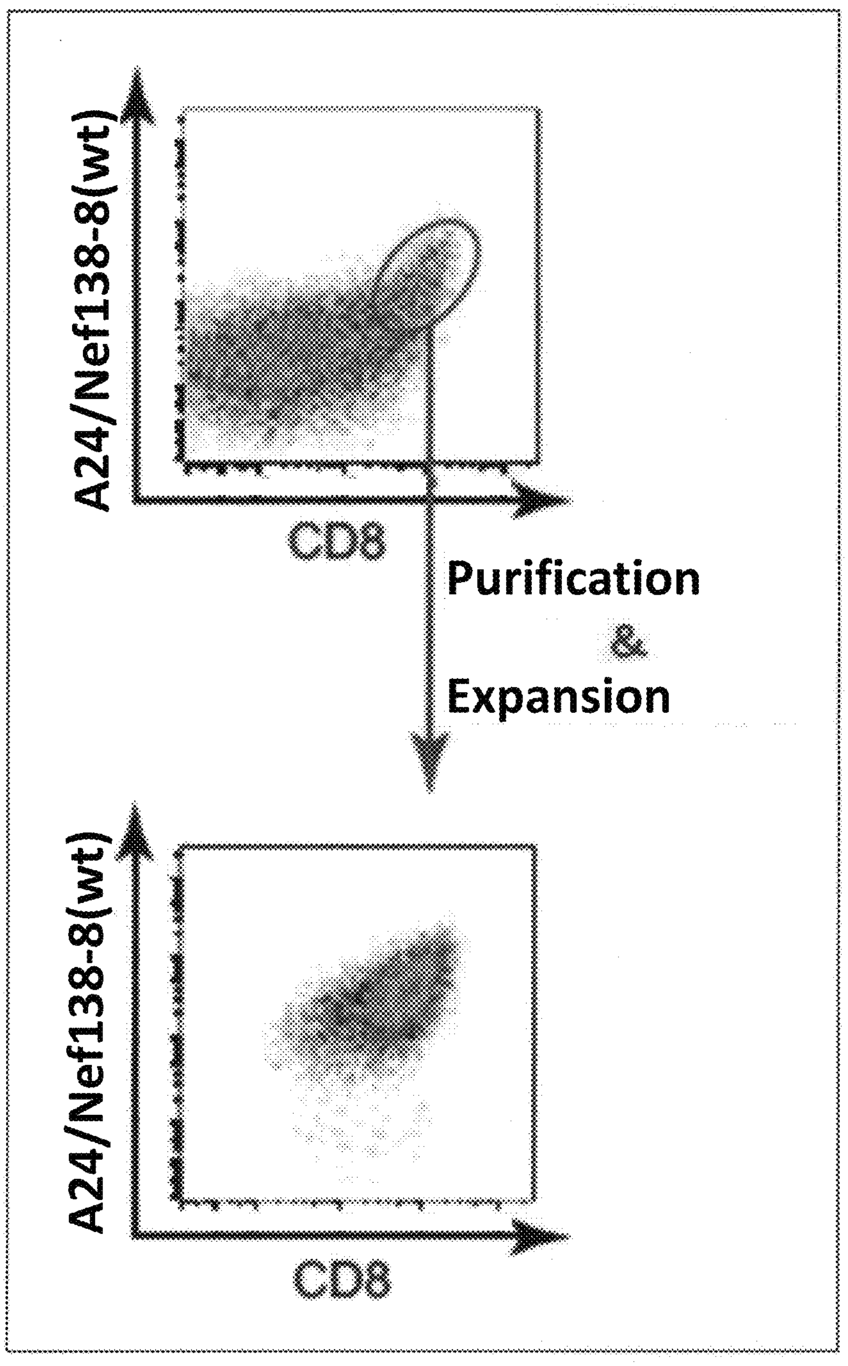
FIG. 55 represents dot plots showing the results of (upper panel) an analysis of cells obtained by re-differentiation of T-iPS cells by the method according to the present invention (cells on days 50 to 60 after the start of the induction of re-differentiation, as shown in FIG. 53), by flow cytometry using A24/Nef-138-8(wt) teratoma, and a re-analysis of T cells expanded by culturing for 14 or more days teratoma-positive cells sorted by FACS or magnetic selection, again by flow cytometry using A24/Nef-138-8(wt) teratoma.

As will be apparent from the results shown in FIG. 55, most of the T-iPS-cell-derived CD8 SP cells were stained with the A24/Nef-138-8(wt) tetramer. The percentage of CD8 SP positive cells (antigen-specific CD8 cells) in the T-iPS-cell-derived CD8 SP cells (CD8 SP tetramer-positive and tetramer-negative cells) was 77%. However, although not shown in any drawings, the T-iPS-cell-derived CD8 SP cells were not stained with an HLA-24 tetramer, used as control, which presents an HIV-1-envelop-derived peptide (RYLRDQQLL, SEQ ID NO:111). Therefore, it turned out that the frequency of T cells having the same gene rearrangement pattern as in the originating T cells, which was observed in Comparative Example B1 (one forth), was greatly improved by stimulating the TCR of redifferentiated T-lineage cells before the transition from the DN stage to the DP stage had been completely finished.

Next, as shown in FIG. 55, CD8+ cells responded to the A24/Nef-138-8(wt) tetramer were collected, expanded, and stimulated again with PHA (this stimulation with PHA is referred as hereinafter to the "second stimulation"). This redifferentiation experiment was repeated independently several times, thereby eventually generating CD8 SP cell lines that responded to the A24/Nef-138-8(wt) tetramer (reT-1, reT-2.1, reT-2.2, and reT-3).

Figure 56:
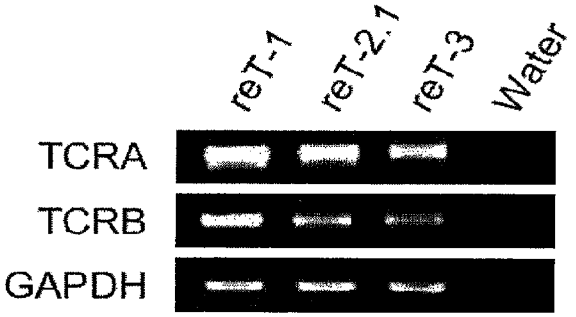
FIG. 56 represents pictures showing that TCR mRNAs were detected by PCR using respective cDNA libraries, synthesized by the SMART method, of various CD8 SP cells (reT-1, reT-2.1, and reT-3) responded to A24/Nef-138-8(wt) teratoma. In the drawing, "Water" indicates the results of RT-PCR without added template DNA (as negative control). GAPDH was used as internal standard in each PCR.

From the results of an analysis of the sequences of TCRα and TCRβ mRNAs in these redifferentiated CD8 SP cell lines, it turned out that their respective rearrangement patterns of the TCR genes were identical to those exhibited by their originating CD8 T-cell clone H25-4, as shown in FIG. 56 and in Tables 17 and 18. Even in cases of antibodies recognizing the above-mentioned tetramer, their amino acid sequences (particularly of the CDR3) are often different; however, the respective rearrangement patterns of these TCR genes were completely identical between the CD8 SP cell lines responding to the A24/Nef-138-8(wt) tetramer (reT-1, reT-2.1, reT-2.2, and reT-3) and their originating CD8 T-cell clone H25-4, as shown in Tables 17 and 18. Also from such date, therefore, it was confirmed that the frequency of T cells having the same gene rearrangement pattern as in the originating T cells, which was observed in Comparative Example B1 (one forth), was greatly improved by stimulating the TCR of redifferentiated T-lineage cells before the transition from the DN stage to the DP stage had been completely finished.

Figure 57:
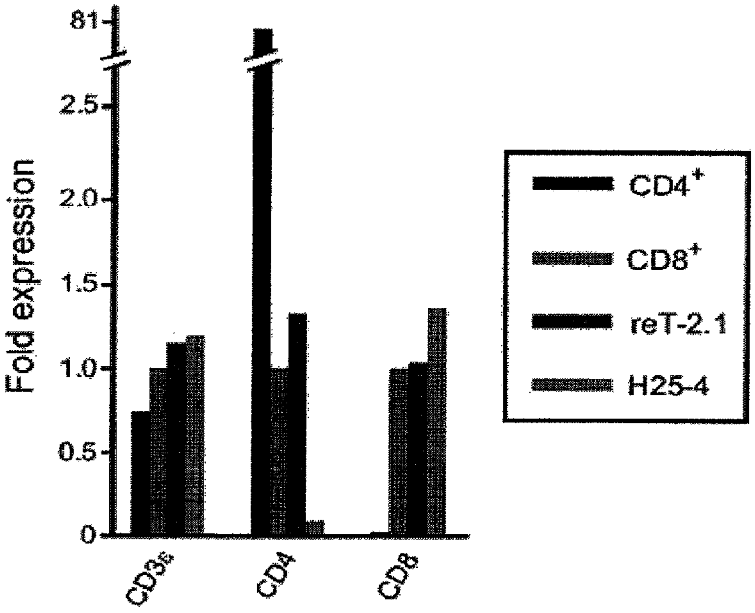
FIG. 57 represents a graph showing the results of comparing the amount of expression of major cell surface molecules among CD4+ cells, CD8+ cells, reT-2.1 cells, and H25-4 cells, using quantitative PCR. In each PCR reaction, the amount of expression of 18S rRNA was used as internal standard. In the drawing, the ordinate axis represents an expression ratio when the amount of expression of each of these genes in the CD8+ cells was set to be 1.0. The abscissa axis represents, from left to right, the results of the respective genes in CD4+ cells, CD8+ cells, reT-2.1 cells, and H25-4 cells.

Further, in order to examine that these redifferentiated CD8 SP cell lines were of the T cell lineage, the gene expression profile in cells of the reT-2.1 cell line was compared to those in peripheral blood (PB) CD4+ T cells, PB CD8+ T cells, and cells of the H25-4 clone by quantitative PCR. The results obtained are shown in FIGS. 57 to 59.

As will be apparent from the results shown in FIG. 57, the respective expression patterns of CD3, CD4, and CD8 were the same in the PB CD8+ T cells, the redifferentiated CD8 SP cells, and the cells of the originating T-cell clone H25-4 (hereinafter referred as to the "H25-4 original T-cell clone"), except for the PB CD4+ T cells.

Figure 58:
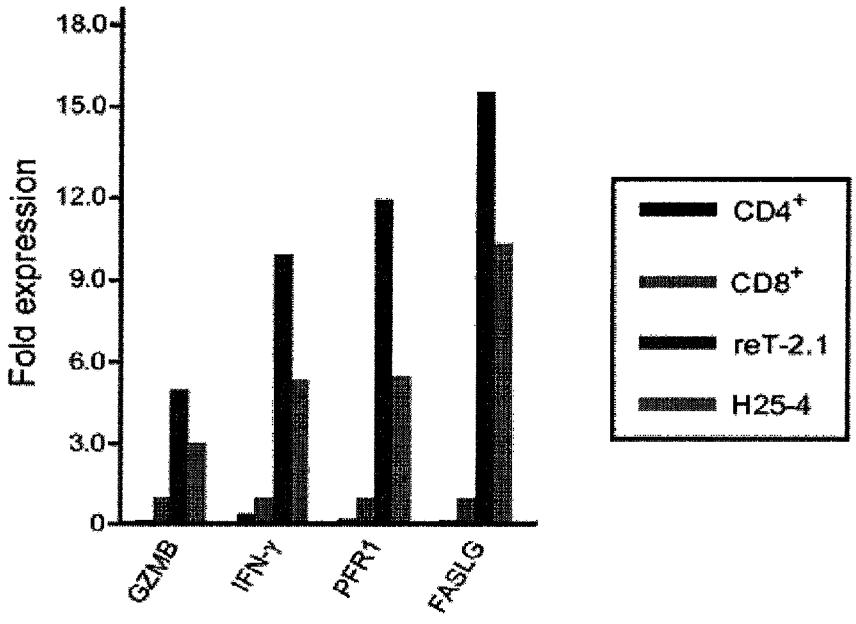
FIG. 58 represents a graph showing the results of comparing the amount of expression of major cytolytic molecules among CD4+ cells, CD8+ cells, reT-2.1 cells, and H25-4 cells, using quantitative PCR. In each PCR reaction, the amount of expression of 18S rRNA was used as internal standard. In the drawing, the ordinate axis represents an expression ratio when the amount of expression of each of these genes in the CD8+ cells was set to be 1.0. The abscissa axis represents, from left to right, the results of the respective genes in CD4+ cells, CD8+ cells, reT-2.1 cells, and H25-4 cells.

As shown in FIG. 58, it was also demonstrated that genes characterized by their cytotoxicity, for example, granzyme B (GZMB), perforin (PFR1), IFN-γ (IFNG), and FAS ligand (FASLG) were expressed on the PB CD8+ T cells and at a relatively high level on the CD8 SP cells, which was a population of T cells that had been already received antigen stimulation, and on the cells of the H25-4 original T-cell clone.

Figure 59:
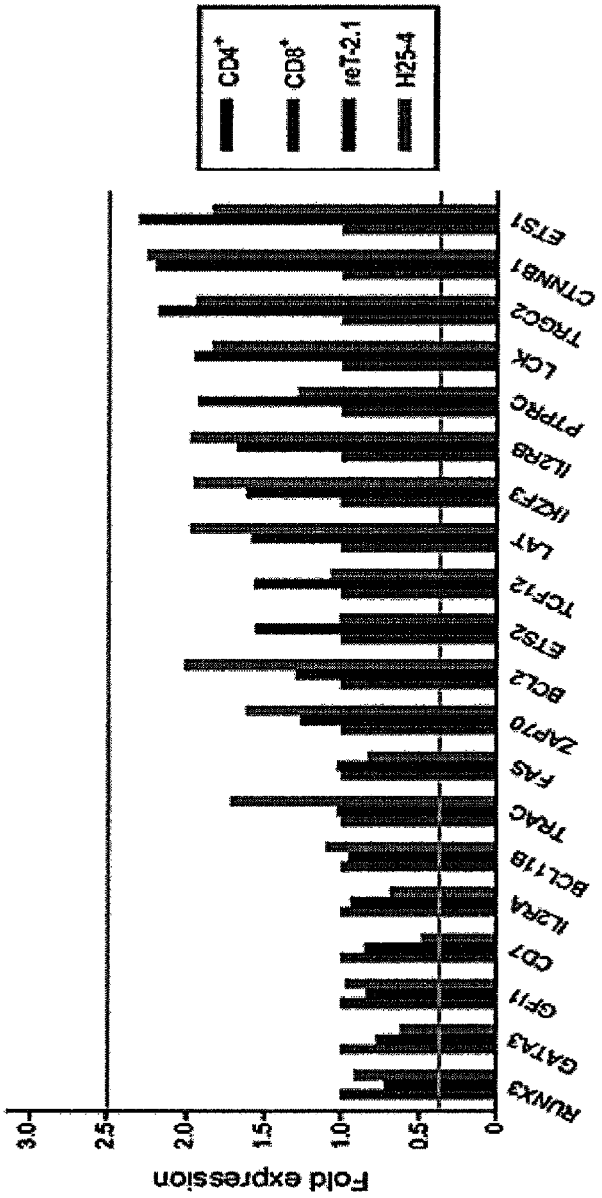
FIG. 59 represents a graph showing the results of comparing the amount of expression of major transcription factors and signaling molecules among CD4+ cells, CD8+ cells, reT-2.1 cells, and H25-4 cells, using quantitative PCR. In each PCR reaction, the amount of expression of 18S rRNA was used as internal standard. In the drawing, the ordinate axis represents an expression ratio when the amount of expression of each of these genes in the CD8+ cells was set to be 1.0. The abscissa axis represents, from left to right, the results of the respective genes in CD4+ cells, CD8+ cells, reT-2.1 cells, and H25-4 cells.

Further, as will be apparent from the results shown in FIG. 59, the expression patterns of several transcription or signaling factors and cell surface molecules were the same in the PB CD8+ T cells, the redifferentiated CD8 SP cells, and the cells of the H25-4 original T-cell clone.

The overall gene expression profile was also analyzed with cDNA microarrays for redifferentiated CD8 cells of the above-mentioned cell line, cells of the H25-4 original T-cell clone, and peripheral blood NK cells, in order to exclude the possibility that the redifferentiated CD8 SP cells might be those which acquired NK-like properties during the period of co-culturing with OP9-DL1 or PBMC cells. The results obtained are shown in FIGS. 60 and 61.

Figure 60:
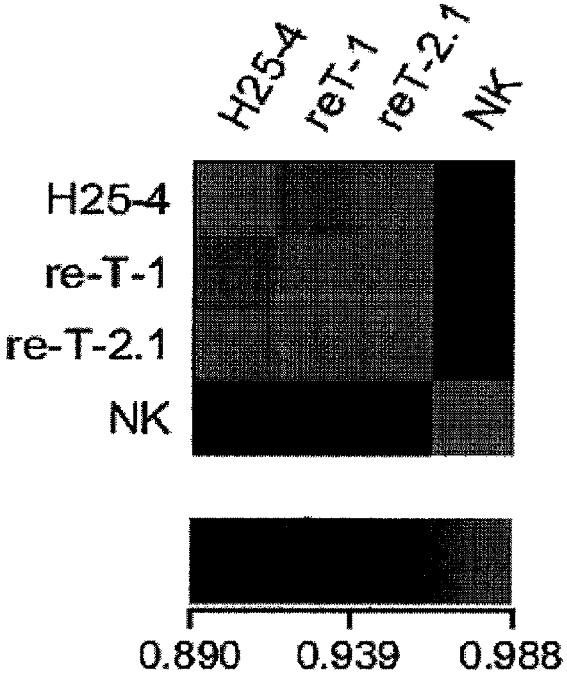
FIG. 60 represents a heat map showing correlation coefficients among samples obtained by a comprehensive analysis of gene expression using cDNA microarrays.
Figure 61:
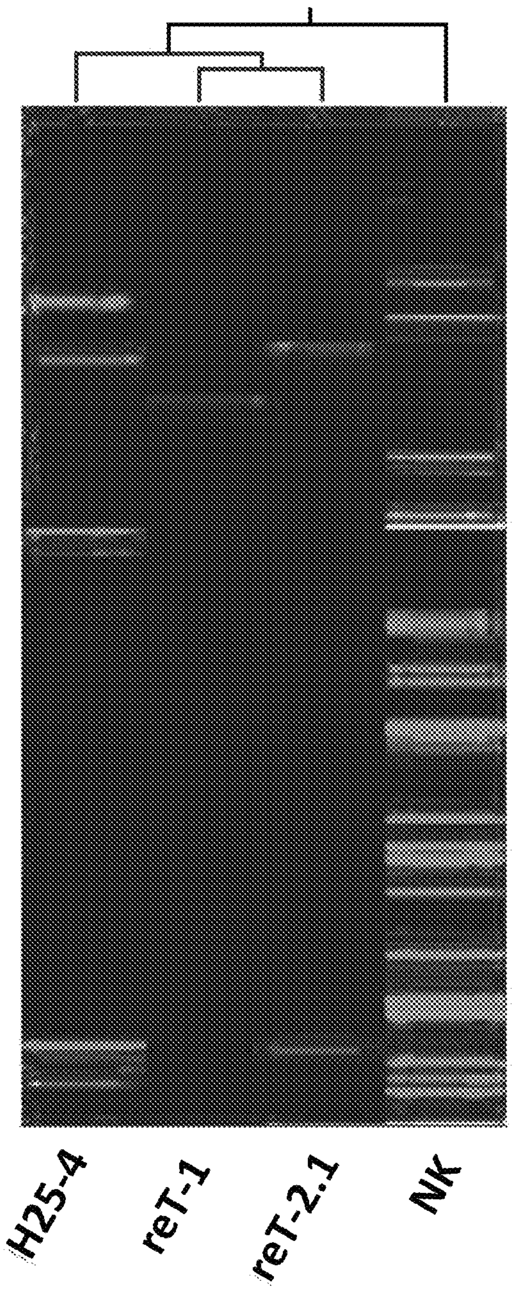
FIG. 61 represents a heat map showing a group of genes exhibiting a more than three-times difference in their expression amount, relative to NK cells, which was obtained by a comprehensive analysis of gene expression using cDNA microarrays. In the drawing, the reds and greens indicate an increase and a decrease in expression, respectively.

As will be apparent from the results shown in FIGS. 60 and 61, it turned out that the gene expression profile of the redifferentiated CD8 SP cells was similar to that of the cells of the H25-4 original T-cell clone. However, the correlation coefficients and cluster analysis did not find any relationship between the redifferentiated CD8 SP cells and the NK cells. Therefore, it was demonstrated that T-iPS cells were capable of redifferentiation into CD8+ T cells exhibiting the same antigen specificity as that exhibited by their originating T cells.

Example B3

<Increased Proliferative Properties of CD8 SP Cells Obtained by the Method According to the Present Invention>

In Example B1, the number of T-lineage cells obtained by co-culturing T-iPS cells with OP9-DL1 cells in a 6-cm dish was less than $10^5$ cells. However, although not shown in any drawings, the first stimulation allowed the number of cells to be increased to more than $10^8$ cells. Based on this finding, cells of each of the cell lines reT-1, reT-2.2, and reT-3 were stimulated with 5 μg/mL PHA, 10 ng/mL IL-7, and 10 ng/mL IL-15, and then subjected to determination of the respective increase (expansion) ratios of these cell lines at two weeks after the stimulation, in order to examine the proliferative properties of CD8 SP cells of these cell lines obtained by the method according to the present invention. The results obtained are shown in FIG. 62.

Figure 62:
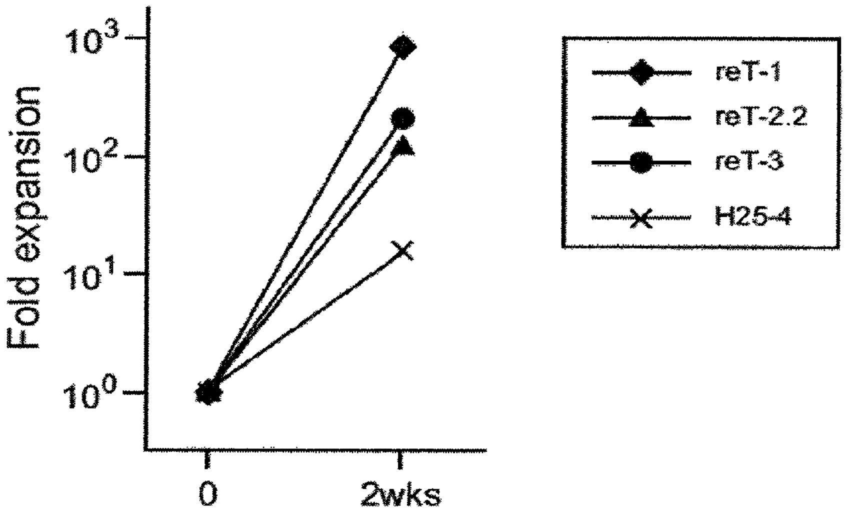
FIG. 62 represents a graph showing the expansion ratio of reT-1, reT-2.2, and reT-3 cells at two weeks after the respective cells were stimulated with PHA, IL-7, and IL-15. The ordinate axis represents an expansion ratio when the number of cells upon the stimulation was set to be $10^0$ for the respective cells.

As will be apparent from FIG. 62, the number of cells of the H25-4 original T-cell clone was expanded about 20 times, whereas the number of CD8+ cells of each of these cell lines was expanded 100 to 1,000 times, at two weeks after the stimulation.

Figure 63:
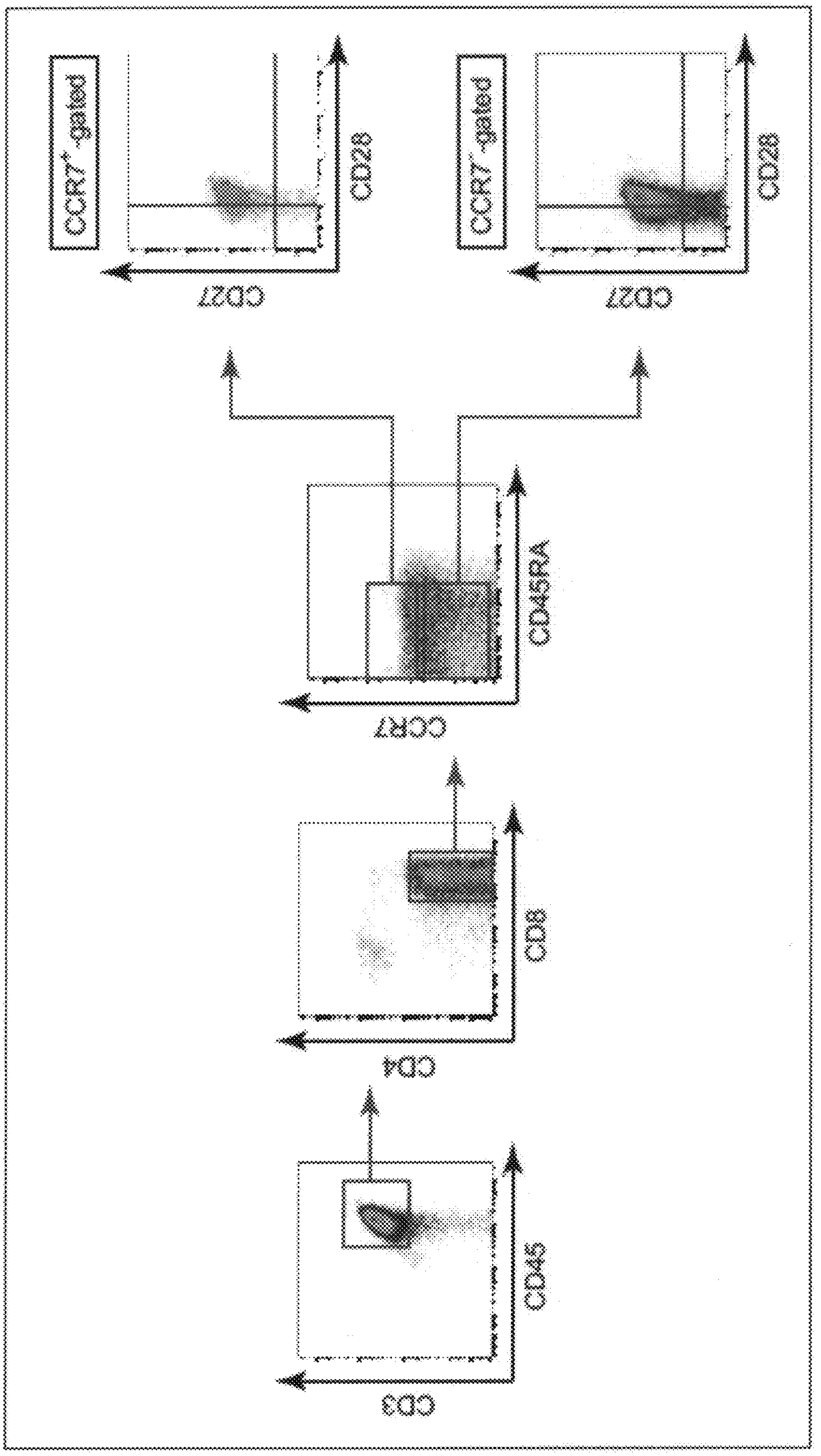
FIG. 63 represents dot plots showing the results of an analysis by flow cytometry of the expression of CD45RA, CCR7, CD27, and CD28 on the cellular surface of the cells purified with A24/Nef-138-8(wt) teratoma and expanded (reT-2.1 and reT-3). In the drawings, the data of reT-2.1 cells are shown as representative results.

In addition, as shown in FIG. 63, a particular population of cells was found to express central memory T-cell markers, for example, CCR7, CD27, and CD28, even after 100 to 1,000 times expansion was achieved (for central memory T-cell markers, see Romero, P. et al., J. Immunol., 2007, Vol. 178, pp. 4112-4119).

Regarding enhanced proliferative (replicative) ability of the CD8 SP cells of the present invention as shown above, it is supposed that by going through a state of iPS cells having an extremely high telomerase activity, the telomere of which the length have become short in cells of the H25-4 original T-cell clone is re-elongated, so that enhanced proliferative ability can be conferred on redifferentiated T cells (see Takahashi, K. et al., Cell, 2007, Vol. 131, pp. 861-872; Marion, R. M. et al., Cell Stem Cell, 2009, Vol. 4, pp. 141-154; Monteiro, J. et al., J. Immunol., 1996, Vol. 156, pp. 3587-3590; and Weng, N. P. et al., Immunity, 1998, Vol. 9, pp. 151-157). Thus, the present inventors determined the telomere length in CD8 SP cells of each of the three cell lines obtained by the method according to the present invention. The results obtained are shown in FIG. 64.

Figure 64:
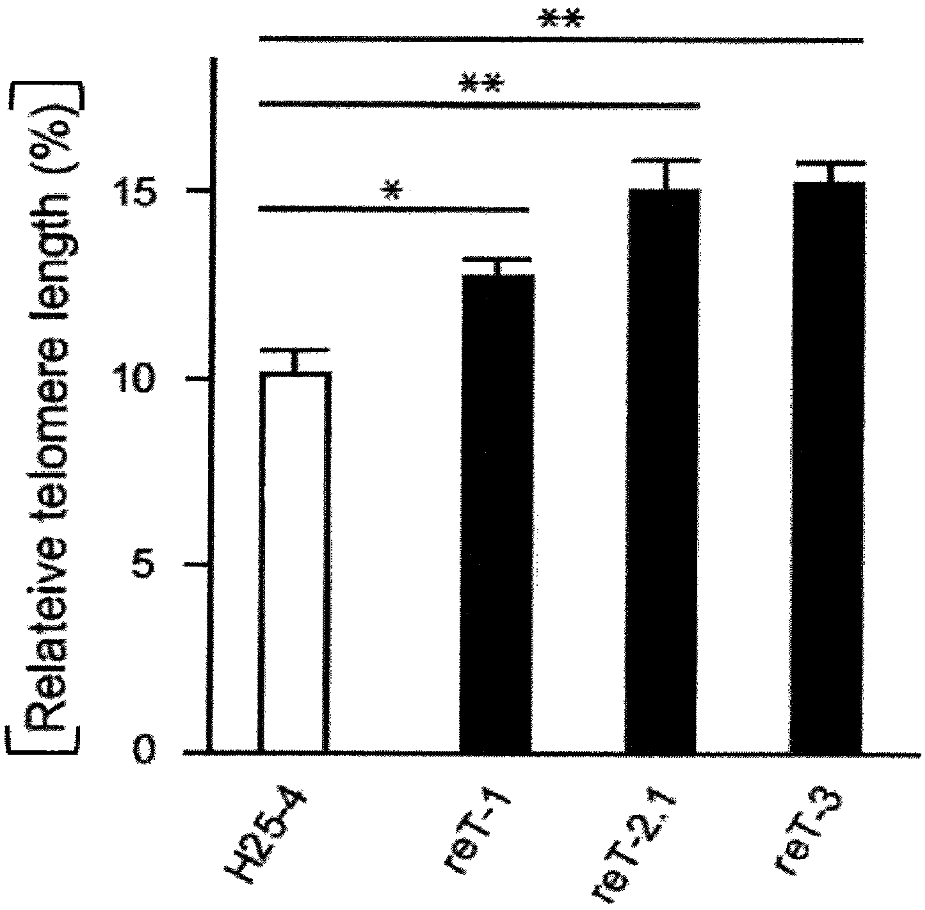
FIG. 64 represents a graph showing the relative telomere length (RTL) as determined by flow-FISH.

As will be apparent from the results shown in FIG. 64, the redifferentiated T cells of each of the three cell lines actually had a longer telomere length than their originating T cells.

Therefore, it is demonstrated that by go through a state of T-iPS cells, the CD8 SP cells obtained by the method according to the present invention (cloned cytotoxic T cells) can be rejuvenated to central memory-like T cells exhibiting superior proliferative ability and viability.

Although not shown in any drawings, there was observed, throughout this Example, neither autonomous cellular proliferation nor survival of abnormal cells in the absence of cytokines.

Example B4

<Antigen-Specific Functions of CD8 SP Cells Obtained by the Method According to the Present Invention>

A major mechanism of cytotoxicity of CTLs is secreting cytolytic molecules which are produced together with TCR signals. Thus, the present inventors examined by intracellular staining as to whether CD8 SP cells of a cell line obtained by the method according to the present invention (reT-2.2) also secreted cytolytic molecules by stimulating TCR with α-CD3/CD28 beads in an amount three times that of the CD8 SP cells. The results obtained are shown in FIG. 65.

Figure 65:
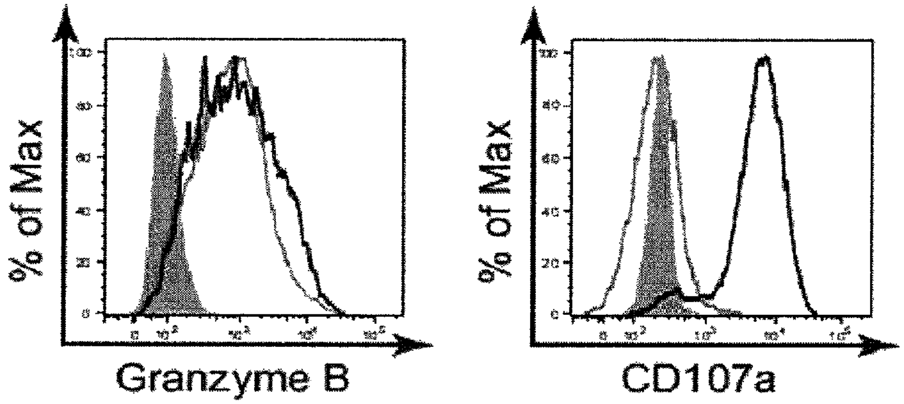
FIG. 65 represents histograms showing the results of an analysis of the secretion of cytolytic molecules in reT-2.1 cells when stimulated with α-CD3/CD28 beads. The left panel is a histogram showing the amount of intracellular production of granzyme B. The open histogram represented by the grey line indicates the reactivity of cells which were not stimulated and an anti-granzyme B antibody, the open histogram represented by the black line indicates the reactivity of cells which were stimulated and an anti-granzyme B antibody, and the closed histogram indicates the reactivity of cells which were stimulated and an antibody used as a negative control (an antibody of the same isotype as that of the anti-granzyme B antibody). The right panel is a histogram showing the results of a CD107a mobilization assay in reT-2.1 cells when stimulated with α-CD3/CD28 beads. The open histogram represented by the grey line indicates the reactivity of cells which were not stimulated and an anti-CD107a antibody, the open histogram represented by the black line indicates the reactivity of cells which were stimulated and an anti-CD107a antibody, and the closed histogram indicates the reactivity of cells which were stimulated and an antibody used as a negative control (an antibody of the same isotype as that of the anti-CD107a antibody).

As shown in FIG. 65, it was demonstrated that after the stimulation with a-CD3/28 beads, granzyme B, a cytolytic molecule, was produced and accumulated in granules of the redifferentiated CD8 T cells (see FIG. 65, left panel).

CD107a, known as lysosome-associated membrane protein 1 (LAMP1), is a granulocyte membrane protein which is transiently expressed when CTLs are stimulated, in conjunction with degranulation in which cytolytic molecules are secreted, and is known to return to the cytoplasm after its secretion (Rubio, V. et al., Nat. Med., 2003, Vol. 9, pp. 1377-1382). Thus, redifferentiated CD8 T cells of an above-mentioned cell line were cultured in the presence or absence of stimulation with a-CD3/28 beads, and then CD107a molecules on the cellular surface of these cells were detected with a fluorescent dye-conjugated antibody. The results obtained are shown in FIG. 65.

As shown in FIG. 65, the incorporation of the antibody was detected only when the redifferentiated T cells of an above-mentioned cell line were stimulated with α-CD3/28 beads (see FIG. 65, right panel).

Next, function assays, an ELISPOT (Enzyme-Linked ImmunoSpot) assay and a $^{51}$Cr-release assay, were carried out using HLA-A24-positive B-LCL cells (cells derived from the patient from which the H25-4 T-cell clone was derived) acting as an antigen-presenting cell, in order to assess whether or not redifferentiated CD8 T cells of the three cell lines of the present invention were capable of exerting cytotoxicity by recognizing a particular peptide in MHC complexes. The results obtained are shown in FIGS. 66 and 67.

Regarding the peptides which were used in these assays, Gag-28-9(wt) (KYKLKHIVW, SEQ ID NO:112) is an antigen peptide of the HIV-1 Gag protein (amino acid residues 28 to 36) and Nef-138-8(2F) (RFPLTFGW, SEQ ID NO:113) is a one-residue mutant of Nef-138-8(wt) in which a tyrosine residue is substituted with phenylalanine, which both are present on HLA-A24.

Figure 66:
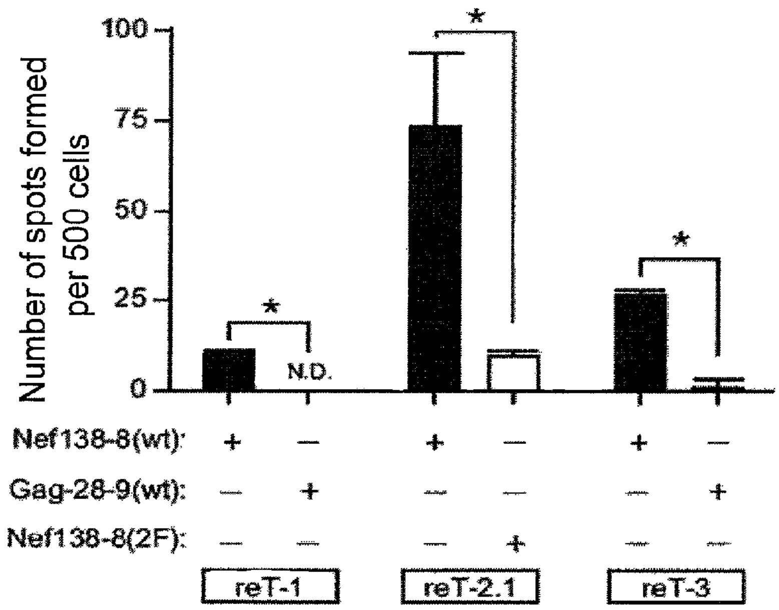
FIG. 66 represents a graph showing the results of an analysis by ELISPOT of IFN-γ produced in response to stimulation with Nef-138-8(wt). Shown in the drawing are representative results of the results of at least three independent experiments. The ordinate axis represents the number of spots formed in 500 cells.
Figure 65:
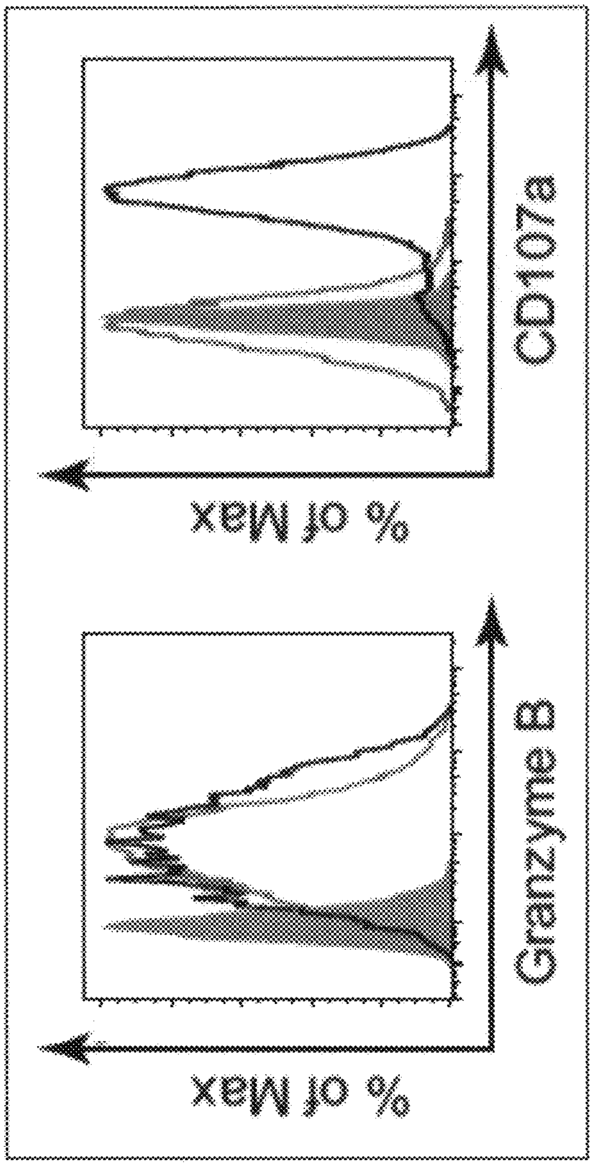
Figure 66:
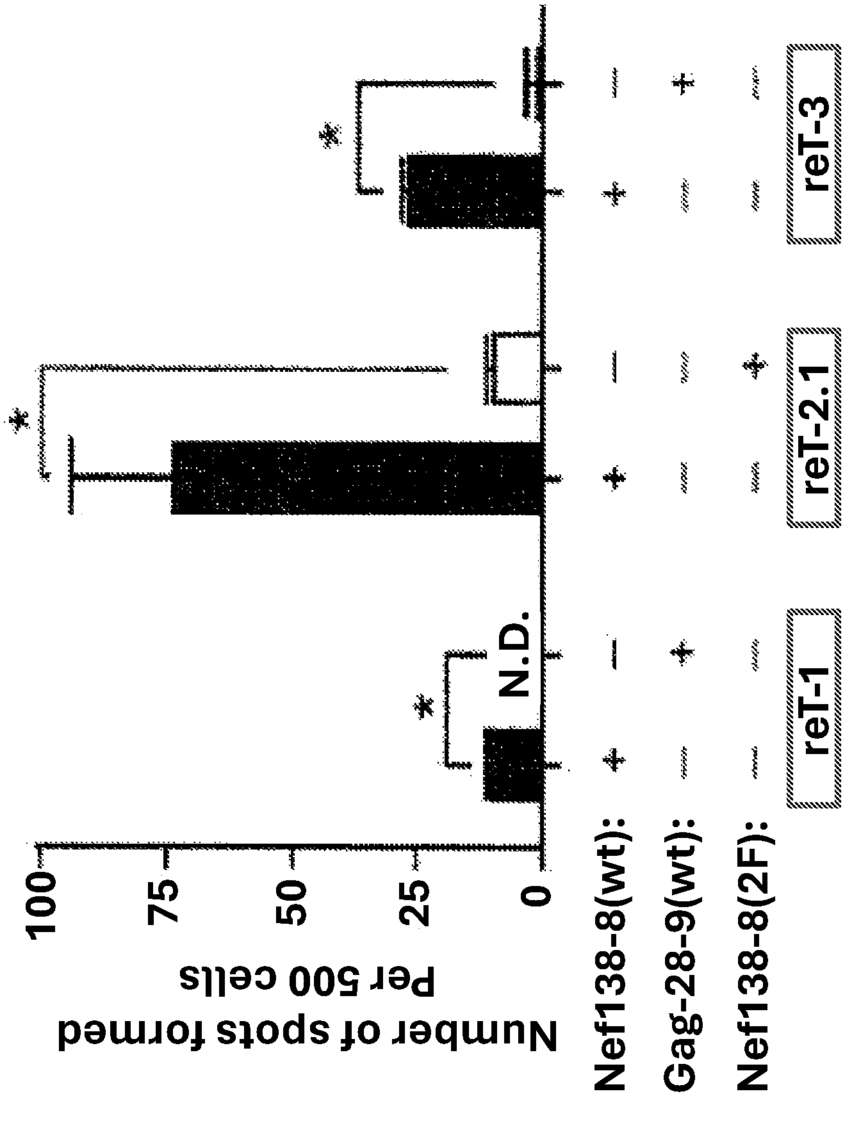

As shown in FIG. 66, from the results of evaluating the cytokine production capability per cell by ELISPOT, it turned out that the redifferentiated CD8 T cells of each of the three cell lines of the present invention remarkably produced IFN-γ, responding to the stimulation with a specific antigen, Nef-138-8(wt).

Figure 67:
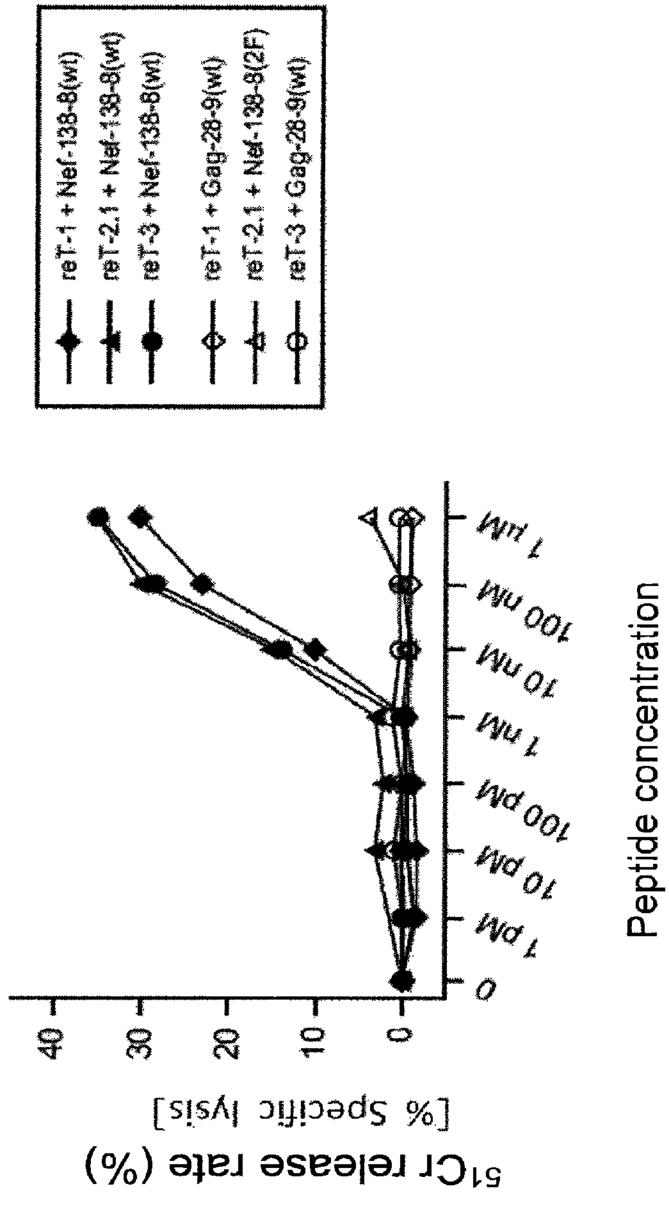
FIG. 67 represents a graph showing the results of a $^{51}$Cr release assay using various concentrations of epitope peptides, including Nef-138-8(wt). The $^{51}$Cr release assay was performed by reacting effector cells and $^{51}$Cr-incorporated target cells at a ratio of 5:1. The ordinate axis represents the percentage of specific $^{51}$Cr-release (%).

As shown in FIG. 67, from the results of examining the cytolytic ability by $^{51}$Cr-release assay, it turned out that only in the presence of Nef-138-8(wt), the redifferentiated CD8 T cells of each of the three cell lines of the present invention lyzed B-LCLs into which 51 Cr was incorporated.

Therefore, it is demonstrated that the CD8 SP cells obtained by the method according to the present invention release cytotoxic molecules and specifically kill target cells expressing a specific antigen, and thus are functional, antigen-specific T cells.

As mentioned above, the method for producing a human T lymphocyte according to the present invention is superior in producing, in particular, a human T lymphocyte specific for an antigen of interest, and eventually a CD4 or CD8 single positive cell which is specific for an antigen of interest and is restricted to a desired human histocompatibility antigen (HLA). Therefore, the present invention can contribute greatly to treatment or prevention of a variety of intractable diseases, such as chronic refractory infections and malignant tumors, or autoimmune diseases.

What is claimed is:

1. A method of treating a tumor in a human subject in need thereof by cell-based immunotherapy, which comprises the steps of:

inducing an iPS cell from an isolated human mature T cell having an antigen specificity against the tumor, differentiating the iPS cell into a CD4/CD8 double-negative cell and then differentiating the CD4/CD8 double-negative cell into a CCR7 positive and PD-1 negative naïve T cell to obtain a population of CCR7 positive and PD-1 negative naïve T cells which have the antigen specificity and have a longer telomere and an improved self-replication ability, compared to the originating mature T cell, and administering to the human subject an effective amount of the resulting population of CCR7 positive and PD-1 negative naïve T cells.

2. A method of treating a tumor in a human subject in need thereof by cell-based immunotherapy, which comprises the steps of:

inducing an iPS cell from an isolated human mature T cells having an antigen specificity against the tumor, differentiating the iPS cell into a CD4/CD8 double-negative cell, stimulating a T cell receptor of the CD4/CD8 double-negative cell, differentiating the CD4/CD8 double-negative cell whose T cell receptor has been stimulated, into a CCR7 positive and PD-1 negative human naïve CD8 single-positive (SP) cell to obtain a population of CCR7 positive and PD-1 negative human naïve CD8 single-positive cells having the antigen specificity and having a longer telomere and an improved self-replication ability, compared to the originating mature T cell, and administering to the human subject an effective amount of the resulting population of CCR7 positive and PD-1 negative human naïve CD8 single-positive (SP) cells.

3. The method according to claim 1, further comprising terminating expression of Rag genes such that the expression will be terminated at the CD4/CD8 double-negative cell.

4. The method according to claim 1, wherein the resulting T cell maintains the same TCR rearrangement pattern as in its originating mature T cell.

5. The method according to claim 2, wherein the resulting T cell maintains the same TCR rearrangement pattern as in its originating mature T cell.

6. The method according to claim 1, wherein the isolated mature T cells are selected from the group consisting of helper/regulatory T cells; cytotoxic T cells (CTLs), CD45RA+CD62L+ naive T cells; CD45RA−CD62L+ central memory T cells; CD45RA−CD62L− effector memory T cells; and CD45RA+CD62L− terminal effector T cells.

7. The method according to claim 2, wherein the isolated mature T cells are selected from the group consisting of helper/regulatory T cells; cytotoxic T cells (CTLs), CD45RA+CD62L+ naive T cells; CD45RA−CD62L+ central memory T cells; CD45RA−CD62L− effector memory T cells; and CD45RA+CD62L− terminal effector T cells.

8. The method according to claim 1, wherein the resulting CCR7 positive and PD-1 negative naïve cells are CCR7 positive and PD-1 negative naïve CD8 single positive (SP) T cells, wherein the CCR7 positive and PD-1 negative naïve CD8 SP T cells incorporate a system that uses a suicide gene into the cell.

9. The method according to claim 8, wherein the suicide gene is a gene encoding an inducible caspase 9 comprising human caspase 9 and a modified FK-binding protein.

10. The method according to claim 2, wherein the CCR7 positive and PD-1 negative human naïve CD8 SP T cells incorporate a system that uses a suicide gene into the cell.

11. The method according to claim 10, wherein the suicide gene is a gene encoding an inducible caspase 9 comprising human caspase 9 and a modified FK-binding protein.

* * * * *

SEQUENCE LISTING

```
<160> NUMBER OF SEQ ID NOS: 258

<210> SEQ ID NO 1
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 1

aacagcctca agatcatcag c                                              21


<210> SEQ ID NO 2
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 2

ttggcaggtt tttctagacg g                                              21


<210> SEQ ID NO 3
<211> LENGTH: 19
<212> TYPE: DNA
<213> ORGANISM: Artificial
<220> FEATURE:
<223> OTHER INFORMATION: Artificially synthesized primer sequence

<400> SEQUENCE: 3

attcagccaa acgaccatc                                                 19


<210> SEQ ID NO 4
<211> LENGTH: 19
<212> TYPE: DNA
<213> ORGANISM: Artificial
<220> FEATURE:
<223> OTHER INFORMATION: Artificially synthesized primer sequence

<400> SEQUENCE: 4

ggaaagggac cgaggagta                                                 19


<210> SEQ ID NO 5
<211> LENGTH: 18
<212> TYPE: DNA
<213> ORGANISM: Artificial
<220> FEATURE:
<223> OTHER INFORMATION: Artificially synthesized primer sequence

<400> SEQUENCE: 5

cagcgcatgg acagttac                                                  18


<210> SEQ ID NO 6
<211> LENGTH: 18
<212> TYPE: DNA
<213> ORGANISM: Artificial
<220> FEATURE:
<223> OTHER INFORMATION: Artificially synthesized primer sequence

<400> SEQUENCE: 6
```

ggagtgggag gaagaggt 18

<210> SEQ ID NO 7
<211> LENGTH: 18
<212> TYPE: DNA
<213> ORGANISM: Artificial
<220> FEATURE:
<223> OTHER INFORMATION: Artificially synthesized primer sequence

<400> SEQUENCE: 7
agtttcatct gcgacccg 18

<210> SEQ ID NO 8
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 8
cctcatcttc ttgttcctcc t 21

<210> SEQ ID NO 9
<211> LENGTH: 18
<212> TYPE: DNA
<213> ORGANISM: Artificial
<220> FEATURE:
<223> OTHER INFORMATION: Artificially synthesized primer sequence

<400> SEQUENCE: 9
gcgggaaggg agaagaca 18

<210> SEQ ID NO 10
<211> LENGTH: 18
<212> TYPE: DNA
<213> ORGANISM: Artificial
<220> FEATURE:
<223> OTHER INFORMATION: Artificially synthesized primer sequence

<400> SEQUENCE: 10
ccggatcgga taggtgaa 18

<210> SEQ ID NO 11
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 11
gacaggggga ggggaggagc tagg 24

<210> SEQ ID NO 12
<211> LENGTH: 26
<212> TYPE: DNA
<213> ORGANISM: Artificial
<220> FEATURE:
<223> OTHER INFORMATION: Artificially synthesized primer sequence

<400> SEQUENCE: 12
cttccctcca accagttgcc ccaaac 26

<210> SEQ ID NO 13
<211> LENGTH: 26
<212> TYPE: DNA
<213> ORGANISM: Artificial

<220> FEATURE:
<223> OTHER INFORMATION: Artificially synthesized primer sequence

<400> SEQUENCE: 13
gggaaatggg aggggtgcaa aagagg 26

<210> SEQ ID NO 14
<211> LENGTH: 26
<212> TYPE: DNA
<213> ORGANISM: Artificial
<220> FEATURE:
<223> OTHER INFORMATION: Artificially synthesized primer sequence

<400> SEQUENCE: 14
ttgcgtgagt gtggatggga ttggtg 26

<210> SEQ ID NO 15
<211> LENGTH: 26
<212> TYPE: DNA
<213> ORGANISM: Artificial
<220> FEATURE:
<223> OTHER INFORMATION: Artificially synthesized primer sequence

<400> SEQUENCE: 15
gcgtcctggg aagggagatc cggagc 26

<210> SEQ ID NO 16
<211> LENGTH: 26
<212> TYPE: DNA
<213> ORGANISM: Artificial
<220> FEATURE:
<223> OTHER INFORMATION: Artificially synthesized primer sequence

<400> SEQUENCE: 16
ttgaggggca tcgtcgcggg aggctg 26

<210> SEQ ID NO 17
<211> LENGTH: 25
<212> TYPE: DNA
<213> ORGANISM: Artificial
<220> FEATURE:
<223> OTHER INFORMATION: Artificially synthesized primer sequence

<400> SEQUENCE: 17
acgatcgtgg ccccggaaaa ggacc 25

<210> SEQ ID NO 18
<211> LENGTH: 28
<212> TYPE: DNA
<213> ORGANISM: Artificial
<220> FEATURE:
<223> OTHER INFORMATION: Artificially synthesized primer sequence

<400> SEQUENCE: 18
tgattgtagt gctttctggc tgggctcc 28

<210> SEQ ID NO 19
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 19
caacgagagg attttgaggc t 21

<210> SEQ ID NO 20
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 20
tgcagtacaa ctccatgacc a 21

<210> SEQ ID NO 21
<211> LENGTH: 26
<212> TYPE: DNA
<213> ORGANISM: Artificial
<220> FEATURE:
<223> OTHER INFORMATION: Artificially synthesized primer sequence

<400> SEQUENCE: 21
caacaaccga aatgcaccag ccccag 26

<210> SEQ ID NO 22
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 22
tgcggcaaaa cctacacaaa g 21

<210> SEQ ID NO 23
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 23
tacaggtggg gtctttcatt c 21

<210> SEQ ID NO 24
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 24
tgtgcaccaa catctacaag 20

<210> SEQ ID NO 25
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 25
gcgttcttgg ctttcaggat 20

<210> SEQ ID NO 26
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 26
cagatcctaa acagctcgca gaat 24

<210> SEQ ID NO 27
<211> LENGTH: 23
<212> TYPE: DNA
<213> ORGANISM: Artificial
<220> FEATURE:
<223> OTHER INFORMATION: Artificially synthesized primer sequence

<400> SEQUENCE: 27
gcgtacgcaa attaaagtcc aga 23

<210> SEQ ID NO 28
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 28
aaatgtttgt gttgcggtca 20

<210> SEQ ID NO 29
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 29
tctggcacag gtgtcttcag 20

<210> SEQ ID NO 30
<211> LENGTH: 25
<212> TYPE: DNA
<213> ORGANISM: Artificial
<220> FEATURE:
<223> OTHER INFORMATION: Artificially synthesized primer sequence

<400> SEQUENCE: 30
cagccctgat tcttccacca gtccc 25

<210> SEQ ID NO 31
<211> LENGTH: 25
<212> TYPE: DNA
<213> ORGANISM: Artificial
<220> FEATURE:
<223> OTHER INFORMATION: Artificially synthesized primer sequence

<400> SEQUENCE: 31
tggaaggttc ccagtcgggt tcacc 25

<210> SEQ ID NO 32
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 32
ggaagcaaac cagaagatgc 20

<210> SEQ ID NO 33

<211> LENGTH: 20
<212> TYPE: DNA
<213> ORGANISM: Artificial
<220> FEATURE:
<223> OTHER INFORMATION: Artificially synthesized primer sequence

<400> SEQUENCE: 33
gaggcagtgt tctccagagg 20

<210> SEQ ID NO 34
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 34
atgtggcagt gtctgctgag 20

<210> SEQ ID NO 35
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 35
agaagggcta ggcttgaagg 20

<210> SEQ ID NO 36
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 36
aagacgtgtt tgcaaatgtc c 21

<210> SEQ ID NO 37
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 37
agctactgct ccaaccctga 20

<210> SEQ ID NO 38
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 38
ggtgaagagg tggaacagga 20

<210> SEQ ID NO 39
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 39
cttgagggtg gacttcttgg 20

<210> SEQ ID NO 40
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 40
cccagttcac atgcttctac 20

<210> SEQ ID NO 41
<211> LENGTH: 19
<212> TYPE: DNA
<213> ORGANISM: Artificial
<220> FEATURE:
<223> OTHER INFORMATION: Artificially synthesized primer sequence

<400> SEQUENCE: 41
gacaacttgg agggagatg 19

<210> SEQ ID NO 42
<211> LENGTH: 19
<212> TYPE: DNA
<213> ORGANISM: Artificial
<220> FEATURE:
<223> OTHER INFORMATION: Artificially synthesized primer sequence

<400> SEQUENCE: 42
gtcaacatca ccaatctgg 19

<210> SEQ ID NO 43
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 43
gtaagatagg atccatctcc 20

<210> SEQ ID NO 44
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 44
aagtgcatga ctcactggag g 21

<210> SEQ ID NO 45
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 45
taggcttcat gatactgctc c 21

<210> SEQ ID NO 46
<211> LENGTH: 20
<212> TYPE: DNA

<213> ORGANISM: Artificial
<220> FEATURE:
<223> OTHER INFORMATION: Artificially synthesized primer sequence

<400> SEQUENCE: 46
atgtgcctcc agtacccatc 20

<210> SEQ ID NO 47
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 47
tcttctggta ggtcatcttc 20

<210> SEQ ID NO 48
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 48
cgaggagaac acgtcagcgg 20

<210> SEQ ID NO 49
<211> LENGTH: 18
<212> TYPE: DNA
<213> ORGANISM: Artificial
<220> FEATURE:
<223> OTHER INFORMATION: Artificially synthesized primer sequence

<400> SEQUENCE: 49
gctcggcctt ctgctctg 18

<210> SEQ ID NO 50
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 50
cccattctgt ttcagccagt 20

<210> SEQ ID NO 51
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 51
tagtcgatga cgtgctggag 20

<210> SEQ ID NO 52
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 52
tcagcctgca tcaccagaga 20

<210> SEQ ID NO 53
<211> LENGTH: 18
<212> TYPE: DNA
<213> ORGANISM: Artificial
<220> FEATURE:
<223> OTHER INFORMATION: Artificially synthesized primer sequence

<400> SEQUENCE: 53
ccattcaact tgtcctcc 18

<210> SEQ ID NO 54
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 54
agggaagggc ccggcagctg 20

<210> SEQ ID NO 55
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 55
ttccggcagg agaggttccc 20

<210> SEQ ID NO 56
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 56
atgggatgag gaaatgcttg 20

<210> SEQ ID NO 57
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 57
tggaggaagg aaagcagaaa 20

<210> SEQ ID NO 58
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 58
gagcaaggta cctcagccag 20

<210> SEQ ID NO 59
<211> LENGTH: 20
<212> TYPE: DNA
<213> ORGANISM: Artificial
<220> FEATURE:

-continued

<223> OTHER INFORMATION: Artificially synthesized primer sequence

<400> SEQUENCE: 59
aacaatggct gagttgggac 20

<210> SEQ ID NO 60
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 60
gattcctgct acctccctcc 20

<210> SEQ ID NO 61
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 61
agcgtcctcc aaagagaaca 20

<210> SEQ ID NO 62
<211> LENGTH: 16
<212> TYPE: DNA
<213> ORGANISM: Artificial
<220> FEATURE:
<223> OTHER INFORMATION: Artificially synthesized primer sequence

<400> SEQUENCE: 62
cactgtgggc gggtcc 16

<210> SEQ ID NO 63
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 63
gttgtattgg ttcggcacca t 21

<210> SEQ ID NO 64
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 64
tcaacacgac accggataaa 20

<210> SEQ ID NO 65
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 65
tgggaatgag gaaagcaaac 20

<210> SEQ ID NO 66
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 66
ccacctcagc attaccgttt 20

<210> SEQ ID NO 67
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 67
gcttctccca gtctttgtgc 20

<210> SEQ ID NO 68
<211> LENGTH: 22
<212> TYPE: DNA
<213> ORGANISM: Artificial
<220> FEATURE:
<223> OTHER INFORMATION: Artificially synthesized primer sequence

<400> SEQUENCE: 68
aaaaagccaa actacagcga ac 22

<210> SEQ ID NO 69
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 69
gaggtgtcag atggaggagg g 21

<210> SEQ ID NO 70
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 70
aactatgttt tggtatcgtc a 21

<210> SEQ ID NO 71
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 71
cacgatgttc tggtaccgtc agca 24

<210> SEQ ID NO 72
<211> LENGTH: 22
<212> TYPE: DNA
<213> ORGANISM: Artificial
<220> FEATURE:
<223> OTHER INFORMATION: Artificially synthesized primer sequence
<400> SEQUENCE: 72
cagtgtgtcc tggtaccaac ag 22

<210> SEQ ID NO 73
<211> LENGTH: 21
<212> TYPE: DNA
<213> ORGANISM: Artificial
<220> FEATURE:
<223> OTHER INFORMATION: Artificially synthesized primer sequence
<400> SEQUENCE: 73
aaccctttat tggtaccgac a 21

<210> SEQ ID NO 74
<211> LENGTH: 22
<212> TYPE: DNA
<213> ORGANISM: Artificial
<220> FEATURE:
<223> OTHER INFORMATION: Artificially synthesized primer sequence
<400> SEQUENCE: 74
atcccttttt tggtaccaac ag 22

<210> SEQ ID NO 75
<211> LENGTH: 22
<212> TYPE: DNA
<213> ORGANISM: Artificial
<220> FEATURE:
<223> OTHER INFORMATION: Artificially synthesized primer sequence
<400> SEQUENCE: 75
aaccctttat tggtatcaac ag 22

<210> SEQ ID NO 76
<211> LENGTH: 21
<212> TYPE: DNA
<213> ORGANISM: Artificial
<220> FEATURE:
<223> OTHER INFORMATION: Artificially synthesized primer sequence
<400> SEQUENCE: 76
cgctatgtat tggtacaagc a 21

<210> SEQ ID NO 77
<211> LENGTH: 25
<212> TYPE: DNA
<213> ORGANISM: Artificial
<220> FEATURE:
<223> OTHER INFORMATION: Artificially synthesized primer sequence
<400> SEQUENCE: 77
ctcccgtttt ctggtacaga cagac 25

<210> SEQ ID NO 78
<211> LENGTH: 22
<212> TYPE: DNA
<213> ORGANISM: Artificial
<220> FEATURE:
<223> OTHER INFORMATION: Artificially synthesized primer sequence
<400> SEQUENCE: 78
cgctatgtat tggtataaac ag 22

<210> SEQ ID NO 79
<211> LENGTH: 26

<212> TYPE: DNA
<213> ORGANISM: Artificial
<220> FEATURE:
<223> OTHER INFORMATION: Artificially synthesized primer sequence

<400> SEQUENCE: 79
ttatgtttac tggtatcgta agaagc 26

<210> SEQ ID NO 80
<211> LENGTH: 22
<212> TYPE: DNA
<213> ORGANISM: Artificial
<220> FEATURE:
<223> OTHER INFORMATION: Artificially synthesized primer sequence

<400> SEQUENCE: 80
caaaatgtac tggtatcaac aa 22

<210> SEQ ID NO 81
<211> LENGTH: 25
<212> TYPE: DNA
<213> ORGANISM: Artificial
<220> FEATURE:
<223> OTHER INFORMATION: Artificially synthesized primer sequence

<400> SEQUENCE: 81
atacatgtac tggtatcgac aagac 25

<210> SEQ ID NO 82
<211> LENGTH: 23
<212> TYPE: DNA
<213> ORGANISM: Artificial
<220> FEATURE:
<223> OTHER INFORMATION: Artificially synthesized primer sequence

<400> SEQUENCE: 82
ggccatgtac tggtatagac aag 23

<210> SEQ ID NO 83
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 83
gtatatgtcc tggtatcgac aaga 24

<210> SEQ ID NO 84
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 84
taacctttat tggtatcgac gtgt 24

<210> SEQ ID NO 85
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 85

```
ggccatgtac tggtaccgac a                                                21


<210> SEQ ID NO 86
<211> LENGTH: 22
<212> TYPE: DNA
<213> ORGANISM: Artificial
<220> FEATURE:
<223> OTHER INFORMATION: Artificially synthesized primer sequence

<400> SEQUENCE: 86

tcatgtttac tggtatcggc ag                                               22


<210> SEQ ID NO 87
<211> LENGTH: 27
<212> TYPE: DNA
<213> ORGANISM: Artificial
<220> FEATURE:
<223> OTHER INFORMATION: Artificially synthesized primer sequence

<400> SEQUENCE: 87

ttatgtttat tggtatcaac agaatca                                          27


<210> SEQ ID NO 88
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 88

caacctatac tggtaccgac a                                                21


<210> SEQ ID NO 89
<211> LENGTH: 22
<212> TYPE: DNA
<213> ORGANISM: Artificial
<220> FEATURE:
<223> OTHER INFORMATION: Artificially synthesized primer sequence

<400> SEQUENCE: 89

taccctttac tggtaccggc ag                                               22


<210> SEQ ID NO 90
<211> LENGTH: 26
<212> TYPE: DNA
<213> ORGANISM: Artificial
<220> FEATURE:
<223> OTHER INFORMATION: Artificially synthesized primer sequence

<400> SEQUENCE: 90

atacttctat tggtacagac aaatct                                           26


<210> SEQ ID NO 91
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 91

cacggtctac tggtaccagc a                                                21


<210> SEQ ID NO 92
<211> LENGTH: 21
<212> TYPE: DNA
<213> ORGANISM: Artificial
```

<220> FEATURE:
<223> OTHER INFORMATION: Artificially synthesized primer sequence

<400> SEQUENCE: 92
cgtcatgtac tggtaccagc a 21

<210> SEQ ID NO 93
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 93
gccaaacagc cttacaaaga c 21

<210> SEQ ID NO 94
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 94
tttccaagcc ccacacagtc 20

<210> SEQ ID NO 95
<211> LENGTH: 25
<212> TYPE: DNA
<213> ORGANISM: Artificial
<220> FEATURE:
<223> OTHER INFORMATION: Artificially synthesized primer sequence

<400> SEQUENCE: 95
cttacctaca actgtgaatc tggtg 25

<210> SEQ ID NO 96
<211> LENGTH: 25
<212> TYPE: DNA
<213> ORGANISM: Artificial
<220> FEATURE:
<223> OTHER INFORMATION: Artificially synthesized primer sequence

<400> SEQUENCE: 96
cttacctaca acggttaacc tggtc 25

<210> SEQ ID NO 97
<211> LENGTH: 25
<212> TYPE: DNA
<213> ORGANISM: Artificial
<220> FEATURE:
<223> OTHER INFORMATION: Artificially synthesized primer sequence

<400> SEQUENCE: 97
cttacctaca acagtgagcc aactt 25

<210> SEQ ID NO 98
<211> LENGTH: 26
<212> TYPE: DNA
<213> ORGANISM: Artificial
<220> FEATURE:
<223> OTHER INFORMATION: Artificially synthesized primer sequence

<400> SEQUENCE: 98
catacccaag acagagagct gggttc 26

<210> SEQ ID NO 99
<211> LENGTH: 25
<212> TYPE: DNA
<213> ORGANISM: Artificial
<220> FEATURE:
<223> OTHER INFORMATION: Artificially synthesized primer sequence

<400> SEQUENCE: 99
cttacctagg atggagagtc gagtc 25

<210> SEQ ID NO 100
<211> LENGTH: 22
<212> TYPE: DNA
<213> ORGANISM: Artificial
<220> FEATURE:
<223> OTHER INFORMATION: Artificially synthesized primer sequence

<400> SEQUENCE: 100
catacctgtc acagtgagcc tg 22

<210> SEQ ID NO 101
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 101
ccttcttacc tagcacggtg a 21

<210> SEQ ID NO 102
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 102
cttacccagt acggtcagcc t 21

<210> SEQ ID NO 103
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 103
cccgcttacc gagcactgtc a 21

<210> SEQ ID NO 104
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 104
ccagcttacc cagcactgag a 21

<210> SEQ ID NO 105
<211> LENGTH: 16
<212> TYPE: DNA
<213> ORGANISM: Artificial
<220> FEATURE:
<223> OTHER INFORMATION: Artificially synthesized primer sequence

<400> SEQUENCE: 105
cgcgcacacc gagcac 16

<210> SEQ ID NO 106
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 106
ctcgcccagc acggtcagcc t 21

<210> SEQ ID NO 107
<211> LENGTH: 22
<212> TYPE: DNA
<213> ORGANISM: Artificial
<220> FEATURE:
<223> OTHER INFORMATION: Artificially synthesized primer sequence

<400> SEQUENCE: 107
cttacctgta accgtgagcc tg 22

<210> SEQ ID NO 108
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 108
agggttgtgt tggaatcagg 20

<210> SEQ ID NO 109
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 109
cgtcgacaac aagtgttgtt ccac 24

<210> SEQ ID NO 110
<211> LENGTH: 8
<212> TYPE: PRT
<213> ORGANISM: Human immunodeficiency virus
<220> FEATURE:
<221> NAME/KEY: DOMAIN
<222> LOCATION: (1)..(8)
<223> OTHER INFORMATION: Nef-138-8(WT)

<400> SEQUENCE: 110

Arg Tyr Pro Leu Thr Phe Gly Trp
1               5

<210> SEQ ID NO 111
<211> LENGTH: 9
<212> TYPE: PRT
<213> ORGANISM: Human immunodeficiency virus
<220> FEATURE:
<221> NAME/KEY: DOMAIN
<222> LOCATION: (1)..(9)
<223> OTHER INFORMATION: HIV-1 envelope-derived peptides

<400> SEQUENCE: 111

Arg Tyr Leu Arg Asp Gln Gln Leu Leu
1 5

<210> SEQ ID NO 112
<211> LENGTH: 9
<212> TYPE: PRT
<213> ORGANISM: Human immunodeficiency virus
<220> FEATURE:
<221> NAME/KEY: DOMAIN
<222> LOCATION: (1)..(9)
<223> OTHER INFORMATION: Gag-28-9(wt)

<400> SEQUENCE: 112

Lys Tyr Lys Leu Lys His Ile Val Trp
1 5

<210> SEQ ID NO 113
<211> LENGTH: 8
<212> TYPE: PRT
<213> ORGANISM: artificial
<220> FEATURE:
<223> OTHER INFORMATION: Artificially synthesized polypeptide sequence (Nef-138-8(2F))

<400> SEQUENCE: 113

Arg Phe Pro Leu Thr Phe Gly Trp
1 5

<210> SEQ ID NO 114
<211> LENGTH: 25
<212> TYPE: DNA
<213> ORGANISM: Artificial
<220> FEATURE:
<223> OTHER INFORMATION: Artificially synthesized primer sequence

<400> SEQUENCE: 114
atttgttttt tgggtagtta aaggt 25

<210> SEQ ID NO 115
<211> LENGTH: 27
<212> TYPE: DNA
<213> ORGANISM: Artificial
<220> FEATURE:
<223> OTHER INFORMATION: Artificially synthesized primer sequence

<400> SEQUENCE: 115
ccaactatct tcatcttaat aacatcc 27

<210> SEQ ID NO 116
<211> LENGTH: 25
<212> TYPE: DNA
<213> ORGANISM: Artificial
<220> FEATURE:
<223> OTHER INFORMATION: Artificially synthesized primer sequence

<400> SEQUENCE: 116
tggttaggtt ggttttaaat ttttg 25

<210> SEQ ID NO 117
<211> LENGTH: 26
<212> TYPE: DNA
<213> ORGANISM: Artificial
<220> FEATURE:
<223> OTHER INFORMATION: Artificially synthesized primer sequence

<400> SEQUENCE: 117
aacccaccct tataaattct caatta 26

<210> SEQ ID NO 118
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 118
aacagcctca agatcatcag c 21

<210> SEQ ID NO 119
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 119
ttggcaggtt tttctagacg g 21

<210> SEQ ID NO 120
<211> LENGTH: 19
<212> TYPE: DNA
<213> ORGANISM: Artificial
<220> FEATURE:
<223> OTHER INFORMATION: Artificially synthesized primer sequence

<400> SEQUENCE: 120
attcagccaa acgaccatc 19

<210> SEQ ID NO 121
<211> LENGTH: 19
<212> TYPE: DNA
<213> ORGANISM: Artificial
<220> FEATURE:
<223> OTHER INFORMATION: Artificially synthesized primer sequence

<400> SEQUENCE: 121
ggaaagggac cgaggagta 19

<210> SEQ ID NO 122
<211> LENGTH: 18
<212> TYPE: DNA
<213> ORGANISM: Artificial
<220> FEATURE:
<223> OTHER INFORMATION: Artificially synthesized primer sequence

<400> SEQUENCE: 122
cagcgcatgg acagttac 18

<210> SEQ ID NO 123
<211> LENGTH: 18
<212> TYPE: DNA
<213> ORGANISM: Artificial
<220> FEATURE:
<223> OTHER INFORMATION: Artificially synthesized primer sequence

<400> SEQUENCE: 123
ggagtgggag gaagaggt 18

<210> SEQ ID NO 124
<211> LENGTH: 18
<212> TYPE: DNA
<213> ORGANISM: Artificial

<220> FEATURE:
<223> OTHER INFORMATION: Artificially synthesized primer sequence

<400> SEQUENCE: 124
agtttcatct gcgacccg 18

<210> SEQ ID NO 125
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 125
cctcatcttc ttgttcctcc t 21

<210> SEQ ID NO 126
<211> LENGTH: 18
<212> TYPE: DNA
<213> ORGANISM: Artificial
<220> FEATURE:
<223> OTHER INFORMATION: Artificially synthesized primer sequence

<400> SEQUENCE: 126
gcgggaaggg agaagaca 18

<210> SEQ ID NO 127
<211> LENGTH: 18
<212> TYPE: DNA
<213> ORGANISM: Artificial
<220> FEATURE:
<223> OTHER INFORMATION: Artificially synthesized primer sequence

<400> SEQUENCE: 127
ccggatcgga taggtgaa 18

<210> SEQ ID NO 128
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 128
gacaggggga ggggaggagc tagg 24

<210> SEQ ID NO 129
<211> LENGTH: 26
<212> TYPE: DNA
<213> ORGANISM: Artificial
<220> FEATURE:
<223> OTHER INFORMATION: Artificially synthesized primer sequence

<400> SEQUENCE: 129
cttccctcca accagttgcc ccaaac 26

<210> SEQ ID NO 130
<211> LENGTH: 26
<212> TYPE: DNA
<213> ORGANISM: Artificial
<220> FEATURE:
<223> OTHER INFORMATION: Artificially synthesized primer sequence

<400> SEQUENCE: 130
gggaaatggg aggggtgcaa aagagg 26

<210> SEQ ID NO 131
<211> LENGTH: 26
<212> TYPE: DNA
<213> ORGANISM: Artificial
<220> FEATURE:
<223> OTHER INFORMATION: Artificially synthesized primer sequence

<400> SEQUENCE: 131
ttgcgtgagt gtggatggga ttggtg 26

<210> SEQ ID NO 132
<211> LENGTH: 26
<212> TYPE: DNA
<213> ORGANISM: Artificial
<220> FEATURE:
<223> OTHER INFORMATION: Artificially synthesized primer sequence

<400> SEQUENCE: 132
gcgtcctggg aagggagatc cggagc 26

<210> SEQ ID NO 133
<211> LENGTH: 26
<212> TYPE: DNA
<213> ORGANISM: Artificial
<220> FEATURE:
<223> OTHER INFORMATION: Artificially synthesized primer sequence

<400> SEQUENCE: 133
ttgaggggca tcgtcgcggg aggctg 26

<210> SEQ ID NO 134
<211> LENGTH: 25
<212> TYPE: DNA
<213> ORGANISM: Artificial
<220> FEATURE:
<223> OTHER INFORMATION: Artificially synthesized primer sequence

<400> SEQUENCE: 134
acgatcgtgg ccccggaaaa ggacc 25

<210> SEQ ID NO 135
<211> LENGTH: 28
<212> TYPE: DNA
<213> ORGANISM: Artificial
<220> FEATURE:
<223> OTHER INFORMATION: Artificially synthesized primer sequence

<400> SEQUENCE: 135
tgattgtagt gctttctggc tgggctcc 28

<210> SEQ ID NO 136
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 136
caacgagagg attttgaggc t 21

<210> SEQ ID NO 137
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 137
tgcagtacaa ctccatgacc a 21

<210> SEQ ID NO 138
<211> LENGTH: 26
<212> TYPE: DNA
<213> ORGANISM: Artificial
<220> FEATURE:
<223> OTHER INFORMATION: Artificially synthesized primer sequence

<400> SEQUENCE: 138
caacaaccga aatgcaccag ccccag 26

<210> SEQ ID NO 139
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 139
tgcggcaaaa cctacacaaa g 21

<210> SEQ ID NO 140
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 140
tacaggtggg gtctttcatt c 21

<210> SEQ ID NO 141
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 141
tgtgcaccaa catctacaag 20

<210> SEQ ID NO 142
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 142
gcgttcttgg ctttcaggat 20

<210> SEQ ID NO 143
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 143
cagatcctaa acagctcgca gaat 24

<210> SEQ ID NO 144

-continued

<211> LENGTH: 23
<212> TYPE: DNA
<213> ORGANISM: Artificial
<220> FEATURE:
<223> OTHER INFORMATION: Artificially synthesized primer sequence

<400> SEQUENCE: 144
gcgtacgcaa attaaagtcc aga 23

<210> SEQ ID NO 145
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 145
aaatgtttgt gttgcggtca 20

<210> SEQ ID NO 146
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 146
tctggcacag gtgtcttcag 20

<210> SEQ ID NO 147
<211> LENGTH: 25
<212> TYPE: DNA
<213> ORGANISM: Artificial
<220> FEATURE:
<223> OTHER INFORMATION: Artificially synthesized primer sequence

<400> SEQUENCE: 147
cagccctgat tcttccacca gtccc 25

<210> SEQ ID NO 148
<211> LENGTH: 25
<212> TYPE: DNA
<213> ORGANISM: Artificial
<220> FEATURE:
<223> OTHER INFORMATION: Artificially synthesized primer sequence

<400> SEQUENCE: 148
tggaaggttc ccagtcgggt tcacc 25

<210> SEQ ID NO 149
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 149
gagcaaggta cctcagccag 20

<210> SEQ ID NO 150
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 150
aacaatggct gagttgggac 20

<210> SEQ ID NO 151
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 151
gattcctgct acctccctcc 20

<210> SEQ ID NO 152
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 152
agcgtcctcc aaagagaaca 20

<210> SEQ ID NO 153
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 153
aactatgttt tggtatcgtc a 21

<210> SEQ ID NO 154
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 154
cacgatgttc tggtaccgtc agca 24

<210> SEQ ID NO 155
<211> LENGTH: 22
<212> TYPE: DNA
<213> ORGANISM: Artificial
<220> FEATURE:
<223> OTHER INFORMATION: Artificially synthesized primer sequence

<400> SEQUENCE: 155
cagtgtgtcc tggtaccaac ag 22

<210> SEQ ID NO 156
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 156 aacccttat tggtaccgac a 21

<210> SEQ ID NO 157
<211> LENGTH: 22
<212> TYPE: DNA

<213> ORGANISM: Artificial
<220> FEATURE:
<223> OTHER INFORMATION: Artificially synthesized primer sequence

<400> SEQUENCE: 157
atcccttttt tggtaccaac ag 22

<210> SEQ ID NO 158
<211> LENGTH: 22
<212> TYPE: DNA
<213> ORGANISM: Artificial
<220> FEATURE:
<223> OTHER INFORMATION: Artificially synthesized primer sequence

<400> SEQUENCE: 158
aaccctttat tggtatcaac ag 22

<210> SEQ ID NO 159
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 159
cgctatgtat tggtacaagc a 21

<210> SEQ ID NO 160
<211> LENGTH: 25
<212> TYPE: DNA
<213> ORGANISM: Artificial
<220> FEATURE:
<223> OTHER INFORMATION: Artificially synthesized primer sequence

<400> SEQUENCE: 160
ctcccgtttt ctggtacaga cagac 25

<210> SEQ ID NO 161
<211> LENGTH: 22
<212> TYPE: DNA
<213> ORGANISM: Artificial
<220> FEATURE:
<223> OTHER INFORMATION: Artificially synthesized primer sequence

<400> SEQUENCE: 161
cgctatgtat tggtataaac ag 22

<210> SEQ ID NO 162
<211> LENGTH: 26
<212> TYPE: DNA
<213> ORGANISM: Artificial
<220> FEATURE:
<223> OTHER INFORMATION: Artificially synthesized primer sequence

<400> SEQUENCE: 162
ttatgtttac tggtatcgta agaagc 26

<210> SEQ ID NO 163
<211> LENGTH: 22
<212> TYPE: DNA
<213> ORGANISM: Artificial
<220> FEATURE:
<223> OTHER INFORMATION: Artificially synthesized primer sequence

<400> SEQUENCE: 163
caaaatgtac tggtatcaac aa 22

<210> SEQ ID NO 164
<211> LENGTH: 25
<212> TYPE: DNA
<213> ORGANISM: Artificial
<220> FEATURE:
<223> OTHER INFORMATION: Artificially synthesized primer sequence

<400> SEQUENCE: 164
atacatgtac tggtatcgac aagac 25

<210> SEQ ID NO 165
<211> LENGTH: 23
<212> TYPE: DNA
<213> ORGANISM: Artificial
<220> FEATURE:
<223> OTHER INFORMATION: Artificially synthesized primer sequence

<400> SEQUENCE: 165
ggccatgtac tggtatagac aag 23

<210> SEQ ID NO 166
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 166
gtatatgtcc tggtatcgac aaga 24

<210> SEQ ID NO 167
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 167
taacctttat tggtatcgac gtgt 24

<210> SEQ ID NO 168
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 168
ggccatgtac tggtaccgac a 21

<210> SEQ ID NO 169
<211> LENGTH: 22
<212> TYPE: DNA
<213> ORGANISM: Artificial
<220> FEATURE:
<223> OTHER INFORMATION: Artificially synthesized primer sequence

<400> SEQUENCE: 169
tcatgtttac tggtatcggc ag 22

<210> SEQ ID NO 170
<211> LENGTH: 27
<212> TYPE: DNA
<213> ORGANISM: Artificial
<220> FEATURE:

```
<223> OTHER INFORMATION: Artificially synthesized primer sequence

<400> SEQUENCE: 170

ttatgtttat tggtatcaac agaatca                                       27


<210> SEQ ID NO 171
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 171

caacctatac tggtaccgac a                                             21


<210> SEQ ID NO 172
<211> LENGTH: 22
<212> TYPE: DNA
<213> ORGANISM: Artificial
<220> FEATURE:
<223> OTHER INFORMATION: Artificially synthesized primer sequence

<400> SEQUENCE: 172

taccctttac tggtaccggc ag                                            22


<210> SEQ ID NO 173
<211> LENGTH: 26
<212> TYPE: DNA
<213> ORGANISM: Artificial
<220> FEATURE:
<223> OTHER INFORMATION: Artificially synthesized primer sequence

<400> SEQUENCE: 173

atacttctat tggtacagac aaatct                                        26


<210> SEQ ID NO 174
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 174

cacggtctac tggtaccagc a                                             21


<210> SEQ ID NO 175
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 175

cgtcatgtac tggtaccagc a                                             21


<210> SEQ ID NO 176
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 176

gccaaacagc cttacaaaga c                                             21
```

<210> SEQ ID NO 177
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 177
tttccaagcc ccacacagtc 20

<210> SEQ ID NO 178
<211> LENGTH: 25
<212> TYPE: DNA
<213> ORGANISM: Artificial
<220> FEATURE:
<223> OTHER INFORMATION: Artificially synthesized primer sequence

<400> SEQUENCE: 178
cttacctaca actgtgaatc tggtg 25

<210> SEQ ID NO 179
<211> LENGTH: 25
<212> TYPE: DNA
<213> ORGANISM: Artificial
<220> FEATURE:
<223> OTHER INFORMATION: Artificially synthesized primer sequence

<400> SEQUENCE: 179
cttacctaca acggttaacc tggtc 25

<210> SEQ ID NO 180
<211> LENGTH: 25
<212> TYPE: DNA
<213> ORGANISM: Artificial
<220> FEATURE:
<223> OTHER INFORMATION: Artificially synthesized primer sequence

<400> SEQUENCE: 180
cttacctaca acagtgagcc aactt 25

<210> SEQ ID NO 181
<211> LENGTH: 26
<212> TYPE: DNA
<213> ORGANISM: Artificial
<220> FEATURE:
<223> OTHER INFORMATION: Artificially synthesized primer sequence

<400> SEQUENCE: 181
catacccaag acagagagct gggttc 26

<210> SEQ ID NO 182
<211> LENGTH: 25
<212> TYPE: DNA
<213> ORGANISM: Artificial
<220> FEATURE:
<223> OTHER INFORMATION: Artificially synthesized primer sequence

<400> SEQUENCE: 182
cttacctagg atggagagtc gagtc 25

<210> SEQ ID NO 183
<211> LENGTH: 22
<212> TYPE: DNA
<213> ORGANISM: Artificial
<220> FEATURE:
<223> OTHER INFORMATION: Artificially synthesized primer sequence

<400> SEQUENCE: 183
catacctgtc acagtgagcc tg 22

<210> SEQ ID NO 184
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 184
ccttcttacc tagcacggtg a 21

<210> SEQ ID NO 185
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 185
cttacccagt acggtcagcc t 21

<210> SEQ ID NO 186
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 186
cccgcttacc gagcactgtc a 21

<210> SEQ ID NO 187
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 187
ccagcttacc cagcactgag a 21

<210> SEQ ID NO 188
<211> LENGTH: 16
<212> TYPE: DNA
<213> ORGANISM: Artificial
<220> FEATURE:
<223> OTHER INFORMATION: Artificially synthesized primer sequence

<400> SEQUENCE: 188
cgcgcacacc gagcac 16

<210> SEQ ID NO 189
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 189
ctcgcccagc acggtcagcc t 21

<210> SEQ ID NO 190
<211> LENGTH: 22

<212> TYPE: DNA
<213> ORGANISM: Artificial
<220> FEATURE:
<223> OTHER INFORMATION: Artificially synthesized primer sequence

<400> SEQUENCE: 190
cttacctgta accgtgagcc tg 22

<210> SEQ ID NO 191
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 191
tctggtatgt gcaatacccc aacc 24

<210> SEQ ID NO 192
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 192
ctgaggaaac cctctgtgca 20

<210> SEQ ID NO 193
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 193
ccgggcagca gacactgctt ctta 24

<210> SEQ ID NO 194
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 194
gatggaaggt ttacagcaca gctc 24

<210> SEQ ID NO 195
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 195
cctcccaggg tccagagtac g 21

<210> SEQ ID NO 196
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 196
ggattgcgct gaaggaagag 20

<210> SEQ ID NO 197
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 197
gcaacatgct ggcggagcac ccac 24

<210> SEQ ID NO 198
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 198
tgaaggtcac ctttgatacc accc 24

<210> SEQ ID NO 199
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 199
aactgcacgt accagacatc 20

<210> SEQ ID NO 200
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 200
accctgagtg tccaggaggg 20

<210> SEQ ID NO 201
<211> LENGTH: 23
<212> TYPE: DNA
<213> ORGANISM: Artificial
<220> FEATURE:
<223> OTHER INFORMATION: Artificially synthesized primer sequence

<400> SEQUENCE: 201
cactgctgac cttaacaaag gcg 23

<210> SEQ ID NO 202
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 202
tcctggtgac agtagttacg 20

<210> SEQ ID NO 203
<211> LENGTH: 24
<212> TYPE: DNA
<213> ORGANISM: Artificial

<220> FEATURE:
<223> OTHER INFORMATION: Artificially synthesized primer sequence

<400> SEQUENCE: 203
aggctcaaag ccttctcagc aggg 24

<210> SEQ ID NO 204
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 204
tccaccagtt ccttcaactt cacc 24

<210> SEQ ID NO 205
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 205
ttcatcaaaa cccttgggga cagc 24

<210> SEQ ID NO 206
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 206
cccagcaggc agatgattct cgtt 24

<210> SEQ ID NO 207
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 207
ggataaacat ctgtctctgc g 21

<210> SEQ ID NO 208
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 208
aagggaatcc tctgactgtg 20

<210> SEQ ID NO 209
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 209
gatagccata cgtccagatg 20

<210> SEQ ID NO 210
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 210
tgccactctt aataccaagg aggg 24

<210> SEQ ID NO 211
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 211
acactggctg caacagcatc 20

<210> SEQ ID NO 212
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 212
ttacaaacga agtggcctcc 20

<210> SEQ ID NO 213
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 213
accctgctga aggtcctaca ttcc 24

<210> SEQ ID NO 214
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 214
cttggagaaa ggctcagttc 20

<210> SEQ ID NO 215
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 215
tgcctcgctg gataaatcat cagg 24

<210> SEQ ID NO 216
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 216
tcccagctca gcgattcagc ctcc 24

<210> SEQ ID NO 217
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 217
gtcctgtcct cttgatagcc 20

<210> SEQ ID NO 218
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 218
aactgcacgt accagacatc 20

<210> SEQ ID NO 219
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 219
agcccagcca tgcaggcatc tacc 24

<210> SEQ ID NO 220
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 220
gaacatcaca gccacccaga ccgg 24

<210> SEQ ID NO 221
<211> LENGTH: 23
<212> TYPE: DNA
<213> ORGANISM: Artificial
<220> FEATURE:
<223> OTHER INFORMATION: Artificially synthesized primer sequence

<400> SEQUENCE: 221
gcaaagctcc ctgtacctta cgg 23

<210> SEQ ID NO 222
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 222
cacagcccct aaacctgaag 20

<210> SEQ ID NO 223

<211> LENGTH: 20
<212> TYPE: DNA
<213> ORGANISM: Artificial
<220> FEATURE:
<223> OTHER INFORMATION: Artificially synthesized primer sequence

<400> SEQUENCE: 223
agcaaaaact tcggaggcgg 20

<210> SEQ ID NO 224
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 224
aaggagagga cttcaccacg 20

<210> SEQ ID NO 225
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 225
ggcaagacgg aaccaatgtt 20

<210> SEQ ID NO 226
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 226
ggggaggtgg tgacagagtc 20

<210> SEQ ID NO 227
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 227
tgacggtgca attttctgct 20

<210> SEQ ID NO 228
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 228
agaaacgcca cgtccaagtt 20

<210> SEQ ID NO 229
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 229
tcctagccag gacgacgatt 20

<210> SEQ ID NO 230
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 230
tcctgggatc agaggaggaa 20

<210> SEQ ID NO 231
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 231
tctcctcccc tgactgtggt 20

<210> SEQ ID NO 232
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 232
tgcaccctga gatggttctt t 21

<210> SEQ ID NO 233
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 233
ctgccccgag acctgataac 20

<210> SEQ ID NO 234
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 234
ttggctgcca cctgtctcta 20

<210> SEQ ID NO 235
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 235
gaatgttttg gaggggcaag 20

<210> SEQ ID NO 236
<211> LENGTH: 20
<212> TYPE: DNA

<213> ORGANISM: Artificial
<220> FEATURE:
<223> OTHER INFORMATION: Artificially synthesized primer sequence

<400> SEQUENCE: 236
ttcaatgctc ccctccactt 20

<210> SEQ ID NO 237
<211> LENGTH: 18
<212> TYPE: DNA
<213> ORGANISM: Artificial
<220> FEATURE:
<223> OTHER INFORMATION: Artificially synthesized primer sequence

<400> SEQUENCE: 237
caacgcagag tacgcggg 18

<210> SEQ ID NO 238
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 238
gctgttgttg aaggcgtttg 20

<210> SEQ ID NO 239
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 239
tctccgagag cccgtagaac 20

<210> SEQ ID NO 240
<211> LENGTH: 43
<212> TYPE: DNA
<213> ORGANISM: Homo sapiens
<220> FEATURE:
<221> NAME/KEY: misc_feature
<222> LOCATION: (1)..(43)
<223> OTHER INFORMATION: TRAV8-3*01 TRAJ10*01

<400> SEQUENCE: 240
tgtgctgtgg gtttcacggg aggaggaaac aaactcacct ttt 43

<210> SEQ ID NO 241
<211> LENGTH: 37
<212> TYPE: DNA
<213> ORGANISM: Homo sapiens
<220> FEATURE:
<221> NAME/KEY: misc_feature
<222> LOCATION: (1)..(37)
<223> OTHER INFORMATION: TRAV13-1*01 TRAJ29*01

<400> SEQUENCE: 241
tgtgcagcaa tcctcaggaa acacacctct tgtcttt 37

<210> SEQ ID NO 242
<211> LENGTH: 39
<212> TYPE: DNA
<213> ORGANISM: Homo sapiens
<220> FEATURE:
<221> NAME/KEY: misc_feature

<222> LOCATION: (1)..(39)
<223> OTHER INFORMATION: TRAV38-2/DV8*01 TRAJ31*01

<400> SEQUENCE: 242
tgtgcttatt ggagtaataa caatgccaga ctcatgttt 39

<210> SEQ ID NO 243
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: TRAV12-1*01 TRAJ7*01

<400> SEQUENCE: 243
tgtgtggtgt actatgggaa caacagactc gctttt 36

<210> SEQ ID NO 244
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: TRAV21*02 TRAJ16*01

<400> SEQUENCE: 244
tgtgctggtt cagatggcca gaagctgctc ttt 33

<210> SEQ ID NO 245
<211> LENGTH: 42
<212> TYPE: DNA
<213> ORGANISM: Homo sapiens
<220> FEATURE:
<221> NAME/KEY: misc_feature
<222> LOCATION: (1)..(42)
<223> OTHER INFORMATION: TRAV1-2*01 TRAJ6*01

<400> SEQUENCE: 245
tgtgctgtga gagcatcagg aggaagctac atacctacat tt 42

<210> SEQ ID NO 246
<211> LENGTH: 42
<212> TYPE: DNA
<213> ORGANISM: Homo sapiens
<220> FEATURE:
<221> NAME/KEY: misc_feature
<222> LOCATION: (1)..(42)
<223> OTHER INFORMATION: TRAV1-2*01 TRAJ7*01

<400> SEQUENCE: 246
tgtgctgtga gagattttta tgggaacaac ggactcgctt tt 42

<210> SEQ ID NO 247
<211> LENGTH: 42
<212> TYPE: DNA
<213> ORGANISM: Homo sapiens
<220> FEATURE:
<221> NAME/KEY: misc_feature
<222> LOCATION: (1)..(42)
<223> OTHER INFORMATION: TRAV1-2*01 TRAJ10*01

<400> SEQUENCE: 247
tgtgctgtga gagatccggg aggaggaaac agactcacct tt 42

<210> SEQ ID NO 248

<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: TRAV1-2*01 TRAJ16*01

<400> SEQUENCE: 248
tgtactgtgt tttcacatgg ccaaaagctg ctcttt 36

<210> SEQ ID NO 249
<211> LENGTH: 42
<212> TYPE: DNA
<213> ORGANISM: Homo sapiens
<220> FEATURE:
<221> NAME/KEY: misc_feature
<222> LOCATION: (1)..(42)
<223> OTHER INFORMATION: TRAV8-1*01 TRAJ6*01

<400> SEQUENCE: 249
tgtgccgtga atgcatcagg aggaagctac atacctacat tt 42

<210> SEQ ID NO 250
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: TRAV12-1*01 TRAJ6*01

<400> SEQUENCE: 250
tgtgtggtgt caggaggaag ctacatacct acattt 36

<210> SEQ ID NO 251
<211> LENGTH: 39
<212> TYPE: DNA
<213> ORGANISM: Homo sapiens
<220> FEATURE:
<221> NAME/KEY: misc_feature
<222> LOCATION: (1)..(39)
<223> OTHER INFORMATION: TRAV12-1*01 TRAJ9*01

<400> SEQUENCE: 251
tgtgtggtga acaatactgg aggattcaaa actatcttt 39

<210> SEQ ID NO 252
<211> LENGTH: 41
<212> TYPE: DNA
<213> ORGANISM: Homo sapiens
<220> FEATURE:
<221> NAME/KEY: misc_feature
<222> LOCATION: (1)..(41)
<223> OTHER INFORMATION: TRAV6*01 TRAJ13*01

<400> SEQUENCE: 252
tgtgctctag acattctggg ggttaccaga aagttacctt t 41

<210> SEQ ID NO 253
<211> LENGTH: 38
<212> TYPE: DNA
<213> ORGANISM: Homo sapiens
<220> FEATURE:
<221> NAME/KEY: misc_feature
<222> LOCATION: (1)..(38)
<223> OTHER INFORMATION: TRAV12-1*01 TRAJ27*01

<400> SEQUENCE: 253
gtgtggtgaa caacaccaat gcaggcaaat caaccttt 38

<210> SEQ ID NO 254
<211> LENGTH: 45
<212> TYPE: DNA
<213> ORGANISM: Homo sapiens
<220> FEATURE:
<221> NAME/KEY: misc_feature
<222> LOCATION: (1)..(45)
<223> OTHER INFORMATION: TRBV7-9*01 TRBD1*01 TRBJ2-5*01

<400> SEQUENCE: 254
tgtgccagca gcttacggga cagggtgccg gagacccagt acttc 45

<210> SEQ ID NO 255
<211> LENGTH: 51
<212> TYPE: DNA
<213> ORGANISM: Homo sapiens
<220> FEATURE:
<221> NAME/KEY: misc_feature
<222> LOCATION: (1)..(51)
<223> OTHER INFORMATION: Germline TRBD1*01 TRBJ2-7*01

<400> SEQUENCE: 255
tacaaagctg taacattgtg gggacaactc tacgagcagt acttcgggcc g 51

<210> SEQ ID NO 256
<211> LENGTH: 47
<212> TYPE: DNA
<213> ORGANISM: Homo sapiens
<220> FEATURE:
<221> NAME/KEY: misc_feature
<222> LOCATION: (1)..(47)
<223> OTHER INFORMATION: TRBV29-1*02 TRBD1*01 TRBJ2-2*01

<400> SEQUENCE: 256
tatatctctg cagcgttgat ggacagggaa acaccgggga gctgttt 47

<210> SEQ ID NO 257
<211> LENGTH: 51
<212> TYPE: DNA
<213> ORGANISM: Homo sapiens
<220> FEATURE:
<221> NAME/KEY: misc_feature
<222> LOCATION: (1)..(51)
<223> OTHER INFORMATION: Germline TRBD2*01/*02 TRBJ2-7*01/*02

<400> SEQUENCE: 257
tatcatggtg taacattgtg gggactagtt taccctacga gcagtacttc g 51

<210> SEQ ID NO 258
<211> LENGTH: 42
<212> TYPE: DNA
<213> ORGANISM: Homo sapiens
<220> FEATURE:
<221> NAME/KEY: misc_feature
<222> LOCATION: (1)..(42)
<223> OTHER INFORMATION: TRBV29-1*01 TRBD1*01 TRBJ2-2*01

<400> SEQUENCE: 258
tgcagcgttg atggacaggg aaacaccggg gagctgtttt tt 42